(12) United States Patent
Biediger et al.

(10) Patent No.: US 7,812,038 B2
(45) Date of Patent: Oct. 12, 2010

(54) CARBOXYLIC ACID DERIVATIVES THAT INHIBIT THE BINDING OF INTEGRINS TO THEIR RECEPTORS

(75) Inventors: Ronald J. Biediger, Houston, TX (US); Qi Chen, Carmel, IN (US); E. Radford Decker, Houston, TX (US); George W. Holland, Houston, TX (US); Jamal M. Kassir, Stafford, TX (US); Wen Li, Pearland, TX (US); Robert V. Market, Pearland, TX (US); Ian L. Scott, Delanson, NY (US); Chengde Wu, Pearland, TX (US); Jian Li, The Woodlands, TX (US)

(73) Assignee: Encysive Pharmaceuticals, Inc., New York, NY (US)

( * ) Notice: Subject to any disclaimer, the term of this patent is extended or adjusted under 35 U.S.C. 154(b) by 1490 days.

(21) Appl. No.: 11/152,695

(22) Filed: Jun. 14, 2005

(65) Prior Publication Data

US 2006/0276476 A1    Dec. 7, 2006

Related U.S. Application Data

(60) Division of application No. 09/973,142, filed on Oct. 9, 2001, now Pat. No. 6,972,296, which is a continuation-in-part of application No. 09/707,068, filed on Nov. 6, 2000, now abandoned, which is a continuation-in-part of application No. 09/565,920, filed on May 5, 2000, now abandoned.

(60) Provisional application No. 60/132,971, filed on May 7, 1999.

(51) Int. Cl.
   *A61K 31/4412* (2006.01)
(52) U.S. Cl. .................. 514/352; 514/345; 514/349; 546/183; 546/290; 546/296; 546/297
(58) Field of Classification Search .................. 546/157, 546/297, 290, 296, 183; 514/311, 349, 312, 514/313, 345, 352
   See application file for complete search history.

(56) References Cited

U.S. PATENT DOCUMENTS

| 5,182,290 | A | 1/1993 | Albaugh |
|---|---|---|---|
| 5,192,746 | A | 3/1993 | Lobl et al. |
| 5,312,822 | A | 5/1994 | Albaugh |
| 5,451,585 | A | 9/1995 | Albaugh |
| 5,484,946 | A | 1/1996 | Abood et al. |
| 5,510,332 | A | 4/1996 | Kogan et al. |
| 5,521,179 | A | 5/1996 | Bernstein et al. |
| 5,656,627 | A | 8/1997 | Bemis et al. |
| 5,710,153 | A | 1/1998 | Ohmoto et al. |
| 5,721,366 | A | 2/1998 | Abood et al. |
| 5,756,466 | A | 5/1998 | Bemis et al. |
| 5,770,573 | A | 6/1998 | Arrhenius et al. |
| 5,821,231 | A | 10/1998 | Arrhenius et al. |
| 5,936,065 | A | 8/1999 | Arrhenius et al. |
| 6,096,773 | A | 8/2000 | Scott et al. |
| 6,194,448 | B1 | 2/2001 | Biediger et al. |
| 6,972,296 | B2 | 12/2005 | Biediger et al. |

FOREIGN PATENT DOCUMENTS

| AU | A-92421/98 | 10/1999 |
|---|---|---|
| DE | 26 14 189 | 10/1977 |
| EP | 0 341 915 | 5/1989 |
| EP | 0 335 819 | 2/1990 |
| EP | 0355819 | 2/1990 |
| EP | 0 422 9038 A1 | 4/1991 |
| EP | 0 508 798 A1 | 10/1992 |
| EP | 0 512 831 A1 | 11/1992 |
| GB | 2288800 | 11/1995 |
| HU | P0104800 | 12/2003 |
| HU | P0201729 | 1/2005 |
| JP | 7-304735 | 11/1995 |
| RU | 94045874 | 9/1996 |
| WO | WO 91/13862 | 9/1991 |
| WO | WO 9422820 | 10/1994 |
| WO | WO 95/15973 | 6/1995 |
| WO | WO 95/26958 | 10/1995 |
| WO | WO 95/32205 | 11/1995 |
| WO | WO 96/06108 | 2/1996 |

(Continued)

OTHER PUBLICATIONS

L. Ismaili, et al.; Synthesis of New Pyrazolo(4,3-c)quinoline-3-one Derivatives and Some Oxazolo(4,5-c)quinoline-2,4-diones; Journal of Hetercyclic Chemistry, vol. 36, No. 3, 1999, pp. 719-722; France.
J. J. Panouse, et al.; Relations structrures-activities des immunomodulateurs. Apport de la modelisation moleculaire; Annales Pharmaceutiques Francaiscs, vol. 58, No. 5, 2000, pp. 291-302.
D. Eric Walters, et al., Genetically Evolved Receptor Models: A Computational Approach to Construction of Receptor Models. J. Med. Chem., vol. 37, No. 16, 1994, pp. 2527-2536.
Andrian et al., *N England J Med* 348:1 (2003).
Arrhenius et al., "Small Molecule Inhibitors of the Leukocyte Integrin VLA-4", in *Peptides: Chemistry, Structure and Biology*, Proceedings of the Fourteenth American Peptide Symposium, Jun. 18-23, 1995, Columbus, Ohio, UsA, pp. 337-339.
Birkofer et al., *Justus Liebigs Ann Chem* 628:162-170 (1959).
Crider et al., *J Pharm Sci* 70(2):192-195 (1981).
Flouzat et al., *Tetrahedron Lett* 33(32):4571-4574 (1992).

(Continued)

*Primary Examiner*—Janet L Andres
*Assistant Examiner*—David E Gallis
(74) *Attorney, Agent, or Firm*—Jones Day

(57) ABSTRACT

A method for the inhibition of the binding of $\alpha_4\beta_1$ integrin to its receptors, for example VCAM-1 (vascular cell adhesion molecule-1) and fibronectin; compounds that inhibit this binding; pharmaceutically active compositions comprising such compounds; and to the use of such compounds either a above, or in formulations for the control or prevention of diseases states in which $\alpha_4\beta_1$ is involved.

7 Claims, No Drawings

FOREIGN PATENT DOCUMENTS

| | | |
|---|---|---|
| WO | WO 98/04247 | 2/1996 |
| WO | WO 96/22966 | 8/1996 |
| WO | WO 97/43650 | 11/1997 |
| WO | WO 98/11896 | 3/1998 |
| WO | WO98/22494 | 5/1998 |
| WO | WO 99/32459 | 1/1999 |
| WO | WO 99/96434 | 2/1999 |
| WO | WO 99/10313 | 3/1999 |
| WO | WO 99/20272 | 4/1999 |
| WO | WO 99/24398 | 5/1999 |
| WO | WO 00/17197 | 9/1999 |
| WO | WO 99/52493 | 10/1999 |
| WO | WO 99/64397 | 12/1999 |
| WO | WO 00/02903 | 1/2000 |
| WO | WO 00/29019 | 5/2000 |
| WO | WO 00/47564 | 8/2000 |
| WO | WO 00/53168 | 9/2000 |
| WO | WO 00/61631 | 10/2000 |
| WO | WO 00/67746 | 11/2000 |
| WO | WO 00/68188 | 11/2000 |
| WO | WO 01/46190 A1 | 6/2001 |
| WO | WO 98/04913 | 2/2008 |

OTHER PUBLICATIONS

Greene et al., In *"Protective Groups in Organic Synthesis"*, John Willey & Sons, p. 271.
Johnson et al., *J Amer Chem Soc* 58:299-301 (1936).
MacLeod et al., *J Med Chem* 38(2)2239-2243 (1995).
Morsch, *Monatsh Chem* 64:333-338 (1934).
Mousa et al., *Cardiovacular Res* 47(4):819-826 (2000).
Rodionow et al., *J Obsc Chim* 3:628-632 (1933).
Sebatine et al., *Am J Med* 109(3):224-237 (2000).
Shantare et al., *Chem Heterocycl Comps* 34(3):351-358 (1998).

CARBOXYLIC ACID DERIVATIVES THAT INHIBIT THE BINDING OF INTEGRINS TO THEIR RECEPTORS

CROSS-REFERENCE TO RELATED APPLICATION

This application is a division of U.S. patent application Ser. No. 09/973,142 filed Oct. 9, 2001 now U.S. Pat. No. 6,972,296 which is a continuation-in-part of U.S. patent application Ser. No. 09/707,068 filed Nov. 6, 2000 now abandoned which is a continuation-in-part of U.S. application Ser. No. 09/565,920, filed May 5, 2000 now abandoned which claims the benefit of U.S. Provisional Patent Application Ser. No. 60/132,971, filed May 7, 1999.

FIELD OF THE INVENTION

This invention is directed generally to the inhibition of the binding of $\alpha_4\beta_1$ integrin to its receptors, for example VCAM-1 (vascular cell adhesion molecule-1) and fibronectin. The invention also relates to compounds that inhibit this binding; to pharmaceutically active compositions comprising such compounds; and to the use of such compounds either as above, or in formulations for the control or prevention of disease states in which $\alpha_4\beta_1$ is involved.

BACKGROUND OF THE INVENTION

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells recognize the invaded or damaged tissue, bind to the wall of the capillary and migrate through the capillary into the affected tissue. These events are mediated by a family of proteins called cell adhesion molecules.

There are three main types of white blood cells: granulocytes, monocytes and lymphocytes. The integrin $\alpha_4\beta_1$ (also called VLA-4 for very late antigen-4) is a heterodimeric protein expressed on the surface of monocytes, lymphocytes and two subclasses of granulocytes: eosinophils and basophils. This protein plays a key role in cell adhesion through its ability to recognize and bind VCAM-1 and fibronectin, proteins associated with the endothelial cells that line the interior wall of capillaries.

Following infection or damage of tissue surrounding a capillary, endothelial cells express a series of adhesion molecules, including VCAM-1, that are critical for binding the white blood cells that are necessary for fighting infection. Prior to binding to VCAM-1 or fibronectin, the white blood cells initially bind to certain adhesion molecules to slow their flow and allow the cells to "roll" along the activated endothelium. Monocytes, lymphocytes, basophils and eosinophils are then able to firmly bind to VCAM-1 or fibronectin on the blood vessel wall via the $\alpha_4\beta_1$ integrin. There is evidence that such interactions are also involved in transmigration of these white blood cells into the damaged tissue as well as the initial rolling event itself.

Although white blood cell migration to the site of injury helps fight infection and destroy foreign material, in many instances this migration can become uncontrolled, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to VCAM-1 and fibronectin.

Some of the diseases that might be treated by the inhibition of $\alpha_4\beta_1$ binding include, but are not limited to, atherosclerosis, rheumatoid arthritis, asthma, allergy, multiple sclerosis, lupus, inflammatory bowel disease, graft rejection, contact hypersensitivity, and type I diabetes. In addition to being found on some white blood cells, $\alpha_4\beta_1$ is also found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

The isolation and purification of a peptide which inhibits the binding of $\alpha_4\beta_1$ to a protein is disclosed in U.S. Pat. No. 5,510,332. Peptides which inhibit binding are disclosed in WO 95/15973, EP 0 341 915, EP 0 422 938 A1, U.S. Pat. No. 5,192,746 and WO 96/06108. Novel compounds which are useful for inhibition and prevention of cell adhesion and cell adhesion-mediated pathologies are disclosed in WO 96/22966, WO 98/04247 and WO 98/04913.

It is therefore an object of the invention to provide novel compounds which are inhibitors of $\alpha_4\beta_1$ binding, and pharmaceutical compositions including such novel compounds.

BRIEF SUMMARY OF THE INVENTION

The present invention is directed to compounds of Formula I

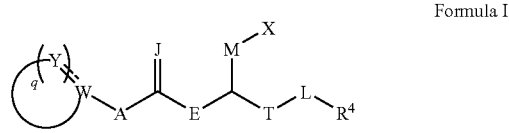

Formula I wherein Y, at each occurrence, is independently selected from the group consisting of C(O), N, $CR^1$, $C(R^2)(R^3)$, $NR^5$, CH, O and S;

q is an integer of from 3 to 10;

A is selected from the group consisting of O, S, $C(R^{16})(R^{17})$ and $NR^6$;

E is selected from the group consisting of $CH_2$, O, S, and $NR^7$;

J is selected from the group consisting of O, S and $NR^8$;

T is selected from the group consisting of C(O) and $(CH_2)_b$, wherein b is an integer of from 0 to 3;

M is selected from the group consisting of $C(R^9)(R^{10})$ and $(CH_2)_u$, wherein u is an integer of from 0 to 3;

L is selected from the group consisting of O, $NR^{11}$, S, and $(CH_2)_n$ wherein n is an integer of 0 or 1;

X is selected from the group consisting of $CO_2B$, $PO_3H_2$, $SO_3H$, $SO_2NH_2$, $SO_2NHCOR^{12}$, $OPO_3H_2$, $C(O)NHC(O)R^{13}$, $C(O)NHSO_2R^{14}$, hydroxyl, tetrazolyl and hydrogen;

W is selected from the group consisting of C, $CR^{15}$ and N; and

B, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ at each occurrence are independently selected from the group consisting of hydrogen, halogen, alkyl, alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$-alkyl), —NHC(O)N($C_1$-$C_3$ alkyl)C(O)—NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl), —SO$_3$—($C_1$-$C_3$ alkyl), sulfonamido, carbamate, aryloxyalkyl and —C(O)NH(benzyl) groups;

wherein B, $R^1$, $R^2$, $R^3$, $R^4$, $R^5$, $R^6$, $R_7$, $R^8$, $R^9$, $R^{10}$, $R^{11}$, $R^{12}$, $R^{13}$, $R^{14}$, $R^{15}$, $R^{16}$ and $R^{17}$ are unsubstituted or substituted with at least one electron donating or electron withdrawing group;

wherein when L is $NR^{11}$, $R^4$ and $R^{11}$ taken together may form a ring;

and wherein when M is $C(R_9)(R^{10})$, $R_9$ and $R^{10}$ taken together may form a ring;

and wherein when A is NR and at least one Y is $CR^1$, $R^1$ and $R^6$ taken together may form a ring;

or a pharmaceutically acceptable salt thereof;

with the proviso that when A is $C(R^{16})(R^{17})$, E is not $NR^7$.

For Formula I, presently preferred compounds may have A as $NR^6$; E as $NR^7$; J as O; M as $C(R^9)(R^{10})$; q as 4 or 5; T as $(CH_2)_b$ wherein b is 0; L as $(CH_2)_n$ wherein n is 0; X as CO$_2$B; W as C or $CR^{15}$; $R^4$ as aryl, alkylaryl, aralkyl, heterocyclyl, alkylheterocyclyl or heterocyclylalkyl; and $R_6$, $R_7$, $R_9$, $R^{10}$ and $R^{15}$ independently as hydrogen or lower alkyl.

More specifically, the compounds of this invention may be described by Formula II

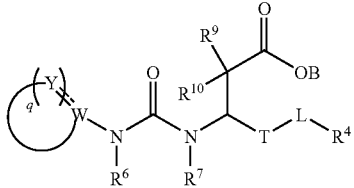

Formula II wherein Y, at each occurrence, is independently selected from the group consisting of C(O), N, $CR^1$, $C(R^2)(R^3)$, $NR_5$, CH, O and S;

q is an integer of from 3 to 7;

T is selected from the group consisting of C(O) and $(CH_2)_b$ wherein b is an integer of 0 to 3;

L is selected from the group consisting of O, $NR^{11}$, S, and $(CH_2)_n$ wherein n is an integer of 0 or 1;

W is selected from the group consisting of C, $CR^{15}$ and N; and

B, $R^1$, $R^2$, $R^3$, $R^4$, $R^5$, $R^6$, $R^7$, $R^9$, $R^{10}$, $R^{11}$ and $R^{15}$ are independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl), —SO$_3$—($C_1$-$C_3$ alkyl), sulfonamido, carbamate, aryloxyalkyl and —C(O)NH(benzyl) groups;

wherein B, $R^1$, $R^2$, $R^3$, $R^4$, $R^5$, $R^6$, $R^7$, $R^9$, $R^{10}$, $R^{11}$ and $R^{15}$ are unsubstituted or substituted with at least one electron donating or electron withdrawing group;

wherein when L is $NR^{11}$, $R^4$ and $R^{11}$ taken together may form a ring;

and wherein $R^9$ and $R^{10}$ taken together may form a ring;

and wherein when at least one Y is $CR^1$, $R^1$ and $R^6$ taken together may form a ring;

or a pharmaceutically acceptable salt thereof.

For Formula II, presently preferred compounds may have q as 4 or 5; W as C or $CR^{15}$; T as $(CH_2)_b$ wherein b is 0; L as $(CH_2)_n$ wherein n is 0; $R^4$ as aryl, alkylaryl, aralkyl, heterocyclyl, alkylheterocyclyl or heterocyclylalkyl; and $R^6$, $R^7$, $R^9$, $R^{10}$ and $R^{15}$ as independently hydrogen or lower alkyl.

More specifically, the compounds of this invention may be described by Formula III

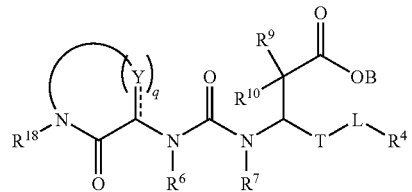

Formula III wherein Y, at each occurrence, is independently selected from the group consisting of C(O), N, $CR^1$, $C(R^2)(R^3)$, $NR^5$, CH, O and S;

q is an integer of from 2 to 5;

T is selected from the group consisting of C(O) and $(CH_2)_b$ wherein b is an integer of 0 to 3;

L is selected from the group consisting of O, $NR^{11}$, S, and $(CH_2)_n$ wherein n is an integer of 0 or 1;

$R^5$, $R^6$, $R^7$, $R^{11}$ and $R^{18}$ are each independently selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups; and B, $R^1$, $R^2$, $R^3$, $R^4$, $R^9$ and $R^{10}$ are independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N $(C_1-C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—$(C_1-C_3$ alkyl), —SO$_3$—$(C_1-C_3$ alkyl), sulfonamido, carbamate, aryloxyalkyl and —C(O)NH(benzyl) groups;

wherein B, $R^1$, $R^2$, $R^3$, $R^4$, $R^5$, $R^6$, $R^7$, $R^9$, $R^{10}$, $R^{11}$ and $R^{18}$ are unsubstituted or substituted with at least one electron donating or electron withdrawing group;

wherein when L is $NR^{11}$, $R^4$ and $R^{11}$ taken together may form a ring;

and wherein $R^9$ and $R^{10}$ taken together may form a ring;

and wherein when at least one Y is $CR^1$, $R^1$ and $R^6$ taken together may form a ring;

or a pharmaceutically acceptable salt thereof.

For Formula III, presently preferred compounds may have $R^{18}$ as hydrogen, alkyl, aryl, aralkyl, cycloalkyl, alkylheterocyclyl, heterocyclylalkyl or heterocyclyl; T as $(CH_2)_b$ wherein b is 0; L as $(CH_2)_n$ wherein n is 0; Y as $CR^1$ and $C(R^2)(R^3)$ and q as 2 or 3.

In Formula III, the portion of the molecule

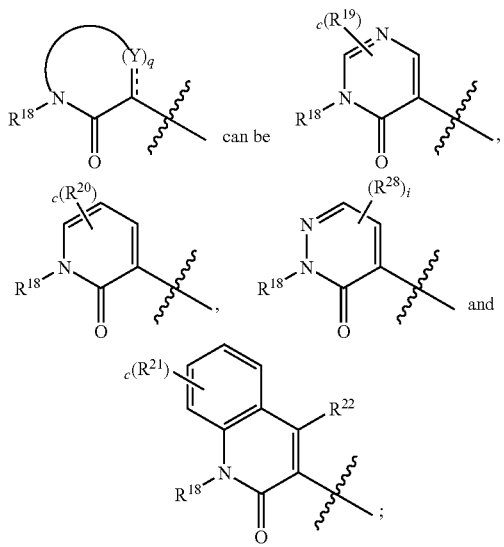

can be and pharmaceutical acceptable salts thereof and pharmaceutical acceptable salts thereof wherein $R_{19}$, $R_{20}$, $R^{21}$ and $R_{28}$ at each occurrence are independently selected from the group consisting of halogen, alkyl, alkenyl, alkynyl, alkoxy, alkenoxy, alkynoxy, thioalkoxy, hydroxyalkyl, aliphatic acyl, —CF$_3$, —OH, —CO$_2$H, —SH, —CN, —NO$_2$, —NH$_2$, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—$(C_1-C_3$ alkyl), —SO$_3$—$(C_1-C_3$ alkyl), sulfonamido, carbamate, aryloxyalkyl and —C(O)NH(benzyl) groups;

$R^{18}$ is selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups;

$R^{22}$ is selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—$(C_1-C_3$ alkyl), —SO$_3$—$(C_1-C_3$ alkyl), sulfonamido, carbamate, aryloxyalkyl and —C(O)NH(benzyl) groups;

c is an integer of zero to two;
d is an integer of zero to three;
e is an integer of zero to four; and
i is an integer of zero to two.

In one embodiment, $R^{18}$ is aralkyl; $R^4$ is aryl; T is $(CH_2)_b$ where b is zero; L is $(CH_2)_n$ where n is zero; and, B, $R^6$, $R^7$, $R^9$ and $R^{10}$ are each independently hydrogen.

More specifically, the compounds of this invention may be described by Formula IV

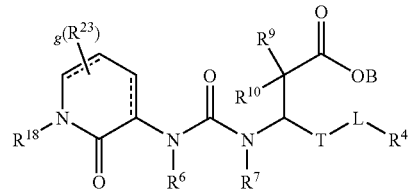

wherein T is selected from the group consisting of C(O) and $(CH_2)_b$ wherein b is an integer of from 0 to 3;

L is selected from the group consisting of O, $NR^{11}$, S, and $(CH_2)_n$ wherein n is an integer of 0 or 1;

g is an integer of from 0 to 7;

B, $R^4$, $R^9$, $R^{10}$ and $R^{23}$ at each occurrence are independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl)-NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)

alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl), —SO$_3$—($C_1$-$C_3$ alkyl), sulfonamido, carbamate, aryloxyalkyl and —C(O)NH(benzyl) groups; and $R^6$, $R^7$, $R^{11}$ and $R^{18}$ are each independently selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups;

wherein B, $R^4$, $R^6$, $R^7$, $R^9$, $R^{10}$, $R^{11}$, $R^{18}$ and $R^{23}$ are unsubstituted or substituted with at least one electron donating or electron withdrawing group;

wherein when L is $NR^{11}$, $R^4$ and $R^{11}$ taken together may form a ring;

and wherein $R^9$ and $R^{10}$ taken together may form a ring;

or a pharmaceutically acceptable salt thereof.

Presently preferred compounds of the present invention may also be described by Formula V.

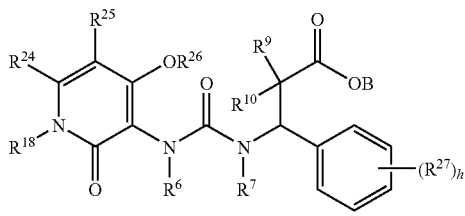

Formula V wherein h is an integer of zero to five;

B, $R^9$, $R^{10}$, $R^{24}$, and $R^{25}$ are each independently selected from the group consisting of hydrogen, halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl), —SO$_3$—($C_1$-$C_3$ alkyl), sulfonamido, carbamate, aryloxyalkyl and —C(O)NH(benzyl) groups;

$R^{27}$, at each occurrence, is independently selected from the group consisting of halogen, alkyl, alkenyl, alkynyl, alkoxy, alkenoxy, alkynoxy, thioalkoxy, hydroxyalkyl, aliphatic acyl, —CF$_3$, —CO$_2$H, —SH, —CN, —NO$_2$, —NH$_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —NHSO$_2$($C_1$-$C_3$ alkyl), —NHSO$_2$(aryl), —N($C_1$-$C_3$ alkyl)SO$_2$($C_1$-$C_3$ alkyl), —N($C_1$-$C_3$ alkyl)SO$_2$(aryl), —C alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —PO$_3$H$_2$, —OPO$_3$H$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—($C_1$-$C_3$ alkyl), —SO$_3$—($C_1$-$C_3$ alkyl), sulfonamido, carbamate, aryloxyalkyl and —C(O)NH(benzyl) groups;

$R^6$, $R^7$ and $R^{18}$ are each independently selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups; and, $R^{26}$ is selected from the group consisting of hydrogen, alkyl, alkenyl, alkynyl, hydroxyalkyl, aliphatic acyl, —CF$_3$, alkoxycarbonyl, heterocycloyl, carboxy, —C(O)O—($C_1$-$C_3$)alkyl, —C(O)NH—($C_1$-$C_3$)alkyl, —C(O)N($C_1$-$C_3$ alkyl)$_2$, —PO$_3$H$_2$, haloalkyl, carboxamide, cycloalkyl, cycloalkenyl, cycloalkynyl, cycloalkylalkyl, aryl, aroyl, biaryl, heterocyclyl, alkylaryl, aralkenyl, aralkyl, alkylheterocyclyl, heterocyclylalkyl, sulfonyl, —SO$_2$—($C_1$-$C_3$ alkyl), sulfonamido, aryloxyalkyl and —C(O)NH(benzyl) groups;

wherein B, $R^6$, $R^7$, $R^9$, $R^{10}$, $R^{18}$, $R^{24}$, $R^{25}$, $R^{26}$ and $R^{27}$ are unsubstituted or substituted with at least one electron donating or electron withdrawing group;

wherein $R^{18}$ and $R^{24}$ taken together may form a ring;

$R^{24}$ and $R^{25}$ taken together may form a ring;

$R^{25}$ and $R^{26}$ taken together may form a ring;

and wherein $R^9$ and $R^{10}$ taken together may form a ring;

or a pharmaceutically acceptable salt thereof.

Presently preferred compounds of Formula V have B, $R^6$, $R^7$, $R^9$, $R^{10}$, $R^{24}$, $R^{25}$ and $R^{26}$ each independently hydrogen and $R^{18}$ as substituted or unsubstituted aralkyl.

Other presently preferred compounds of the present invention may be described by Formula VI.

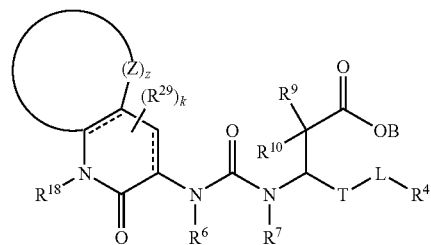

Formula VI wherein Z, at each occurrence, is independently selected from the group consisting of C(O), N, $CR^{30}$, $C(R^{31})(R^{32})$, $NR^{33}$, CH, O and S;

z is an integer of from 3 to 6;

k is an integer of from 0 to 5;

T is selected from the group consisting of C(O) and $(CH_2)_b$ wherein b is an integer of from 0 to 3;

L is selected from the group consisting of O, $NR^{11}$, S, and $(CH_2)_n$ wherein n is an integer of 0 or 1;

$R^6$, $R^7$, $R^{11}$, $R^{18}$ and $R^{33}$ are each independently selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups;

B, $R^4$, $R^9$, $R^{10}$, $R^{30}$, $R^{31}$ and $R^{32}$ at each occurrence are independently selected from the group consisting of hydrogen, halogen, alkyl, alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups; and, $R^{29}$, at each occurrence, is independently selected from the group consisting of halogen, alkyl, alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups;

wherein B, $R^4$, $R^6$, $R^7$, $R^9$, $R^{10}$, $R^{11}$, $R^{18}$, $R^{29}$, $R^{30}$, $R^{31}$, $R^{32}$ and $R^{33}$ are unsubstituted or substituted with at least one electron donating or electron withdrawing group;

wherein when L is $NR^{11}$, $R^4$ and $R^{11}$ taken together may form a ring;

and wherein $R^9$ and $R^{10}$ taken together may form a ring;

or a pharmaceutically acceptable salt thereof.

Some compounds of Formulae I-VI can be prepared from novel intermediates of Formula VII and Formula VIII.

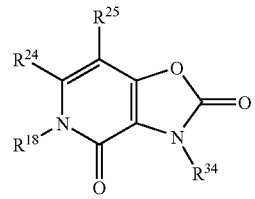

Formula VII wherein $R^{24}$ and $R^{25}$ are each independently selected from the group consisting of hydrogen, halogen, alkyl, alkenyl, alkynyl, alkoxy, alkenoxy, alkynoxy, thioalkoxy, hydroxyalkyl, aliphatic acyl, —$CF_3$, —SH, —OH, —$CO_2H$, —CN, —$NO_2$, —$NH_2$, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), alkylamino, —$NHSO_2$($C_1$-$C_3$ alkyl), —$NHSO_2$(aryl), alkoxyalkyl, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups; and $R^{18}$ and $R^{34}$ are each independently selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups;

wherein $R^{18}$, $R^{24}$, $R^{25}$ and $R^{34}$ are unsubstituted or substituted with at least one electron donating or electron withdrawing group;

and wherein $R^{24}$ and $R^{25}$ taken together may form a ring; with the proviso that when $R^{24}$ and $R^{25}$ taken together form a ring, the ring formed is not benzene. Presently preferred compounds of Formula VII have $R^{34}$ as hydrogen; $R^{18}$ as aralkyl; and $R^{24}$ and $R^{25}$ each independently as hydrogen, lower alkyl or lower alkyl wherein $R^{24}$ and $R^{25}$ are taken together to form a ring.

Formula VIII shows presently preferred novel intermediates.

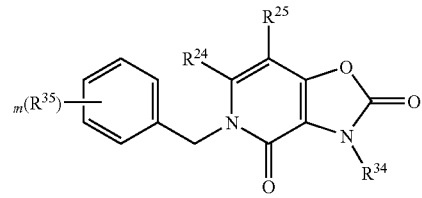

Formula VIII wherein $R^{24}$ and $R^{25}$ are each independently selected from the group consisting of hydrogen, halogen, alkyl, alkenyl, alkynyl, alkoxy, alkenoxy, alkynoxy, thioalkoxy, hydroxyalkyl, aliphatic acyl, —$CF_3$, —SH, —OH, —$CO_2H$, —CN, —$NO_2$, —$NH_2$, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups;

$R^{34}$ is selected from the group consisting of alkyl, alkenyl, alkynyl, hydroxyalkyl, aliphatic acyl, alkynylamino, alkoxycarbonyl, heterocycloyl, —CH=NOH, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, carbamate, aryloxyalkyl, hydrogen and —C(O)NH(benzyl) groups; and, $R^{35}$, at each occurrence, is independently selected from the group consisting of halogen, alkyl, alkenyl, alkynyl, alkoxy, alkenoxy, alkynoxy, thioalkoxy, hydroxyalkyl, aliphatic acyl, —$CF_3$, —$CO_2H$, —SH, —CN, —$NO_2$, —$NH_2$, —OH, alkynylamino, alkoxycarbonyl, heterocycloyl, carboxy, —N($C_1$-$C_3$ alkyl)-C(O)($C_1$-$C_3$ alkyl), —NHC(O)N($C_1$-$C_3$ alkyl)C(O)NH($C_1$-$C_3$ alkyl), —NHC(O)NH($C_1$-$C_6$ alkyl), —$NHSO_2$($C_1$-$C_3$ alkyl), —$NHSO_2$(aryl), alkoxyalkyl, alkylamino, alkenylamino, di($C_1$-$C_3$)amino, —C(O)O—($C_1$-$C_3$)alkyl, —C(O)NH—($C_1$-$C_3$)alkyl, —C(O)N($C_1$-$C_3$ alkyl)$_2$, —CH=NOH, —$PO_3H_2$, —$OPO_3H_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —$SO_2$—($C_1$-$C_3$ alkyl), —$SO_3$—($C_1$-$C_3$ alkyl), sulfonamido, carbamate, aryloxyalkyl and —C(O)NH(benzyl) groups;

wherein $R^{24}$, $R^{25}$, $R^{34}$ and $R^{35}$ are unsubstituted or substituted with at least one electron donating or electron withdrawing group; and, m is an integer of from 0 to 5. Presently preferred compounds of Formula VIII have $R^{34}$ as hydrogen; m as an integer of one to three and $R^{35}$ at each occurrence as alkyl, halogen, alkoxy, haloalkyl, sulfonyl, —OH or —CN.

Presently preferred compounds of Formula I include: (3S)-3-[({[2-methyl-4-(2-methylpropyl)-6-oxo-1-(phenylmethyl)-1,6-dihydro-5-pyrimidinyl]amino}carbonyl)amino]-3-(4-methylphenyl)propanoic acid, (3S)-3-(1,3-benzodioxol-5-yl)-3-[({2-oxo-1-(phenylmethyl)-4-propyl-1,2-dihydro-3-pyridinyl]amino}carbonyl)amino]propanoic acid, (3S)-3-{[({1-[(2-chlorophenyl)methyl]-4-ethyl-2-oxo-1,2-dihydro-3-pyridinyl}amino)carbonyl]amino}-3-(4-methylphenyl)propanoic acid, (3S)-3-{[({1-[(2-chlorophenyl)methyl]-2-oxo-4-propyl-1,2-dihydro-3-pyridinyl}amino)carbonyl]amino}-3-(4-methylphenyl)propanoic acid, (3S)-3-{[({1-[(2-chlorophenyl)methyl]-4-methyl-2-oxo-1,2-dihydro-3-pyridinyl}amino)carbonyl]amino}-3-(4-methylphenyl)propanoic acid, (3S)-3-{[({6-methyl-2-oxo-1-(phenylmethyl)-4-[(phenylmethyl)oxy]-1,2-dihydro-3-pyridinyl}amino)carbonyl]amino}-3-(4-methylphenyl)propanoic acid, (3S)-3-{[({1-[(2-chlorophenyl)methyl]-2,4-dimethyl-6-oxo-1,6-dihydro-5-pyrimidinyl}amino)carbonyl]amino}-3-(4-methylphenyl)propanoic acid, (3S)-3-{[({4-amino-1-[(2-chlorophenyl)methyl]-6-methyl-2-oxo-1,2-dihydro-3-pyridinyl}amino)carbonyl]amino}-3-(4-methylphenyl)propanoic acid, (3S)-3-{[({1-[(2-chlorophenyl)methyl]-4-methyl-2-oxo-1,2-dihydro-3-pyridinyl}amino)carbonyl]amino}-3-[4-(methyloxy)phenyl]propanoic acid, (3S)-3-{[({1-[(2-chlorophenyl)methyl]-4-methyl-2-oxo-1,2-dihydro-3-pyridinyl}amino)carbonyl]amino}-3-(3,4-dimethylphenyl)propanoic acid, (3S)-3-{[({4-amino-1-[(2-chlorophenyl)methyl]-2-oxo-1,2-dihydro-3-pyridinyl}amino)carbonyl]amino}-3-(4-methylphenyl)propanoic acid, (3S)-3-{[({1-[(2-chlorophenyl)methyl]-4-hydroxy-2-oxo-1,2-dihydro-3-pyridinyl}amino)carbonyl]amino}-3-(4-methylphenyl)propanoic acid, (3S)-3-[({[1-[(2-chlorophenyl)methyl]-4-(1,4-oxazinan-4-yl)-2-oxo-1,2-dihydro-3-pyridinyl]amino}carbonyl)amino]-3-(4-methylphenyl)propanoic acid, (3S)-3-[({[1-[(2-chlorophenyl)methyl]-2-oxo-4-(propylamino)-1,2-dihydro-3-pyridinyl]amino}carbonyl)amino]-3-(4-methylphenyl)propanoic acid, (3S)-3-{[({1-[(2-bromophenyl)methyl]-4-methyl-2-oxo-1,2-dihydro-3-pyridinyl}amino)carbonyl]amino}-3-(4-methylphenyl)propanoic acid, (3S)-3-{[({1-[(2-chlorophenyl)methyl]-4-hydroxy-2-oxo-1,2-dihydro-3-pyridinyl}amino)carbonyl]amino}-3-[3-methyl-4-(methyloxy)phenyl]propanoic acid, (3S)-3-{[({1-[(2-chlorophenyl)methyl]-2-oxo-4-phenyl-1,2-dihydro-3-pyridinyl}amino)carbonyl]amino}-3-(4-methylphenyl)propanoic acid, (3S)-3-{[({1-[(2-chlorophenyl)methyl]-4-[2-{2-(methyloxy)ethyl]oxy}ethyl)oxy]-2-oxo-1,2-dihydro-3-pyridinyl}amino)carbonyl]amino}-3-(4-methylphenyl)propanoic acid, (3S)-3-{[({1-[(2-chlorophenyl)methyl]-4-hydroxy-6-methyl-2-oxo-1,2-dihydro-3-yridinyl}amino)carbonyl]amino}-3-(4-methylphenyl)propanoic acid, (3S)-3-{[({1-[(2-chlorophenyl)methyl]-4-[(1,1-dimethylethyl)amino]-2-oxo-1,2-dihydro-3-pyridinyl}amino)carbonyl]amino}-3-(4-methylphenyl)propanoic acid, (3S)-3-{[({1-[(2-chlorophenyl)methyl]-4-hydroxy-2-oxo-1,2-dihydro-3-pyridinyl}amino)carbonyl]amino}-3-phenylpropanoic acid, (3S)-3-{[({1-[(2-chlorophenyl)methyl]-4-[4-methyltetrahydro-1(2H)-pyrazinyl]-2-oxo-1,2-dihydro-3-pyridinyl}amino)carbonyl]amino}-3-(4-methylphenyl)propanoic acid, (3S)-3-{[({1-[(2-chlorophenyl)methyl]-4-hydroxy-2-oxo-1,2-dihydro-3-pyridinyl}amino)carbonyl]amino}-3-[4-(methyloxy)phenyl]propanoic acid, (3S)-3-{[({1-[(2-chlorophenyl)methyl]-4-hydroxy-2-oxo-1,2-dihydro-3-pyridinyl}amino)carbonyl]amino}-3-(3,5-dimethylphenyl)propanoic acid, (3S)-3-{[({1-[(2-chlorophenyl)methyl]-4-hydroxy-2-oxo-1,2-dihydro-3-pyridinyl}amino)carbonyl]amino}-3-(3-methylphenyl)propanoic acid, (3S)-3-{[({1-[(2-chlorophenyl)methyl]-4-hydroxy-2-oxo-1,2-dihydro-3-pyridinyl}amino)carbonyl]amino}-3-[3-(methyloxy)phenyl]propanoic acid, (3S)-3-[3,5-bis(methyloxy)phenyl]-3-{[({1-[(2-chlorophenyl)methyl]-4-hydroxy-2-oxo-1,2-dihydro-3-pyridinyl}amino)carbonyl]amino}propanoic acid, (3S)-3-{[({1-[(2-chlorophenyl)methyl]-4-hydroxy-2-oxo-1,2-dihydro-3-quinolinyl}amino)carbonyl]amino}-3-(4-methylphenyl)propanoic acid, (3S)-3-{[({1-[(2-chlorophenyl)methyl]-4-hydroxy-2-oxo-1,2-dihydro-3-pyridinyl}amino)carbonyl]amino}-3-[3-(trifluoromethyl)phenyl]propanoic acid, (3S)-

3-{[({1-[(2-chlorophenyl)methyl]-4-[({ethyl[(ethylamino)carbonyl]amino}carbonyl)amino]-2-oxo-1,2-dihydro-3-pyridinyl}amino)carbonyl]amino}-3-(4-methylphenyl)propanoic acid, (3S)-3-{[({4-(1-azetanyl)-1-[(2-chlorophenyl)methyl]-2-oxo-1,2-dihydro-3-yridinyl}amino)carbonyl]amino}-3-(4-methylphenyl)propanoic acid, (3S)-3-[({1-[(2-chlorophenyl)methyl]-4-({2-[(2-{[2-(methyloxy)ethyl]oxy}ethyl)oxy]ethyl}oxy)-2-oxo-1,2-dihydro-3-pyridinyl]amino}carbonyl)amino]-3-(4-methylphenyl)propanoic acid, (3S)-3-{[({1-[(2-fluorophenyl)methyl]-4-hydroxy-2-oxo-1,2-dihydro-3-pyridinyl}amino)carbonyl]amino}-3-(4-methylphenyl)propanoic acid, (3S)-3-{[({1-[(2-chloro-6-fluorophenyl)methyl]-4-hydroxy-2-oxo-1,2-dihydro-3-pyridinyl}amino)carbonyl]amino}-3-(4-methylphenyl)propanoic acid, (3S)-3-{[({1-[(2-chlorophenyl)methyl]-5-methyl-2-oxo-1,2-dihydro-3-pyridinyl}amino)carbonyl]amino}-3-(4-methylphenyl)propanoic acid, (3S)-3-(1,3-benzodioxol-5-yl)-3-((((2-oxo-1-((4-(trifluoromethyl)phenyl)methyl)-1,2 dihydro-3-pyridinyl)amino)carbonyl)amino)propanoic acid, (3S)-3-((((1-((2-chlorophenyl)methyl)-2-oxo-1,2-dihydro-3-pyridinyl)amino)carbonyl)amino)-3-(4-methylphenyl)propanoic acid, (3S)-3-((((1-((2-fluorophenyl)methyl)-2-oxo-1,2-dihydro-3-pyridinyl)amino)carbonyl)amino)-3-(4-methylphenyl)propanoic acid, (3S)-3-((((1-((2-bromophenyl)methyl)-2-oxo-1,2-dihydro-3-pyridinyl)amino)carbonyl)amino)-3-(4-methylphenyl)propanoic acid, (3S)-3-((((1-((2,4-dichlorophenyl)methyl)-2-oxo-1,2-dihydro-3-pyridinyl)amino)carbonyl)amino)-3-(4-methylphenyl)propanoic acid, (3S)-3-((((1-((2-chloro-6-fluorophenyl)methyl)-2-oxo-1,2-dihydro-3-pyridinyl)amino)carbonyl)amino)-3-(4-methylphenyl)propanoic acid, (3S)-3-((((1-((2-chlorophenyl)methyl)-4-hydroxy-2-oxo-1,2-dihydro-3-pyridinyl)amino)carbonyl)amino)-3-(4-trifluoromethyl)oxy)phenyl)propanoic acid, (3S)-3-[({[1-(2-chloro-6-methoxybenzyl)-2-oxo-1,2-dihydropyridin-3-yl]amino}carbonyl)amino]-3-(4-methylphenyl)propanoic acid, 4-{[3-[({[(1S)-2-carboxy-1-(4-methylphenyl)ethyl]amino}carbonyl)amino]-1-(2-chlorobenzyl)-2-oxo-1,2-dihydropyridin-4-yl]amino}benzoic acid, (3S)-3-{[({1-(2-chlorobenzyl)-4-[(2,2-dimethylpropanoyl)amino]-2-oxo-1,2-dihydropyridin-3-yl}amino)carbonyl]amino}-3-(4-methylphenyl)propanoic acid, (3S)-3-[({[4-{[(tert-butylamino)carbonyl]amino}-1-(2-chlorobenzyl)-2-oxo-1,2-dihydropyridin-3-yl]amino}carbonyl)amino]-3-(4-methylphenyl)propanoic acid, (3S)-3-[({[1-(2-cyanobenzyl)-4-hydroxy-2-oxo-1,2-dihydropyridin-3-yl]amino}carbonyl)amino]-3-(4-methylphenyl)propanoic acid, (3S)-3-[({[1-(2-chlorobenzyl)-4-hydroxy-2-oxo-1,2-dihydropyridin-3-yl]amino}carbonyl)amino]-3-(2,3-dihydro-1,4-benzodioxin-6-yl)propanoic acid, (3S)-3-[({[1-(2-chlorobenzyl)-4-hydroxy-2-oxo-1,2-dihydropyridin-3-yl]amino}carbonyl)amino]-3-(7-methoxy-1,3-benzodioxol-5-yl)propanoic acid, (3S)-3-[({[1-(2-chlorobenzyl)-4-hydroxy-2-oxo-1,2-dihydropyridin-3-yl]amino}carbonyl)amino]-3-(3-ethoxy-4-methoxyphenyl)propanoic acid, (3S)-3-[({[1-(2-chlorobenzyl)-4-hydroxy-2-oxo-1,2-dihydropyridin-3-yl]amino}carbonyl)amino]-3-(3,4-dimethoxyphenyl)propanoic acid, (3S)-3-[({[1-(4-chlorobenzyl)-4-hydroxy-2-oxo-1,2-dihydropyridin-3-yl]amino}carbonyl)amino]-3-(4-methylphenyl)propanoic acid, (3S)-3-[({[1-(2-chloro-6-methoxybenzyl)-4-hydroxy-2-oxo-1,2-dihydropyridin-3-yl]amino}carbonyl)amino]-3-(4-methylphenyl)propanoic acid, (3S)-3-[({[1-(2-chlorobenzyl)-4-hydroxy-5-methyl-2-oxo-1,2-dihydropyridin-3-yl]amino}carbonyl)amino]-3-(4-methylphenyl)propanoic acid, (3S)-3-[({[1-(2,6-difluorobenzyl)-4-hydroxy-2-oxo-1,2-dihydropyridin-3-yl]amino}carbonyl)amino]-3-(4-methylphenyl)propanoic acid, (3S)-3-[({[1-(2-chloro-6-methoxybenzyl)-4-hydroxy-2-oxo-1,2-dihydropyridin-3-yl]amino}carbonyl)amino]-3-(3,5-dimethoxyphenyl)propanoic acid, (3S)-3-[({[1-(2-chlorobenzyl)-4-hydroxy-2-oxo-1,2-dihydropyridin-3-yl]amino}carbonyl)amino]-3-(3,4-diethoxyphenyl)propanoic acid, (3S)-3-[({[1-(2-chlorobenzyl)-4-hydroxy-2-oxo-1,2-dihydropyridin-3-yl]amino}carbonyl)amino]-3-(3-ethoxyphenyl)propanoic acid, (3S)-3-[({[1-(2-chlorobenzyl)-4-hydroxy-2-oxo-1,2-dihydropyridin-3-yl]amino}carbonyl)amino]-3-(3-methoxy-4-methylphenyl)propanoic acid, (3S)-3-[({[1-(2-chlorobenzyl)-4-hydroxy-2-oxo-1,2-dihydropyridin-3-yl]amino}carbonyl)amino]-3-(3,5-dimethoxy-4-methylphenyl)propanoic acid, (3S)-3-[({[1-(2-chlorobenzyl)-4-hydroxy-2-oxo-1,2-dihydropyridin-3-yl]amino}carbonyl)amino]-3-(3,4-dimethylphenyl)propanoic acid, (3S)-3-[({[1-(2-chlorobenzyl)-5-ethyl-4-hydroxy-2-oxo-1,2-dihydropyridin-3-yl]amino}carbonyl)amino]-3-(4-methylphenyl)propanoic acid, (3S)-3-{[({1-[2-chloro-5-(trifluoromethyl)benzyl]-4-hydroxy-2-oxo-1,2-dihydropyridin-3-yl}amino)carbonyl]amino}-3-(4-methylphenyl)propanoic acid, (3S)-3-[({[1-(2-chloro-6-methoxybenzyl)-4-hydroxy-2-oxo-1,2-dihydropyridin-3-yl]amino}carbonyl)amino]-3-(3-methylphenyl)propanoic acid, (3S)-3-[({[1-(2-chloro-6-methylbenzyl)-4-hydroxy-5-methyl-2-oxo-1,2-dihydropyridin-3-yl]amino}carbonyl)amino]-3-(4-methylphenyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-methylphenyl)propanoic acid, (3S)-3-[({[1-(2,6-dimethoxybenzyl)-4-hydroxy-2-oxo-1,2-dihydropyridin-3-yl]amino}carbonyl)amino]-3-(4-methylphenyl)propanoic acid, (3S)-3-[({[1-(2-chlorobenzyl)-4-hydroxy-2-oxo-1,2-dihydropyridin-3-yl]amino}carbonyl)amino]-3-(3-propoxyphenyl)propanoic acid, (3S)-3-[({[1-(2-chlorobenzyl)-4-hydroxy-2-oxo-5-propyl-1,2-dihydropyridin-3-yl]amino}carbonyl)amino]-3-(3-ethoxyphenyl)propanoic acid, (3S)-3-[({[1-(2-chlorobenzyl)-4-hydroxy-5,6-dimethyl-2-oxo-1,2-dihydropyridin-3-yl]amino}carbonyl)amino]-3-(4-methylphenyl)propanoic acid, (3S)-3-[({[1-(2-chlorobenzyl)-4-hydroxy-2-oxo-5-propyl-1,2-dihydropyridin-3-yl]amino}carbonyl)amino]-3-(3,4-diethoxyphenyl)propanoic acid, (3S)-3-(3-butoxyphenyl)-3-[({[1-(2-chlorobenzyl)-4-hydroxy-2-oxo-1,2-dihydropyridin-3-yl]amino}carbonyl)amino]propanoic acid, (3S)-3-{[({1-[2-chloro-5-(methylsulfonyl)benzyl]-4-hydroxy-2-oxo-1,2-dihydropyridin-3-yl}amino)carbonyl]amino}-3-(4-methylphenyl)propanoic acid, (3S)-3-[({[1-(2-chlorobenzyl)-4-hydroxy-2-oxo-1,2-dihydropyridin-3-yl]amino}carbonyl)amino]-3-[3-(2-methoxyethoxy)phenyl]propanoic acid, (3S)-3-[({[1-(2-chlorobenzyl)-4-hydroxy-2-oxo-1,2-dihydropyridin-3-yl]amino}carbonyl)amino]-3-(3,4-dipropoxyphenyl)propanoic acid, (3S)-3-[({[1-(2-chlorobenzyl)-4-hydroxy-2-oxo-1,2-dihydropyridin-3-yl]amino}carbonyl)amino]-3-[3-(difluoromethoxy)phenyl]propanoic acid, (3S)-3-[({[1-(2-chlorobenzyl)-4-hydroxy-5-methyl-2-oxo-1,2-dihydropyridin-3-yl]amino}carbonyl)amino]-3-(3,4-diethoxyphenyl)propanoic acid, (3S)-3-[({[1-(2-chlorobenzyl)-4-hydroxy-5-methyl-2-oxo-1,2-dihydropyridin-3-yl]amino}carbonyl)amino]-3-(3-ethoxyphenyl)propanoic acid, (3S)-3-[({[1-(2-chloro-6-methylbenzyl)-4-hydroxy-5,6-dimethyl-2-oxo-1,2-dihydropyridin-3-yl]amino}carbonyl)amino]-3-(3,4-diethoxyphenyl)propanoic acid, (3S)-3-[({[1-(2-chloro-6-cyanobenzyl)-4-hydroxy-2-oxo-1,2-dihydropyridin-3-yl]amino}carbonyl)amino]-3-(4-methylphenyl)propanoic acid, 3-[({[1-(2-chlorobenzyl)-4-hydroxy-2-oxo-1,2-dihydropyridin-3-yl]amino}carbonyl)amino]-3-(2-naphthyl)propanoic acid and (3S)-3-[({[1-(2-chlorobenzyl)-4-hydroxy-5,6-dimethyl-2-oxo-1,2-dihydropyridin-3-yl]amino}carbonyl)amino]-3-(3,4-diethoxyphenyl)propanoic acid, (3S)-3-[({[1-(2-chloro-6-methoxybenzyl)-4-hydroxy-5-methyl-2-oxo-1,2-dihydropyridin-3-yl]amino}carbonyl)amino]-3-(3,4-diethoxyphenyl)propanoic acid, (3S)-3-[({[1-(2-chlorobenzyl)-4-hydroxy-2-oxo-1,2-dihydropyridin-3-yl]amino}carbonyl)amino]-3-(3-isopropoxyphenyl)propanoic acid, (3S)-3-[({[1-(2-chlorobenzyl)-4-hydroxy-5-methyl-2-oxo-1,2-dihydropyridin-3-yl]amino}carbonyl)amino]-3-(4-methoxyphenyl)propanoic acid, (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid, (3S)-3-[({[1-(2-chloro-6-ethoxybenzyl)-4-hydroxy-2-oxo-1,2-dihydropyridin-3-yl]amino}carbonyl)amino]-3-(3-ethoxyphenyl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(3-isopropoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(1-methyl-1H-indol-5-yl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(2,3-dihydro-1-benzofuran-5-yl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3,5-diethoxyphenyl)propanoic acid, (3S)-3-[({[5-chloro-1-(2-chloro-6-ethoxybenzyl)-4-hydroxy-2-oxo-1,2-dihydropyridin-3-yl]amino}carbonyl)amino]-3-(3-ethoxyphenyl)propanoic acid, (3S)-3-[({[1-(2-chloro-6-ethoxybenzyl)-4-hydroxy-2-oxo-1,2-dihydropyridin-3-yl]amino}carbonyl)amino]-3-(3-isopropoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-propoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-phenylpropanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1,3-diethyl-2-oxo-2,3-dihydro-1H-benzimidazol-5-yl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-[3-(trifluoromethoxy)phenyl]propanoic acid, (3S)-3-[({[1-(2-chloro-6-ethoxybenzyl)-4-hydroxy-5,6-dimethyl-2-oxo-1,2-dihydropyridin-3-yl]amino}carbonyl)amino]-3-(3-isopropoxyphenyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1-methyl-1H-indol-5-yl)propanoic acid, (3S)-3-[({[1-(2-chloro-6-ethoxybenzyl)-5-cyclopropyl-4-hydroxy-2-oxo-1,2-dihydropyridin-3-yl]amino}carbonyl)amino]-3-(3-isopropoxyphenyl)propanoic acid, (3S)-3-[({[1-(2-chloro-6-ethoxybenzyl)-5-cyclopropyl-4-hydroxy-2-oxo-1,2-dihydropyridin-3-yl]amino}carbonyl)amino]-3-(4-methylphenyl)propanoic acid, (3S)-3-[({[1-(2-chloro-5-methoxybenzyl)-4-hydroxy-5-methyl-2-oxo-1,2-dihydropyridin-3-yl]amino}carbonyl)amino]-3-(4-methylphenyl)propanoic acid, (3S)-3-[({[1-(2-chloro-6-ethoxybenzyl)-4-hydroxy-6-methyl-2-oxo-1,2-dihydropyridin-3-yl]amino}carbonyl)amino]-3-(3-isopropoxyphenyl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(1-methyl-1H-indol-6-yl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopropyloxy)phenyl]propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3,5-dimethylphenyl)propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(difluoromethyl)oxy]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(1,1,2,2-tetrafluoroethyl)oxy]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(1-ethyl-1H-indol-5-yl)propanoic acid and (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[3-(diethylamino)phenyl]propanoic acid, (3S)-3-[({[1-(2-chlorobenzyl)-4-hydroxy-5-methyl-2-oxo-1,2-dihydropyridin-3-yl]amino}carbonyl)amino]-3-(4-methylphenyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-methylphenyl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(4-methylphenyl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(3-ethoxyphenyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid, (3S)-3-[({[1-(2-chloro-6-ethoxybenzyl)-4-hydroxy-5-methyl-2-oxo-1,2-dihydropyridin-3-yl]amino}carbonyl)amino]-3-(6-methoxy-2-naphthyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-methylphenyl)propanoic acid, (3S)-3-[({[1-(2-chlorobenzyl)-4-hydroxy-5-methyl-2-oxo-1,2-dihydropyridin-3-yl]amino}carbonyl)amino]-3-[3-(diethylamino)phenyl]propanoic acid, and (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(1-methyl-1H-indol-5-yl)propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[(methylsulfonyl)amino]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[methyl(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3- yl}amino)carbonyl]amino}-3-{3-[methyl(methylsulfonyl)amino]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[ethyl(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[ethyl(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(1H-indol-5-yl)propanoic acid and pharmaceutically acceptable salts thereof of the above compounds.

Presently preferred compounds of Formula VII include: 5-(2-chlorobenzyl)-3,5-dihydro[1,3]oxazolo[4,5-c]pyridine-2,4-dione, 5-(2-chlorobenzyl)-6-methyl-3,5-dihydro[1,3]oxazolo[4,5-c]pyridine-2,4-dione, 5-(2-fluorobenzyl)-3,5-dihydro[1,3]oxazolo[4,5-c]pyridine-2,4-dione, 5-(2-chloro-6-fluorobenzyl)-3,5-dihydro[1,3]oxazolo[4,5-c]pyridine-2,4-dione, 5-benzyl-6-methyl-3,5-dihydro[1,3]oxazolo[4,5-c]pyridine-2,4-dione, 5-benzyl-3,5-dihydro[1,3]oxazolo[4,5-c]pyridine-2,4-dione, 5-(2,5-dimethylbenzyl)-3,5-dihydro[1,3]oxazolo[4,5-c]pyridine-2,4-dione, 5-(2-methylbenzyl)-3,5-dihydro[1,3]oxazolo[4,5-c]pyridine-2,4-dione, 5-(2,4-dichlorobenzyl)-3,5-dihydro[1,3]oxazolo[4,5-c]pyridine-2,4-dione, 5-(2-methoxybenzyl)-3,5-dihydro[1,3]oxazolo[4,5-c]pyridine-2,4-dione, 5-(2,5-difluorobenzyl)-3,5-dihydro[1,3]oxazolo[4,5-c]pyridine-2,4-dione, 5-[2-chloro-5-(methylthio)benzyl]-3,5-dihydro[1,3]oxazolo[4,5-c]pyridine-2,4-dione, 5-(4-fluorobenzyl)-3,5-dihydro[1,3]oxazolo[4,5-c]pyridine-2,4-dione, 5-(2-chloro-5-methoxybenzyl)-3,5-dihydro[1,3]oxazolo[4,5-c]pyridine-2,4-dione, 5-[3,5-bis(trifluoromethyl)benzyl]-3,5-dihydro[1,3]oxazolo[4,5-c]pyridine-2,4-dione, 5-(4-tert-butylbenzyl)-3,5-dihydro[1,3]oxazolo[4,5-c]pyridine-2,4-dione, 5-(3-chlorobenzyl)-3,5-dihydro[1,3]oxazolo[4,5-c]pyridine-2,4-dione, 5-(4-chlorobenzyl)-3,5-dihydro[1,3]oxazolo[4,5-c]pyridine-2,4-dione, 5-[3-(trifluoromethyl)benzyl]-3,5-dihydro[1,3]oxazolo[4,5-c]pyridine-2,4-dione, 5-(2-bromobenzyl)-3,5-dihydro[1,3]oxazolo[4,5-c]pyridine-2,4-dione, 5-(3,4-dichlorobenzyl)-3,5-dihydro[1,3]oxazolo[4,5-c]pyridine-2,4-dione, 5-(4-methylbenzyl)-3,5-dihydro[1,3]oxazolo[4,5-c]pyridine-2,4-dione, 5-(2-chloro-6-methoxybenzyl)-3,5-dihydro[1,3]oxazolo[4,5-c]pyridine-2,4-dione, 5-[4-(trifluoromethyl)benzyl]-3,5-dihydro[1,3]oxazolo[4,5-c]pyridine-2,4-dione, 5-(3-methylbenzyl)-3,5-dihydro[1,3]oxazolo[4,5-c]pyridine-2,4-dione, 5-(pyridin-2-ylmethyl)-3,5-dihydro[1,3]oxazolo[4,5-c]pyridine-2,4-dione, 5-(2-chlorobenzyl)-7-methyl-3,5-dihydro-[1,3]oxazolo[4,5-c]pyridine-2,4-dione, 5-(2,4-difluorobenzyl)-3,5-dihydro[1,3]oxazolo[4,5-c]pyridine-2,4-dione, 5-(2,6-difluorobenzyl)-3,5-dihydro[1,3]oxazolo[4,5-c]pyridine-2,4-dione, 5-[3-(trifluoromethoxy)benzyl]-3,5-dihydro[1,3]oxazolo[4,5-c]pyridine-2,4-dione, 5-[4-(trifluoromethoxy)benzyl]-3,5-dihydro[1,3]oxazolo[4,5-c]pyridine-2,4-dione, 5-[2-(trifluoromethyl)benzyl]-3,5-dihydro[1,3]oxazolo[4,5-c]pyridine-2,4-dione, 5-(3-methoxybenzyl)-3,5-dihydro[1,3]oxazolo[4,5-c]pyridine-2,4-dione, 5-(2,3-dichlorobenzyl)-3,5-dihydro[1,3]oxazolo[4,5-c]pyridine-2,4-dione, 5-(3,5-dimethylbenzyl)-3,5-dihydro[1,3]oxazolo[4,5-c]pyridine-2,4-dione, 5-(2-chlorobenzyl)-7-pentyl-3,5-dihydro[1,3]oxazolo[4,5-c]pyridine-2,4-dione, 5-(2,4-dichlorobenzyl)-7-methyl-3,5-dihydro[1,3]oxazolo[4,5-c]pyridine-2,4-dione, 5-(2-chlorobenzyl)-7-ethyl-3,5-dihydro[1,3]oxazolo[4,5-c]pyridine-2,4-dione, 7-butyl-5-(2-chlorobenzyl)-3,5-dihydro[1,3]oxazolo[4,5-c]pyridine-2,4-dione, 5-[2-chloro-5-(trifluoromethyl)benzyl]-3,5-dihydro[1,3]oxazolo[4,5-c]pyridine-2,4-dione, 5-(2,6-dichlorobenzyl)-3,5-dihydro[1,3]oxazolo[4,5-c]pyridine-2,4-dione, 5-(2-chloro-5-fluorobenzyl)-3,5-dihydro[1,3]oxazolo[4,5-c]pyridine-2,4-dione, 5-(2-chloro-6-methylbenzyl)-7-methyl-3,5-dihydro[1,3]oxazolo[4,5-c]pyridine-2,4-dione, 5-(4-chlorobenzyl)-7-methyl-3,5-dihydro[1,3]oxazolo[4,5-c]pyridine-2,4-dione, 5-(2-chlorobenzyl)-5,6,7,8-tetrahydro-2H-cyclopenta[b][1,3]oxazolo[5,4-d]pyridine-2,4(3H)-dione, 7-methyl-5-[4-(methylsulfonyl)benzyl]-3,5-dihydro[1,3]oxazolo[4,5-c]pyridine-2,4-dione, 5-(4-methoxybenzyl)-3,5-dihydro[1,3]oxazolo[4,5-c]pyridine-2,4-dione, 5-(2-chlorobenzyl)-7-propyl-3,5-dihydro[1,3]oxazolo[4,5-c]pyridine-2,4-dione, 4-[(2,4-dioxo-2,3-dihydro[1,3]oxazolo[4,5-c]pyridin-5(4H)-yl)methyl]-N,N-dimethylbenzenesulfonamide, 5-(mesitylmethyl)-3,5-dihydro[1,3]oxazolo[4,5-c]pyridine-2,4-dione, 5-(2-chlorobenzyl)-3,5,6,7,8,9-hexahydro[1,3]oxazolo[4,5-c]quinoline-2,4-dione, 5-(2-chlorobenzyl)-7-ethyl-6-methyl-3,5-dihydro[1,3]oxazolo[4,5-c]pyridine-2,4-dione, 5-[2-(methylthio)benzyl]-3,5-dihydro[1,3]oxazolo[4,5-c]pyridine-2,4-dione, 2-[(2,4-dioxo-2,3-dihydro[1,3]oxazolo[4,5-c]pyridin-5(4H)-yl)methyl]-N,N-dimethylbenzenesulfonamide, 5-(2,6-dimethoxybenzyl)-3,5-dihydro[1,3]oxazolo[4,5-c]pyridine-2,4-dione, 5-[2-(trifluoromethoxy)benzyl]-3,5-dihydro[1,3]oxazolo[4,5-c]pyridine-2,4-dione, 5-(2-chlorobenzyl)-6,7-dimethyl-3,5-dihydro[1,3]oxazolo[4,5-c]pyridine-2,4-dione, 5-[2-chloro-5-(methylsulfonyl)benzyl]-3,5-dihydro[1,3]oxazolo[4,5-c]pyridine-2,4-dione, 5-(4-chloro-2-methoxybenzyl)-3,5-dihydro[1,3]oxazolo[4,5-c]pyridine-2,4-dione, 5-(2-chlorobenzyl)-5,6,7,8,9,10-hexahydro-2H-cyclohepta[b][1,3]oxazolo[5,4-d]pyridine-2,4(3H)-dione, 5-[2-(difluoromethoxy)benzyl]-3,5-dihydro[1,3]oxazolo[4,5-c]pyridine-2,4-dione, 7-methyl-5-[(1R)-1-phenylethyl]-3,5-dihydro[1,3]oxazolo[4,5-c]pyridine-2,4-dione, 5-(4-chlorobenzyl)-7-propyl-3,5-dihydro[1,3]oxazolo[4,5-c]pyridine-2,4-dione, 5-[2-(methylsulfonyl)benzyl]-3,5-dihydro[1,3]oxazolo[4,5-c]pyridine-2,4-dione, 5-(2,6-dimethylbenzyl)-3,5-dihydro[1,3]oxazolo[4,5-c]pyridine-2,4-dione, 3-chloro-2-[(2,4-dioxo-2,3-dihydro[1,3]oxazolo[4,5-c]pyridin-5(4H)-yl)methyl]benzonitrile, 5-(2-chloro-6-methylbenzyl)-6,7-dimethyl-3,5-dihydro[1,3]oxazolo[4,5-c]pyridine-2,4-dione, 2-[(2,4-dioxo-2,3-dihydro[1,3]oxazolo[4,5-c]pyridin-5(4H)-yl)methyl]benzonitrile, 5-(2-chloro-6-methoxybenzyl)-7-methyl-3,5-dihydro[1,3]oxazolo[4,5-c]pyridine-2,4-dione, 5-[3-(methylthio)benzyl]-3,5-dihydro[1,3]oxazolo[4,5-c]pyridine-2,4-dione, 5-(2-chlorobenzyl)-7-cyclopropyl-3,5-dihydro[1,3]oxazolo[4,5-c]pyridine-2,4-dione, 5-(3-chlorobenzyl)-7-methyl-3,5-dihydro[1,3]oxazolo[4,5-c]pyridine-2,4-dione, 5-(2,6-dichlorobenzyl)-7-methyl-3,5-dihydro[1,3]oxazolo[4,5-c]pyridine-2,4-dione, 7-methyl-5-(4-methylbenzyl)-3,5-dihydro[1,3]oxazolo[4,5-c]pyridine-2,4-dione, 5-(3,5-dimethoxybenzyl)-7-methyl-3,5-dihydro[1,3]oxazolo[4,5-c]pyridine-2,4-dione, 5-(2,6-difluorobenzyl)-7-methyl-3,5-dihydro[1,3]oxazolo[4,5-c]pyridine-2,4-dione, 5-[3-(methylsulfonyl)benzyl]-3,5-dihydro[1,3]oxazolo[4,5-c]pyridine-2,4-dione, 5-(2-chloro-6-ethoxybenzyl)-3,5-dihydro[1,3]oxazolo[4,5-c]pyridine-2,4-dione, 5-(2-chloro-6-ethoxybenzyl)-7-methyl-3,5-dihydro[1,3]oxazolo[4,5-c]pyridine-2,4-dione, 5-(2-fluoro-6-methoxybenzyl)-7-methyl-3,5-dihydro[1,3]oxazolo[4,5-c]pyridine-2,4-dione, 5-(2-chloro-6-methoxybenzyl)-7-propyl-3,5-dihydro[1,3]oxazolo[4,5-c]pyridine-2,4-dione, 5-(5-chloro-2-fluorobenzyl)-7-methyl-3,5-dihydro[1,3]oxazolo[4,5-c]pyridine-2,4-dione, 5-(2-chlorobenzyl)-7-isopropyl-3,5-dihydro[1,3]oxazolo[4,5-c]pyridine-2,4-dione, 5-(5-fluoro-2-methylbenzyl)-7-methyl-3,5-dihydro[1,3]oxazolo[4,5-c]

pyridine-2,4-dione, 7-methyl-5-[(1S)-1-phenylethyl]-3,5-dihydro[1,3]oxazolo[4,5-c]pyridine-2,4-dione, 5-(2-chloro-5-isopropoxybenzyl)-7-methyl-3,5-dihydro[1,3]oxazolo[4,5-c]pyridine-2,4-dione, 5-(5-acetyl-2-methoxybenzyl)-3,5-dihydro[1,3]oxazolo[4,5-c]pyridine-2,4-dione, 5-(2-chlorobenzyl)-7-methyl-3,5-dihydro[1,3]oxazolo[4,5-d]pyridazine-2,4-dione, 5-[2-fluoro-6-(trifluoromethyl)benzyl]-7-methyl-3,5-dihydro[1,3]oxazolo[4,5-c]pyridine-2,4-dione, 5-(2-chloro-6-methylbenzyl)-5,6,7,8-tetrahydro-2H-cyclopenta[b][1,3]oxazolo[5,4-d]pyridine-2,4(3H)-dione, 5-(2-chloro-6-ethoxybenzyl)-7-ethyl-3,5-dihydro[1,3]oxazolo[4,5-c]pyridine-2,4-dione, 5-(2-chloro-6-propoxybenzyl)-7-methyl-3,5-dihydro[1,3]oxazolo[4,5-c]pyridine-2,4-dione, 5-(2-chloro-6-isobutoxybenzyl)-7-methyl-3,5-dihydro[1,3]oxazolo[4,5-c]pyridine-2,4-dione, 5-(2-chloro-6-ethoxybenzyl)-5,6,7,8-tetrahydro-2H-cyclopenta[b][1,3]oxazolo[5,4-d]pyridine-2,4(3H)-dione, 5-(2-chloro-6-isopropoxybenzyl)-7-methyl-3,5-dihydro[1,3]oxazolo[4,5-c]pyridine-2,4-dione, 5-[2-chloro-6-(2,2,2-trifluoroethoxy)benzyl]-7-methyl-3,5-dihydro[1,3]oxazolo[4,5-c]pyridine-2,4-dione, 5-(2-chloro-6-ethoxybenzyl)-7-methyl-3,5-dihydro[1,3]oxazolo[4,5-d]pyridazine-2,4-dione, 5-[2-chloro-6-(2-methoxyethoxy)benzyl]-5,6,7,8-tetrahydro-2H-cyclopenta[b][1,3]oxazolo[5,4-d]pyridine-2,4(3H)-dione, 5-(2-chloro-6-ethoxybenzyl)-6,7-dimethyl-3,5-dihydro[1,3]oxazolo[4,5-c]pyridine-2,4-dione, 5-(2-chloro-6-ethoxybenzyl)-7-ethyl-6-methyl-3,5-dihydro[1,3]oxazolo[4,5-c]pyridine-2,4-dione, 5-(2-chlorobenzyl)-7-ethyl-3,5-dihydro[1,3]oxazolo[4,5-d]pyridazine-2,4-dione, 5-(2-chloro-6-ethoxybenzyl)-7-propyl-3,5-dihydro[1,3]oxazolo[4,5-c]pyridine-2,4-dione, 5-(2-chloro-6-ethoxybenzyl)-7-cyclopropyl-3,5-dihydro[1,3]oxazolo[4,5-c]pyridine-2,4-dione, 5-(2-chloro-5-propoxybenzyl)-7-methyl-3,5-dihydro[1,3]oxazolo[4,5-c]pyridine-2,4-dione, 5-(2-chloro-5-methoxybenzyl)-7-methyl-3,5-dihydro[1,3]oxazolo[4,5-c]pyridine-2,4-dione, 5-(2-chloro-6-ethoxybenzyl)-6-methyl-3,5-dihydro[1,3]oxazolo[4,5-c]pyridine-2,4-dione, 5-(2-chloro-5-ethoxybenzyl)-7-methyl-3,5-dihydro[1,3]oxazolo[4,5-c]pyridine-2,4-dione, 5-[2-chloro-5-(piperidin-1-ylsulfonyl)benzyl]-7-methyl-3,5-dihydro[1,3]oxazolo[4,5-c]pyridine-2,4-dione, 5-[2-chloro-5-(pyrrolidin-1-ylsulfonyl)benzyl]-7-methyl-3,5-dihydro[1,3]oxazolo[4,5-c]pyridine-2,4-dione, 5-[2-chloro-6-(cyclopentylmethoxy)benzyl]-7-methyl-3,5-dihydro[1,3]oxazolo[4,5-c]pyridine-2,4-dione, 5-[2-(benzyloxy)-6-chlorobenzyl]-7-methyl-3,5-dihydro[1,3]oxazolo[4,5-c]pyridine-2,4-dione, 5-(2,3-dichloro-6-ethoxybenzyl)-5,6,7,8-tetrahydro-2H-cyclopenta[b][1,3]oxazolo[5,4-d]pyridine-2,4(3H)-dione, 5-[2-chloro-5-(trifluoromethyl)benzyl]-7-methyl-3,5-dihydro[1,3]oxazolo[4,5-c]pyridine-2,4-dione and 5-(2-chloro-5-fluorobenzyl)-7-methyl-3,5-dihydro[1,3]oxazolo[4,5-c]pyridine-2,4-dione.

Derivatives such as esters, carbamates, aminals, amides, optical isomers and pro-drugs are also contemplated.

The present invention also relates to pharmaceutical compositions comprising a physiologically acceptable diluent and at least one compound of the present invention.

The present invention further relates to a process of inhibiting the binding of $\alpha_4\beta_1$ integrin to VCAM-1 comprising exposure of a cell expressing $\alpha_4\beta_1$ integrin to a cell expressing VCAM-1 in the presence of an effective inhibiting amount of a compound of the present invention. The VCAM-1 may be on the surface of a vascular endothelial cell, an antigen presenting cell, or other cell type. The $\alpha_4\beta_1$ may be on a white blood cell such as a monocyte, lymphocyte, granulocyte; a stem cell; or any other cell that naturally expresses $\alpha_4\beta_1$.

The invention also provides a method for treating disease states mediated by $\alpha_4\beta_1$ binding which comprises administration of an effective amount of a compound of the present invention, either alone or in formulation, to an afflicted patient.

DETAILED DESCRIPTION OF THE INVENTION

Definitions of Terms

The term "alkyl" as used herein, alone or in combination, refers to $C_1$-$C_{12}$ straight or branched, substituted or unsubstituted saturated chain radicals derived from saturated hydrocarbons by the removal of one hydrogen atom, unless the term alkyl is preceded by a $C_x$-$C_y$ designation. Representative examples of alkyl groups include methyl, ethyl, n-propyl, iso-propyl, n-butyl, sec-butyl, iso-butyl, and tert-butyl among others.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$-$C_6$ unit for a particular functionality. For example lower alkyl means $C_1$-$C_6$ alkyl.

The term "aliphatic acyl" as used herein, alone or in combination, refers to radicals of formula alkyl-C(O)—, alkenyl-C(O)— and alkynyl-C(O)— derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl and methylpropiolyl, among others.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

"Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkoxyalkyl" as used herein, refers to $R_y$—O—$R_z$, wherein $R_y$ is lower alkyl as defined above, and $R_z$ is alkylene (—$(CH_2)_w$—) wherein w is an integer of from one to six. Representative examples include methoxymethyl, methoxyethyl, and ethoxyethyl among others.

The term "alkenoxy" as used herein, alone or in combination, refers to a radical of formula alkenyl-O, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy" as used herein, alone or in combination, refers to a radical of formula alkynyl-O, provided that the radical is not an -ynol ether. Examples of suitable alkynoxy radicals include, but are not limited to, propargyloxy, 2-butynyloxy and the like.

The term "carboxy" as used herein refers to —C(O)O—.

The term "thioalkoxy" refers to a thioether radical of formula alkyl-S—, wherein "alkyl" is as defined above.

The term "sulfonamido" as used herein refers to —$SO_2NH_2$.

The term "carboxaldehyde" as used herein refers to —C(O)R wherein R is hydrogen.

The terms "carboxamide" or "amide" as used herein refer to —C(O)$NR_aR_b$ wherein $R_a$ and $R_b$ are each independently hydrogen, alkyl or any other suitable substituent.

The term "alkoxyalkoxy" as used herein refers to $R_c$O—$R_d$O— wherein $R_c$ is lower alkyl as defined above and $R_d$ is alkylene wherein alkylene is —$(CH_2)_{n'}$— wherein n' is an integer from 1 to 6. Representative examples of alkoxyalkoxy groups include methoxymethoxy, ethoxymethoxy, t-butoxymethoxy among others.

The term "alkylamino" as used herein refers to $R_e$NH— wherein $R_e$ is a lower alkyl group, for example, ethylamino, butylamino, among others.

The term "alkenylamino" as used herein, alone or in combination, refers to a radical of formula alkenyl-NH— or (alkenyl)$_2$N—, wherein the term "alkenyl" is as defined above, provided that the radical is not an enamine. An example of such alkenylamino radical is the allylamino radical.

The term "alkynylamino" as used herein, alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to $R_fR_g$N— wherein $R_f$ and $R_g$ are independently selected from lower alkyl, for example diethylamino, and methyl propylamino, among others.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl" as used herein, alone or in combination, refers to an aryl substituted alkenyl radical, wherein the terms "aryl" and "alkenyl" are as defined above.

The term "arylamino" as used herein, alone or in combination, refers to a radical of formula aryl-NH—, wherein "aryl" is as defined above. Examples of arylamino radicals include, but are not limited to, phenylamino(anilido), naphthlamino, 2-, 3-, and 4-pyridylamino and the like.

The term "benzyl" as used herein refers to $C_6H_5$—$CH_2$—.

The term "biaryl" as used herein, alone or in combination, refers to a radical of formula aryl-aryl, wherein the term "aryl" is as defined above.

The term "thioaryl" as used herein, alone or in combination, refers to a radical of formula aryl-S—, wherein the term "aryl" is as defined above. An example of a thioaryl radical is the thiophenyl radical.

The term "aroyl" as used herein, alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group, including but not limited to 2-methyl-5-thiazolyl, 2-methyl-1-pyrrolyl and 5-ethyl-2-thienyl.

The term "heterocyclylalkyl" as used herein refers to a heterocyclyl group as previously defined appended to the parent molecular moiety through an alkyl group, including but not limited to 2-thienylmethyl, 2-pyridinylmethyl and 2-(1-piperidinyl)ethyl.

The term "heterocycloyl" as used herein refers to radicals of the formula heterocyclyl-C(O)—, wherein the term "heterocyclyl" is as defined above.

The term "aminal" as used herein refers to a hemi-acetal of the structure $R_hC(NR_iR_j)(NR_kR_l)$— wherein $R_h$, $R_i$, $R_j$, $R_k$ and $R_l$ are each independently hydrogen, alkyl or any other suitable substituent.

The term "ester" as used herein refers to —C(O)$R_m$, wherein $R_m$ is hydrogen, alkyl or any other suitable substituent.

The term "carbamate" as used herein refers to compounds based on carbamic acid $NH_2C(O)OH$.

The term "optical isomers" as used herein refers to compounds which differ only in the stereochemistry of at least one atom, including enantiomers, diastereomers and racemates.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —NH—, —S—, —S(O)—, —O—, —C(O)O— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, sulfonyl and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio, carboxy lower alkyl, arylalkoxy, alkanoylamino, alkanoyl(lower alkyl)amino, lower alkylsufonylamino, arylsulfonylamino, alkylsulfonyl(lower alkyl)amino, arylsulfonyl(lower alkyl)amino, lower alkylcarboxamide, di(lower alkyl)carboxamide, sulfonamide, lower alkylsulfonamide, di(lower alkyl)sulfonamide, lower alkylsulfonyl, arylsulfonyl and alkyldithio.

As used herein, the term "composition" is intended to encompass a product comprising the specified ingredients in the specified amounts, as well as any product which results, directly or indirectly, from a combination of the specified ingredients in the specified amounts.

As used herein, the term "mammals" includes humans and other animals. The ring defined by Y in Formulae I, II and III can be a mono-cyclic heterocycle or aromatic ring, or can be a bicyclic ring.

The dotted lines used in Formulae I, II, III, IV and VI indicate that the bond at that location can be either single or double. The bond between the atoms Y and W for example can be a single or double bond if Y and/or W is a substitutent such as N, C or CH. Therefore, the ring defined by Y in the Formulae can be either saturated or unsaturated, depending upon which W and/or Y is selected. In Formulae IV and VI, the dotted line indicates that the nitrogen-containing ring optionally contains double bonds at the indicated locations.

In the Formulae, certain R groups potentially substitute their associated rings a number of times. $R^{19}$, $R^{20}$, $R^{21}$, $R^{23}$, $R^{27}$, $R^{28}$, $R^{29}$ and $R^{25}$ may each substitute their associated rings more than once. For example for $R^{19}$, when c is zero, the associated ring is unsubstituted, having hydrogens at the C-2 and C-4 positions; and for $R^{23}$, when g is zero, hydrogens are at the C-2-C-5 positions.

Suitable substituents for the aryl, alkyl, cycloalkyl, heterocyclyl groups or the ring defined by Y and W in the formulae described above, when present, include alcohols, amines, heteroatoms, or any combination of aryl, alkoxy, alkoxyalkoxy, alkyl, cycloalkyl or heterocyclyl groups either attached directly, or via suitable linkers. The linkers are typically short chains of 1-3 atoms containing any combination of C, C=O, $CO_2$, O, N, S, S=O, $SO_2$, as for example ethers, amides, amines, ureas, sulfamides, sulfonamides, among others.

For example, $R^1$, $R^2$, $R^3$, $R^5$, $R^6$, $R^7$ and $R^8$ in the above formulae may independently be, but are not limited to: hydrogen, alkyl, phenyl, thienylmethyl, isobutyl, n-butyl, 2-thienylmethyl, 1,3-thiazol-2-yl-methyl, benzyl, thienyl, 3-pyridinylmethyl, 3-methyl-1-benzothiophen-2-yl, allyl, 3-methoxybenzyl, propyl, 2-ethoxyethyl, cyclopropylmethyl, benzylsulfanylmethyl, benzylsulfonylmethyl, phenylsulfanylmethyl, phenethylsulfanylmethyl, 3-phenylpropylsulfanylmethyl, 4-((2-toluidinocarbonyl)amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, 4-(acetylamino)phenyl, 4-methoxyphenyl, 4-aminophenyl, 4-chlorophenyl, (4-(benzylsulfonyl)amino)phenyl, (4-(methylsulfonyl)amino)phenyl, 2-aminophenyl, 2-methylphenyl, isopropyl, 2-oxo-1-pyrrolidinyl, 3-(methylsulfanyl)propyl, (propylsulfanyl)methyl, octylsulfanylmethyl, 3-aminophenyl, 4-((2-toluidinocarbonyl)amino)phenyl, 2-((methylbenzyl)amino)benzyl, methylsulfanylethyl, hydroxy, chloro, fluoro, bromo, ureido, amino, methanesulfonylamino, acetylamino, ethylsulfanylmethyl, 2-chlorobenzyl, 2-bromobenzyl, 2-fluorobenzyl, 2-chloro-6-fluorobenzyl, 2-chloro-4-fluorobenzyl, 2,4-dichlorobenzyl, 2-chloro-6-methoxybenzyl, 2-cyanobenzyl, 2,6-difluorobenzyl, 2-chloro-5-(trifluoromethyl)benzyl, 2-chloro-6-methylbenzyl, 2,6-dimethoxybenzyl, 2-chloro-5-(methylsulfonyl)benzyl, 2-chloro-6-cyanobenzyl, 2-chloro-6-ethoxybenzyl, 2-chloro-5-methoxybenzyl, 2-chloro-5-fluorobenzyl, 5-chloro-2-fluorobenzyl, ethyl, propyl, butyl, pentyl, cyclopropyl, tert-butylamino, propylamino, 4-methyl-1-piperazinyl, 1-azetidinyl, 4-morpholino, (4-carboxyphenyl)amino, pivaloylamino, ((tert-butylamino)carbonyl)amino, trifluoromethyl, benzyloxy, 2-(2-methoxyethoxy)ethoxy, 2-(2-(2-methoxyethoxy)ethoxy)ethoxy and 2-(2-(2-(2-methoxyethoxy)ethoxy)ethoxy)ethoxy.

The $R^4$ substituent for the formulae above may be, but is not limited to 1,3-benzodioxol-5-yl, 1-naphthyl, thienyl, 4-isobutoxyphenyl, 2,6-dimethylphenyl, allyloxyphenyl, 3-bromo-4-methoxyphenyl, 4-butoxyphenyl, 1-benzofuran-2-yl, 2-thienylmethyl, phenyl, methylsulfanyl, phenylsulfanyl, phenethylsulfanyl, 4-bromo-2-thienyl, 3-methyl-2-thienyl, 4-methylphenyl, 3,5-bis(methyloxy)phenyl, 4-(methyloxy)phenyl, 4-fluorophenyl, 3-(methyloxy)phenyl, 3,4,5-tris(methyloxy)phenyl, 2,3-dihydro-1-benzofuran-5-yl, 3-fluorophenyl, 4-(trifluoromethyl)phenyl, 4-fluoro-3-(trifluoromethyl)phenyl, 4-(1,1,1-dimethylethyl)phenyl, 3,5-dimethylphenyl, 4-hydroxyphenyl, 3,4-dimethylphenyl, 3-methyl-4-(methyloxy)phenyl, 4-hydroxy-3-methylphenyl, 3-methylphenyl, 2,3-dihydro-inden-5-yl, 2-methylphenyl, 2,6-bis(methyloxy)phenyl, 2,6-dihydroxyphenyl, 4-chlorophenyl, 3-chlorophenyl, 3,4-dichlorophenyl, 4-((trifluoromethyl)oxy)phenyl, 4-ethylphenyl, 4-(ethyloxy)phenyl, methyl, 2-propyl, 4,5-dihydro-1,3-oxazol-2-yl, 3-(trifluoromethyl)phenyl, 4-(trifluoromethoxy)phenyl, 2,3-dihydro-1,4-benzodioxin-6-yl, 7-methoxy-1,3-benzodioxol-5-yl, 3-ethoxy-4-methoxyphenyl, 3,4-dimethoxyphenyl, 3,4-diethoxyphenyl, 3-ethoxyphenyl, 3-methoxy-4-methylphenyl, 3,5-dimethoxy-4-methylphenyl, 3-propoxyphenyl, 3-butoxyphenyl, 3-(2-methoxyethoxy)phenyl, 3,4-dipropoxyphenyl, 3-(difluoromethoxy)phenyl, 2-naphthyl, 3-isopropoxyphenyl, 1-methyl-1H-indol-5-yl, 2,3-dihydro-1-benzofuran-5-yl, 1,3-diethyl-2-oxo-2,3-dihydro-1H-benzimidazol-5-yl, 3-(trifluoromethoxy)phenyl, 1-methyl-1H-indol-6-yl, 3-(cyclopropoxy)phenyl, 3-(cyclopropylmethoxy)phenyl, 3-(difluoromethoxy)phenyl, 3-(1,1,2,2-tetrafluoroethoxy)phenyl, 1-ethyl-1H-indol-5-yl, 3-(diethylamino)phenyl, 6-methoxy-2-naphthyl, 3-[(methylsulfonyl)amino]phenyl, 3-[methyl(methylsulfonyl)amino]phenyl, 3-[ethyl(methylsulfonyl)amino]phenyl, 1H-indol-5-yl, 3-fluoro-4-methoxyphenyl and 3-(difluoromethyl)phenyl.

Two independent $R^1$, $R^2$, $R^3$ or $R^5$ groups taken together may be linked to form a ring.

$R^4$ and $R^{11}$ may be linked to form a ring such as 1-pyrrolidino, 1-piperidino, 4-methyl-1-piperazino, 4-acetyl-1-piperazino and 4-morpholino among others.

$R^9$ and $R^{10}$ may be linked to form a ring such as cyclopropyl, cyclobutyl, cyclopentyl, and cyclohexyl among others.

Abbreviations

Abbreviations which have been used in the schemes and the examples which follow are: BOC for t-butyloxycarbonyl; DMF for dimethylformamide; THF for tetrahydrofuran; DME for dimethoxyethane; DMSO for dimethylsulfoxide; NMM for N-methyl morpholine; DIPEA for diisopropylethylamine; CDI for 1,1'-carbonyldiimidazole; TBS for TRIS-buffered saline; Ms for methanesulfonyl, TMEDA for N,N,N',N'-tetramethylethylenediamine, DCE for 1,2-dichloroethane, NCS for N-chlorosuccinimide, NBS for N-bromosuccinimide, DPPA for diphenylphosphorylazide, DEAD for diethyl azodicarboxylate, m-CPBA for 3-chloroperoxybenzoic acid, TFAA for trifluoroacetic anhydride, DCM for dichloromethane, LHMDS for lithium bis(trimethylsilyl)amide and Cbz for benzyloxycarbonyl. Amino acids are abbreviated as follows: C for L-cysteine; D for L-aspartic acid; E for L-glutamic acid; G for glycine; H for L-histidine; I for L-isoleucine; L for L-leucine; N for L-asparagine; P for L-proline; Q for L-glutamine; S for L-serine; T for L-threonine; V for L-valine and W for L-tryptophan.

Examples of the procedures that may be used to synthesize compounds of the Formulae described above are shown in the Schemes which follow. A detailed description of the representative compounds of the present invention is set forth in the Examples below.

Scheme 1 below illustrates the procedure described in Example 1.

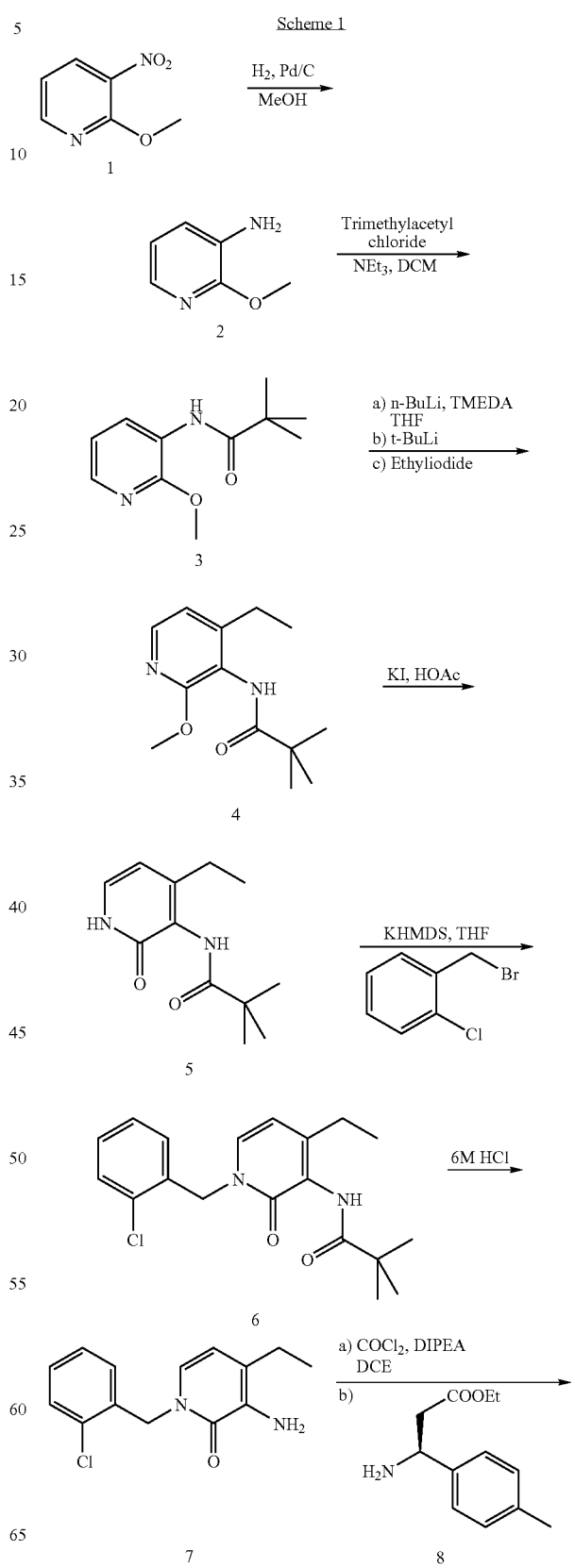

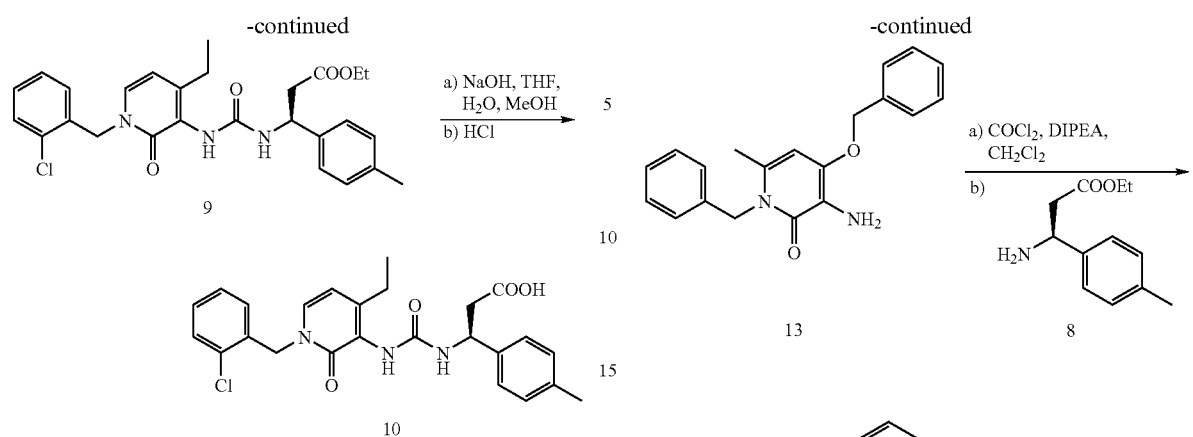
Scheme 2, illustrating the procedure of Example 2, is shown below.
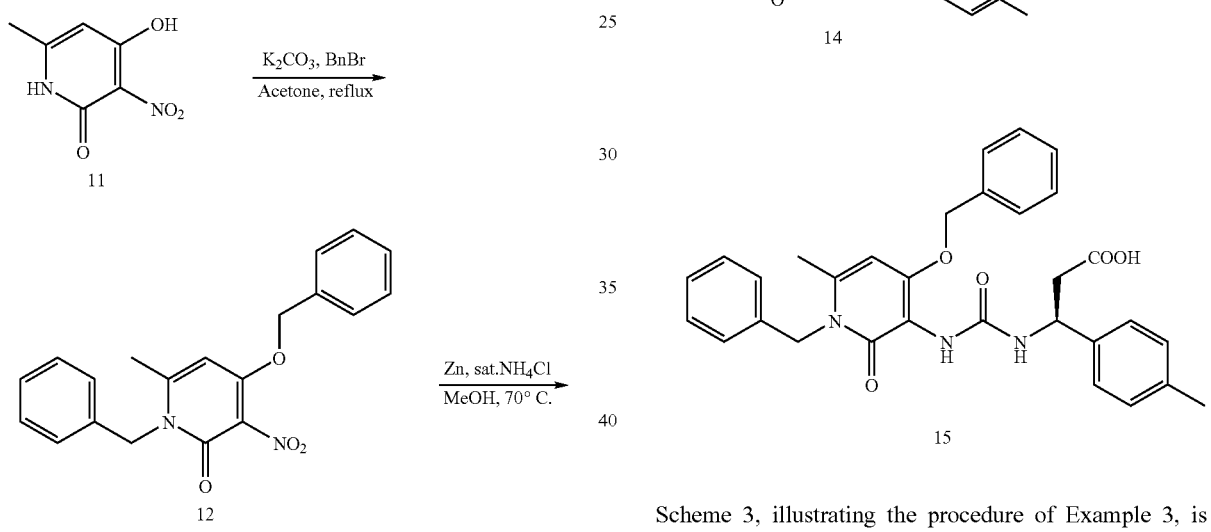
Scheme 3, illustrating the procedure of Example 3, is shown below.
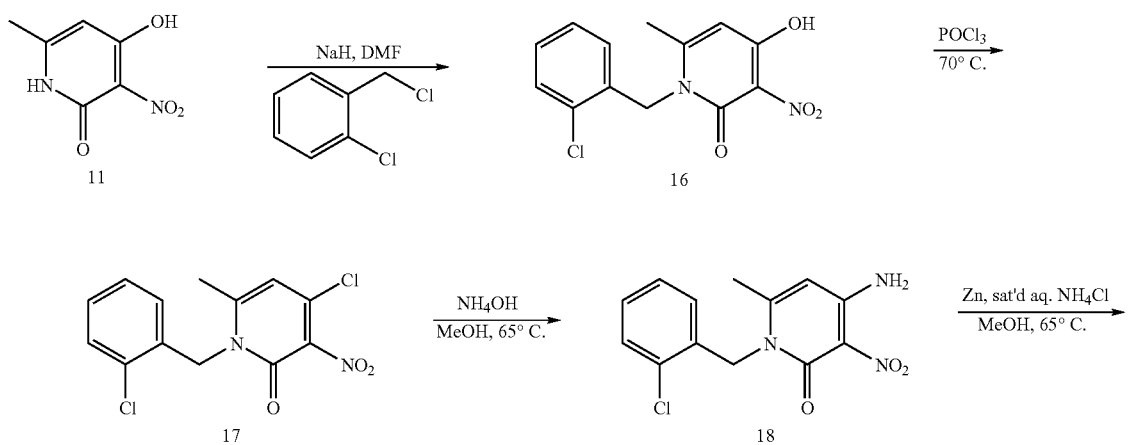

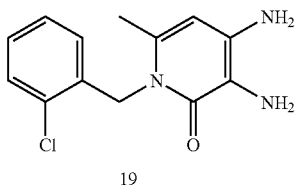
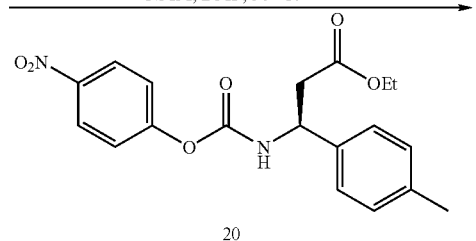
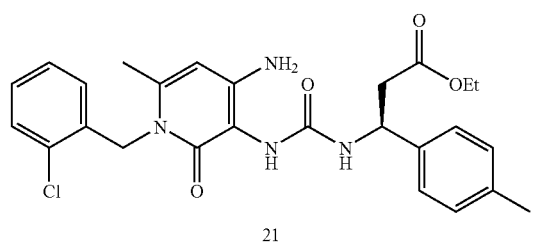
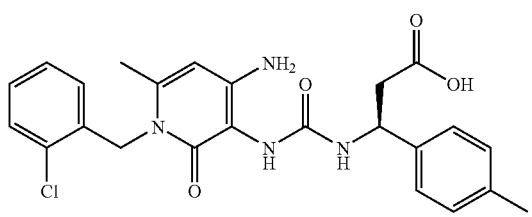
Scheme 4, illustrating the procedure of Example 4, is shown below.
Scheme 5, illustrating the procedure of Example 5, is shown below.
Scheme 4
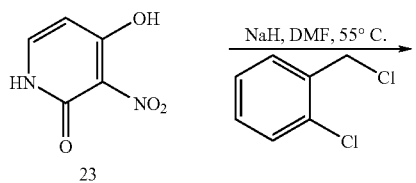
Scheme 5
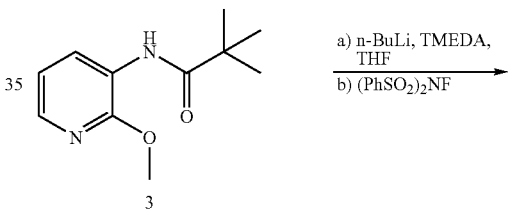
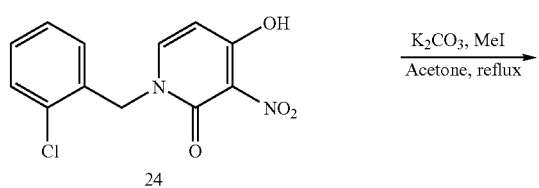
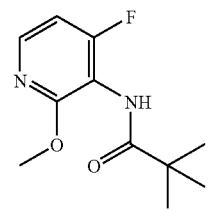
Scheme 6, illustrating the procedure of Example 6, is shown below.
Scheme 6
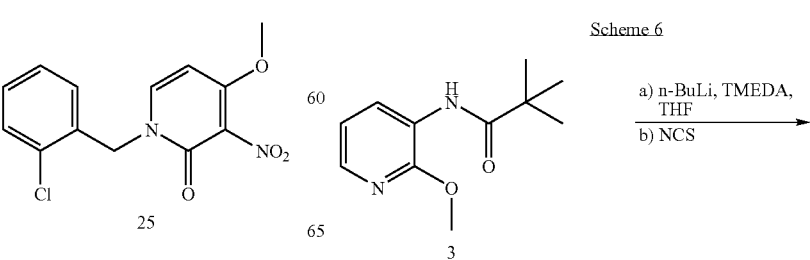

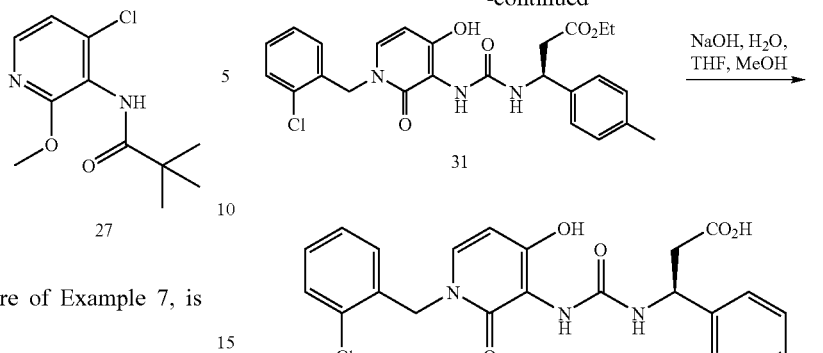
Scheme 7, illustrating the procedure of Example 7, is shown below.
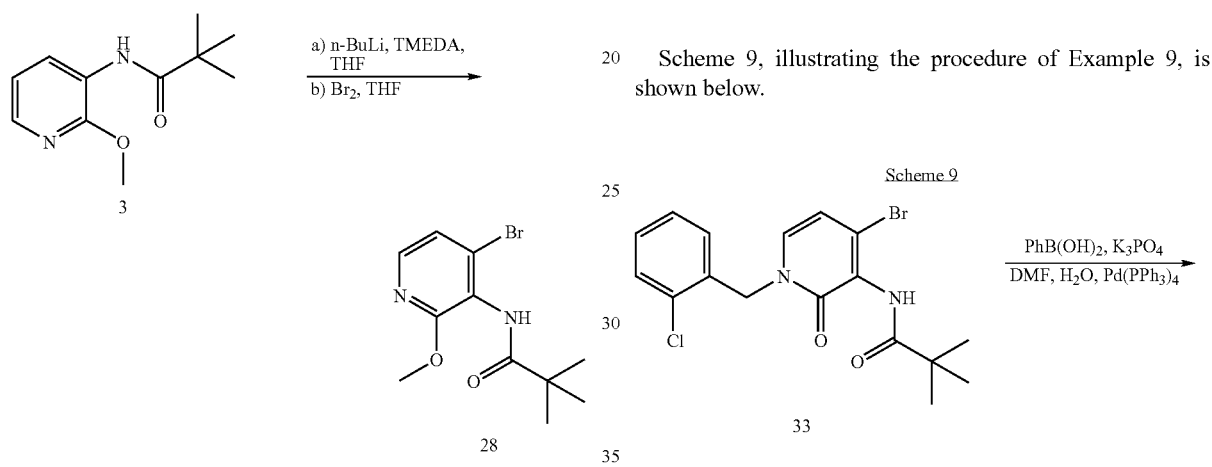
Scheme 8, illustrating the procedure of Example 8, is shown below.
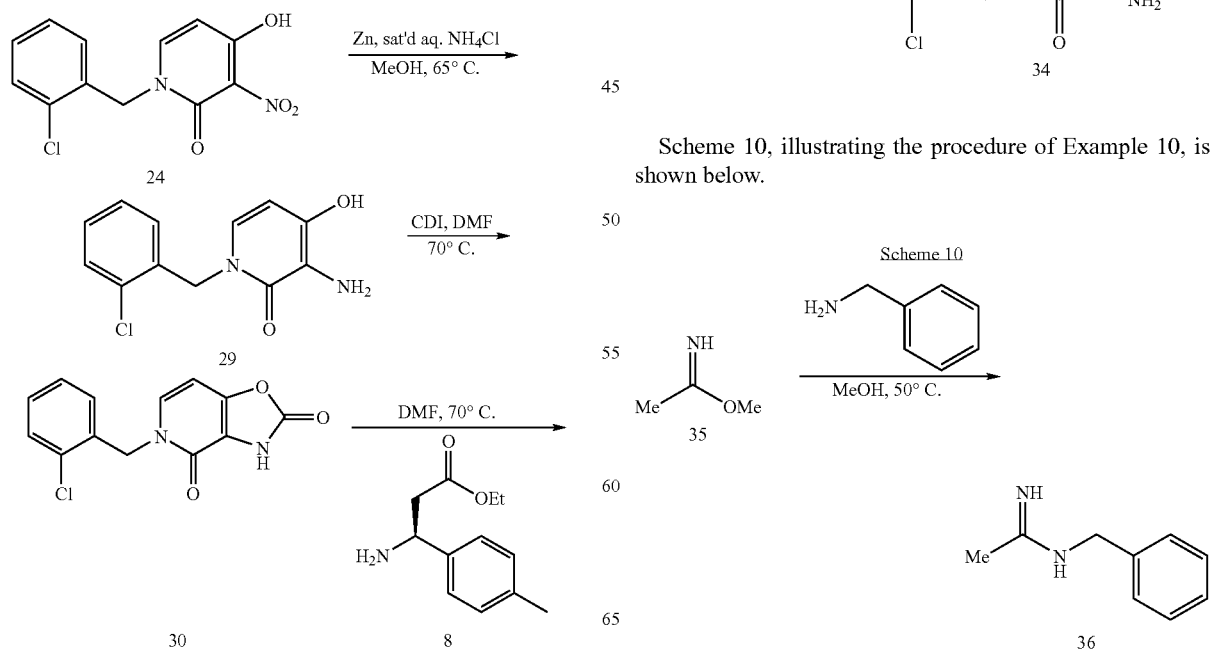
Scheme 9, illustrating the procedure of Example 9, is shown below.
Scheme 10, illustrating the procedure of Example 10, is shown below.

Scheme 11, illustrating the procedure of Example 11, is shown below.
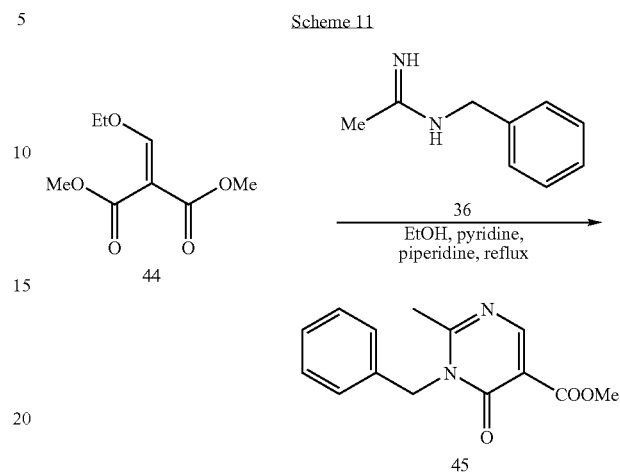
Scheme 12, illustrating the procedure of Example 12, is shown below.
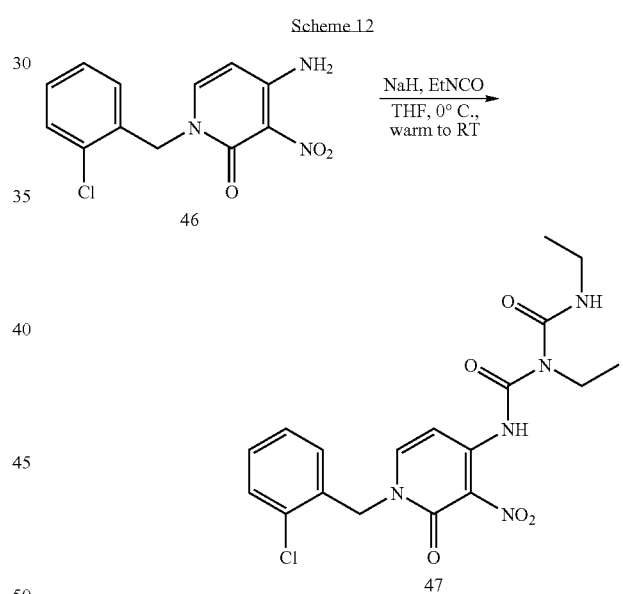
Scheme 13, illustrating the procedure of Example 13, is shown below.
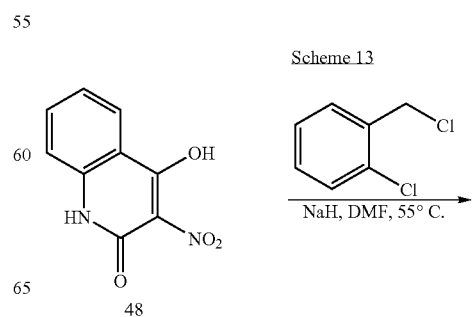

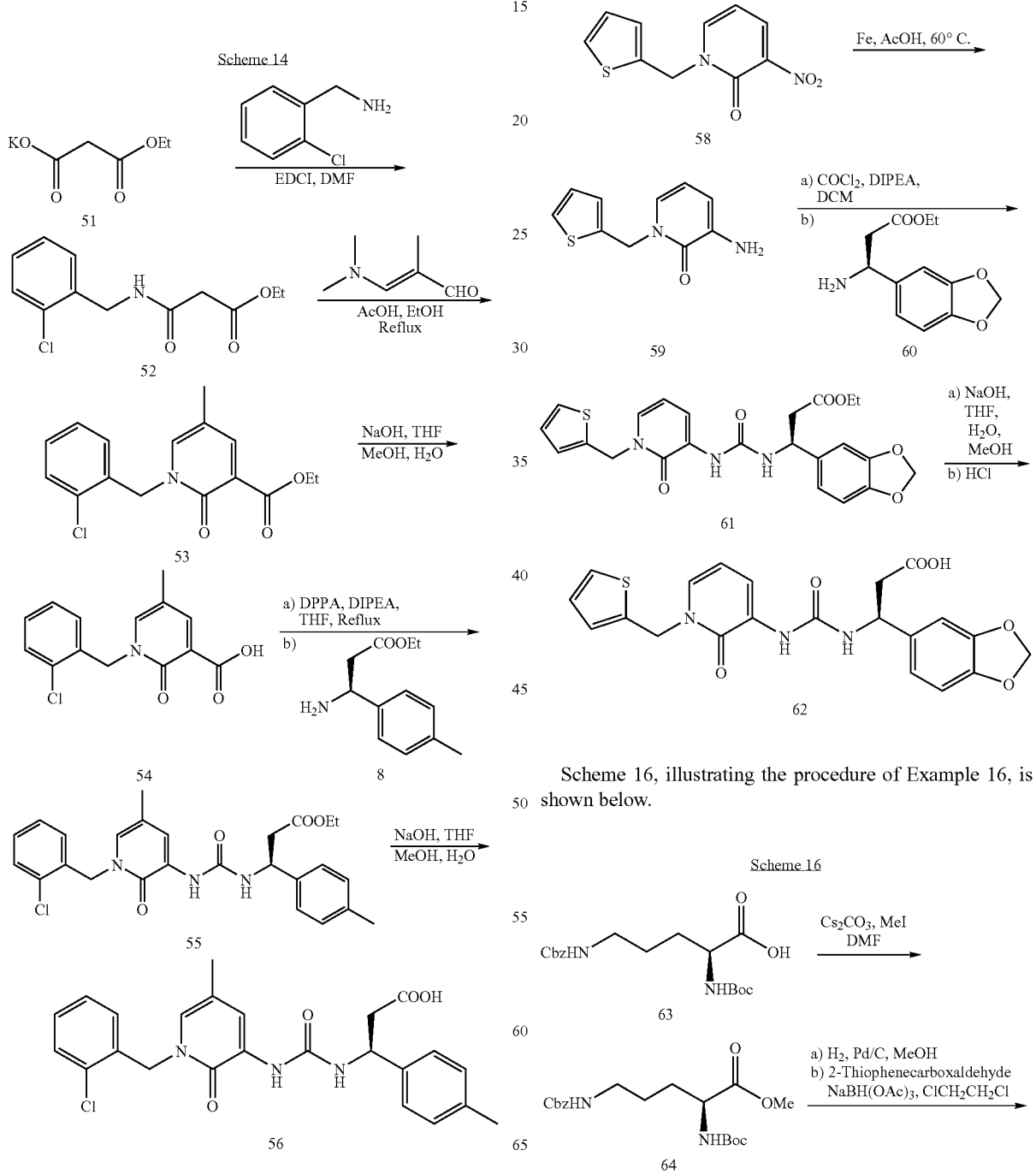
Scheme 14, illustrating the procedure of Example 14, is shown below.
Scheme 15, illustrating the procedure of Example 15, is shown below.
Scheme 16, illustrating the procedure of Example 16, is shown below.

-continued
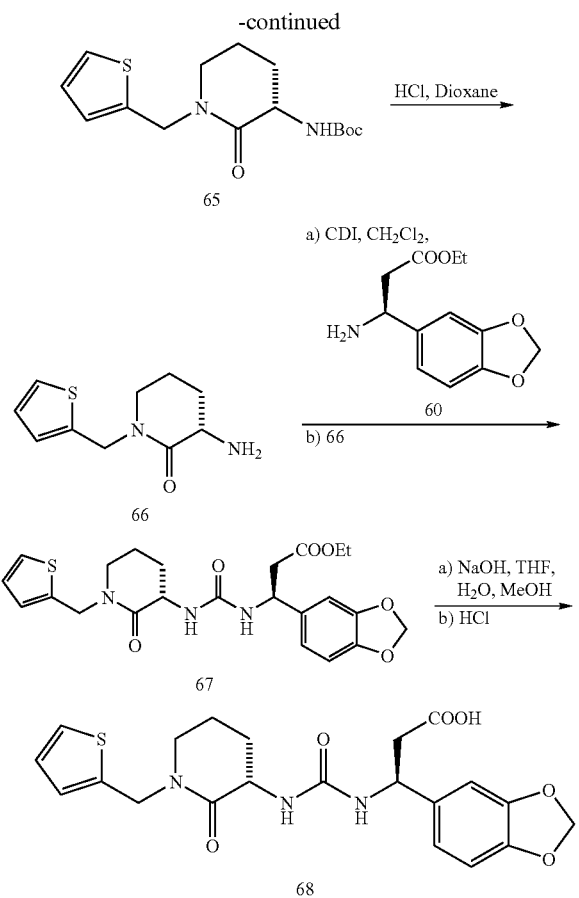
Scheme 17, illustrating the procedure of Example 17, is shown below
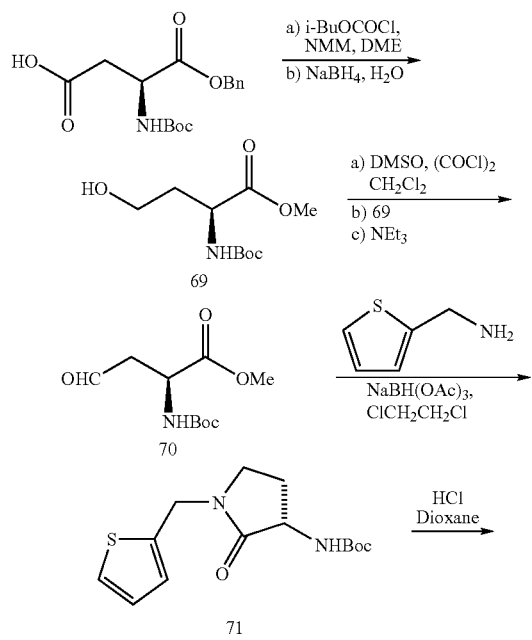
-continued
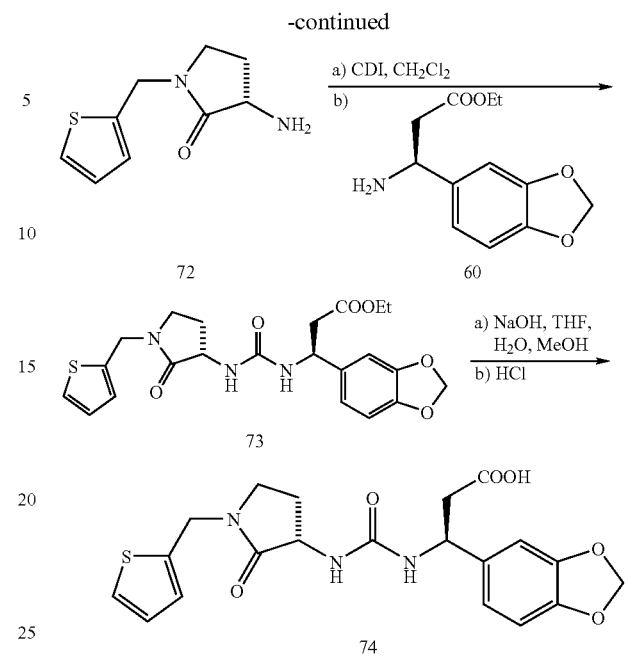
Scheme 18, illustrating the procedure of Example 18, is shown below.
Scheme 18
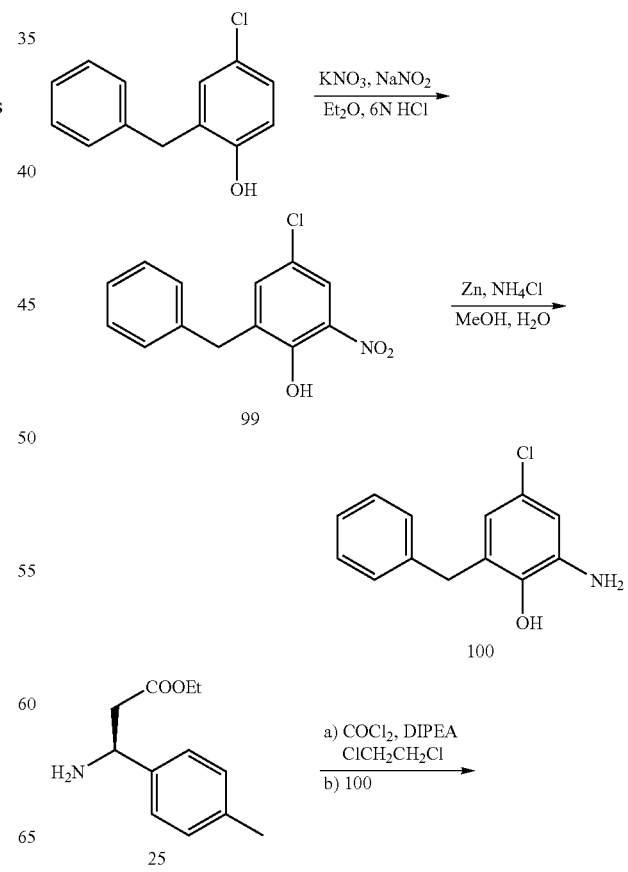

-continued
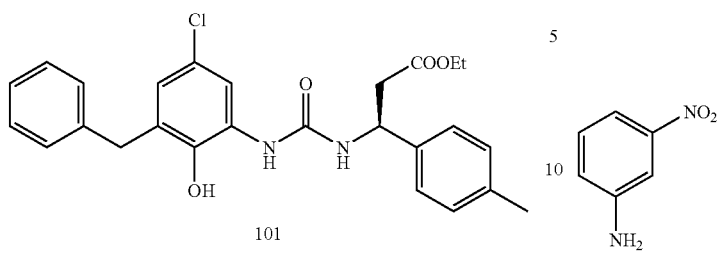
101
Scheme 19, illustrating the procedure of Example 19, is shown below.
Scheme 21, illustrating the procedure of Example 21, is shown below.
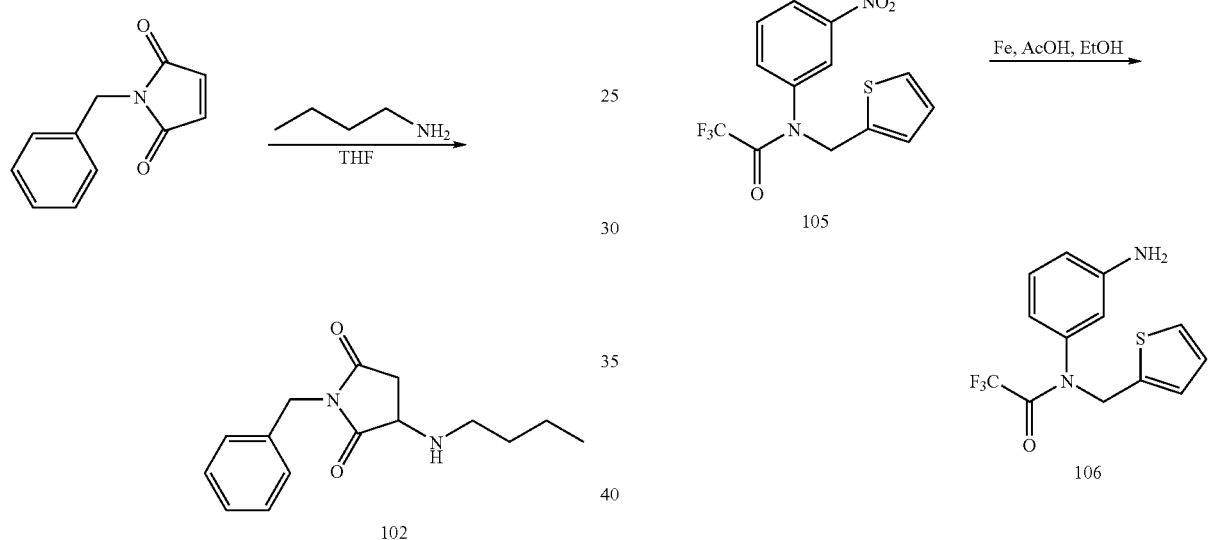
Scheme 22, illustrating the procedure of Example 22, is shown below.
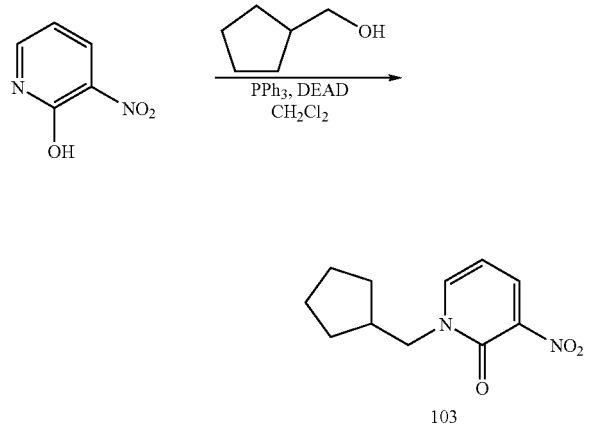
Scheme 20, illustrating the procedure of Example 20, is shown below.

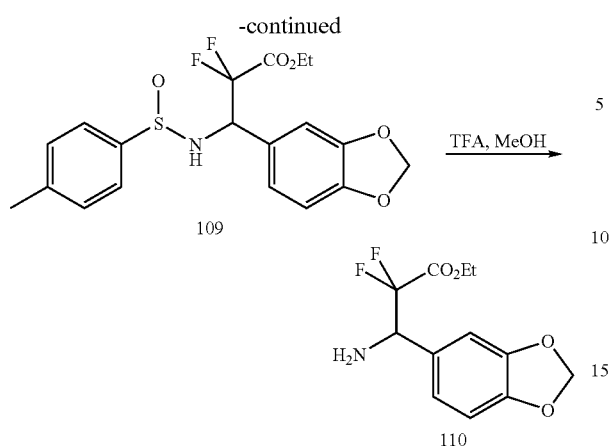
Scheme 23, illustrating the procedure of Example 23, is shown below.
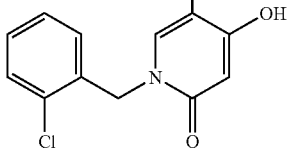
Scheme 24, illustrating the procedure of Example 24, is shown below.
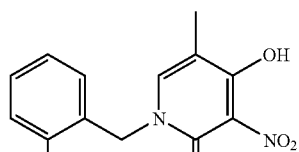
Scheme 25, illustrating the procedure of Example 25, is shown below.
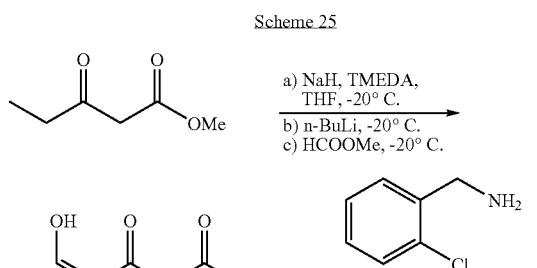
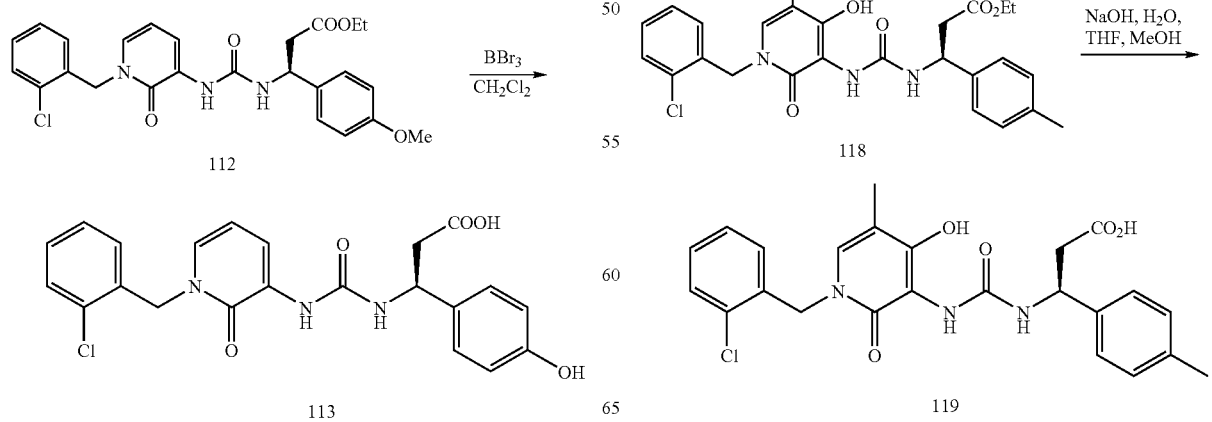

Scheme 26, illustrating Example 26 is shown below.
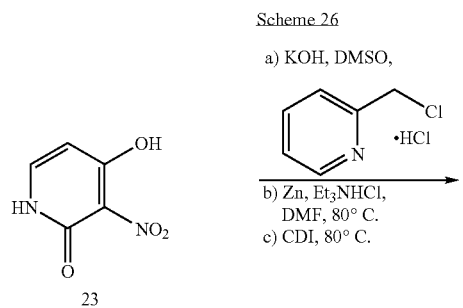
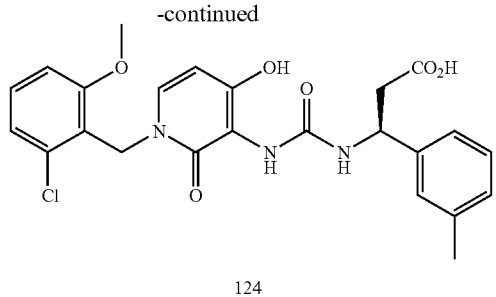
Scheme 29, illustrating Example 29, is shown below.
Scheme 27, illustrating Example 27, is shown below.
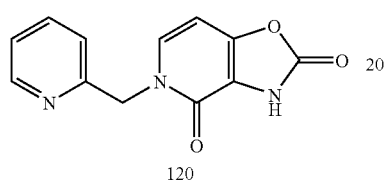
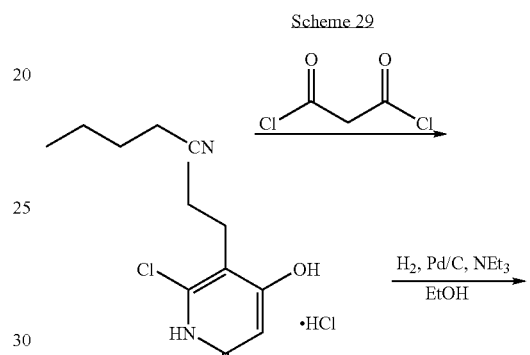
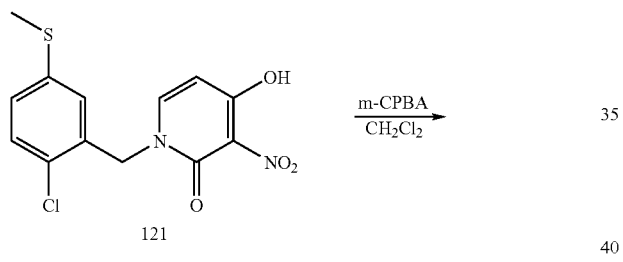
Scheme 30, illustrating Example 30, is shown below.
Scheme 28, illustrating Example 28, is shown below.
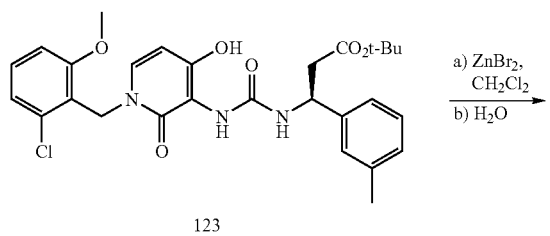
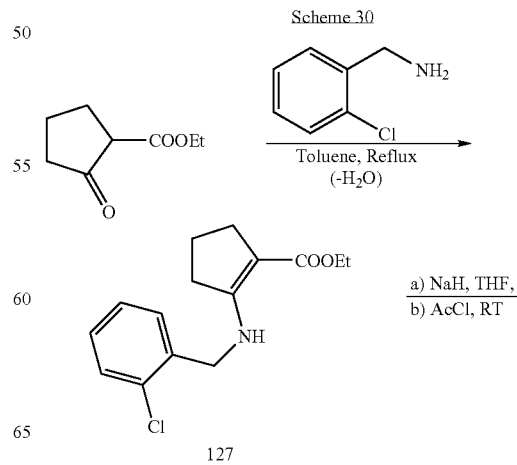
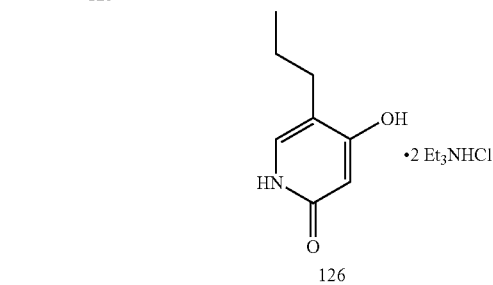

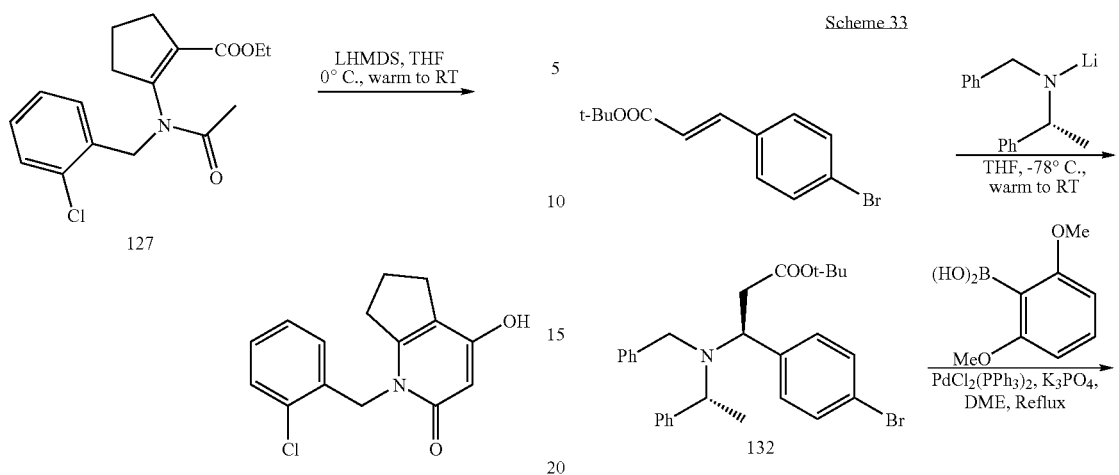
Scheme 31, illustrating Example 31, is shown below.
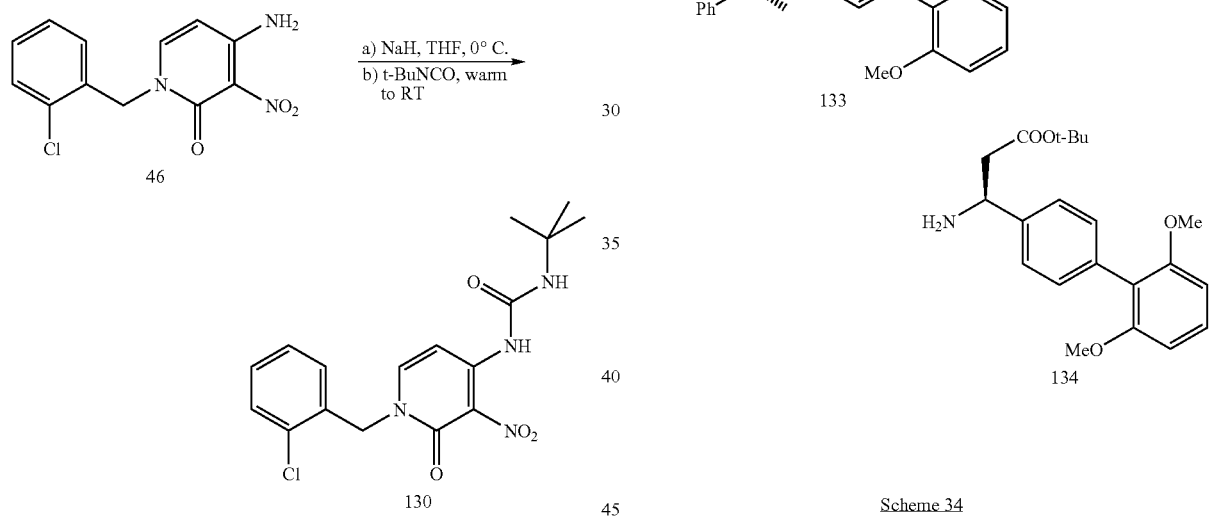
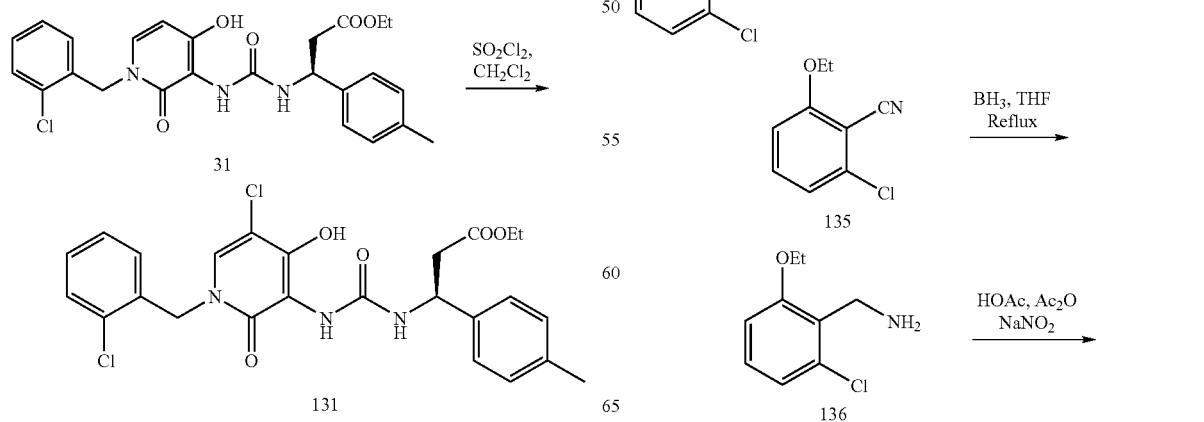

-continued
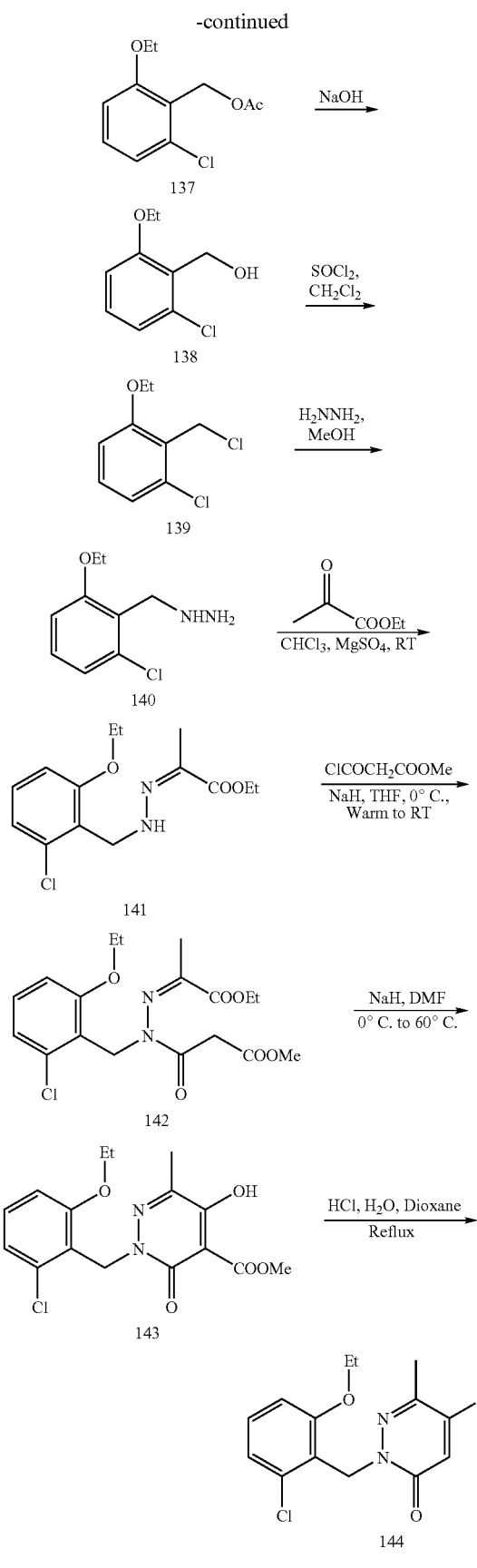
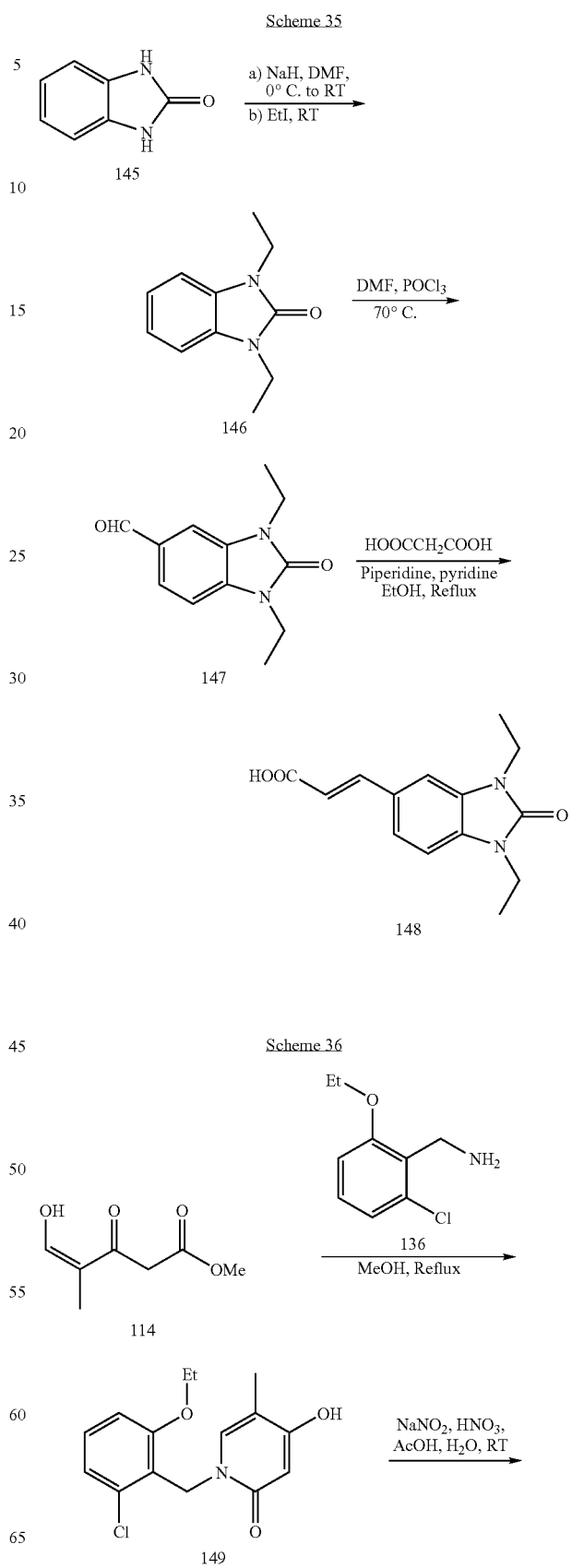

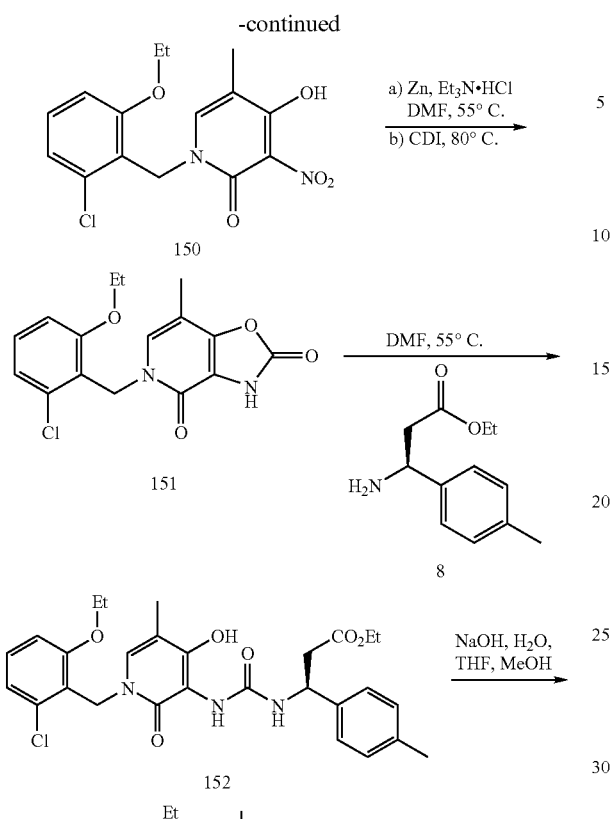
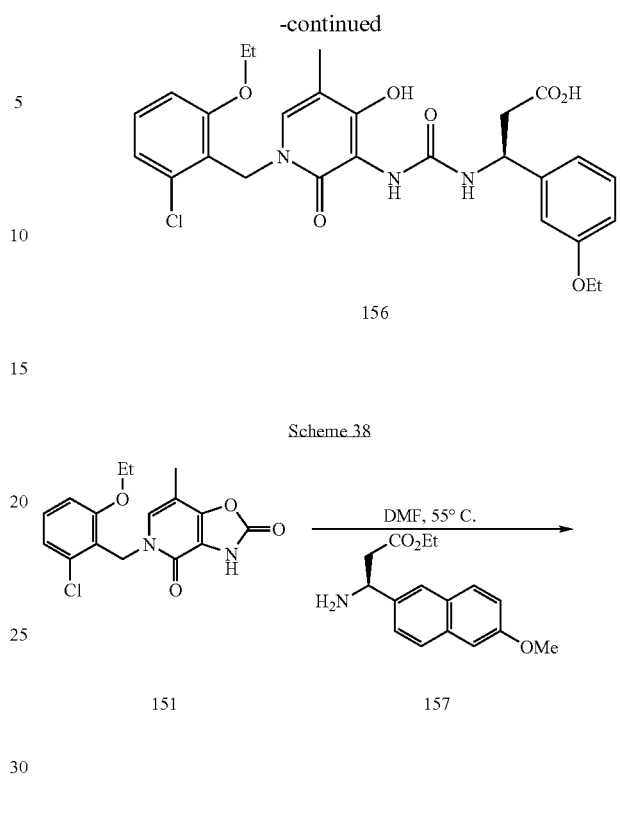
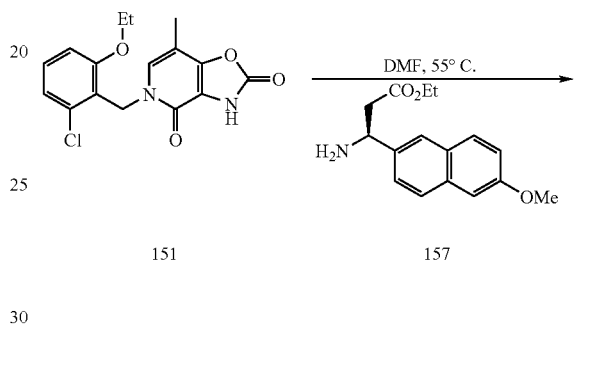
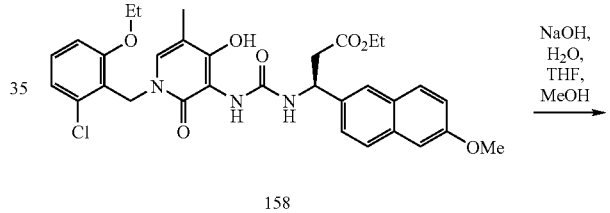
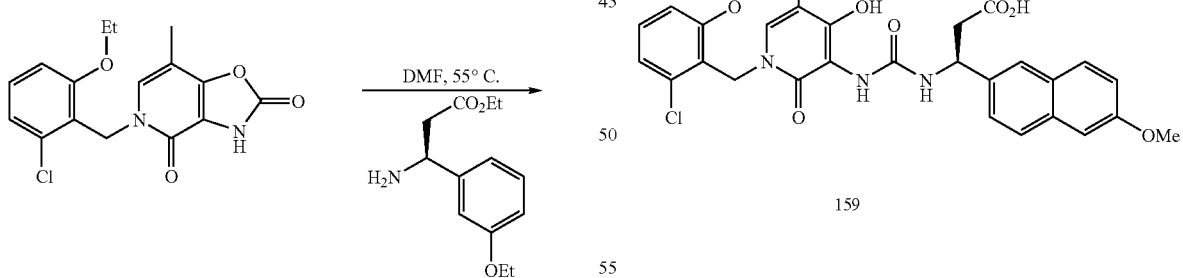
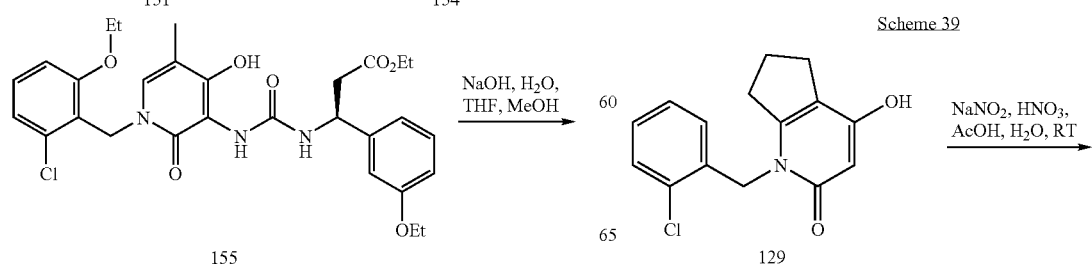

-continued
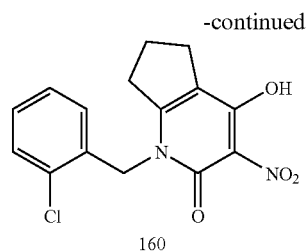
160
a) Zn, Et₃N·HCl
DMF, 55° C.
b) CDI, 80° C.
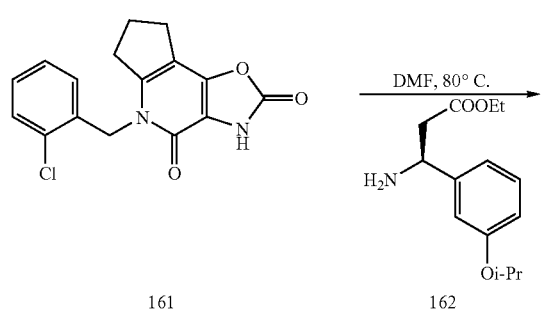
161
DMF, 80° C.
162
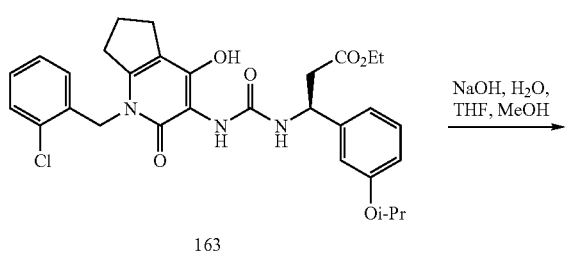
163
NaOH, H₂O,
THF, MeOH
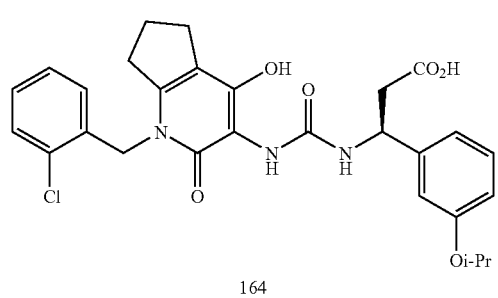
164
Scheme 40
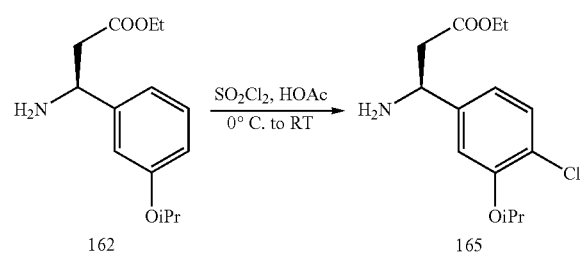
162     165
SO₂Cl₂, HOAc
0° C. to RT
Scheme 41
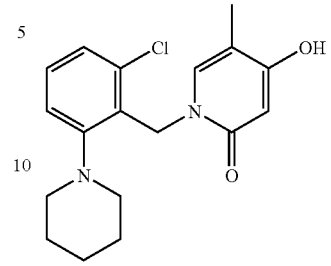
166
NaNO₂, HOAc
MeOH, H₂O
0° C. to RT
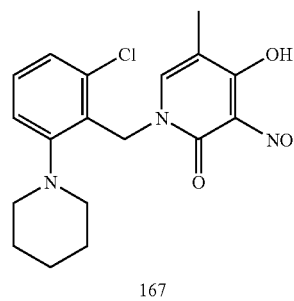
167
Scheme 42
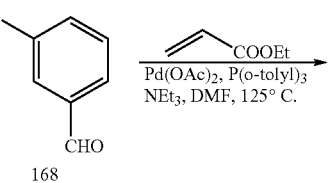
168
COOEt
Pd(OAc)₂, P(o-tolyl)₃
NEt₃, DMF, 125° C.
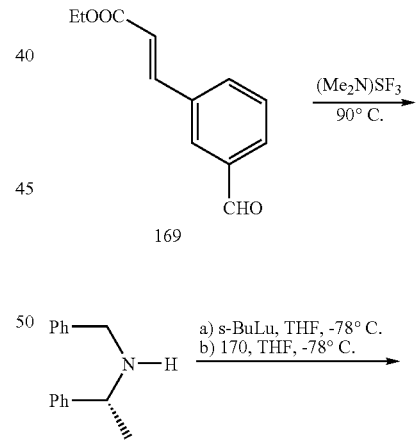
169     169
(Me₂N)SF₃
90° C.
a) s-BuLi, THF, −78° C.
b) 170, THF, −78° C.
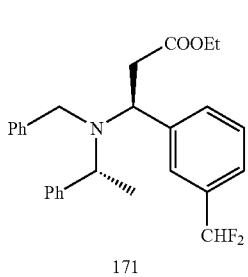
171
H₂, Pd/C, AcOH
EtOH, 35° C.

-continued

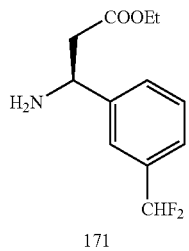

171

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

In another aspect, the present invention contemplates a process of inhibiting the binding of $\alpha_4\beta_1$ integrin to VCAM-1. A process of the present invention can be used either in vitro or in vivo. In accordance with a process of the present invention, a cell expressing $\alpha_4\beta_1$ integrin is exposed to a cell expressing VCAM-1 in the presence of an effective inhibiting amount of a compound of the present invention.

A cell expressing $\alpha_4\beta_1$ integrin can be a naturally occurring white blood cell, mast cell or other cell type that naturally expresses $\alpha_4\beta_1$ on the cell surface, or a cell transfected with an expression vector that contains a poly-nucleotide (e.g., genomic DNA or cDNA) that encodes $\alpha_4\beta_1$ integrin. In an especially preferred embodiment, $\alpha_4\beta_1$ integrin is present on the surface of a white blood cell such as a monocyte, a lymphocyte or a granulocyte (e.g., an eosinophil or a basophil).

A cell that expresses VCAM-1 can be a naturally occurring cell (e.g. an endothelial cell) or a cell transfected with an expression vector containing a polynucleotide that encodes VCAM-1. Methods for producing transfected cells that express VCAM-1 are well known in the art.

Where VCAM-1 exists on the surface of cell, the expression of that VCAM-1 is preferably induced by inflammatory cytokines such as tumor necrosis factor-$\alpha$ interleukin-4 and interleukin-1$\beta$.

Where the cells expressing $\alpha_4\beta_1$ integrin and VCAM-1 are in a living organism, a compound of the present invention is administered in an effective amount to the living organism. Preferably, the compound is in a pharmaceutical composition of this invention.

A process of the present invention is especially useful in treating diseases associated with uncontrolled migration of white blood cells to damaged tissue. Such diseases include, but are not limited to, asthma, atherosclerosis, rheumatoid arthritis, allergy, multiple sclerosis, lupus, inflammatory bowel disease, graft rejection, contact hypersensitivity, type I diabetes, leukemia, and brain cancer. Administration is preferably accomplished via intravascular, subcutaneous, intranasal, transdermal or oral delivery.

The present invention also provides a process of selectively inhibiting the binding of $\alpha_4\beta_1$ integrin to a protein comprising exposing the integrin to the protein in the presence of an effective inhibiting amount of a compound of the present invention. In a preferred embodiment, the $\alpha_4\beta_1$ integrin is expressed on the surface of a cell, either naturally occurring or a cell transformed to express $\alpha_4\beta_1$ integrin.

The protein to which the $\alpha_4\beta_1$ integrin binds can be expressed either on a cell surface or be part of the extracellular matrix. Especially preferred proteins are fibronectin or invasin.

The ability of compounds of the present invention to inhibit binding is described in detail hereinafter in the Examples. These Examples are presented to describe preferred embodiments and utilities of the invention and are not meant to limit the invention unless otherwise stated in the claims appended hereto.

The ability of compounds of the present invention to inhibit binding is described in detail hereinafter in the Examples. These Examples are presented to describe preferred embodiments and utilities of the invention and are not meant to limit the invention unless otherwise stated in the claims appended hereto.

EXAMPLE 1

Synthesis of (3S)-3-{[({1-[(2-chlorophenyl)methyl]-4-ethyl-2-oxo-1,2-dihydro-3-pyridinyl}amino)carbonyl]amino}-3-(4-methylphenyl)propanoic acid (10)

Step One: Compound 1 (20.8 g, 135 mmol) was dissolved in methanol (270 mL) and palladium on carbon (10% Pd dry weight basis, Degussa type E101 NE/W, ~50% water content, 5.75 g, 2.7 mmol Pd) was added. The atmosphere was replaced with hydrogen (toggle between vacuum and hydrogen from a balloon five times), the mixture was stirred overnight, then filtered. The filtrate was concentrated under vacuum and the residue was taken up in a 1:1 hexanes:ethyl acetate mixture and washed with a 4:1 mixture of water and saturated $NaHCO_3$, saturated $NaHCO_3$ and brine. The organic layer was dried over $MgSO_4$ and filtered and the filtrate was concentrated under reduced pressure to give compound 2 (12.43 g, 74%) as a white solid. This material was used without purification.

Step Two: Compound 2 (2.64 g, 21.3 mmol) was dissolved in dichloromethane (50 mL) and chilled to 0° C. The cold solution was treated sequentially with triethylamine (3.6 mL, 25.6 mmol) and trimethylacetyl chloride (2.90 mL, 23.4 mmol). The solution was stirred at room temperature for 6 hours, then refluxed overnight. The mixture was partitioned between dichloromethane and aqueous NaOH (2N). The organic layer was washed with brine, dried over $MgSO_4$ and filtered and the filtrate was concentrated to give compound 3 (3.33 g, 75%).

Step Three: Compound 3 (0.50 g, 2.4 mmol) was dissolved in dry THF, (9.6 mL) and TMEDA (1.1 mL, 7.2 mmol) under a dry nitrogen atmosphere. The resulting solution was chilled to between −20 and −10° C. and treated sequentially with n-butyllithium (1.6 M in hexanes 2.25 mL) and t-butyllithium (1.7 M in pentane, 2.1 mL) dropwise via syringe. After 30 minutes the bath temperature was allowed to come to −5 to 0° C. and treated with ethyl iodide via a syringe (0.77 mL, 9.6 mmol). The solution was stirred at 0° C. for 2 hours, then room temperature overnight. The mixture was quenched with methanol and concentrated to dryness. The residue was purified by filtering through silica gel, eluting with 3:1 hexanes:ethyl acetate and then recrystallizing from hexanes to yield compound 4 (0.32 g, 56%).

Step Four: Compound 4 (0.32 g, 1.3 mmol) was dissolved in glacial acetic acid (4.5 mL) and treated with potassium iodide (0.65 g, 3.9 mmol). The resulting mixture was heated in an oil bath regulated at 115° C. for 1.0 hour. The mixture was cooled, diluted with water and adjusted to pH 6 using 2N NaOH and 2N HCl. The mixture was extracted with chloroform (4 times). The combined extracts were washed with aqueous sodium thiosulfate, dried over $MgSO_4$ and filtered. The filtrate was concentrated under reduced pressure to give compound 5 (0.25 g, 86%) as a white solid. This material was used without further purification.

Step Five: Compound 5 (0.25 g, 1.1 mmol) was dissolved in THF (45 mL) and treated dropwise with a solution of potassium bis(trimethylsilyl)amide (0.5 M in toluene, 2.7 mL) at 0° C. The resulting solution was treated with 2-chlorobenzylbromide (0.16 mL, 1.2 mmol) and the solution was allowed to warm to room temperature overnight. The mixture was partitioned between 2N HCl and ethyl acetate. The organic layer was washed with brine, dried over $MgSO_4$ and filtered. The filtrate was concentrated under reduced pressure and the residue was purified by chromatography ($SiO_2$, gradient elution 4:1 switching to 2:1 hexanes:ethyl acetate) to give compound 6 (0.16 g, 41%).

Step Six: Compound 6 (0.16 g, 0.46 mmol) was suspended in 1:1 water:concentrated HCl (4.6 mL). The suspension was brought to reflux for 4 hours, during which time the compound dissolved. The mixture was cooled, diluted with water and extracted with diethyl ether. The aqueous layer adjusted basic with excess saturated sodium bicarbonate solution, and the mixture was extracted with ethyl acetate. The extracts were combined, washed with brine, dried over $MgSO_4$ and filtered. The filtrate was concentrated under reduced pressure to give compound 7 (0.081 g, 67%).

Step Seven: Compound 7 (0.080 g, 0.30 mmol) was dissolved in 1,2-dichloroethane (1.2 mL) and DIPEA (0.115 mL, 0.66 mmol) and chilled to 0° C. The cold solution was treated rapidly with a solution of phosgene (1.93 M in toluene, 0.170 mL, 0.33 mmol). After 30 minutes a solution of compound 8 (0.068 g, 0.33 mmol) in 1,2-dichloroethane (0.5 mL) was added rapidly via syringe. The resulting mixture was heated to 55° C. for 1 hour. The mixture was partitioned between dichloromethane and 2N HCl. The organic layer was washed with saturated aqueous $NaHCO_3$ and brine, dried over $MgSO_4$ and filtered. The filtrate was concentrated to give compound 9 (0.110 g, 74%).

Step Eight: Compound 9 (0.11 g, 0.22 mmol) was dissolved in 2:1 THF:$H_2O$ (0.88 mL) and treated with a solution of 2N NaOH (0.33 mL). Methanol was added dropwise until a homogeneous solution was obtained. The mixture was stirred for 20 minutes, diluted with water and washed with ethyl ether. The aqueous layer was acidified with 2N HCl and extracted with ethyl acetate. The ethyl acetate layer was washed with brine, dried over $MgSO_4$ and filtered. The filtrate was concentrated to give (3S)-3-{[({1-[(2-chlorophenyl)methyl]-4-ethyl-2-oxo-1,2-dihydro-3-pyridinyl}amino)carbonyl]amino}-3-(4-methylphenyl)propanoic acid (10, 0.095 g, 92%).

EXAMPLE 2

Synthesis of (3S)-3-{[({6-methyl-2-oxo-1-(phenylmethyl)-4-[(phenylmethyl)oxy]-1,2-dihydro-3-pyridinyl}amino)carbonyl]amino}-3-(4-methylphenyl)propanoic acid (15)

Step One: To a suspension of compound 11 (1.0 g, 5.9 mmol) and $K_2CO_3$ (2.40 g 17.6 mmol) in acetone (50 mL) was added benzylbromide (2.31 g, 13.5 mmol). After refluxing overnight, the reaction was cooled and the mixture was partitioned between ethyl acetate and saturated $NaHCO_3$. The organic layer was washed with dilute HCl and brine, dried over $MgSO_4$ and filtered and the filtrate was concentrated to give compound 12 (1.60 g, 80%).

Step Two: Compound 12 (0.30 g, 0.86 mmol), zinc powder (0.30 g, 4.6 mmol) and saturated aqueous $NH_4Cl$ (0.30 mL) were mixed in MeOH (18 mL). This mixture was allowed to stir at room temperature for 1 hour before additional zinc (0.30 g, 4.6 mmol) was added. The resulting heterogeneous mixture was refluxed overnight. After filtration of the hot mixture and concentration of the filtrate under reduced pressure, the residue was dissolved in ethyl acetate and washed with saturated aqueous $NaHCO_3$ and brine. The organic layer was dried over $MgSO_4$ and filtered and the filtrate was concentrated under reduced pressure to give compound 13 (0.18 g, 66%).

Step Three: Compound 13 (0.30 g, 0.94 mmol.) and DIPEA (0.40 mL, 2.3 mmol.) were dissolved in $CH_2Cl_2$ and the mixture was cooled to 0° C. Phosgene (1.9 M in toluene, 0.55 mL, 1.0 mmol) was added to the solution dropwise. The reaction mixture was stirred at 0° C. for 15 minutes before compound 8 (0.19 g, 0.94 mmol) in $CH_2Cl_2$ (2 mL) was added. The resulting solution was stirred at room temperature overnight then poured into ethyl acetate and washed with saturated aqueous $NaHCO_3$, 1 N HCl and brine. The organic layer was dried over $MgSO_4$ and filtered and the filtrate was concentrated under reduced pressure. The residue was purified by flash chromatography on silica gel, eluting with 1:1 increasing to 1:2 hexanes:ethyl acetate to give compound 14 (0.33 g, 64%).

Step Four: A solution of compound 14 (0.33 g, 0.6 mmol) in THF (6 mL) was treated with 2N NaOH (2 mL). MeOH was added until homogeneous solution was achieved. The reaction mixture was stirred at room temperature for 30 minutes and poured into $H_2O$ (50 mL). The aqueous layer was washed with diethyl ether (twice), and then acidified with 1N HCl. The aqueous layer was extracted with ethyl acetate (twice). The combined ethyl acetate extracts were washed with brine (twice), dried over $MgSO_4$ and filtered. The filtrate was concentrated under reduced pressure to give (3S)-3-{[({6-methyl-2-oxo-1-(phenylmethyl)-4-[(phenylmethyl)oxy]-1,2-dihydro-3-pyridinyl}amino)carbonyl]amino}-3-(4-methylphenyl)propanoic acid (15, 0.26 g, 90%) as an off-white solid. Melting point: 124-126° C.

EXAMPLE 3

Synthesis of (3S)-3-{[({4-amino-1-[(2-chlorophenyl)methyl]-6-methyl-2-oxo-1,2-dihydro-3-pyridinyl}amino)carbonyl]amino}-3-(4-methylphenyl)propanoic acid (22)

Step One: To a solution of compound 11 (10.00 g, 58.8 mmol) in anhydrous DMF (120 mL) at 0° C. was added NaH (60% dispersion in mineral oil, 5.40 g, 135 mmol). The mixture was stirred at 0° C. for 15 minutes before the addition of 2-chlorobenzylchloride (12.3 g, 76.4 mmol). After stirring at 55° C. overnight, the mixture was poured into ice-water and washed with $Et_2O$ twice. The aqueous layer was acidified and filtration of the resulting precipitate gave compound 16 (14.7 g, 85%).

Step Two: To a flask containing compound 16 (8.00 g, 28.6 mmol) sealed with a rubber septum and balloon at room temperature under dry nitrogen atmosphere, $POCl_3$ (30.0 ml, 322 mmol) was added via syringe. The nitrogen line was removed and the reaction mixture was stirred overnight at 70° C., then poured over ice (300 ml) and stirred for 30 minutes. The resulting mixture was extracted with dichloromethane (300 ml) and the organic phase was dried over $MgSO_4$ and filtered. The filtrate was concentrated under reduced pressure to give compound 17 (7.3 g, 86%) as a dark brown solid.

Step Three: To a 250 ml flask equipped with condenser and rubber septum fitted with a balloon, a solution of compound 17 (2.1 g, 7.05 mmol), methanol (55 ml) and aqueous ammonium hydroxide (28-30%, 70.0 ml, 1.14 mol) were added at room temperature. The reaction mixture was heated to 65° C. for 60 hours open only to the balloon. The mixture was filtered and the filtrate was concentrated under reduced pressure to yield compound 18 (1.5 g, 76%) as a brown solid.

Step Four: To a solution of compound 18 (0.3 g, 1.02 mmol) in methanol (50 ml) at room temperature, saturated aqueous ammonium chloride (2 ml) and zinc dust (0.30 g, 4.6 mmol) were added sequentially. After stirring 30 minutes at room temperature, additional zinc was added (0.30 g, 4.6 mmol) and the reaction mixture was refluxed overnight. The reaction mixture was filtered hot and the filtrate was concentrated under reduced pressure. The residue was partitioned between ethyl acetate and 1N NaOH. The solution was filtered and the aqueous phase extracted with ethyl acetate. The combined organic phases were dried over $MgSO_4$ and filtered. The filtrate was concentrated under reduced pressure to yield compound 19 (0.21 g, 78%) as a brown solid.

Step Five: A solution of compound 19 (0.10 g, 0.38 mmol), NMM (0.040 mL, 0.38 mmol) and compound 20 (0.14 g, 0.38 mmol) in anhydrous DMF (5 mL) was heated to 50° C. overnight. The mixture was cooled and diluted with ethyl acetate (60 mL). The organic layer was washed with 0.5N NaOH (3×30 mL) and brine, dried over $MgSO_4$ and filtered. The filtrate was concentrated under reduced pressure and the residue was purified by flash chromatography on silica gel, eluting with 9:1 increasing to 17:3 $CHCl_3$:MeOH to give compound 21 (0.120 g, 65%) as a yellow foam.

Step Six: A solution of compound 21 (0.120 g, 0.25 mmol) in THF (6 mL) was treated with 2N NaOH (2 mL). Methanol was added until a homogeneous solution was achieved. The reaction mixture was stirred at room temperature for 30 minutes and poured into $H_2O$ (50 mL). The aqueous layer was washed with diethyl ether (twice), and then acidified with 1N HCl. The aqueous layer was extracted with ethyl acetate (twice). The combined ethyl acetate extracts were washed with brine (twice), dried over $MgSO_4$ and filtered. The filtrate was concentrated under reduced pressure to give (3S)-3-{[({4-amino-1-[(2-chlorophenyl)methyl]-6-methyl-2-oxo-1,2-dihydro-3-pyridinyl}amino)-carbonyl]amino}-3-(4-methylphenyl)propanoic acid (22, 0.100 g, 89%) as an off-white solid. Melting point: 145-147° C.

EXAMPLE 4

Synthesis of (3S)-3-[({[1-[(2-chlorophenyl)methyl]-4-(methyloxy)-2-oxo-1,2-dihydro-3-pyridinyl]amino}carbonyl)amino]-3-(4-methylphenyl)propanoic acid Step One: To a solution of compound 23 (10.00 g, 64.0 mmol) in anhydrous DMF (130 mL) at 0° C. was added NaH (60% dispersion in mineral oil, 5.90 g, 147 mmol). The mixture was stirred at 0° C. for 15 minutes before the addition of 2-chlorobenzylchloride (13.4 g, 83.3 mmol). After stirring at 55° C. overnight, the mixture was poured into ice water and washed with $Et_2O$ (twice). The aqueous layer was acidified and filtration of the resulting precipitate gave compound 24 (13.5 g, 75%).

Step Two: A suspension of compound 24 (1.0 g, 3.6 mmol), $K_2CO_3$ (0.85 g, 6.2 mmol) and MeI (1.18 g, 8.3 mmol) in acetone (20 mL) was refluxed overnight. The reaction mixture was diluted with ethyl acetate and washed with saturated aqueous $NaHCO_3$, 1N HCl and brine. The organic layer was dried over $MgSO_4$ and filtered and the filtrate was concentrated under reduced pressure to give Compound 25 (0.74 g, 70%).

(3S)-3-[({[1-[(2-chlorophenyl)methyl]-4-(methyloxy)-2-oxo-1,2-dihydro-3-pyridinyl]amino}carbonyl)amino]-3-(4-methylphenyl)propanoic acid was prepared from compound 25 according to procedures described in Example 3. MS: Calculated: $(M+H)^+=469.93$; Found: $(M+H)^+=470.01$.

EXAMPLE 5

Synthesis of (3S)-3-{[({1-[(2-chlorophenyl)methyl]-4-fluoro-2-oxo-1,2-dihydro-3-pyridinyl}amino)carbonyl]amino}-3-(4-methylphenyl)propanoic acid Step One: Compound 3 (0.65 g, 3.1 mmol) was dissolved in dry THF (12.4 mL) and TMEDA (0.90 mL, 6 mmol) under a dry nitrogen atmosphere. The resulting solution was chilled to between −15 and −10° C. and n-butyllithium (1.6 M in hexanes, 7.75 mL, 12.4 mmol) was added dropwise via syringe. After 1.5 hours, a solution of N-fluorobenzenesulfonimide (1.07 g, 3.4 mmol) in THF (5 mL) was added to the cold solution rapidly via syringe. The solution was stirred at 0° C. for 1 hour, then room temperature for 3 hours. The mixture was quenched with water and extracted with chloroform (4 times). The combined organic extracts were washed with brine, dried over MgSO$_4$ and filtered. The filtrate was concentrated under reduced pressure and the residue was purified by chromatography, (SiO$_2$, plug gel, using 4:1 switching to 3:1 hexanes:ethyl acetate) to yield compound 26 (0.177 g, 25%).

(3S)-3-{[({1-[(2-Chlorophenyl)methyl]-4-fluoro-2-oxo-1,2-dihydro-3-pyridinyl}amino)carbonyl]amino}-3-(4-methylphenyl)propanoic acid was prepared from Compound 26 according to procedures described in Example 1. MS: Calculated: (M+H)$^+$=458.12; Found: (M+H)$^+$=458.01.

EXAMPLE 6

Synthesis of (3S)-4-chloro-3-{[({1-[(2-chlorophenyl)methyl]-2-oxo-1,2-dihydro-3-pyridinyl}amino)carbonyl]amino}-3-(4-methylphenyl)propanoic acid Step One: Compound 3 (0.65 g, 3.1 mmol) was dissolved in THF (21 mL) and TMEDA (1.20 mL, 7.75 mmol) and chilled to −15° C. The solution was treated with n-butyllithium (1.6 M in hexanes, 4.8 mL, 7.8 mmol). The mixture was maintained between −20 and −10° C. for 1 hour, then cooled to −78° C. Solid N-chlorosuccinimide (0.45 g, 3.4 mmol) was added while the apparatus was under a positive flow of nitrogen. The reaction was allowed to gradually warm to room temperature then stirred overnight. The mixture was quenched with water and extracted with chloroform (4 times). The organic layers were combined, dried over MgSO$_4$ and filtered. The filtrate was concentrated under reduced pressure and the residue was recrystallized from hexanes to give compound 27 (0.25 g, 33%).

(3S)-4-Chloro-3-{[({1-[(2-chlorophenyl)methyl]-2-oxo-1,2-dihydro-3-pyridinyl}amino)carbonyl]amino}-3-(4-methylphenyl)propanoic acid was prepared from compound 27 according to procedures described in Example 1.

EXAMPLE 7

Synthesis of (3S)-4-bromo-3-{[({1-[(2-chlorophenyl)methyl]-2-oxo-1,2-dihydro-3-pyridinyl}amino)carbonyl]amino}-3-(4-methylphenyl)propanoic acid Step One: Compound 3 (2.00 g, 9.6 mmol) was dissolved in dry THF (32 mL) and TMEDA (2.20 mL, 14.4 mmol) under a dry nitrogen atmosphere. The resulting solution was chilled to between −20 and −10° C. and n-butyl lithium (1.60 M in hexanes, 18.0 mL, 28.8 mmol) was added dropwise via syringe. Upon completion of the addition, the solution was chilled to −78° C. and bromine (0.49 mL, 10.5 mmol) was added dropwise via syringe. The solution was allowed to warm slowly to room temperature overnight, then was quenched with water and extracted with chloroform. The organic layer was dried over MgSO$_4$ and filtered and the filtrate was concentrated under reduced pressure. The residue was recrystallized from hexanes to give compound 28 (1.32 g, 48%) as a tannish white solid.

(3S)-4-Bromo-3-{[({1-[(2-chlorophenyl)methyl]-2-oxo-1,2-dihydro-3-pyridinyl}amino)carbonyl]amino}-3-(4-methylphenyl)propanoic acid was prepared from compound 28 according to procedures described in Example 1.

EXAMPLE 8

Synthesis of (3S)-3-{[({1-[(2-chlorophenyl)methyl]-4-hydroxy-2-oxo-1,2-dihydro-3-pyridinyl}amino)carbonyl]amino}-3-(4-methylphenyl)propanoic acid (32)

Step One: To a solution of compound 24 (1.5 g, 5.3 mmol) in methanol (50 ml) at room temperature, saturated ammonium chloride (1.5 mL) and zinc dust (1.5 g, 23 mmol) were added sequentially. After stirring 30 minutes at room temperature, additional zinc dust (1.5 g, 23 mmol) was added and the reaction mixture was refluxed overnight. The reaction mixture was filtered while hot and the filtrate was concentrated under reduced pressure. HCl (1 N) was added to the resulting residue until the pH was approximately 4 and the resulting precipitate was collected by filtration to give compound 29 (0.80 g, 57%) as a brown solid.

Step Two: A solution of compound 29 (0.26 g, 1.0 mmol) and CDI (0.25 g, 1.6 mmol) in DMF (10 mL) was heated to 70° C. overnight. After cooling to room temperature, the mixture was diluted with ethyl acetate and washed with 1N HCl (3 times) and brine. The organic layer was dried over MgSO$_4$ and filtered and the filtrate was concentrated under reduced pressure to give compound 30 (0.14 g, 50%) as a brown solid.

Step Three: A solution of compound 30 (0.1 g, 0.36 mmol) and compound 8 (0.082 g, 0.40 mmol) in anhydrous DMF (5 mL) was heated to 70° C. overnight. The mixture was cooled, diluted with ethyl acetate and washed with 1N HCl (3 times) and brine. The organic layer was dried over MgSO$_4$ and filtered and the filtrate was concentrated under reduced pressure. The residue was purified by flash chromatography (SiO$_2$), eluting with 9:1 CHCl$_3$:MeOH to give compound 31 (0.17 g, 97%).

Step Four: A solution of compound 31 (0.170 g, 0.35 mmol) in THF (3 mL) was treated with 2N NaOH (1 mL). Methanol was added until a homogeneous solution was achieved. The reaction mixture was stirred at room temperature for 30 minutes and poured into H$_2$O (50 mL). The aqueous layer was washed with diethyl ether (twice), and then acidified with 1N HCl. The aqueous layer was extracted with ethyl acetate (twice). The combined ethyl acetate extracts were washed with brine (twice), dried over MgSO$_4$ and filtered. The filtrate was concentrated under reduced pressure to give (3S)-3-{[({1-[(2-chlorophenyl)methyl]-4-hydroxy-2-oxo-1,2-dihydro-3-pyridinyl}amino)carbonyl]amino}-3-(4-methylphenyl)propanoic acid (32, 0.150 g, 94%) as an off-white solid. Melting point: 113-115° C.

EXAMPLE 9

Synthesis of (3S)-3-{[({1-[(2-chlorophenyl)methyl]-2-oxo-4-phenyl-1,2-dihydro-3-pyridinyl}amino)carbonyl]amino}-3-(4-methylphenyl)propanoic acid Step One: Compound 33 (prepared from compound 28 according to procedures described in Example 1, 0.20 g, 0.50 mmol) was dissolved in DMF (1.8 mL) and water (0.7 mL) and treated with K$_3$PO$_4$ (0.39 g, 1.86 mmol) and phenyl boronic acid (0.113 g, 0.93 mmol). The resulting mixture was deoxygenated (switching between vacuum and nitrogen 5 times), then tetrakis(triphenylphosine)palladium(0) (8.7 mg, 0.050 mmol) was added. The mixture was deoxygenated as before and heated at 90° C. overnight. The mixture was cooled, diluted with water and extracted with ethyl acetate (2 times). The combined extracts were washed with brine, dried over MgSO$_4$ and filtered through silica gel and concentrated under reduced pressure. The residue was suspended in 1:1 water:concentrated HCl (2 mL) and acetonitrile (0.5 mL). The suspension was brought to reflux for 1 hour, then cooled, and partitioned between ethyl acetate and saturated aqueous NaHCO$_3$. The ethyl acetate layer was washed with brine, dried over MgSO$_4$, filtered, and concentrated under reduced pressure. The residue was purified by flash chromatography (SiO$_2$, 3:1 hexanes/ethyl acetate) to give compound 34 (0.115 g, 94%). This material was used without purification.

(3S)-3-{[({1-[(2-Chlorophenyl)methyl]-2-oxo-4-phenyl-1,2-dihydro-3-pyridinyl}amino)carbonyl]amino}-3-(4-methylphenyl)propanoic acid was prepared from Compound 34 according procedures described in Example 1. $^1$H NMR (400 MHz, CD$_3$OD): δ 2.25 (s, 3H), 2.50 (m, 2H), 4.89 (t, J=5.9 Hz, 1H), 5.34 (s, 2H), 6.40 (d, J=7.0 Hz, 1H), 7.0 (d, J=8.0 Hz, 2H), 7.10 (d, J=8.0 Hz, 2H), 7.18 (m, 1H), 7.28 (m, 2H), 7.35 (m, 3H), 7.43 (m, 1H), 7.49 (m, 3H).

EXAMPLE 10

Synthesis of (3S)-3-[({[2-methyl-4-(2-methylpropyl)-6-oxo-1-(phenylmethyl)-1,6-dihydro-5-pyrimidinyl]amino}carbonyl)amino]-3-(4-methylphenyl) propanoic acid (43)

Step One: Compound 35 (2.00 g 18.2 mmol) was dissolved in 30 mL of dry methanol. To this was added benzylamine (1.97 g 18.2 mmol) and triethylamine (2.0 g 20.0 mmol). The reaction mixture was stirred at 50° C. for 3 hours, and then concentrated under reduced pressure. The residue was partitioned between H$_2$O and CH$_2$Cl$_2$. The organic layer was dried over MgSO$_4$ and filtered and the filtrate was concentrated under reduced pressure to give compound 36 (2.3 g, 82%).

Step Two: To a solution of compound 37 (3.50 g, 26.5 mmol) in ethanol (10 mL) and pyridine (5 mL) was added isovaleraldehyde (2.8 mL 27 mmol) and piperidine (1 mL). The reaction mixture was heated to reflux for 3 hours and concentrated under reduced pressure. The residue was partitioned between 2N HCl (15 mL) and ethyl acetate (30 mL). The organic layer was dried over MgSO$_4$, and filtered and the filtrate was concentrated under reduced pressure. The residue was purified by silica gel chromatography, eluting with 2:1 hexanes:ethyl acetate to give compound 38 (3.6 g, 67%).

Step Three: A solution of compound 38 (2.5 g, 12.48 mmol) and compound 36 (2.52 g, 13.7 mmol) in dry methanol (25 mL) was heated to vigorous reflux for 3 hours, cooled and concentrated under reduced pressure. The residue was chromatographed on silica gel eluting with 2:1 hexanes:ethylacetate to give compound 39 (2.75 g, 69%).

Step Four: To a solution of compound 39 (2.5 g, 7.9 mmol) in CCl$_4$ (15 mL) was added NBS (1.4 g, 8.0 mmoL), K$_2$CO$_3$ (11.0 g, 80.0 mmol), and benzoyl peroxide (50 mg, 0.20 mmol). The reaction mixture was heated to reflux for 1 hour, cooled to room temperature, diluted with H$_2$O and extracted with CH$_2$Cl$_2$. The organic layer was dried over MgSO$_4$ and filtered and the filtrate was concentrated under reduced pressure. The residue was chromatographed on silica gel eluting with 3:1 hexanes:ethyl acetate to give compound 40 (0.62 g, 25%).

Step Five: Compound 40 (0.60 g, 1.9 mmol) was treated with 2N NaOH (5 mL) and THF (3 mL). The resulting mixture was stirred at room temperature for 2 hours, acidified with 2N HCl and extracted with ethyl acetate. The organic layer was dried over MgSO$_4$ and filtered and the filtrate was concentrated under reduced pressure to give compound 41 (560 mg, 98%).

Step Six: To a solution of compound 41 (0.56 g, 1.86 mmol) in dry benzene (10 mL), diphenylphosphorylazide (0.56 g, 2.0 mmol) and triethylamine (2.02 g, 2.0 mmol) were added. The reaction mixture was heated to 90° C. for 1 hour then a solution of compound 8 (0.39 g, 1.9 mmol) in benzene (2 mL) was added. The reaction was stirred at 90° C. for an additional 1 hour, cooled to room temperature, diluted with 10% aqueous ammonium chloride and extracted with ethyl acetate. The organic layer was dried over MgSO$_4$ and filtered and the filtrate was concentrated under reduced pressure. The residue was chromatographed on silica gel, eluting with 7:3 ethyl acetate:hexane to give compound 42 (0.38 g, 40%).

Step Seven: To a solution of compound 42 (0.35 g 0.7 mmol) in 1:1 mixture of THF:MeOH (8 mL) was added 2N NaOH (8 mL). The reaction was stirred at room temperature for 3 hours, acidified with 2N HCl (10 mL) and extracted with ethyl acetate (20 mL). The organic layer was dried over MgSO$_4$ and filtered and the filtrate was concentrated under reduced pressure to give (3S)-3-[({[2-methyl-4-(2-methylpropyl)-6-oxo-1-(phenylmethyl)-1,6-dihydro-5-pyrimidinyl]amino}carbonyl)amino]-3-(4-methylphenyl)propanoic acid (43, 250 mg, 75%). MS: Calculated: (M+H)$^+$=477.25 m/z. Found: (M+H)$^+$=477.17 m/z.

EXAMPLE 11

Synthesis of (3S)-3-[({[2-methyl-6-oxo-1-(phenylmethyl)-1,6-dihydro-5-pyrimidinyl]amino}carbonyl) amino]-3-(4-methylphenyl)propanoic acid Step One: A solution of compound 36 (2.3 g, 15.5 mmol) and compound 44 (3.36 g, 15.5 mmol) in absolute ethanol (35 mL) was refluxed for 3 hours and concentrated. The residue was chromatographed on silica gel, eluting with 1:1 ethyl acetate:hexane to give compound 45 (1.87 g, 55% yield).

(3S)-3-[({[2-Methyl-6-oxo-1-(phenylmethyl)-1,6-dihydro-5-pyrimidinyl]amino}carbonyl)amino]-3-(4-methylphenyl)propanoic acid was prepared from compound 45 according to procedures described in Example 10. $^1$H NMR (400 MHz, CD$_3$OD) δ 2.28 (s, 3H), 2.35 (s, 3H), 2.57 (m, 2H), 5.16 (m, 1H), 5.30 (s, 2H), 7.13 (m, 4H), 7.30 (m, 5H), 8.50 (s, 1H).

EXAMPLE 12

Synthesis of (3S)-3-{[({1-[(2-chlorophenyl)methyl]-4-[({ethyl[(ethylamino)carbonyl]amino}carbonyl) amino]-2-oxo-1,2-dihydro-3-pyridinyl}amino)carbonyl]amino}-3-(4-methylphenyl)propanoic acid Step One: To a solution of compound 46 (prepared according to procedures described in Example 3, 0.50 g, 1.8 mmol) in THF (10 mL) at 0° C. was added NaH (60% dispersion in mineral oil, 0.23 g, 5.1 mmol). The mixture was stirred for 10 minutes at 0° C., then ethyl isocyanate (0.65 g, 9.15 mmol) was added. The mixture was stirred at room temperature over the weekend, was quenched with 1 N HCl and extracted with ethyl acetate. The organic layer was dried over MgSO$_4$ and filtered and the filtrate was concentrated under reduced pressure to give compound 47 (0.60 g). This material was used without purification.

(3S)-3-{[({1-[(2-Chlorophenyl)methyl]-4-[({ethyl[(ethylamino)carbonyl]amino}carbonyl)amino]-2-oxo-1,2-dihydro-3-pyridinyl}amino)carbonyl]amino}-3-(4-methylphenyl)propanoic acid was prepared from compound 47 according to procedures described in Example 3. Melting point: 128-130° C.

EXAMPLE 13

Synthesis of (3S)-3-{[({1-[(2-chlorophenyl)methyl]-4-hydroxy-2-oxo-1,2-dihydro-3-quinolinyl}amino)carbonyl]amino}-3-(4-methylphenyl)propanoic acid Step One: To a solution of compound 48 (2.00 g, 9.70 mmol) in anhydrous DMF (25 mL) at 0° C. was added NaH (60% dispersion in mineral oil, 0.89 g, 22 mmol). The mixture was stirred at 0° C. for 15 minutes before the addition of 2-chlorobenzylchloride (2.03 g, 12.6 mmol). After stirring at 55° C. overnight, the mixture was poured into ice-water and washed with Et$_2$O (twice). The aqueous layer was acidified and filtration of the resulting precipitate gave compound 49 (3.45 g). This material was used without purification.

(3S)-3-{[({1-[(2-chlorophenyl)methyl]-4-hydroxy-2-oxo-1,2-dihydro-3-quinolinyl}amino)carbonyl]amino}-3-(4-methylphenyl)propanoic acid was prepared from compound 49 according to procedures described in Example 8. Melting point: 134-136° C.

EXAMPLE 14

Synthesis of (3S)-3-{[({1-[(2-chlorophenyl)methyl]-5-methyl-2-oxo-1,2-dihydro-3-pyridinyl}amino)carbonyl]amino}-3-(4-methylphenyl)propanoic acid (56)

Step One: To a suspension of compound 51 (1.67 g, 9.81 mmol) in DMF (33 mL) at room temperature under a dry, nitrogen atmosphere, 2-chlorobenzylamine (1.30 mL, 10.8 mmol) and EDCI (2.35 g, 12.3 mmol) were added sequentially. The resulting mixture was vigorously stirred at room temperature for 5 hours, diluted with ethyl acetate and washed with 2 N HCl, H$_2$O (3 times), saturated aqueous NaHCO$_3$ and brine. The organic layer was dried over MgSO$_4$ and filtered and the filtrate was concentrated under reduced pressure to give compound 52 (2.55 g, 100%) as a pale yellow solid.

Step Two: A solution of compound 52 (555 mg, 2.17 mmol) and 3-dimethylamino-2-methylpropenal (738 mg, 6.5 mmol) in absolute ethanol (4.3 mL) and glacial acetic acid (0.22 mL) was heated to reflux overnight. The resulting mixture was cooled to room temperature, diluted with ethyl acetate and washed with 2 N HCl (twice), H$_2$O and brine. The organic layer was dried over MgSO$_4$ and filtered and the filtrate was concentrated under reduced pressure. The pressure was purified by chromatography on silica gel, eluting with 7:3 increasing to 1:1 hexanes:ethyl acetate and finally 19:19:2 hexanes:ethyl acetate:methanol to yield compound 53 (182 mg, 27%) as a yellow oil.

Step Three: To a solution of compound 53 (167 mg, 0.55 mmol) in THF (3 mL), 2 N NaOH (1 mL) and methanol (2 mL) were added. The resulting mixture was stirred for 15 minutes, diluted with H$_2$O and extracted with ethyl ether. The aqueous layer was acidified with 2 N HCl and extracted with ethyl acetate. The ethyl acetate layer was washed with H$_2$O and brine, dried over MgSO$_4$ and filtered. The filtrate was concentrated under reduced pressure to give compound 54 (139 mg, 91%) as a white solid.

Step Four: To a suspension of compound 54 (175 mg, 0.63 mmol) in THF (6.7 mL) and DIPEA (0.23 mL, 1.34 mmol) at room temperature under a dry, nitrogen atmosphere, DPPA (0.29 mL, 1.34 mmol) was added via syringe. The resulting mixture was stirred at room temperature for 15 minutes, then heated to reflux for 3.5 hours. The mixture was allowed to cool to room temperature and a solution of compound 8 (278 mg, 1.34 mmol) in THF (6.0 mL) was added via cannula along with a THF (0.7 mL) rinse. The resulting mixture was stirred at room temperature overnight, diluted with ethyl acetate and washed with 2 N HCl (twice), saturated aqueous NaHCO$_3$ and brine. The organic layer was dried over MgSO$_4$ and filtered and the filtrate was concentrated under reduced pressure. The residue was purified by silica gel chromatography, eluting with 7:3 then 3:2 and finally 1:1 hexanes:ethyl acetate to yield compound 55 (60 mg, 20%) as a colorless oil.

Step Five: To a solution of compound 55 (60 mg, 0.12 mmol) in THF (3 mL), 0.192 N NaOH (0.65 mL, 0.12 mmol) and methanol (2 mL) were added. The resulting mixture was stirred at room temperature for 24 hours, then was diluted with H$_2$O. The organic solvents were removed under reduced pressure and the resulting aqueous mixture was extracted with ethyl ether. The aqueous phase was lyophilized to give (3S)-3-{[({1-[(2-chlorophenyl)methyl]-5-methyl-2-oxo-1,2-dihydro-3-pyridinyl}amino)carbonyl]amino}-3-(4-methylphenyl)propanoic acid, sodium salt (56, 56 mg, 95%) as an off-white solid. MS: Calculated for (C$_{24}$H$_{23}$ClN$_3$O$_4$)$^-$: 452.14 m/z. Found: 451.99 m/z.

EXAMPLE 15

Synthesis of (3S)-3-(1,3-benzodioxol-5-yl)-3-[({[2-oxo-1-(2-thienylmethyl)-1,2-dihydro-3-pyridinyl]amino}carbonyl)amino]propanoic acid (62)

Step One: To a solution of 2-thiophenemethanol (1.015 g, 8.89 mmol) in CH$_2$Cl$_2$ (17.8 ml) cooled to 0° C. under a dry nitrogen atmosphere, triethylamine (2.98 ml, 21.4 mmol) and methanesulfonyl chloride (0.69 ml, 8.9 mmol) were added sequentially by syringe. The resulting mixture was stirred at 0° C. for 15 minutes, then 2-hydroxy-3-nitropyridine (1.496 g, 10.7 mmol) and 4-dimethylaminopyridine (catalytic) were added. The mixture was allowed to gradually warm to room temperature and then was stirred overnight. The mixture was diluted with ethyl acetate and washed with 2N HCl, H$_2$O, saturated NaHCO$_3$ and brine. The organic phase was dried over MgSO4 and filtered and the filtrate was concentrated under reduced pressure to give 58 (395 mg) as a yellow waxy solid. This material was used without purification.

Step Two: To a solution of 58 (330 mg, 1.40 mmol) in glacial acetic acid (6.6 ml) at room temperature under a dry nitrogen atmosphere, iron powder (154 mg, 2.8 mmol, −325 mesh) was added. The resulting solution was heated to 60° C. in an oil bath with vigorous stirring for 20 minutes. The mixture was cooled to room temperature, diluted with ethyl acetate and filtered through Celite. The filtrate was washed with H$_2$O, saturated NaHCO$_3$ and brine. The organic phase was dried over MgSO$_4$ and filtered and the filtrate was concentrated under reduced pressure. The residue was filtered through silica gel, eluting with 1:1 hexanes:ethyl acetate increasing to 1:3 hexanes:ethyl acetate to yield 59 (188 mg, 12% for two steps) as a greenish solid.

Step Three: To a solution of 59 (111 mg, 0.54 mmol) in CH$_2$Cl$_2$ (2.7 ml) cooled to 0° C. under a dry nitrogen atmosphere, N,N-diisopropylethylamine (0.23 ml, 1.30 mmol) and phosgene (0.31 ml, 1.9M in toluene, 0.59 mmol) were added sequentially by syringe. The resulting mixture was stirred at 0° C. for 15 minutes, then a solution of β-amino ester 60 (167 mg, 0.70 mmol) in CH$_2$Cl$_2$ (2.7 ml) was added by cannula along with a CH$_2$Cl$_2$ rinse (1.0 ml). The resulting mixture was allowed to warm to room temperature, was stirred for 2 hours, was diluted with ethyl acetate and washed with 2N HCl, H$_2$O, saturated NaHCO$_3$ and brine. The organic phase was dried over MgSO$_4$ and filtered and the filtrate was concentrated under reduced pressure. The residue was purified by silica gel chromatography, eluting with 1:1 hexanes: ethyl acetate to yield 61 (231 mg, 91%) as a purple foam.

Step Four: To a solution of ester 61 (227 mg, 0.48 mmol) in THF (6 ml) at room temperature, NaOH (2 ml, 2N in $H_2O$, 4 mmol) and methanol (enough to give a clear solution, approximately 2 ml) were added. The resulting mixture was stirred for 15 minutes, then was diluted with water and extracted with ether. The aqueous phase was acidified with HCl (2N) and extracted with ethyl acetate. The organic phase was washed with brine, dried over $MgSO_4$ and filtered and the filtrate was concentrated under reduced pressure to give 62 (191 mg, 90%) as a white solid. $^1$H NMR (400 MHz, $CD_3SOCD_3$) δ 2.63 (d, J=7.3 Hz, 2H), 4.99 (dt, J=8.4, 7.3 Hz, 1H), 5.30 (s, 2H), 5.98 (m, 2H), 6.21 (dd, J=7.5, 7.0 Hz, 1H), 6.78 (dd, J=8.1, 1.6 Hz, 1H), 6.85 (d, J=8.1 Hz, 1H), 6.88 (d, J=1.6 Hz, 1H), 6.97 (dd, J=5.1, 3.5 Hz, 1H), 7.17 (dd, J=3.5, 1.1 Hz, 1H), 7.35 (dd, J=7.0, 1.8 Hz, 1H), 7.44 (dd, J=5.1, 1.1 Hz, 1H), 7.67 (d, J=8.4 Hz, 1H), 7.94 (dd, J=7.5, 1.8 Hz, 1H), 8.40 (s, 1H).

EXAMPLE 16

Synthesis of (3S)-3-(1,3-benzodioxol-5-yl)-3-[({[(3S)-2-oxo-1-(2-thienylmethyl)hexahydro-3-pyridinyl]amino}carbonyl)amino]propanoic acid (68)

Step One: To a solution of N-α-tert-butoxycarbonyl-N-δ-benzyloxycarbonyl-L-ornithine 63 (1.00 g, 2.73 mmol) and cesium carbonate (1.33 g, 4.1 mmol) in DMF (10 ml) at room temperature under a dry nitrogen atmosphere, iodomethane (0.22 ml, 3.3 mmol) was added by syringe. The resulting mixture was stirred at room temperature for 18 hours then was diluted with ethyl acetate and washed with $H_2O$, 10% $Na_2S_2O_5$, saturated $NaHCO_3$ and brine. The organic phase was dried over $MgSO_4$ and filtered and the filtrate was concentrated under reduced pressure to give ester 64 (1.21 g) as a pale yellow oil. This material contained DMF but was used without purification.

Step Two: To a solution of 64 (0.86 g of crude material prepared in previous procedure, 1.94 mmol theoretical) in methanol (10 ml) at 0° C. under a dry nitrogen atmosphere, palladium on charcoal (300 mg, 10% Pd, Degussa type E101 NE/W, wet, 50% water by weight) was added. The nitrogen atmosphere was replaced by hydrogen (alternate five times between vacuum and hydrogen supplied by balloon) and the mixture was stirred at 0° C. for 30 minutes then filtered directly into a flask containing 2-thiophenecarboxaldehyde (177 mg, 1.58 mmol). The mixture was concentrated (water bath at room temperature) and the residue was taken up in dichloroethane (6 ml). To this solution, sodium triacetoxyborohydride (479 mg, 2.26 mmol) was added and the mixture was stirred for 2 hours, diluted with ethyl acetate and washed with saturated $NaHCO_3$ (2 times) and brine. The organic phase was dried over $MgSO_4$ and filtered and the filtrate was concentrated under reduced pressure. The residue was filtered through silica gel, eluting with 7:3 hexanes:ethyl acetate to yield lactam 65 (75 mg, 12% for two steps) as a colorless oil.

Step Three: To a flask containing 65 (89 mg, 0.29 mmol) sealed with a rubber septum at room temperature under a dry nitrogen atmosphere, HCl (7.2 ml, 4.0M in dioxane, 28.8 mmol) was added by syringe. The nitrogen needle was removed and the mixture in the sealed flask was stirred overnight. The mixture was diluted with $CH_2Cl_2$ and washed with saturated $NaHCO_3$. The organic phase was dried over $MgSO_4$ and filtered and the filtrate was concentrated under reduced pressure to give amine 66 (60 mg, 100%) as a light yellow oil. This material was used without purification.

Step Four: To a solution of β-amino ester 60 (75 mg, 0.32 mmol) in $CH_2Cl_2$ (0.6 ml) at room temperature under a dry nitrogen atmosphere, carbonyldiimidazole (51 mg, 0.32 mmol) was added. The resulting mixture was stirred at room temperature for 5 minutes and a solution of amine 66 (60 mg, 0.29 mmol) in $CH_2Cl_2$ (0.6 ml) was added by cannula along with a $CH_2Cl_2$ (0.2 ml) rinse. The resulting mixture was stirred at room temperature for 3 days, then was diluted with ethyl acetate and washed with 2N HCl (2 times), $H_2O$, saturated $NaHCO_3$ and brine. The organic phase was dried over $MgSO_4$ and filtered and the filtrate was concentrated under reduced pressure. The residue was filtered through silica gel, eluting with 1:1 hexanes:ethyl acetate increasing to 2:3 hexanes:ethyl acetate to yield urea 67 (110 mg, 80%).

Step Five: To a solution of urea 67 (108 mg, 0.23 mmol) in THF (3 ml) at room temperature, NaOH (1 ml, 2N in $H_2O$, 2 mmol) and methanol (enough to give a clear solution, approximately 2 ml) were added. The resulting mixture was stirred for 15 minutes, then was diluted with water and extracted with ether. The aqueous phase was acidified with HCl (2N) and extracted with ethyl acetate. The ethyl acetate layer was washed with brine, dried over $MgSO_4$ and filtered and the filtrate was concentrated under reduced pressure to give 68 (92 mg, 90%) as a white foam. $^1$H NMR (400 MHz, $CD_3SOCD_3$) δ 1.45 (m, 1H), 1.76 (m, 2H), 2.62 (m, 2H), 3.25 (m overlapping $H_2O$, 2H), 4.01 (m, 1H), 4.59 (d, J=15.0 Hz, 1H), 4.68 (d, J=15.0 Hz, 1H), 4.96 (m, 1H), 5.97 (s, 2H), 6.24 (d, J=6.6 Hz, 1H), 6.71 (d, J=8.4 Hz, 1H), 6.75 (dd, J=8.1, 1.5 Hz, 1H), 6.82 (d, J=8.1 Hz, 1H), 6.85 (d, J=1.5 Hz, 1H), 6.97 (dd, J=5.1, 3.3 Hz, 1H), 7.03 (dd, J=3.3, 1.5 Hz, 1H), 7.42 (dd, J=5.1, 1.5 Hz, 1H), 12.06 (br. s, 1H).

EXAMPLE 17

Synthesis of (3S)-3-(1,3-benzodioxol-5-yl)-3-[({[(3S)-2-oxo-1-(2-thienylmethyl)tetrahydro-1H-pyrrol-3-yl]amino}carbonyl)amino]propanoic acid (74)

Step One: To a solution of N-tert-butoxycarbonyl-L-aspartic acid α-benzylester (2.10 g, 6.5 mmol) in dimethoxyethane (15 ml) cooled to −15° C. (bath temperature) under a dry nitrogen atmosphere, 4-methylmorpholine (0.71 ml, 6.5 mmol) and isobutyl chloroformate (0.84 ml, 6.5 mmol) were added sequentially by syringe. The resulting mixture was stirred for 2 minutes, then was filtered, washing the solid cake with dimethoxyethane (10 ml). The filtrate was recooled to −15° C. (bath temperature) and a solution of sodium borohydride (370 mg, 9.7 mmol) in $H_2O$ (3 ml) was added followed immediately by the addition of $H_2O$ (100 ml). The mixture was extracted with ethyl acetate (3 times) and the organic layers were combined and washed with cold (0° C.) HCl (0.2N), $H_2O$, saturated $NaHCO_3$ and brine. The resulting organic layer was dried over $MgSO_4$ and filtered and the filtrate was concentrated under reduced pressure to give 69 (2.50 g) as a colorless oil. This material contains some of the unreduced mixed-anhydride but was used without purification.

Step Two: To a solution of oxalyl chloride (2.4 ml, 2.0 M in $CH_2Cl_2$, 4.8 mmol) in $CH_2Cl_2$ (30 ml) cooled to −65° C. under a dry nitrogen atmosphere, a solution of methylsulfoxide (0.55 ml, 7.8 mmol) in $CH_2Cl_2$ (8 ml) was added by syringe. The resulting mixture was stirred at −65° C. for 15 minutes, then a solution of alcohol 69 (1.00 g, 3.2 mmol) in $CH_2Cl_2$ (29 ml) was added by cannula along with a $CH_2Cl_2$ (3 ml) rinse. The mixture was stirred at −65° C. for 3 hours, then was allowed to warm to −20° C. (bath temperature). Triethylamine (0.96 ml, 6.9 mmol) was added, followed by H₂O (20 ml). The aqueous layer was extracted with CH₂Cl₂ and the combined organic phases were dried over MgSO₄ and filtered. The filtrate was concentrated under reduced pressure to give aldehyde 70 as a white solid. This material was used immediately without purification.

Step Three: To a solution of the crude aldehyde 70 (3.2 mmol theoretical) and 2-aminomethylthiophene (402 mg, 3.55 mmol) in dichloroethane (13 ml) at room temperature under a dry nitrogen atmosphere, sodium triacetoxyborohydride (959 mg, 4.5 mmol) was added. The resulting mixture was stirred at room temperature overnight, then was diluted with ethyl acetate and washed with saturated NaHCO₃ and brine. The organic phase was dried over MgSO₄ and filtered and the filtrate was concentrated under reduced pressure. The residue was purified by silica gel chromatography, eluting with 1:1 hexanes:ethyl acetate to yield lactam 71 (220 mg, 23% for 3 steps) as a white solid.

Step Four: To a solution of 71 (220 mg, 0.74 mmol) in dioxane (1.5 ml) sealed with a rubber septum at room temperature under a dry nitrogen atmosphere, HCl (1.50 ml, 4.0M in dioxane, 6.0 mmol) was added by syringe. The nitrogen needle was removed and the mixture in the sealed flask was stirred for 5 hours. The mixture was diluted with CH₂Cl₂ and washed with saturated NaHCO₃. The organic phase was dried over MgSO₄ and filtered and the filtrate was concentrated under reduced pressure to give amine 72 (129 mg, 89%) as a light yellow oil. This material was used without purification.

Step Five: To a solution of amine 72 (123 mg, 0.63 mmol) in CH₂Cl₂ (1.5 ml) at room temperature under a dry nitrogen atmosphere, carbonyldiimidazole (112 mg, 0.69 mmol) was added. The resulting mixture was stirred at room temperature for 5 minutes and a solution of amino ester 60 (164 mg, 0.69 mmol) in CH₂Cl₂ (0.8 ml) was added by cannula along with a CH₂Cl₂ (0.2 ml) rinse. The resulting mixture was stirred at room temperature overnight, then was diluted with ethyl acetate and washed with 2N HCl (2 times), H₂O, saturated NaHCO₃ and brine. The organic phase was dried over MgSO₄ and filtered and the filtrate was concentrated under reduced pressure. The residue was filtered through silica gel, eluting with 49:1 chloroform:methanol to yield urea 73 (230 mg, 80%) as a colorless oil which slowly solidified on standing.

Step Six: To a solution of urea 73 (230 mg, 0.50 mmol) in THF (3 ml) at room temperature, NaOH (1 ml, 2N in H₂O, 2 mmol) and methanol (1 ml) were added. The resulting mixture was stirred for 1 hour, then was diluted with water and extracted with ether. The aqueous phase was acidified with HCl (2N) and extracted with ethyl acetate. The ethyl acetate layer was washed with brine, dried over MgSO₄ and filtered and the filtrate was concentrated under reduced pressure to give 74 (181 mg, 84%) as a white foam. ¹H NMR (400 MHz, CD₃SOCD₃) δ 1.64 (m, 1H), 2.30 (m, 1H), 2.64 (m, 2H), 3.20 (m, 2H), 4.17 (dd, J=8.8, 8.4 Hz, 1H), 4.56 (s, 2H), 4.96 (m, 1H), 5.97 (s, 2H), 6.30 (d, J=7.0 Hz, 1H), 6.58 (d, J=8.8 Hz, 1H), 6.77 (m, 1H), 6.80-6.90 (m, 2H), 6.96-7.04 (m, 2H), 7.45 (dd, J=5.1, 0.7 Hz, 1H), 12.10 (br. s, 1H).

EXAMPLE 18

Synthesis of (3S)-3-[({[5-chloro-2-hydroxy-3-(phenylmethyl)phenyl]amino}carbonyl)amino]-3-(4-methylphenyl)propanoic acid Step One: To a mixture of 2-phenylmethyl-3-chlorophenol (5.00 g, 22.9 mmol) in Et₂O (20 mL) and 6N HCl (50 mL), KNO₃ (2.30 g, 22.9 mmol) and NaNO₂ (20 mg, catalytic) were added sequentially. The resulting mixture was stirred for 2 hours, diluted with water and extracted with ethyl acetate. The organic layer was washed with water and brine, dried over MgSO₄ and filtered. The filtrate was concentrated under reduced pressure to give 99 (6.0 g, 100%).

Step Two: To a solution of 99 (6.0 g, 22.8 mmol) in methanol (360 mL), zinc powder (6.0 g, 92 mmol) and saturated aqueous NH₄Cl (6 mL) were added. The resulting heterogeneous mixture was refluxed overnight. After filtration of the hot mixture and concentration of the filtrate under reduced pressure, the residue was dissolved in ethyl acetate and washed with saturated aqueous NaHCO₃ and brine. The organic layer was dried over MgSO₄ and filtered and the filtrate was concentrated under reduced pressure to give compound 100 (2.93 g, 55%).

Step Three: To a solution of 25 (0.20 g, 0.96 mmol) in CH₂Cl₂ at 0° C., DIPEA (0.40 mL, 2.4 mmol) and phosgene (1.93 M in toluene, 0.60 mL, 1.2 mmol) were added sequentially. The resulting mixture was allowed to warm to room temperature, stirred for 20 minutes, then recooled to 0° C. To this mixture, a solution of 100 (0.25 g, 1.1 mmol) in CH₂Cl₂ was added dropwise. The resulting mixture was allowed to warm to room temperature overnight, was diluted with water and was extracted with CH₂Cl₂. The organic layer was washed with water and brine, dried over MgSO₄ and filtered. The filtrate was concentrated under reduced pressure and the residue was purified by silica gel chromatography, eluting with 9:1 and increasing to 5:1 hexanes:ethyl acetate to give 101 (60 mg, 12%). (3S)-3-[({[5-Chloro-2-hydroxy-3-(phenylmethyl)phenyl]amino}carbonyl)amino]-3-(4-methylphenyl)propanoic acid was prepared from 101 by procedures described in Example 1. ¹H NMR (400 MHz, CD₃SO₂CD₃) δ 2.26 (s, 3H), 2.58 (dd, J=15.8, 6.6 Hz, 1H), 2.67 (dd, J=15.8, 8.4 Hz, 1H), 3.49 (s, 2H), 4.88 (m, 1H), 7.00-7.70 (m, 13H), 11.95 (br. s, 1H).

EXAMPLE 19

Synthesis of (3S)-3-(1,3-benzodioxol-5-yl)-3-[({butyl[2,5-dioxo-1-(phenylmethyl)tetrahydro-1H-pyrrol-3-yl]amino}carbonyl)amino]propanoic acid Step One: A solution of N-benzylmaleimide (2.60 g, 13.9 mmol) and n-butylamine (1.00 g, 13.7 mmol) in THF (15 mL) was stirred at room temperature overnight and concentrated under reduced pressure. The residue was purified by silica gel chromatography, eluting with 4:1 increasing to 2:1 hexanes:ethyl acetate to give 102 (3.25 g, 90%).

(3S)-3-(1,3-Benzodioxol-5-yl)-3-[({butyl[2,5-dioxo-1-(phenylmethyl)tetrahydro-1H-pyrrol-3-yl]amino}carbonyl)amino]propanoic acid was prepared from 102 according to procedures described in Example 1. MP: 80-85° C.

EXAMPLE 20

Synthesis of (3S)-3-(1,3-benzodioxol-5-yl)-3-[({[1-(cyclopentylmethyl)-2-oxo-1,2-dihydro-3-pyridinyl]amino}carbonyl)amino]propanoic acid Step One: To a solution of 2-hydroxy-3-nitropyridine (200 mg, 1.4 mmol) in CH₂Cl₂ (14 mL) at 0° C. under a nitrogen atmosphere, cyclopentanemethanol (178 mg, 1.78 mmol) was added followed by triphenylphosphine (551 mg, 2.1 mmol). The solution was stirred at 0° C. for 15 minutes and diethyl azodicarboxylate (366 mg, 2.1 mmol) was added dropwise via syringe. The reaction was allowed to stir at 0° C.

for one hour and then at room temperature overnight. The mixture was quenched with methanol (20 mL) and washed with water (twice). The aqueous layer was extracted with dichloromethane and the combined organic layers were dried over magnesium sulfate and filtered. The filtrate was concentrated and the residue was purified by silica gel chromatography, eluting with 1:1 hexanes:ethyl acetate to afford 103 (299 mg, 96% yield) as a yellow solid.

(3S)-3-(1,3-Benzodioxol-5-yl)-3-[({[1-(cyclopentylmethyl)-2-oxo-1,2-dihydro-3-pyridinyl]amino}carbonyl) amino]propanoic acid was prepared from 103 according to procedures described in Example 1. $^1$H NMR (400 MHz, CDCl$_3$): δ 1.2-1.7 (m, 8H), 2.34 (m, 1H), 2.81 (dd, J=, 1H), 2.95 (dd, J=, 1H), 3.92 (d, J=7.7 Hz, 2H), 5.30 (m, 1H), 5.92 (m, 2H), 6.30 (t, J=7.1 Hz, 1H), 6.68-7.00 (m, 5H), 8.33 (d, J=7.7 Hz, 1H), 8.89 (s, 1H).

EXAMPLE 21

Synthesis of (3S)-3-(1,3-benzodioxol-5-yl)-3-{[({3-[(2-thiophenylmethyl)amino]phenyl}amino)carbonyl]amino}propanoic acid Step One: To a solution of 2-thiophenecarboxaldehyde (0.48 g, 4.0 mmol) in dichloromethane was added 3-nitroaniline (0.51 g, 3.7 mmol). The solution was concentrated to dryness and brought up in 1,2-dichloroethane (16 mL). Molecular sieves (3 Å, 1.1 g) were added followed by NaBH(OAc)$_3$ (1.01 g, 4.8 mmol). The solution was stirred overnight at room temperature, diluted with chloroform and washed with water. The organic layer was dried over MgSO$_4$ and filtered and the filtrate was concentrated under reduced pressure to give 104 (0.72 g, 84%).

Step Two: To a solution of 104 (0.30 g, 1.3 mmol) in CH$_2$Cl$_2$ (5.2 mL) and triethylamine (0.215 mL, 1.5 mmol) at 0° C. was added trifluoroacetic anhydride (0.193 mL, 1.4 mmol). The solution was stirred 15 minutes at 0° C., the ice bath was removed and the mixture was stirred for an additional 15 minutes. The mixture was diluted with CH$_2$Cl$_2$, washed with 2N HCl, water and brine. The organic layer was dried over Na$_2$SO$_4$ and filtered and the filtrate was concentrated under reduced pressure to give 105 (0.38 g, 100%) as a yellow solid.

Step Three: To a solution of 105 (0.38 g, 1.4 mmol) in ethanol (2.6 mL) and acetic acid (2.6 mL) at room temperature, Fe powder (0.36 g, 6.5 mmol) was added and the suspension was stirred vigorously at 40° C. until TLC indicated complete consumption of 105. The mixture was filtered through Celite, washing with chloroform. The filtrate was diltuted with saturated sodium bicarbonate and the chloroform layer was dried over Na$_2$SO$_4$ and filtered. The filtrate was concentrated under reduced pressure and the residue was purified by chromatography on silica gel (gradient elution 6:1 to 4:1 hexanes:ethyl acetate) to give compound 106 (0.102 g, 25%)

(3S)-3-(1,3-Benzodioxol-5-yl)-3-{[({3-[(2-thiophenylmethyl)amino]phenyl}amino)carbonyl]amino}propanoic acid was prepared from 106 according to procedures described in Example 1. $^1$H NMR (400 MHz, CD$_3$SO$_2$CD$_3$) δ 2.50 (m, 2H overlapping DMSO), 4.37 (d, J=5.9 Hz, 2H), 4.94 (m, 1H), 5.94 (m, 2H), 6.06 (t, J=5.8 Hz, 1H), 6.16 (m, 1H), 6.59 (d, J=8.8 Hz, 1H), 6.78 (m, 3H), 6.85 (dd, J=8.8, 7.7 Hz, 1H), 6.90 (s, 1H), 6.94 (dd, J=5.2, 3.7 Hz, 1H), 7.00 (d, J=3.3 Hz, 1H), 7.33 (dd, J=5.1, 1.1 Hz, 1H), 8.5 (s, 1H).

EXAMPLE 22

Synthesis of 3-(1,3-benzodioxol-5-yl)-2,2-difluoro-3-[({[2-oxo-1-(2-thiophenylmethyl)1,2-dihydro-3-pyridinyl]amino}carbonyl)amino]propanoic acid Step One: To a solution of (1S,2R,5S)-(+)-menthyl (R)-p-toluenesulfinate (3.00 g, 10.2 mmol) in THF (25.5 mL) chilled to −78° C., lithium bis(trimethylsilyl)amide (1.0 M in THF, 15.3 mL) was added dropwise over 15 minutes. The resulting mixture was stirred at room temperature for 6 hours, then chilled to 0° C. Piperonal (3.06 g, 20.4 mmol) and CsF (3.10 g, 20.4 mmol) were added rapidly and the suspension stirred 36 hours at room temperature. The reaction was quenched with saturated NH$_4$Cl and extracted with ethyl acetate. The organic layer was washed with brine, dried over Na$_2$SO$_4$ and filtered and the filtrate was concentrated under reduced pressure. The residue was recrystallized from hexanes and dichloromethane to give compound 108 (1.36 g, 46%)

Step Two: Ethyl bromodifluoroacetate (0.78 mL, 6.1 mmol) was added to a suspension of Zn dust (2.00 g, 30.5 mmol) in THF (20.2 mL) and refluxed for 15 minutes. The suspension was chilled to 0° C. and 108 (0.87 g, 3.0 mmol) was added. The suspension was allowed to warm to room temperature and stirred overnight. The mixture was quenched with a minimum amount of saturated NH$_4$Cl and extracted with ethyl acetate. The organic layer was washed with saturated aqueous NaHCO$_3$ and brine, dried over Na$_2$SO$_4$ and filtered. The filtrate was concentrated under reduced pressure and the residue was purified by chromatography on silica gel (gradient elution 6:1 to 4:1 hexanes:ethyl acetate to give 109 (0.607 g, 61% at 80% conversion).

Step Three: To a solution of 109 (0.700 g, 1.70 mmol) in methanol (4.3 mL) at 0° C., trifluoroacetic acid (0.26 mL 3.4 mmol) was added. The solution was stirred at 0° C. for 2 hours, then concentrated to dryness under reduced pressure, while maintaining the external temperature below 30° C. The residue was taken up in diethyl ether and washed with 2N HCl (2 times). The combined aqueous layers were carefully basified with excess saturated NaHCO$_3$ and extracted with diethyl ether. The ether layer was dried over MgSO$_4$ and filtered and the filtrate was concentrated under reduced pressure to give 110 (0.326 g, 80%).

3-(1,3-Benzodioxol-5-yl)-2,2-difluoro-3-[({[2-oxo-1-(2-thiophenylmethyl)-1,2-dihydro-3-pyridinyl] amino}carbonyl)amino]propanoic acid was prepared from 110 according to procedures described in Example 1. MS: Calculated (M−H)$^-$=476.07; Found (M−H)$^-$=476.00.

EXAMPLE 23

Synthesis of (3S)-3-(1,3-benzodioxol-5-yl)-3-({[9-oxo-8-(phenylmethyl)-2,3,4,5,8,9-hexahydro-1H-pyrido[3,4-b]azepin-1-yl]carbonyl}amino)propanoic acid Step One: To a solution of 3 (0.74 g, 3.6 mmol) in THF (14.4 mL) and TMEDA (1.60 mL, 10.8 mmol) at −20° C., n-butyllithium (1.6 M in hexanes, 3.4 mL, 5.4 mmol) and tert-butyllithium (1.7M in pentane, 2.5 mL, 4.3 mmol) were sequentially added dropwise by syringe. The temperature was allowed to warm to between −10 and 0° C. and maintained there for 2 hours. To the resulting mixture, 1,4-dibromobutane (1.75 mL, 14.7 mmol) was added rapidly and the solution was allowed to warm to room temperature and stirred for 4 days. The reaction was quenched with water and extracted with CHCl$_3$ (3 times). The combined extracts were washed with brine, dried over NaSO$_4$ and filtered. The filtrate was concentrated under reduced pressure and the residue was purified by chromatography on silica gel, eluting with 4:1 hexanes:ethyl acetate to give 111 (0.41 g, 44%).

(3S)-3-(1,3-Benzodioxol-5-yl)-3-({[9-oxo-8-(phenylmethyl)-2,3,4,5,8,9-hexahydro-1H-pyrido[3,4-b]azepin-1-yl]carbonyl}amino)propanoic acid was prepared from 111 according to the procedures described in Example 4. MS: Calculated (M–H)$^-$=488.18; Found (M–H)$^-$=488.21.

EXAMPLE 24

Synthesis of (3S)-3-{[({1-[(2-chlorophenyl)methyl]-2-oxo-1,2-dihydro-3-pyridinyl}amino)carbonyl]amino}-3-(4-hydroxyphenyl)propanoic acid Step One: To a solution of 112 (prepared according to procedures described in Example 15, 0.19 g, 0.39 mmol) in CH$_2$Cl$_2$ at 0° C. under nitrogen, BBr$_3$ (1.0 M in CH$_2$Cl$_2$, 1.2 mL, 1.2 mmol) was added by syringe. The mixture was allowed to gradually warm to room temperature and then stirred overnight. The mixture was diluted with water and stirred for 30 minutes and further diluted with saturated aqueous NaHCO$_3$. The organic layer was washed with water and the aqueous layers were combined and acidified with 2N HCl and extracted with ethyl acetate (3 times). The combined ethyl acetate layers were dried over MgSO$_4$ and filtered and the filtrate was concentrated under reduced pressure to yield (3S)-3-{[({1-[(2-chlorophenyl)methyl]-2-oxo-1,2-dihydro-3-pyridinyl}amino)carbonyl]amino}-3-(4-hydroxyphenyl)propanoic acid (113, 120 mg, 70%). $^1$H NMR (400 MHz, CD$_3$SO$_2$CD$_3$) δ 2.95 (d, J=5.2 Hz, 2H), 5.28 (s, 2H), 5.35 (ddd, J=9.2, 4.8, 4.4 Hz, 1H), 6.33 (t, J=7.1 Hz, 1H), 6.60 (d, J=8.8 Hz, 2H), 7.04 (m, 5H), 7.22 (m, 3H), 7.37 (dd, J=7.7, 1.5 Hz, 1H), 8.35 (dd, J=7.6, 1.5 Hz, 1H), 8.80 (s, 1H).

EXAMPLE 25

Synthesis of (3S)-3-[({[1-(2-chlorobenzyl)-4-hydroxy-5-methyl-2-oxo-1,2-dihydropyridin-3-yl]amino}carbonyl)amino]-3-(4-methylphenyl)propanoic acid, 119

Step One: To a suspension of sodium hydride (3.6 g of 60% dispersion in mineral oil, 90 mmol) in THF (300 mL) under a dry nitrogen atmosphere, TMEDA (13.2 mL, 87.5 mmol) was added and the mixture was cooled to −20° C. Methyl propionylacetate (9.60 mL, 76.5 mmol) was added dropwise and the solution was stirred for an additional 15 minutes. A solution of n-butyllithium (90 mL, 1.6M in hexanes, 144 mmol) was added dropwise and the resulting mixture was stirred at −20° C. for 15 minutes. Methyl formate (6.0 mL, 97 mmol) was then added rapidly and the mixture was allowed to stir for 15 minutes before quenching with HCl (2 N, 250 mL). The reaction was diluted with diethyl ether (150 mL) and the organic layer was washed twice more with water. The aqueous layers were combined and sodium chloride was added until saturated. This mixture was extracted with ethyl acetate (3 times). The original ether layer was washed with saturated sodium bicarbonate solution and water. The combined aqueous washes were acidified with excess HCl (2 N), saturated with sodium chloride and extracted with ethyl acetate (3 times). All of the ethyl acetate extracts were combined and dried over MgSO$_4$. The resulting mixture was vacuum filtered through coarse silica gel and the filtrate was concentrated under reduced pressure to give 114 (8.27 g, 68%) as a light yellow oil. This material was used without further purification.

Step Two: To a solution of 114 (3.95 g, 25.0 mmol) in anhydrous methanol (225 mL) at room temperature, a solution of 2-chlorobenzylamine (4.2 g, 30 mmol) in anhydrous methanol (25 mL) was added dropwise from an addition funnel. The solution was heated at 45° C. overnight then refluxed for two hours. The reaction mixture was cooled to room temperature and concentrated to dryness. The residue was brought up in dichloromethane and filtered. The solid was collected and dried under vacuum to give 115 (2.20 g 35%) as a light yellow solid.

Step Three: To a suspension of 115 (840 mg, 3.4 mmol) in glacial acetic acid (11 mL) at room temperature, NaNO$_2$ (46 mg, 0.67 mmol), water (0.92 mL) and HNO3 (70%, 0.85 mL, 13.4 mmol) were added sequentially. The resulting bright yellow solution was stirred at room temperature overnight, then was diluted with CH$_2$Cl$_2$ and water. The aqueous phase was extracted with CH$_2$Cl$_2$, the organic layers were combined and washed with water (3 times) and brine. The organic layer was dried over MgSO$_4$ and filtered and the filtrate was concentrated under reduced pressure to give 116 (910 mg, 92%) as a bright yellow solid. This material was used without purification.

Step Four: To a solution of 116 (910 mg, 3.1 mmol) in DMF (10.3 mL) at room temperature under a dry nitrogen atmosphere, Zn powder (909 mg, 13.9 mmol) and triethylamine hydrochloride (2340 mg, 17.0 mmol) were added. The resulting mixture was heated to 55° C. for 2 hours, then was cooled to room temperature. To the resulting mixture, CDI (1002 mg, 6.18 mmol) was added as a solid. Upon addition, gas evolution occurred. The mixture was then heated to 80° C. for 1 hour, cooled to room temperature, and diluted with CH$_2$Cl$_2$ and HCl (2 N). The aqueous phase was extracted with CH$_2$Cl$_2$, the organic layers were combined and washed with water (4 times) and brine. The organic layer was dried over MgSO$_4$ and filtered and the filtrate was concentrated under reduced pressure to give 117 (920 mg) as a yellow solid. This material contained a small amount of DMF and was used without purification.

Step Five: A suspension of 117 (920 mg crude material, 3.1 mmol theoretical) and 8 (800 mg, 3.86 mmol) in 21 ml THF under a dry nitrogen atmosphere was heated to 55° C. overnight, cooled to room temperature and then diluted with ethyl acetate. The resulting mixture was washed twice with HCl (2N) and brine and the organic layer was dried over MgSO$_4$ and filtered. The filtrate was concentrated under reduced pressure and the resulting residue was purified by silica gel chromatography, eluting with 7:3 hexanes:ethyl acetate to give 118 (1098 mg, 71% for two steps) as a pale yellow foam.

Step Six: To a solution of 118 (1091 mg, 2.19 mmol) in THF (18 mL) a room temperature sodium hydroxide (2 N, 6 ml) and methanol (12 mL) were added. The mixture was stirred for 20 minutes, then was diluted with water and extracted with ethyl ether. The aqueous phase was acidified with HCl (2 N) and extracted with ethyl acetate. The ethyl acetate layer was washed with water and brine, dried over MgSO$_4$ and filtered. The filtrate was concentrated under reduced pressure to give (3S)-3-[({[1-(2-chlorobenzyl)-4-hydroxy-5-methyl-2-oxo-1,2-dihydropyridin 3-yl]amino}carbonyl)amino]-3-(4-methylphenyl)propanoic acid, 119, (1045 mg, quantitative) as a white foam. MS: Calculated (M–H)$^-$=468.13 m/z. Found (M–H)$^-$=467.99 m/z.

EXAMPLE 26

Synthesis of (3S)-3-[({[4-hydroxy-2-oxo-1-(pyridin-2-ylmethyl)-1,2-dihydropyridin-3-yl]amino}carbonyl)amino]-3-(4-methylphenyl)propanoic acid Step One: To a solution of 23 (0.50 g, 3.2 mmol) in DMSO (12.5 ml) at room temperature, powdered KOH (0.89 g, 16 mmol) was added and the mixture was stirred for 1.5 hours. To the resulting mixture, 2-picolylchloride hydrochloride (0.63 g, 3.8 mmol) was added as a solid and the mixture was stirred overnight. At this point, triethylamine hydrochloride (3.52 g, 25.6 mmol) and DMF (5 mL) were added followed by zinc powder (1.04 g, 16.0 mmol). The mixture was heated to 80° C. for 2 hours then cooled to room temperature. To this mixture, CDI (1.00 g, 6.2 mmol) was added and the resulting mixture was heated to 80° C. overnight. The mixture was diluted with ethyl acetate and saturated aqueous NaHCO$_3$. The organic layer was dried over MgSO$_4$ and filtered and the filtrate was concentrated under reduced pressure. The residue was filtered through a pad of silica gel, eluting with 9:1 CHCl$_3$:CH$_3$OH to give 120 (0.14 g, 18%).

(3S)-3-[({[4-Hydroxy-2-oxo-1-(pyridin-2-ylmethyl)-1,2-dihydropyridin-3-yl]amino}carbonyl)amino]-3-(4-methylphenyl)propanoic acid was prepared from 120 according to procedures described in Example 25. MS: Calculated (M−H)$^-$=421.15 m/z. Found (M−H)$^-$=421.06 m/z.

EXAMPLE 27

Synthesis of (3S)-3-{[({1-[2-chloro-5-(methylsulfonyl)benzyl]-4-hydroxy-2-oxo-1,2-dihydropyridin-3-yl}amino)carbonyl]amino}-3-(4-methylphenyl)propanoic acid Step One: To a solution of 121 (prepared from 23 according to procedures described in Example 4, 220 mg, 0.67 mmol) in anhydrous CH$_2$Cl$_2$ (14 mL) cooled to 0° C. under a dry, nitrogen atmosphere, m-CPBA (610 mg, 3.6 mmol) was added. The resulting mixture was allowed to warm to room temperature and stirred for 4 hours. The reaction was diluted with water (50 ml) and the aqueous phase was extracted with CH$_2$Cl$_2$ (2 times). The combined organic layers were dried over MgSO$_4$ and filtered and the filtrate was concentrated under reduced pressure. The residue was purified by silica gel chromatography, eluting with 9:1 CHCl$_3$:MeOH to give 122 (219 mg, 91% yield) as a yellow solid.

(3S)-3-{[({1-[2-Chloro-5-(methylsulfonyl)benzyl]-4-hydroxy-2-oxo-1,2-dihydropyridin-3-yl}amino)carbonyl]amino}-3-(4-methylphenyl)propanoic acid was prepared from 122 according to procedures described in Example 25. MS: Calculated (M−H)$^-$=532.10 m/z. Found (M−H)$^-$=531.94 m/z.

EXAMPLE 28

Synthesis of (3S)-3-[({[1-(2-chloro-6-methoxybenzyl)-4-hydroxy-2-oxo-1,2-dihydropyridin-3-yl]amino}carbonyl)amino]-3-(3-methylphenyl)propanoic acid Step One: To a solution of the 123 (70 mg, 0.13 mmol) in anhydrous CH$_2$Cl$_2$ (3 mL), stirring under a nitrogen atmosphere, ZnBr$_2$ (200 mg, 0.82 mmol) was added. The solution was stirred at 0° C. for one hour. The reaction mixture was allowed to warm to room temperature and was stirred overnight. At this point, water (50 ml) was added and the mixture was stirred for an additional three hours. The layers were separated and the aqueous layer was extracted with CH$_2$Cl$_2$ (2 times). The combined organic layers were dried over MgSO$_4$ and filtered and the filtrate was concentrated under reduced pressure to give (3S)-3-[({[1-(2-chloro-6-methoxybenzyl)-4-hydroxy-2-oxo-1,2-dihydropyridin-3-yl]amino}carbonyl)amino]-3-(3-methylphenyl)propanoic acid, 124 (60 mg, 95% yield). MS: Calculated (M−H)$^-$=484.13 m/z. Found (M−H)$^-$=484.00 m/z.

EXAMPLE 29

Synthesis of (3S)-3-[({[1-(2-chlorobenzyl)-4-hydroxy-2-oxo-5-propyl-1,2-dihydropyridin-3-yl]amino}carbonyl)amino]-3-(4-methylphenyl)propanoic acid Step One: A mixture of malonyl dichloride (25.0 g, 177 mmol) and valeronitrile (25.0 g, 300.7 mmol) under an anhydrous atmosphere was vigorously stirred at room temperature for 24 hours. Diethyl ether (50 mL) was added to the resulting heterogeneous mixture. The precipitate was collected and washed with diethyl ether to give 125.HCl as a white solid (20.2 g, 64%).

Step Two: To a suspension of 125.HCl (6.10 g, 27.2 mmol) in EtOH (100 mL), triethylamine (5.8 g, 57.3 mmol) and palladium on carbon (10% Pd dry weight basis, Degussa type E101 NE/W, ~50% water content, 3.5 g, 1.6 mmol Pd) were added. The atmosphere was replaced with hydrogen (toggle between vacuum and hydrogen from a balloon five times) and the mixture was stirred overnight, then filtered. The filtrate was concentrated under reduced pressure to give 126.2Et$_3$NHCl (11.0 g, 94%). This material was used without further purification.

(3S)-3-[({[1-(2-Chlorobenzyl)-4-hydroxy-2-oxo-5-propyl-1,2-dihydropyridin-3-yl]amino}carbonyl)amino]-3-(4-methylphenyl)propanoic acid was prepared from 126.2Et$_3$NHCl according to procedures described in Example 25. MS: Calculated (M−H)$^-$=496.16 m/z. Found (M−H)$^-$=495.94 m/z.

EXAMPLE 30

Synthesis of (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-methylphenyl)propanoic acid Step One: To a solution of ethyl 2-oxocyclopentanecarboxylate (3.30 g, 21.1 mmol) in toluene (45 ml), 4-chlorobenzylamine (2.56 mL, 21.1 mmol) was added. The resulting mixture was refluxed overnight with azeotropic removal of water via a Dean-Stark trap. The reaction mixture was concentrated under reduced pressure to give 127 (5.90 g, 99%) as a red oil. This material was used without purification.

Step Two: To a solution of 127 (11.0 g, 39.3 mmol) in anhydrous THF (75 mL) cooled to 0° C. under a dry, nitrogen atmosphere, NaH (60% dispersion in mineral oil, 1.73 g, 43.2 mmol) was added. The reaction was stirred for 10 minutes at 0° C., then acetyl chloride (3.9 mL, 55 mmol) was added. The reaction mixture was allowed to gradually warm to room temperature, then was stirred overnight. The resulting mixture was concentrated under reduced pressure and a mixture of ice water (200 mL) and HCl (1 N, 200 mL) was added to the residue. This mixture was extracted with ethyl acetate (300 mL) and the ethyl acetate layer was dried over MgSO$_4$ and filtered. The filtrate was concentrated under reduced pressure to give 128 (13.4 g) as a brown oil. This material contained mineral oil but was used without purification.

Step Three: To a solution of crude 128 (13.4 g, 39.3 mmol theoretical) in anhydrous THF (50 ml) cooled to 0° C. under a dry, nitrogen atmosphere, lithium bis(trimethylsilyl)amide (1.0 M in THF, 125 mL, 125 mmol) was added slowly via syringe. The reaction mixture was allowed to warm to room temperature, then was stirred overnight. The mixture was concentrated under reduced pressure and the residue was triturated with ethyl acetate/hexane and filtered. The solid was washed with HCl (1 N, 250 ml) and water (500 ml) to give 129 (5.48 g, 48% for two steps) as a brown solid.

(3S)-3-[({[1-(2-Chlorobenzyl)-4-hydroxy-2-oxo-2,5,6,7-tetrahydro-1H-cyclopenta[b]pyridin-3-yl]amino}carbonyl) amino]-3-(4-methylphenyl)propanoic acid was synthesized from 129 according to procedures described in Example 25. MS: Calculated $(M+H)^+=496.16$ m/z. Found $(M+H)^+=495.99$ m/z.

EXAMPLE 31

Synthesis of (3S)-3-[({[4-{[(tert-butylamino)carbonyl]amino}-1-(2-chlorobenzyl)-2-oxo-1,2-dihydropyridin-3-yl]amino}carbonyl)amino]-3-(4-methylphenyl)propanoic acid Step One: To a solution of 46 (500 mg, 1.79 mmol) in anhydrous THF (10 mL) cooled to 0° C. under a dry nitrogen atmosphere, NaH (60% dispersion in mineral oil, 210 mg, 5.37 mmol) was added and the resulting mixture was stirred for 20 minutes. To this mixture, tert-butyl isocyanate (0.31 mL, 2.68 mmol) was added and the reaction mixture was allowed to warm to room temperature, then was stirred for 2 days. The reaction mixture was quenched with water and extracted twice with ethyl acetate. The organic layers were combined, dried over $MgSO_4$ and filtered and the filtrate was concentrated under reduced pressure to give 130 (660 mg, 97%) as a brown solid.

(3S)-3-[({[4-{[(tert-butylamino)carbonyl]amino}-1-(2-chlorobenzyl)-2-oxo-1,2-dihydropyridin-3-yl] amino}carbonyl)amino]-3-(4-methylphenyl)propanoic acid was prepared from 130 according to procedures described in Example 3. MS: Calculated $(M-H)^-=552.20$ m/z. Found $(M-H)^-=551.89$ m/z.

Synthetic procedures similar to those described above may be utilized to obtain the compounds of Tables 2, 3, 4 and 5.

EXAMPLE 32

Synthesis of (3S)-3-[({[5-chloro-1-(2-chlorobenzyl)-4-hydroxy-2-oxo-1,2-dihydropyridin-3-yl]amino}carbonyl)amino]-3-(4-methylphenyl)propanoic acid Step One: To a solution of 31 (350 mg, 0.72 mmol) in $CH_2Cl_2$ at room temperature under a dry nitrogen atmosphere, sulfurylchloride (1.0 M in $CH_2Cl_2$, 0.65 mL, 0.65 mmol) was added by syringe. The resulting mixture was stirred at room temperature for 1 hour, then was partitioned between $CH_2Cl_2$ and water. The organic layer was washed with brine and dried over $MgSO_4$ and the filtrate was concentrated under reduced pressure. The residue was purified by silica gel chromatography, eluting with 8:1, then 4:1 and finally 1:1 hexanes:ethyl acetate to give 131 (240 mg, 64%).

(3S)-3-[({[5-Chloro-1-(2-chlorobenzyl)-4-hydroxy-2-oxo-1,2-dihydropyridin-3-yl]amino}carbonyl)amino]-3-(4-methylphenyl)propanoic acid was synthesized from 131 according to procedures described in Example 1. MS: Calculated $(M-H)^-=488.08$; Found $(M-H)^-=487.97$.

EXAMPLE 33

Synthesis of (3S)-3-[({[1-(2-chlorobenzyl)-4-hydroxy-5-methyl-2-oxo-1,2-ddihydropyridin-3-yl]amino}carbonyl)amino]-3-(2',6'-dimethoxy-1,1'-biphenyl-4-yl)propanoic acid Step One: To a solution of (R)-(+)-N-benzyl-α-methylbenzyl amine (5.07 g, 24 mmol) in THF (85 mL) under nitrogen in a flame-dried flask, cooled to −78° C., sec-butyllithium (1.3 M solution in cyclohexane, 18.0 mL, 23.4 mmol) was added dropwise over a 30 minute period. The mixture was stirred an additional 30 minutes at −78° C., then a solution of t-butyl 4-bromocinnamate (5.1 g, 20 mmol) in THF (20 mL) was added dropwise and the mixture was allowed to come to room temperature overnight. The reaction was quenched by addition of saturated ammonium chloride (~50 mL) and the organic layer was washed with saturated sodium chloride, dried over $MgSO_4$ then filtered. The filtrate was concentrated under reduced pressure and the residue was purified by silica gel chromatography eluting with hexanes and increasing to 3:1 hexanes:ethyl acetate to give 132 (4.33 g, 47%) as a pale yellow oil.

Step Two: To a solution of 132 (7.4 g, 15 mmol) and 2,6-dimethoxyphenyl boronic acid (4.9 g, 27 mmol) in DME (100 mL) at room temperature under a dry, nitrogen atmosphere, finely-powdered potassium phosphate (8.0 g, 37.5 mM) and dichlorobis(triphenylphosphine)palladium (0) (0.5 g, 0.75 mmol) were added. The mixture was deoxygenated (toggle between vacuum and nitrogen gas 5 times) and then heated to reflux for 8 hours. The mixture was then cooled and filtered through Celite® 521, and the filtrate was concentrated under reduced pressure. The residue was purified by silica gel chromatography, eluting with hexanes increasing to 3:1 hexanes:ethyl acetate to give 133 (7.8 g, 95% yield).

Step Three: To a solution of 133 (3.39 g, 6.1 mmol) in ethanol (80 mL) in a 250 mL flask, acetic acid (0.5 mL) and palladium on carbon (10% Pd dry weight basis, water content ~50%, Degussa type E101 NE/W, 2.5 g, 1.2 mmol Pd) were added sequentially. The mixture was stirred under a hydrogen atmosphere from a balloon for 36 hours. The reaction mixture was filtered through Celite® 521 and the filtrate was concentrated under reduced pressure. The residue was recrystallized from ethyl acetate to give 134.HOAc (1.0 g, 71%) as a white solid.

(3S)-3-[({[1-(2-chlorobenzyl)-4-hydroxy-5-methyl-2-oxo-1,2-dihydropyridin-3-yl]amino}carbonyl)amino]-3-(2',6'-dimethoxy-1,1'-biphenyl-4-yl)propanoic acid was synthesized from 134.HOAc by procedures described in Example 25. MS: Measured $(M+H)^+=592.04$; Calculated $(M+H)^+=592.19$.

EXAMPLE 34

Synthesis of (3S)-3-[({[2-(2-chloro-6-ethoxybenzyl)-5-hydroxy-6-methyl-3-oxo-2,3-dihydropyridazin-4-yl]amino}carbonyl)amino]-3-(3-ethoxyphenyl)propanoic acid Step One: To a solution of sodium 1-butoxide (65 g, 0.642 mol) in THF (1 L), at room temperature under a dry nitrogen atmosphere, ethanol (250 mL, 5.35 mol) was added over a 10 minute period. To the resulting solution, 2-chloro-6-fluorobenzonitrile (100 g, 0.642 mol) was added in portions. The reaction mixture was stirred at room temperature for 30 minutes and then reduced to a volume of approximately 250 mL under reduced pressure. The resulting mixture was poured into chloroform and water and the layers separated. The organic layer was washed with water (twice) and brine, dried over $MgSO_4$ and filtered. The filtrate was concentrated under reduced pressure to afford a light yellow solid. This material was recrystallized from hexanes to provide the 2-chloro-6-ethoxybenzonitrile, 135, (101 g, 87% yield) as a white crystalline solid.

Step Two: To a solution of 2-chloro-6-ethoxybenzonitrile, 135, (93.2 g, 0.513 mol) in THF (350 mL) at room temperature under a dry nitrogen atmosphere was added borane in THF (1.0 M, 620 mL, 0.62 mol). The resulting mixture was heated to reflux for 3 hours and then cooled to room temperature. Water (250 mL) was added very slowly to the solution allowing for the evolution of hydrogen. Concentrated HCl (50 mL) was then added over several minutes and the solution was heated to 50° C. for 2 hours. The mixture was cooled and partitioned between chloroform and water. The aqueous layer was washed 6 times with chloroform. The combined organic fractions were washed with HCl (1 M) and this organic layer was discarded. Chloroform was added to the combined aqueous layers and solid KOH was added until the aqueous phase was basic (pH>9). The aqueous layer washed with chloroform an additional five times. The organic fractions were combined and washed with water, brine, and dried over $MgSO_4$ and silica gel (2 g). This mixture was filtered and the filtrate was concentrated under reduced pressure to give 2-chloro-6-ethoxybenzylamine, 136, (60.1 g, 64% yield) as a light yellow oil.

Step Three: To a solution of 2-chloro-6-ethoxybenzylamine, 136, (7.30 g, 39.3 mmol) in glacial acetic acid (50 mL) and acetic anhydride (50 mL) at room temperature, sodium nitrite (6.00 g, 85.7 mmol) was added in small portions. The resulting mixture was stirred at room temperature overnight then was poured into ice water and extracted with ethyl acetate. The organic layer was washed with aqueous NaOH (1N, 2×100 mL) and brine (twice). The organic layer was dried over $Na_2SO_4$ and filtered and the filtrate was concentrated under reduced pressure to give 137 (9.00 g, 100%) as a light yellow solid.

Step Four: To a solution of 137 (9.00 g, 39.3 mmol) and tetrabutylammonium bromide (1.0 g, 3.1 mmol) in THF (50 ml) at room temperature, aqueous NaOH (2N, 50 mL, 100 mmol) was slowly added and the mixture was heated to 45° C. overnight. The reaction mixture was cooled to room temperature, then was diluted with water and extracted with ethyl acetate. The organic layer was washed with brine, dried over $Na_2SO_4$ and filtered and the filtrate was concentrated under reduced pressure to give 138 (7.08 g, 96% yield).

Step Five: To a solution of 138 (7.08 g, 37.9 mmol) in $CH_2Cl_2$ (55 mL) at room temperature under a dry nitrogen atmosphere, a solution of $SOCl_2$ (9.0 mL, 120 mmol) in $CH_2Cl_2$ (30 mL) was added dropwise. The resulting mixture was stirred at room temperature overnight, then was poured into ice water. The aqueous layer was extracted with $CH_2Cl_2$ and the combined organic layers were washed with aqueous NaOH (1N, twice), water (3 times) and brine (twice). The organic layer was dried over $Na_2SO_4$ and filtered and the filtrate was concentrated under reduced pressure to give 2-chloro-6-ethoxybenzylchloride, 139, (6.69 g, 86% yield) as a viscous, brown oil.

Step Six: A solution of 2-chloro-6-ethoxybenzychloride, 139, (6.90 g, 33.7 mmol) and hydrazine (21.60 g, 673 mmol) in MeOH (22 mL) was stirred at room temperature for 3 hours. The mixture was then partitioned between $CH_2Cl_2$ and water. The organic layer was dried over $MgSO_4$ and filtered and the filtrate was concentrated under reduced pressure to give 140 (6.18 g, 92%).

Step Seven: To a suspension of ethyl pyruvate (3.85 mL, 33.7 mmol) and $MgSO_4$ in $CHCl_3$ (65 mL), a solution of 140 (6.14 g, 30.6 mmol) in $CHCl_3$ (30 mL) was slowly added. The resulting mixture was stirred at room temperature overnight. The resulting mixture was filtered and the filtrate was concentrated under reduced pressure to give 141 (8.43 g, 92%). This material was used in the next step without purification.

Step Eight: To a solution of 141 (8.43 g, 28.2 mmol) in dry THF (110 mL) cooled to 0° C. under a dry nitrogen atmosphere, sodium hydride (60% dispersion in mineral oil, 1.88 g, 47.1 mmol) was added in one portion. The resulting mixture was stirred at 0° C. for 30 minutes, then methyl malonylchloride (6.63 g, 47.10 mmol) was slowly added. The mixture was allowed to warm to room temperature, stirred overnight, carefully quenched with water then extracted with ethyl acetate (twice). The organic layers were combined, washed with brine, dried over $MgSO_4$ and filtered. The filtrate was concentrated under reduced pressure to give 142 (14.29 g). This material was used in the next step without further purification.

Step Nine: To a solution of crude 142 (14.29 g) in dry DMF (60 mL) cooled to 0° C. under a dry nitrogen atmosphere, sodium hydride (60% dispersion in mineral oil, 2.90 g, 72.2 mmol) was added in one portion. This solution was heated to 60° C. overnight, cooled down in an ice bath, then shaken with hexane. The layers were separated and the DMF layer was poured into ice water. The mixture was acidified (pH 1) by adding HCl (2N). The precipitate was collected by filtration the dissolved in ethyl acetate. The organic solution was dried over $MgSO_4$ and filtered and the filtrate was concentrated to give 143 (8.42 g, 85% yield for two steps).

Step Ten: A solution of 143 (8.42 g, 23.9 mmol) in dioxane (100 mL) and aqueous HCl (60 mL, 5.2 N) was refluxed overnight. The mixture was cooled to room temperature, diluted with water and extracted with ethyl acetate. The organic layer was washed with brine, dried over $MgSO_4$ and filtered. The filtrate was concentrated under reduced pressure and the residue was purified by silica gel chromatography eluting with 1:1 ethyl acetate:hexanes, then ethyl acetate and finally 9:1 ethyl acetate:methanol to give 144 (2.0 g, 28%).

Synthesis of (3S)-3-[({[2-(2-chloro-6-ethoxybenzyl)-5-hydroxy-6-methyl-3-oxo-2,3-dihydropyridazin-4-yl] amino}carbonyl)amino]-3-(3-ethoxyphenyl)propanoic acid was prepared from 144 by procedures provided in Example 25. MS: Measured $(M+H)^+$=545.05; Calculated $(M+H)^+$=545.18.

EXAMPLE 35

Synthesis of (3 S)-3-[({[1-(2-chlorobenzyl)-4-hydroxy-2-oxo-2,5,6,7-tetrahydro-1H-cyclopenta[b] pyridin-3-yl]amino}carbonyl)amino]-3-(1,3-diethyl-2-oxo-2,3-dihydro-1H-benzimidazol-5-yl)propanoic acid Step One: An ice-cold mixture of sodium hydride (8.00 g, 60% dispersion in mineral oil, 200 mmol) and 145 (8.94 g, 66.6 mmol) in DMF (250 mL) under a dry nitrogen atmosphere was allowed to gradually warm to room temperature. To the resulting mixture, iodoethane (16 ml, 200 mmol) was added and the mixture was stirred at room temperature overnight. The reaction mixture was poured into ice and extracted with ethyl acetate. The organic layer was washed with water and brine, dried over Na$_2$SO$_4$ and filtered. The filtrate was concentrated under reduced pressure and the residue was taken up in hexanes and filtered. The resulting brown solid was dried under reduced pressure to give 146 (9.00 g, 71% yield). This material was used without purification.

Step Two: A mixture of DMF (3.6 g, 49 mmol) and POCl$_3$ (9.6 mL, 100 mmol) was stirred at room temperature under a dry nitrogen atmosphere for 1 hour. The flask containing this mixture was then placed in a 45° C. oil bath and 146 (7.6 g, 40 mmol) was added in small portions. The oil bath temperature was raised to 70° C. and the mixture was stirred overnight, then cooled to room temperature. The mixture was diluted with water and extracted with ethyl acetate. The organic layer was washed with water and brine, dried over Na$_2$SO$_4$ and filtered. The filtrate was concentrated under reduced pressure to give a 7:3 mixture of 147:146 (6.69 g). This material was used without purification.

Step Three: To a solution of the 147:146 mixture obtained above (2.2 g) in ethanol (2.2 mL), malonic acid (1.16 g, 11.2 mmol), pyridine (0.44 mL) and piperidine (0.99 mL) were added sequentially. The resulting mixture was heated to reflux for 6 hours, then cooled to room temperature. The mixture was diluted with aqueous NaOH (1N) and extracted with ethyl acetate (4 times). The aqueous phase was acidified to pH 3 with HCl (1N) and the resulting suspension was filtered, washing the solid with water. The white solid was collected and dried under reduced pressure to give 148 (1.69 g, 49% for two steps).

(3S)-3-[({[1-(2-chlorobenzyl)-4-hydroxy-2-oxo-2,5,6,7-tetrahydro-1H-cyclopenta[b]pyridin-3-yl]amino}carbonyl) amino]-3-(1,3-diethyl-2-oxo-2,3-dihydro-1H-benzimidazol-5-yl)propanoic acid was prepared from 148 by procedures described in Examples 33 and 25. MS: Measured (M+H)$^+$=594.05; Calculated (M+H)$^+$=594.21.

EXAMPLE 36

Synthesis of give (3S)-3-[({[1-(2-chloro-6-ethoxy-benzyl)-4-hydroxy-5-methyl-2-oxo-1,2-dihydropyridin-3-yl]amino}carbonyl)amino]-3-(4-methylphenyl) propanoic acid, 153

Step One: To a solution of 114 (20.3 g, 129 mmol) in anhydrous methanol (430 mL) at room temperature under a dry nitrogen atmosphere, 2-chloro-6-ethoxybenzylamine, 136, (31.1 g, 168 mmol) was added. The solution was heated at 45° C. for 1 hour then refluxed overnight. The reaction mixture was cooled to room temperature and concentrated to dryness. The residue was brought up in dichloromethane and filtered. The solid was collected and dried under vacuum to give 149 (14.7 g, 39%).

Step Two: To a suspension of 149 (11.02 g, 37.8 mmol) in glacial acetic acid (126 mL) at room temperature, NaNO$_2$ (522 mg, 7.6 mmol), water (10.5 mL) and HNO3 (70%, 9.6 mL, 151.2 mmol) were added sequentially. The resulting bright yellow solution was stirred at room temperature overnight, then was diluted with CH$_2$Cl$_2$ and water. The aqueous phase was extracted with CH$_2$Cl$_2$, the organic layers were combined and washed with water (3 times) and brine. The organic layer was dried over MgSO$_4$ and filtered and the filtrate was concentrated under reduced pressure. The residue was recrystallized from CH$_2$Cl$_2$/ethyl acetate to give 150 (10.9 g, 85%) as a bright yellow solid.

Step Three: To a solution of 150 (10.9 g, 32.2 mmol) in DMF (107 mL) at room temperature under a dry nitrogen atmosphere, Zn powder (9.48 g, 145 mmol) and triethylamine hydrochloride (24.4 g, 177 mmol) were added. The resulting mixture was heated to 55° C. for 1 h, then was cooled to room temperature. To the resulting mixture, CDI (10.4 g, 64.4 mmol) was added as a solid. Upon addition, gas evolution occurred. The mixture was then heated to 80° C. for 2 hours, cooled to room temperature and poured into HCl (2 N, 1 L). The resulting suspension was stirred for 20 minutes and then was diluted with water (1 L) and filtered. The solid was resuspended in water (1 L) and then filtered. The solid was dried under vacuum to give 151 (10.78 g, 100% yield) as a white powder.

Step Four: A mixture of 151 (10.68 g, 31.9 mmol) and 8 (8.27 g, 39.9 mmol) in DMF (64 mL) under a dry nitrogen atmosphere was heated to 55° C. overnight, cooled to room temperature and then diluted with ethyl acetate. The resulting mixture was washed with HCl (2N), water (4 times) and brine and the organic layer was dried over MgSO$_4$ and filtered. The filtrate was concentrated under reduced pressure and the resulting residue was purified by silica gel chromatography, eluting with 7:3 hexanes:ethyl acetate to give 152 (14.2 g, 82%) as a pale yellow foam.

Step Five: To a solution of 152 (11.60 g, 21.4 mmol) in THF (138 mL) at room temperature, aqueous sodium hydroxide (2 N, 46 mL) and methanol (92 mL) were added. The mixture was stirred for 20 minutes, then was diluted with water and extracted with ethyl ether. The aqueous phase was acidified with HCl (2 N) and extracted with ethyl acetate. The ethyl acetate layer was washed with water and brine, dried over MgSO$_4$ and filtered. The filtrate was concentrated under reduced pressure to give (3S)-3-[({[1-(2-chloro-6-ethoxy-benzyl)-4-hydroxy-5-methyl-2-oxo-1,2-dihydropyridin-3-yl]amino}carbonyl)amino]-3-(4-methylphenyl)propanoic acid, 153, (10.82, 98% yield) as a light tan foam. MS: Calculated (M–H)$^-$=512.16; Measured (M–H)$^-$=512.03.

EXAMPLE 37

Synthesis of (3S)-3-[({[1-(2-chloro-6-ethoxybenzyl)-4-hydroxy-5-methyl-2-oxo-1,2-dihydropyridin-3-yl] amino}carbonyl)amino]-3-(3-ethoxyphenyl)propanoic acid, 156

Step One: A mixture of 151 (8.40 g, 28.8 mmol) and 154 (8.2 g, 35 mmol) in DMF (100 mL) under a dry nitrogen atmosphere was heated to 55° C. overnight, cooled to room temperature and then diluted with ethyl acetate. The resulting mixture was washed with HCl (2N), water (4 times) and brine and the organic layer was dried over MgSO$_4$ and filtered. The filtrate was concentrated under reduced pressure and the resulting residue was purified by silica gel chromatography, eluting with 8:2 increasing to 1:1 hexanes:ethyl acetate to give 155 (11.1 g, 67% yield).

Step Two: To a solution of 155 (9.12 g, 15.9 mmol) in THF (100 mL) at room temperature, aqueous sodium hydroxide (1 N, 88 mL) and methanol (63 mL) were added. The mixture was stirred for 20 minutes, then was diluted with water and extracted with ethyl ether. This ether layer was discarded. The aqueous phase was acidified with HCl (2 N) and extracted with ethyl ether (4 times). The organic layers were washed with water and brine, dried over MgSO$_4$ and filtered. The filtrate was concentrated under reduced pressure to give (3S)-3-[({[1-(2-chloro-6-ethoxybenzyl)-4-hydroxy-5-methyl-2-oxo-1,2-dihydropyridin-3-yl]amino}carbonyl)amino]-3-(3-ethoxyphenyl)propanoic acid, 156, (8.13 g, 93%) as a white foam. MS: Calculated (M+H)$^+$=544.19; Measured (M+H)$^+$=544.04.

EXAMPLE 38

Synthesis of (3S)-3-[({[1-(2-chloro-6-ethoxybenzyl)-4-hydroxy-5-methyl-2-oxo-1,2-dihydropyridin-3-yl]amino}carbonyl)amino]-3-(6-methoxy-2-naphthyl)propanoic acid, 159

Step One: A mixture of 151 (110 mg, 0.29 mmol), 157 (130 mg, 0.34 mmol) and NMM (0.50 mL, 4.5 mmol) in DMF (1.0 mL) under a dry nitrogen atmosphere was heated to 55° C. overnight, cooled to room temperature and then diluted with ethyl acetate. The resulting mixture was washed with HCl (2N), water (4 times) and brine and the organic layer was dried over $MgSO_4$ and filtered. The filtrate was concentrated under reduced pressure and the resulting residue was purified by silica gel chromatography, eluting with 1:1 hexanes:ethyl acetate to give 158 (130 mg, 73% yield).

Step Two: To a solution of 158 (130 mg, 0.21 mmol) in THF (3 mL) at room temperature, aqueous sodium hydroxide (2 N, 1 mL) and methanol (2 mL) were added. The mixture was stirred for 20 minutes, then was diluted with water and extracted with ethyl ether. The aqueous phase was acidified with HCl (2 N) and extracted with ethyl acetate. The ethyl acetate layer was washed with water and brine, dried over $MgSO_4$ and filtered. The filtrate was concentrated under reduced pressure to give (3S)-3-[({[1-(2-chloro-6-ethoxybenzyl)-4-hydroxy-5-methyl-2-oxo-1,2-dihydropyridin-3-yl]amino}carbonyl)amino]-3-(6-methoxy-2-naphthyl)propanoic acid, 159, (90 mg, 74% yield). MS: Measured $(M+H)^+=580.07$; Calculated $(M+H)^+=580.19$.

EXAMPLE 39

Synthesis of (3S)-3-[({[1-(2-chlorobenzyl)4-hydroxy-2-oxo-2,5,6,7-tetrahydro-1H-cyclopenta[b]pyridin-3-yl]amino}carbonyl)amino]-3-(3-isopropoxyphenyl)propanoic acid, 164

Step One: To a suspension of 129 (5.30 g, 19.2 mmol) in glacial acetic acid (64 mL) at room temperature, $NaNO_2$ (266 mg, 3.9 mmol), water (5.3 mL) and $HNO_3$ (70%, 4.9 mL, 77 mmol) were added sequentially. The resulting bright yellow solution was stirred at room temperature overnight, then was poured into water and filtered, washing with water. The yellow solid was dried under reduced pressure to give 160 (5.35 g, 87%).

Step Two: To a solution of 160 (5.35 g, 16.7 mmol) in DMF (56 mL) at room temperature under a dry nitrogen atmosphere, Zn powder (4.88 g, 74.7 mmol) and triethylamine hydrochloride (12.6 g, 91.5 mmol) were added. The resulting mixture was heated to 55° C. for 1 h, then was cooled to room temperature. To the resulting mixture, CDI (5.41 g, 33.4 mmol) was added as a solid. Upon addition, gas evolution occurred. The mixture was then heated to 80° C. for 2 hours, cooled to room temperature and poured into HCl (2 N, 500 mL). The resulting suspension was stirred for 20 minutes and then was diluted with water (500 mL) and filtered. The solid was resuspended in water (500 mL) and then filtered. The solid was dried under vacuum to give 161 (5.0 g, 95% yield) as a white powder.

Step Three: A mixture of 161 (6.14 g, 19.4 mmol) and 162 (5.12 g, 20.3 mmol) in DMF (90 mL) under a dry nitrogen atmosphere was heated to 80° C. overnight, cooled to room temperature and then diluted with ethyl acetate. The resulting mixture was washed with HCl (2 N), water (4 times) and brine and the organic layer was dried over $MgSO_4$ and filtered. The filtrate was concentrated under reduced pressure and the resulting residue was purified by silica gel chromatography, eluting with 7:3 hexanes:ethyl acetate to give 163 (8.90 g, 81%) as a pale yellow foam.

Step Four: To a solution of 163 (8.69 g, 15.3 mmol) in THF (35 mL) at room temperature, aqueous sodium hydroxide (2 N, 30 mL) and methanol (30 mL) were added. The mixture was stirred overnight, then was diluted with water and extracted with ethyl ether. The aqueous phase was acidified with HCl (2 N) and extracted with ethyl acetate. The ethyl acetate layer was washed with water and brine, dried over $MgSO_4$ and filtered. The filtrate was concentrated under reduced pressure to give (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid, 164, (7.50 g, 91% yield). MS: Measured $(M+H)^+=540.09$; Calculated $(M+H)^+=540.19$.

EXAMPLE 40

Synthesis of (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-chloro-3-isopropoxyphenyl)propanoic acid Step One: To a mixture of 162 (200 mg, 0.80 mmol) in glacial acetic acid (1.65 mL) cooled to 0° C. under a dry nitrogen atmosphere, a mixture of $SO_2Cl_2$ (1.2 mL, 15 mmol) in glacial acetic acid (1.0 mL) was added dropwise by syringe. The resulting mixture was stirred at 0° C. for 30 minutes then was warmed to room temperature. After stirring for an additional 4 hours, the mixture was recooled to 0° C. and quenched by careful addition of saturated aqueous $NaHCO_3$. The mixture was extracted with ethyl acetate and the organic layer was washed with saturated aqueous $NaHCO_3$, dried over $MgSO_4$ and filtered. The filtrate was concentrated under reduced pressure and the residue was purified by silica gel chromatography, eluting with 2:1 hexanes:ethyl acetate to give 165 (148 mg, 65%).

(3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-chloro-3-isopropoxyphenyl)propanoic acid was prepared from 165 according to procedures described in Examples 25 and 30. MS: Calculated $(M-H)^-=586.15$; Found $(M-H)^-=585.92$.

EXAMPLE 41

Synthesis of (3S)-3-({[(1-{[2-chloro-6-tetrahydro-1(2H)-pyridinylphenyl]methyl}-4-hydroxy-5-methyl-2-oxo-1,2-dihydro-3-pyridinyl)amino]carbonyl}amino)-3-(4-methylphenyl)propanoic acid Step One: To a suspension of 166 (0.35 g, 1.06 mmol, prepared according to procedures described in Examples 34 and 25) in methanol (7 mL) and water (3.5 mL) cooled to 0° C., glacial acetic acid (189 μL, 3.2 mmol) and sodium nitrite (178 mg, 2.65 mmol) were added sequentially. The mixture was allowed to slowly warm to room temperature overnight and then was diluted with chloroform and water. The pH of the aqueous phase was checked to ensure a pH of 4-5. The organic layer was washed with brine, dried over $MgSO_4$ and filtered and the filtrate was concentrated under reduced pressure to give 167 (0.35 g, 92%) as a yellow solid.

(3S)-3-({[(1-{[2-chloro-6-tetrahydro-1(2H)-pyridinylphenyl]methyl}-4-hydroxy-5-methyl-2-oxo-1,2-dihydro-3-pyridinyl)amino]carbonyl}amino)-3-(4-methylphenyl)propanoic acid was synthesized from 167 according to the procedures described in Example 25. MS:
Calculated (M−H)⁻=551.21; Found (M−H)⁻=551.06.

EXAMPLE 42

Synthesis of (3 S)-3-{[({1-[(2-chlorophenyl)methyl]-4-hydroxy-5-methyl-2-oxo-1,2-dihydro-3-pyridinyl}amino)carbonyl]amino}-3-[3-(difluoromethyl)phenyl]propanoic acid Step One: To a solution of 3-bromobenzaldehyde, 168, (3.00 g, 16.2 mmol) in DMF (69 mL) under a dry nitrogen atmosphere, palladium acetate (73 mg, 0.32 mmol), tri-o-tolylphosphine (197 mg, 0.65 mmol), ethyl acrylate (2.20 mL, 20.3 mmol) and triethylamine (4.50 mL, 32.4 mmol) were added. The system was deoxygenated (toggle between vacuum and nitrogen five times), the mixture was heated to 125° C. for 19 hours and then cooled to room temperature. The reaction was poured into water and extracted with ether. The organic layer was washed with HCl (4N) and brine, dried over $MgSO_4$ and filtered. The filtrate was concentrated under reduced pressure to give 169 (2.74 g, 83%), which was used without further purification.

Step Two: To a flask containing 169 (1.00 g, 4.9 mmol) under a dry nitrogen atmosphere, (dimethylamino)sulfur trifluoride (0.96 mL, 9.8 mmol) was added by syringe.

The mixture was heated to 90° C. behind a blast shield for 25 minutes then was cooled to room temperature. The resulting mixture was diluted with $CH_2Cl_2$ and washed with saturated aqueous $NaHCO_3$ and $H_2O$. The organic layer was dried over $MgSO_4$ and filtered and the filtrate was concentrated under reduced pressure. The residue was purified by silica gel chromatography, eluting with 1:5 ethyl actetate:hexanes to give 170 (0.62 g, 56%).

Step Three: To a solution of (R)-(+)-N-benzyl-α-methylbenzylamine (0.70 g, 3.3 mmol) in THF (6.7 mL) cooled to −78° C. under a dry nitrogen atmosphere, sec-BuLi (4.22 mL, 1.3M in cyclohexane, 5.5 mmol) was added dropwise. The resulting mixture was stirred at −78° C. for 30 minutes and then a solution of 170 (0.62 g, 2.74 mmol) in THF (3.4 mL) was added dropwise by syringe. The mixture was stirred at −78° C. for 5 hours and then quenched with glacial AcOH (2 mL) in THF (5 mL). The reaction mixture was warmed to room temperature, poured into a 1:1 mixture of saturated aqueous $NaHCO_3$:EtOAc. The organic layer was washed with $H_2O$ (2 times) and brine, dried over $MgSO_4$ and filtered. The filtrate was concentrated under reduced pressure and the residue was purified by silica gel chromatography, eluting with 1:5 ethyl actetate:hexanes to give 171 (1.2 g, 100%). This material still contained minor impurities but was used without further purification.

Step Four: To a solution of 171 (0.50 g, 1.14 mmol) in EtOH (10 mL) at room temperature under a dry nitrogen atmosphere, Pd/C (10% Pd dry weight basis, 50% water by weight, Degussa type E101 NE/W, 0.25 g) and glacial AcOH (0.5 mL) were added. The atmosphere was replaced by hydrogen (toggle between vacuum and hydrogen from a balloon five times) and the mixture was heated to 35° C. for 6 hours. The reaction was cooled to room temperature, filtered through a plug of Celite® 521 and the filtrate was concentrated under reduced pressure. The residue was diluted with $CHCl_3$ and washed with saturated aqueous $NaHCO_3$. The aqueous layer was extracted with $CHCl_3$ (2 times) and the combined organic layers were dried over $MgSO_4$ and filtered. The filtrate was concentrated under reduced pressure and the residue was purified by silica gel chromatography, eluting with 1:10 MeOH:$CHCl_3$ to give 172 (180 mg, 67%).

(3S)-3-{[({1-[(2-chlorophenyl)methyl]-4-hydroxy-5-methyl-2-oxo-1,2-dihydro-3-pyridinyl}amino)carbonyl]amino}-3-[3-(difluoromethyl)phenyl]propanoic acid was synthesized from 172 according to procedures described in Example 25. MS: Calculated (M−H)⁻=504.11; Found (M−H)⁻=503.96.

EXAMPLE 43

The procedures described in Examples 3, 4, 8, 25, 26, 27, 29, 30, 34, 36, 39 and 41 were utilized to synthesize several compounds of general Formula VII and general Formula VIII, by varying starting materials. In Table 1 shown below, characterization data is provided for compounds synthesized.

TABLE 1

| Compound | ¹H NMR (400 MHz) |
|---|---|
| 5-(2-chlorobenzyl)-3,5-dihydro[1,3]oxazolo[4,5-c]pyridine-2,4-dione | ($CD_3SO_2CD_3$) δ 5.27(s, 2H), 6.67(d, J=7.4 Hz, 1H), 6.88(dd, J=7.3, 1.4 Hz, 1H), 7.27-7.37(m, 2H), 7.51(dd, J=7.9, 1.5 Hz, 1H), 7.65(d, J=7.4 Hz, 1H), 12.01(br. s, 1H). |
| 5-(2-chlorobenzyl)-6-methyl-3,5-dihydro[1,3]oxazolo[4,5-c]pyridine-2,4-dione | ($CD_3SO_2CD_3$) δ 2.27(s, 3H), 5.36(s, 2H), 6.60(d, J=7.3 Hz, 1H), 6.63(s, 1H), 7.27-7.37(m, 2H), 7.51(d, J=7.7 Hz, 1H), 11.9(br. s, 1H). |
| 5-(2-fluorobenzyl)-3,5-dihydro[1,3]oxazolo[4,5-c]pyridine-2,4-dione | ($CD_3SO_2CD_3$) δ 5.26(s, 2H), 6.65(d, J=7.3 Hz, 1H), 6.88, 7.12-7.26(m, 3H), 7.37(m, 1H), 7.69(d, J=7.3 Hz, 1H), 11.93(br. s, 1H). |
| 5-(2-chloro-6-fluorobenzyl)-3,5-dihydro[1,3]oxazolo[4,5-c]pyridine-2,4-dione | ($CD_3SO_2CD_3$) δ 5.30(s, 2H), 6.56(d, J=7.3 Hz, 1H), 7.25(ddd, J=9.4, 8.9, 1.1 Hz, 1H), 7.37(d, J=8.0 Hz, 1H), 7.43(m, 2H), 11.93(br. s, 1H). |
| 5-benzyl-6-methyl-3,5-dihydro[1,3]oxazolo[4,5-c]pyridine-2,4-dione | ($CD_3SO_2CD_3$) δ 2.30(s, 3H), 5.37(s, 2H), 6.55(s, 1H), 7.10(d, J=7.0 Hz, 2H), 7.24-7.36(m, 3H), 11.88(br. s, 1H). |
| 5-benzyl-3,5-dihydro[1,3]oxazolo[4,5-c]pyridine-2,4-dione | ($CD_3SO_2CD_3$) δ 5.20(s, 2H), 6.60(d, J=7.3 Hz, 1H), 7.28-7.36(m, 5H), 7.72(d, J=7.3 Hz, 1H), 11.97(br. s, 1H). |
| 5-(2,5-dimethylbenzyl)-3,5-dihydro[1,3]oxazolo[4,5-c]pyridine-2,4-dione | ($CDCl_3$) δ 2.27(s, 3H), 2.32(s, 3H), 5.27(s, 2H), 6.42(d, J=7.3 Hz, 1H) 6.90(s, 1H), 7.09(m, 3H), 10.68(br s, 1H). |

TABLE 1-continued

| Compound | $^1$H NMR (400 MHz) |
|---|---|
| 5-(2-methylbenzyl)-3,5-dihydro[1,3]oxazolo[4,5-c]pyridine-2,4-dione | (CDCl$_3$) δ 2.30(s, 3H), 5.28(s, 2H), 6.39(d, J=7.3 Hz, 1H), 7.06(d, J=7.3 Hz, 1H), 7.09(d, J=7.7 Hz, 1H), 7.18-7.28(m, 3H) 10.91(br s, 1H). |
| 5-(2,4-dichlorobenzyl)-3,5-dihydro[1,3]oxazolo[4,5-c]pyridine-2,4-dione | (CDCl$_3$) δ 5.33(s, 2H), 6.47(d, J=7.3 Hz, 1H), 7.29(m, 1H), 7.38(d, J=7.3 Hz, 1H), 7.42-7.48(m, 2H) 10.77(br s, 1H) |
| 5-(2-methoxybenzyl)-3,5-dihydro[1,3]oxazolo[4,5-c]pyridine-2,4-dione | (CDCl$_3$) δ 3.87(s, 1H), 5.24(s, 2H), 6.36(d, J=7.5 Hz, 1H), 6.88(d, J=8.1 Hz, 1H), 6.97(m, 1H), 7.30(m, 1H), 7.45(d, J=7.5 Hz, 1H), 7.55(m, 1H), 10.75(br. s, 1H). |
| 5-(2,5-difluorobenzyl)-3,5-dihydro[1,3]oxazolo[4,5-c]pyridine-2,4-dione | (CDCl$_3$) δ 5.26(s, 2H), 6.46(d, J=7.4 Hz, 1H), 6.96-7.05(m, 2H), 7.30-7.37(m, 1H), 7.39(m, 1H), 10.68(br. s, 1H). |
| 5-[2-chloro-5-(methylthio)benzyl]-3,5-dihydro[1,3]oxazolo[4,5-c]pyridine-2,4-dione | (CD$_3$SO$_2$CD$_3$) δ 2.41(s, 3H), 5.24(s, 2H), 6.65(d, J=7.2 Hz, 1H), 6.83(d, J=2.6 Hz, 1H), 7.25(dd, J=8.0, 2.6 Hz, 2H), 7.45(d, J=8.0 Hz, 1H), 7.62(d, J=7.2 Hz, 1H), 12.01(br. s, 1H). |
| 5-(4-fluorobenzyl)-3,5-dihydro[1,3]oxazolo[4,5-c]pyridine-2,4-dione | (CD$_3$SO$_2$CD$_3$) δ 5.18(s, 2H), 6.61(d, J=7.4 Hz, 1H), 7.14-7.2(m, 2H), 7.35-7.39(m, 2H), 7.74(d, J=7.3 Hz, 1H), 11.96(br. s, 1H). |
| 5-(2-chloro-5-methoxybenzyl)-3,5-dihydro[1,3]oxazolo[4,5-c]pyridine-2,4-dione | (CD$_3$SO$_2$CD$_3$) δ 3.69(s, 3H), 5.22(s, 2H), 6.42(d, J=2.9 Hz, 1H), 6.65(d, J=7.3 Hz, 1H), 6.94(dd, J=8.8, 2.9 Hz, 1H), 7.43(d, J=8.8 Hz, 1H), 7.62(d, J=7.3 Hz, 1H), 12.05(br. s, 1H). |
| 5-[3,5-bis(trifluoromethyl)benzyl]-3,5-dihydro[1,3]oxazolo[4,5-c]pyridine-2,4-dione | (CD$_3$SO$_2$CD$_3$) δ 5.36(s, 2H), 6.69(d, J=7.5 Hz, 1H), 7.91(d, J=7.5 Hz, 1H), 8.08(s, 3H), 12.04(br. S, 1H). |
| 5-(4-tert-butylbenzyl)-3,5-dihydro[1,3]oxazolo[4,5-c]pyridine-2,4-dione | (CD$_3$SO$_2$CD$_3$) δ 1.24(s, 9H), 5.15(s, 2H), 6.61(d, J=7.3 Hz, 1H), 7.23(d, J=8.4 Hz, 2H), 7.35(d, J=8.4 Hz, 2H), 7.74(d, J=7.3 Hz, 1H), 12.02(br. s, 1H). |
| 5-(3-chlorobenzyl)-3,5-dihydro[1,3]oxazolo[4,5-c]pyridine-2,4-dione | (CD$_3$SO$_2$CD$_3$) δ 5.20(s, 2H), 6.63(d, J=7.4 Hz, 1H), 7.25(m, 1H), 7.35-7.39(m, 3H), 7.76(d, J=7.4 Hz, 1H), 11.97(br. s, 1H). |
| 5-(4-chlorobenzyl)-3,5-dihydro[1,3]oxazolo[4,5-c]pyridine-2,4-dione | (CD$_3$SO$_2$CD$_3$) δ 5.19(s, 2H), 6.62(d, J=7.3 Hz, 1H), 7.29-7.33(m, 2H), 7.37-7.42(m, 2H), 7.73(d, J=7.3 Hz, 1H), 11.97(br. s, 1H). |
| 5-[3-(trifluoromethyl)benzyl]-3,5-dihydro[1,3]oxazolo[4,5-c]pyridine-2,4-dione | n.d. |
| 5-(2-bromobenzyl)-3,5-dihydro[1,3]oxazolo[4,5-c]pyridine-2,4-dione | (CD$_3$SO$_2$CD$_3$) δ 5.23(s, 2H), 6.68(d, J=7.4 Hz, 1H), 6.79(m, 1H), 7.26(m, 1H), 7.34(m, 1H), 7.64(d, J=7.4 Hz, 1H), 7.68(m, 1H), 12.02(br. s, 1H). |
| 5-(3,4-dichlorobenzyl)-3,5-dihydro[1,3]oxazolo[4,5-c]pyridine-2,4-dione | (CD$_3$SO$_2$CD$_3$) δ 5.19(s, 2H), 6.64(d, J=7.3 Hz, 1H), 7.29(m, 1H), 7.61(m, 2H), 7.77(d, J=7.3 Hz, 1H), 11.98(br. s, 1H). |
| 5-(4-methylbenzyl)-3,5-dihydro[1,3]oxazolo[4,5-c]pyridine-2,4-dione | (CD$_3$SO$_2$CD$_3$) δ 2.27(s, 3H), 5.14(s, 2H), 6.59(d, J=7.5 Hz, 1H), 7.14(d, J=8.2 Hz, 2H), 7.20(d, J=8.2 Hz, 2H), 7.69(d, J=7.5 Hz, 1H), 11.95(br. s, 1H). |
| 5-(2-chloro-6-methoxybenzyl)-3,5-dihydro[1,3]oxazolo[4,5-c]pyridine-2,4-dione | (CD$_3$SO$_2$CD$_3$) δ 3.80(s, 3H), 5.23(s, 2H), 6.48(d, J=7.4 Hz, 1H), 7.05-7.15(m, 3H), 7.42(m, 1H), 11.95(br. s, 1H). |
| 5-[4-(trifluoromethyl)benzyl]-3,5-dihydro[1,3]oxazolo[4,5-c]pyridine-2,4-dione | (CD$_3$SO$_2$CD$_3$) δ 5.30(s, 2H), 6.65(d, J=7.3 Hz, 1H), 7.48(d, J=8.0 Hz, 2H), 7.71(d, J=8.0 Hz, 2H), 7.76(d, J=7.3 Hz, 1H), 11.96(br. s, 1H). |
| 5-(3-methylbenzyl)-3,5-dihydro[1,3]oxazolo[4,5-c]pyridine-2,4-dione | (CD$_3$SO$_2$CD$_3$) δ 2.27(s, 3H), 5.15(s, 2H), 6.62(d, J=7.3 Hz, 1H), 7.10(m, 4H), 7.72(d, J=7.3 Hz, 1H), 12.53(br. s, 1H). |
| 5-(pyridin-2-ylmethyl)-3,5-dihydro[1,3]oxazolo[4,5-c]pyridine-2,4-dione | (CD$_3$SO$_2$CD$_3$) δ 5.29(s, 2H), 6.62(d, J=7.3 Hz, 1H), 7.22-7.33(m, 2H), 7.71(d, J=7.3 Hz, 1H), 7.79(m, 1H), 8.50(m, 1H), 11.96(br. s, 1H). |
| 5-(2-chlorobenzyl)-7-methyl-3,5-dihydro[1,3]oxazolo[4,5-c]pyridine-2,4-dione | (CD$_3$SO$_2$CD$_3$) δ 2.10(s, 3H), 5.23(s, 2H), 6.86(dd, J=7.7, 1.5 Hz, 1H), 7.31(m, 2H), 7.50(m, 2H), 12.01(br s, 1H) |
| 5-(2,4-difluorobenzyl)-3,5-dihydro[1,3]oxazolo[4,5-c]pyridine-2,4-dione | (CD$_3$SO$_2$CD$_3$) δ 5.21(s, 2H), 6.63(d, J=7.3 Hz, 1H), 7.02-7.07(m, 1H), 7.20-7.29(m, 2H), 7.65(d, J=7.3 Hz, 1H), 11.97(br. s, 1H). |

TABLE 1-continued

| Compound | $^1$H NMR (400 MHz) |
|---|---|
| 5-(2,6-difluorobenzyl)-3,5-dihydro[1,3]oxazolo[4,5-c]pyridine-2,4-dione | (CD$_3$SO$_2$CD$_3$) δ 5.25(s, 2H), 6.58(d, J=7.3 Hz, 1H), 7.02-7.12(m, 2H) 7.38-7.55(m, 1H), 7.63(d, J=7.3 Hz, 1H), 11.91(br. s, 1H). |
| 5-[3-(trifluoromethoxy)benzyl]-3,5-dihydro[1,3]oxazolo[4,5-c]pyridine-2,4-dione | (CD$_3$SO$_2$CD$_3$) δ 5.24(s, 2H), 6.64(d, J=7.3 Hz, 1H), 7.22-7.35(m, 3H), 7.46(t, J=7.7 Hz, 1H), 7.78(d, J=7.3 Hz, 1H), 11.99(br. s, 1H). |
| 5-[4-(trifluoromethoxy)benzyl]-3,5-dihydro[1,3]oxazolo[4,5-c]pyridine-2,4-dione | (CD$_3$SO$_2$CD$_3$) δ 5.23(s, 2H), 6.63(d, J=7.3 Hz, 1H), 7.29-7.45(m, 4H), 7.76(d, J=7.3 Hz, 1H), 11.98(br. s, 1H). |
| 5-[2-(trifluoromethyl)benzyl]-3,5-dihydro[1,3]oxazolo[4,5-c]pyridine-2,4-dione | (CD$_3$SO$_2$CD$_3$) δ 5.40(s, 2H), 6.73(d, J=7.3 Hz, 1H), 6.81(d, J=7.5 Hz, 1H), 7.51(t, J=7.5 Hz, 1H), 7.61(t, J=7.5 Hz, 1H), 7.70(d, J=7.3 Hz, 1H), 7.80(d, J=7.5 Hz, 1H), 12.04(br. s, 1H). |
| 5-(3-methoxybenzyl)-3,5-dihydro[1,3]oxazolo[4,5-c]pyridine-2,4-dione | n.d. |
| 5-(2,3-dichlorobenzyl)-3,5-dihydro[1,3]oxazolo[4,5-c]pyridine-2,4-dione | n.d. |
| 5-(3,5-dimethylbenzyl)-3,5-dihydro[1,3]oxazolo[4,5-c]pyridine-2,4-dione | (CD$_3$SO$_2$CD$_3$) δ 2.23(s, 6H), 5.11(s, 2H), 6.61(d, J=7.3 Hz, 1H), 6.91(m, 3H), 7.69(d, J=7.3 Hz, 1H), 12.00(br. s, 1H). |
| 5-(2-chlorobenzyl)-7-pentyl-3,5-dihydro[1,3]oxazolo[4,5-c]pyridine-2,4-dione | (CD$_3$SO$_2$CD$_3$) δ 0.86(t, J=6.2 Hz, 3H), 1.27(m, 6H), 1.65(t, J=6.7 Hz, 2H), 5.24(s, 2H), 6.83(d, J=6.6 Hz, 1H), 7.24-7.34(m, 2H), 7.48(s, 1H), 7.50(d, J=7.7 Hz, 1H), 12.00(br. s, 1H). |
| 5-(2,4-dichlorobenzyl)-7-methyl-3,5-dihydro[1,3]oxazolo[4,5-c]pyridine-2,4-dione | (CD$_3$SO$_2$CD$_3$) δ 2.10(s, 3H), 5.19(s, 2H), 6.87(d, J=8.4 Hz, 1H), 7.38(dd, J=8.4, 2.2 Hz, 1H), 7.50(s, 1H), 7.69(d, J=2.2 Hz, 1H), 12.02(br. s, 1H). |
| 5-(2-chlorobenzyl)-7-ethyl-3,5-dihydro[1,3]oxazolo[4,5-c]pyridine-2,4-dione | (CD$_3$SO$_2$CD$_3$) δ 1.17(t, J=7.5 Hz, 3H), 2.50(m, 2H overlapping DMSO), 5.25(s, 2H), 6.84(m, 1H), 7.30(m, 2H), 7.49(m, 2H), 12.02(br. s, 1H). |
| 7-butyl-5-(2-chlorobenzyl)-3,5-dihydro[1,3]oxazolo[4,5-c]pyridine-2,4-dione | (CD$_3$SO$_2$CD$_3$) δ 0.87(t, J=7.3 Hz, 3H), 1.28(m, 4H), 1.54(t, J=7.1 Hz, 2H), 5.24(s, 2H), 6.83(d, J=6.8 Hz, 1H), 7.24-7.34(m, 2H), 7.48-7.56(m, 2H), 12.00(br. s, 1H). |
| 5-[2-chloro-5-(trifluoromethyl)benzyl]-3,5-dihydro[1,3]oxazolo[4,5-c]pyridine-2,4-dione | (CD$_3$SO$_2$CD$_3$) δ 5.33(s, 2H), 6.68(d, J=7.3 Hz, 1H), 7.35(s, 1H), 7.69-7.79(m, 3H), 11.96(br. s, 1H). |
| 5-(2,6-dichlorobenzyl)-3,5-dihydro[1,3]oxazolo[4,5-c]pyridine-2,4-dione | (CD$_3$SO$_2$CD$_3$) δ 5.38(s, 2H), 6.53(d, J=7.4 Hz, 1H), 7.07(d, J=7.7 Hz, 1H), 7.45-7.50(m, 1H), 7.52-7.59(m, 2H), 11.99(br. s, 1H). |
| 5-(2-chloro-5-fluorobenzyl)-3,5-dihydro[1,3]oxazolo[4,5-c]pyridine-2,4-dione | (CD$_3$SO$_2$CD$_3$) δ 5.27(s, 2H), 6.67(d, J=7.3 Hz, 1H), 6.72(dd, J=7.3, 3.2 Hz, 1H), 7.21-7.23(m, 1H), 7.55-7.59(m, 1H), 7.65(d, J=7.3 Hz, 1H), 12.00(br. s, 1H). |
| 5-(2-chloro-6-methylbenzyl)-7-methyl-3,5-dihydro[1,3]oxazolo[4,5-c]pyridine-2,4-dione | (CDCl$_3$) δ 2.07(s, 3H), 2.29(s, 3H), 5.48(s, 2H), 6.63(s, 1H), 7.16(d, J=7.7 Hz, 1H), 7.25(t, J=7.7 Hz, 1H), 7.34(d, J=7.7 Hz, 1H), 11.33(br. S, 1H). |
| 5-(4-chlorobenzyl)-7-methyl-3,5-dihydro[1,3]oxazolo[4,5-c]pyridine-2,4-dione | (CD$_3$SO$_2$CD$_3$) δ 2.08(s, 3H), 5.14(s, 2H), 7.31(d, J=8.4 Hz, 2H), 7.41(d, J=8.4 Hz, 2H), 7.58(s, 1H), 12.03(br. s, 1H). |
| 5-(2-chlorobenzyl)-5,6,7,8-tetrahydro-2H-cyclopenta[b][1,3]oxazolo[5,4-d]pyridine-2,4(3H)-dione | (CD$_3$SO$_2$CD$_3$) δ 2.04(m, 2H), 2.80(m, 4H), 5.28(s, 2H), 6.68(d, J=7.3 Hz, 1H), 7.18-7.34(m, 2H), 7.51(d, J=7.7 Hz, 1H), 11.92(br. s, 1H). |
| 7-methyl-5-[4-(methylsulfonyl)benzyl]-3,5-dihydro[1,3]oxazolo[4,5-c]pyridine-2,4-dione | (CD$_3$SO$_2$CD$_3$) δ 2.11(s, 3H), 2.58(s, 3H), 5.28(s, 2H), 7.58(d, J=7.3 Hz, 2H), 7.64(s, 1H), 7.91(d, J=7.3 Hz, 2H), 12.06(br. s, 1H). |
| 5-(4-methoxybenzyl)-3,5-dihydro[1,3]oxazolo[4,5-c]pyridine-2,4-dione | (CD$_3$SO$_2$CD$_3$) δ 3.73(s, 3H), 5.10(s, 2H), 6.56(br. d, J=5.9 Hz, 1H), 6.89(d, J=8.8 Hz, 2H), 7.27(d, J=8.8 Hz, 2H), 7.67(br. m, 1H), 12.06(br. s, 1H). |

TABLE 1-continued

| Compound | $^1$H NMR (400 MHz) |
|---|---|
| 5-(2-chlorobenzyl)-7-propyl-3,5-dihydro[1,3]oxazolo[4,5-c]pyridine-2,4-dione | (CD$_3$SO$_2$CD$_3$) δ 0.88(t, J=7.4 Hz, 3H), 1.57(m, 2H), 2.46(m, 2H), 5.24(s, 2H), 6.84(d, J=6.2 Hz, 1H), 7.26-7.38(m, 2H), 7.48(s, 1H), 7.50(d, J=7.7 Hz, 1H), 12.00(br. s, 1H). |
| 4-[(2,4-dioxo-2,3-dihydro[1,3]oxazolo[4,5-c]pyridin-5(4H)-yl)methyl]-N,N-dimethylbenzenesulfonamide | (CD$_3$SO$_2$CD$_3$) δ 2.55(s, 6H), 5.31(s, 2H), 6.67(d, J=7.3 Hz, 1H), 7.43-7.51(m, 2H), 7.66-7.74(m, 2H), 7.77(d, J=7.3 Hz, 1H), 12.00(br. s, 1H). |
| 5-(mesitylmethyl)-3,5-dihydro[1,3]oxazolo[4,5-c]pyridine-2,4-dione | (CDCl$_3$) δ 2.19(s, 6H), 2.30(s, 3H), 5.25(s, 2H), 6.31(d, J=7.3 Hz, 1H), 6.73(d, J=7.3 Hz, 1H), 6.94(s, 2H), 11.01(br. s, 1H). |
| 5-(2-chlorobenzyl)-3,5,6,7,8,9-hexahydro[1,3]oxazolo[4,5-c]quinoline-2,4-dione | (CD$_3$SO$_2$CD$_3$) δ 1.64(m, 4H), 2.50(m, 4H), 5.34(s, 2H), 6.59(d, J=8.1 Hz, 1H), 7.25-7.34(m, 2H), 7.51(d, J=7.7 Hz, 1H), 11.92(br. s, 1H). |
| 5-(2-chlorobenzyl)-7-ethyl-6-methyl-3,5-dihydro[1,3]oxazolo[4,5-c]pyridine-2,4-dione | (CD$_3$SO$_2$CD$_3$) δ 1.10(t, J=7.4 Hz, 3H), 2.22(s, 3H), 2.56(m, 2H), 5.40(s, 2H), 6.58(d, J=7.0 Hz, 1H), 7.23-7.34(m, 2H), 7.52(d, J=8.1 Hz, 1H), 11.92(br. s, 1H). |
| 5-[2-(methylthio)benzyl]-3,5-dihydro[1,3]oxazolo[4,5-c]pyridine-2,4-dione | (CD$_3$SO$_2$CD$_3$) δ 2.52(s, 3H), 5.19(s, 2H), 6.63(d, J=7.3 Hz, 1H), 6.76(d, J=7.7 Hz, 1H), 7.09-7.17(m, 1H), 7.29-7.37(m, 2H), 7.55(d, J=7.3 Hz, 1H), 11.99(s, 1H). |
| 2-[(2,4-dioxo-2,3-dihydro[1,3]oxazolo[4,5-c]pyridin-5(4H)-yl)methyl]-N,N-dimethylbenzenesulfonamide | (CD$_3$SO$_2$CD$_3$) δ 2.81(s, 6H), 5.54(s, 2H), 6.71(d, J=7.3 Hz, 1H), 6.81(d, J=7.3 Hz, 1H), 7.49-7.61(m, 2H), 7.69(d, J=7.3 Hz, 1H), 7.85(d, J=7.3 Hz, 1H), 12.05(br. s, 1H). |
| 5-(2,6-dimethoxybenzyl)-3,5-dihydro[1,3]oxazolo[4,5-c]pyridine-2,4-dione | (CD$_3$SO$_2$CD$_3$) δ 3.76(s, 6H), 5.07(s, 2H), 6.43(d, J=7.7 Hz, 1H), 6.73(d, J=8.4 Hz, 2H), 7.00(d, J=7.7 Hz, 1H), 7.37(t, J=8.4 Hz, 1H), 11.92(br. s, 1H). |
| 5-[2-(trifluoromethoxy)benzyl]-3,5-dihydro[1,3]oxazolo[4,5-c]pyridine-2,4-dione | (CD$_3$SO$_2$CD$_3$) δ 5.27(s, 2H), 6.65(d, J=7.3 Hz, 1H), 7.08(dd, J=7.3, 1.4 Hz, 1H), 7.30-7.49(m, 3H), 7.63(d, J=7.3 Hz, 1H), 11.99(br. s, 1H). |
| 5-(2-chlorobenzyl)-6,7-dimethyl-3,5-dihydro[1,3]oxazolo[4,5-c]pyridine-2,4-dione | (CD$_3$SO$_2$CD$_3$) δ 2.12(s, 3H), 2.19(s, 3H), 5.40(s, 2H), 6.59(d, J=6.6 Hz, 1H), 7.25-7.34(m, 2H), 7.52(d, J=7.7 Hz, 1H), 11.91(br. s, 1H). |
| 5-[2-chloro-5-(methylsulfonyl)benzyl]-3,5-dihydro[1,3]oxazolo[4,5-c]pyridine-2,4-dione | (CD$_3$SO$_2$CD$_3$) δ 3.20(s, 3H), 5.35(s, 2H), 6.70(d, J=7.3 Hz, 1H), 7.55(m, 1H), 7.69(m, 1H), 7 90(m, 2H), 12.04(br. s, 1H). |
| 5-(4-chloro-2-methoxybenzyl)-3,5-dihydro[1,3]oxazolo[4,5-c]pyridine-2,4-dione | (CD$_3$SO$_2$CD$_3$) δ 3.86(s, 3H), 5.09(s, 2H), 6.60(d, J=7.3 Hz, 1H), 6.90-6.98(m, 2H), 7.12(d, J=2.2 Hz, 1H), 7.59(d, J=7.3 Hz, 1H), 11.95(br. s, 1H). |
| 5-(2-chlorobenzyl)-5,6,7,8,9,10-hexahydro-2H-cyclohepta[b][1,3]oxazolo[5,4-d]pyridine-2,4(3H)-dione | (CD$_3$SO$_2$CD$_3$) δ 1.34(m, 2H), 1.56(m, 2H), 1.69(m, 2H), 2.70(m, 4H), 5.45(s, 2H), 6.69(d, J=6.6 Hz, 1H), 7.24-7.35(m, 2H), 7.52(d, J=7.7 Hz, 1H), 11.91(br. s, 1H). |
| 5-[2-(difluoromethoxy)benzyl]-3,5-dihydro[1,3]oxazolo[4,5-c]pyridine-2,4-dione | (CD$_3$SO$_2$CD$_3$) δ 5.21(s, 2H), 6.64(d, J=7.3 Hz, 1H), 7.02(d, J=7.3 Hz, 1H), 7.20-7.25(m, 2H), 7.27(t, J=74.0 Hz, 1H), 7.62(d, J=7.3 Hz, 1H), 12.00(br. s, 1H). |
| 7-methyl-5-[(1R)-1-phenylethyl]-3,5-dihydro[1,3]oxazolo[4,5-c]pyridine-2,4-dione | (CD$_3$SO$_2$CD$_3$) δ 1.72(d, J=7.3 Hz, 3H), 2.07(s, 3H), 6.27(q, J=7.3 Hz, 1H), 7.27-7.40(m, 6H), 11.95(br. s, 1H). |
| 5-(4-chlorobenzyl)-7-propyl-3,5-dihydro[1,3]oxazolo[4,5-c]pyridine-2,4-dione | (CD$_3$SO$_2$CD$_3$) δ 0.89(t, J=7.3 Hz, 3H), 1.54(m, 2H), 2.44(t, J=7.7 Hz, 2H), 5.15(s, 2H), 7.30(d, J=8.4 Hz, 2H), 7.39(d, J=8.4 Hz, 2H), 7.57(s, 1H), 11.97(br. s, 1H). |
| 5-[2-(methylsulfonyl)benzyl]-3,5-dihydro[1,3]oxazolo[4,5-c]pyridine-2,4-dione | (CD$_3$SO$_2$CD$_3$) δ 3.43(s, 3H), 5.60(s, 2H), 6.75(d, J=7.3 Hz, 1H), 7.49-7.61(m, 2H), 7.65-7.70(m, 2H) 7.89-7.91(m, 1H), 12.02(br. s, 1H). |
| 5-(2,6-dimethylbenzyl)-3,5-dihydro[1,3]oxazolo[4,5-c]pyridine-2,4-dione | (CD$_3$SO$_2$CD$_3$) δ 2.21(s, 6H), 5.16(s, 2H), 6.47(d, J=7.3 Hz, 1H), 6.80(d, J=7.3 Hz, 1H), 7.09-7.22(m, 3H), 12.00(br. s, 1H). |
| 3-chloro-2-[(2,4-dioxo-2,3-dihydro[1,3]oxazolo[4,5-c]pyridin-5(4H)-yl)methyl]benzonitrile | (CD$_3$SO$_2$CD$_3$) δ 5.38(s, 2H), 6.61(d, 7.4 Hz, 1H), 7.55(t, J=8.0 Hz, 1H), 7.62(d, J=7.4 Hz, 1H), 7.82(d, J=8.0 Hz, 1H), 7.87(d, J=8.0 Hz, 1H), 11.96(br. s, 1H). |

TABLE 1-continued

| Compound | ¹H NMR (400 MHz) |
|---|---|
| 5-(2-chloro-6-methylbenzyl)-6,7-dimethyl-3,5-dihydro[1,3]oxazolo[4,5-c]pyridine-2,4-dione | (CD$_3$SO$_2$CD$_3$) δ 2.06(s, 3H), 2.09(s, 3H), 2.10(s, 3H), 5.58(s, 2H), 7.13(d, J=7.7 Hz, 1H), 7.20(t, J=7.7 Hz, 2H), 7.27(d, J=7.7 Hz, 1H), 11.84(br. s, 1H). |
| 2-[(2,4-dioxo-2,3-dihydro[1,3]oxazolo[4,5-c]pyridin-5(4H)-yl)methyl]benzonitrile | (CD$_3$SO$_2$CD$_3$) δ 5.40(s, 2H), 6.70(d, J=7.4 Hz, 1H), 7.11(d, J=7.7 Hz, 1H), 7.50(t, J=7.7 Hz, 1H), 7.66(td, J=7.7, 1.1 Hz, 1H), 7.74(d, J=7.4 Hz, 1H), 7.88(dd, J=7.7, 1.1 Hz, 1H), 12.01(br. s, 1H). |
| 5-(2-chloro-6-methoxybenzyl)-7-methyl-3,5-dihydro[1,3]oxazolo[4,5-c]pyridine-2,4-dione | (CD$_3$SO$_2$CD$_3$) δ 2.01(s, 3H), 3.81(s, 3H), 5.21(s, 2H), 6.86(s, 1H), 7.11(m, 2H), 7.41(t, J=8.2 Hz, 1H), 11.96(br. s, 1H). |
| 5-[3-(methylthio)benzyl]-3,5-dihydro[1,3]oxazolo[4,5-c]pyridine-2,4-dione | (CD$_3$SO$_2$CD$_3$) δ 2.45(s, 3H), 5.16(s, 2H), 6.61(d, J=7.3 Hz, 1H), 7.04(d, J=7.3 Hz, 1H), 7.16-7.34(m, 3H), 7.73(d, J=7.3 Hz, 1H), 11.97(br. s, 1H). |
| 5-(2-chlorobenzyl)-7-cyclopropyl-3,5-dihydro[1,3]oxazolo[4,5-c]pyridine-2,4-dione | (CD$_3$SO$_2$CD$_3$) δ 0.70(m, 2H), 0.87(m, 2H), 1.79(m, 1H), 5.22(s, 2H), 6.79(d, J=7.3 Hz, 1H), 7.31(m, 1H), 7.45(s, 1H), 7.50(d, J=7.7 Hz, 1H), 12.01(br. s, 1H). |
| 5-(3-chlorobenzyl)-7-methyl-3,5-dihydro[1,3]oxazolo[4,5-c]pyridine-2,4-dione | (CD$_3$SO$_2$CD$_3$) δ 2.09(d, J=1.1 Hz, 3H), 5.15(s, 2H), 7.26(m, 1H), 7.33-7.41(m, 3H), 7.59(q, J=1.1 Hz, 1H), 11.97(br. s, 1H). |
| 5-(2,6-dichlorobenzyl)-7-methyl-3,5-dihydro[1,3]oxazolo[4,5-c]pyridine-2,4-dione | (CD$_3$SO$_2$CD$_3$) δ 2.03(d, J=1.1 Hz, 3H), 5.36(s, 2H), 6.87(q, J=1.1 Hz, 1H), 7.46(dd, J=8.8, 7.4 Hz, 1H), 7.56(d, J=7.4 Hz, 1H), 7.57(d, J=8.8 Hz, 1H), 11.99(br. s, 1H). |
| 7-methyl-5-(4-methylbenzyl)-3,5-dihydro[1,3]oxazolo[4,5-c]pyridine-2,4-dione | (CD$_3$SO$_2$CD$_3$) δ 2.07(s, 3H), 2.27(s, 3H), 5.10(s, 2H), 7.08-7.23(m, 4H), 7.52(s, 1H), 11.95(br. s, 1H). |
| 5-(3,5-dimethoxybenzyl)-7-methyl-3,5-dihydro[1,3]oxazolo[4,5-c]pyridine-2,4-dione | (CD$_3$SO$_2$CD$_3$) δ 2.09(s, 3H), 3.71(s, 6H), 5.06(s, 2H), 6.42(t, J=2.2 Hz, 1H), 6.46(d, J=2.2 Hz, 2H), 7.51(s, 1H), 11.96(br. s, 1H). |
| 5-(2,6-difluorobenzyl)-7-methyl-3,5-dihydro[1,3]oxazolo[4,5-c]pyridine-2,4-dione | (CD$_3$SO$_2$CD$_3$) δ 2.09(d, J=1.1 Hz, 3H), 5.21(s, 2H), 7.04-7.13(m, 2H), 7.38-7.47(m, 2H), 11.91(br. s, 1H). |
| 5-[3-(methylsulfonyl)benzyl]-3,5-dihydro[1,3]oxazolo[4,5-c]pyridine-2,4-dione | (CD$_3$SO$_2$CD$_3$) δ 3.20(s, 3H), 5.31(s, 2H), 6.66(d, J=7.3 Hz, 1H), 7.5-7.7(m, 2H), 7.81(d, J=7.3 Hz, 1H), 7.83-7.96(m, 2H), 11.99(br. s, 1H). |
| 5-(2-chloro-6-ethoxybenzyl)-3,5-dihydro[1,3]oxazolo[4,5-c]pyridine-2,4-dione | (CD$_3$SO$_2$CD$_3$) δ 1.25(t, J=7.0 Hz, 3H), 4.05(q, J=7.0 Hz, 2H), 5.25(s, 2H), 6.49(d, J=7.3 Hz, 1H), 7.06(d, J=8.4 Hz, 1H), 7.10(d, J=8.1 Hz, 1H), 7.12(d, J=7.3 Hz, 1H), 7.37(dd, J=8.4, 8.1 Hz, 1H), 11.95(br. s, 1H). |
| 5-(2-chloro-6-ethoxybenzyl)-7-methyl-3,5-dihydro[1,3]oxazolo[4,5-c]pyridine-2,4-dione | (CD$_3$SO$_2$CD$_3$) δ 1.25(t, J=7.0 Hz, 3H), 2.02(s, 3H), 4.04(q, J=7.0 Hz, 2H), 5.23(s, 2H), 6.97(s, 1H), 7.04(d, J=8.4 Hz, 1H), 7.09(d, J=8.0 Hz, 1H), 7.36(dd, J=8.4, 8.0 Hz, 1H), 11.93(br. s, 1H). |
| 5-(2-fluoro-6-methoxybenzyl)-7-methyl-3,5-dihydro[1,3]oxazolo[4,5-c]pyridine-2,4-dione | (CD$_3$SO$_2$CD$_3$) δ 2.05(s, 3H), 3.82(s, 3H), 5.12(s, 2H), 6.82(dd, J=9.5, 8.4 Hz, 1H), 6.91(d, J=8.4 Hz, 1H), 7.18(s, 1H), 7.37(td, J=8.4, 6.6 Hz, 1H), 11.89(br. s, 1H). |
| 5-(2-chloro-6-methoxybenzyl)-7-propyl-3,5-dihydro[1,3]oxazolo[4,5-c]pyridine-2,4-dione | (CD$_3$SO$_2$CD$_3$) δ 0.82(t, J=7.3 Hz, 3H), 1.47(sextet, J=7.3 Hz, 2H), 2.38(t, J=7.3 Hz, 2H), 3.80(s, 3H), 5.21(s, 2H), 6.89(s, 1H), 7.08-7.13(m, 2H), 7.40(t, J=8.3 Hz, 1H), 11.93(br. s, 1H). |
| 5-(5-chloro-2-fluorobenzyl)-7-methyl-3,5-dihydro[1,3]oxazolo[4,5-c]pyridine-2,4-dione | (CD$_3$SO$_2$CD$_3$) δ 2.10(s, 3H), 5.18(s, 2H), 7.20(dd, J=6.6, 3.0 Hz, 1H), 7.29(dd, J=9.6, 8.8 Hz, 1H), 7.42(ddd, J=8.8, 4.4, 3.0 Hz, 1H), 7.51(s, 1H), 11.96(br. s, 1H). |
| 5-(2-chlorobenzyl)-7-isopropyl-3,5-dihydro[1,3]oxazolo[4,5-c]pyridine-2,4-dione | (CD$_3$SO$_2$CD$_3$) δ 1.23(d, J=7.0 Hz, 6H), 2.92(m, 1H), 5.25(s, 2H), 6.83(dd, J=7.4, 2.2 Hz, 1H), 7.27-7.35(m, 2H), 7.49(s, 1H), 7.51(dd, J=7.3, 1.8 Hz, 1H), 12.01(br. s, 1H). |
| 5-(5-fluoro-2-methylbenzyl)-7-methyl-3,5-dihydro[1,3]oxazolo[4,5-c]pyridine-2,4-dione | (CD$_3$SO$_2$CD$_3$) δ 2.10(d, J=1.1 Hz, 3H), 2.30(s, 3H), 5.13(s, 2H), 6.55(dd, J=9.9, 2.6 Hz, 1H), 7.01(td, J=8.4, 2.6 Hz, 1H), 7.25(dd, J=8.4, 5.9 Hz, 1H), 7.42(q, 1.1 Hz, 1H), 11.99(br. s, 1H). |

TABLE 1-continued

| Compound | ¹H NMR (400 MHz) |
| --- | --- |
| 7-methyl-5-[(1S)-1-phenylethyl]-3,5-dihydro[1,3]oxazolo[4,5-c]pyridine-2,4-dione | (CD$_3$SO$_2$CD$_3$) δ 1.72(d, J=7.3 Hz, 3H), 2.07(s, 3H), 6.27(q, J=7.3 Hz, 1H), 7.27-7.40(m, 6H), 11.95(br. s, 1H). |
| 5-(2-chloro-5-isopropoxybenzyl)-7-methyl-3,5-dihydro[1,3]oxazolo[4,5-c]pyridine-2,4-dione | (CD$_3$SO$_2$CD$_3$) δ 1.20(d, J=6.0 Hz, 6H), 2.11(s, 3H), 4.50(m, 1H), 5.16(s, 2H), 6.34(d, J=3.0 Hz, 1H), 6.91(dd, J=8.8, 3.0 Hz, 1H), 7.38(d, J=8.8 Hz, 1H), 7.47(s, 1H), 12.01(br. s, 1H). |
| 5-(5-acetyl-2-methoxybenzyl)-3,5-dihydro[1,3]oxazolo[4,5-c]pyridine-2,4-dione | (CD$_3$SO$_2$CD$_3$) δ 2.47(s, 3H), 3.93(s, 3H), 5.16(s, 2H), 6.62(d, J=7.3 Hz, 1H), 7.16(d, J=8.4 Hz, 1H), 7.59(d, J=2.2 Hz, 1H), 7.63(d, J=7.3 Hz, 1H), 7.97(dd, J=8.4, 2.2 Hz, 1H), 11.96(br. s, 1H). |
| 5-(2-chlorobenzyl)-7-methyl-3,5-dihydro[1,3]oxazolo[4,5-d]pyridazine-2,4-dione | (CD$_3$SO$_2$CD$_3$) δ 2.29(s, 3H), 5.39(s, 2H), 7.00(d, J=7.4 Hz, 1H), 7.26-7.37(m, 2H), 7.51(d, J=7.7 Hz, 1H), 12.80(br. s, 1H). |
| 5-[2-fluoro-6-(trifluoromethyl)benzyl]-7-methyl-3,5-dihydro[1,3]oxazolo[4,5-c]pyridine-2,4-dione | (CD$_3$SO$_2$CD$_3$) δ 2.04(s, 3H), 5.33(s, 2H), 7.05(s, 1H), 7.51-7.72(m, 3H), 11.98(br. s, 1H). |
| 5-(2-chloro-6-methylbenzyl)-5,6,7,8-tetrahydro-2H-cyclopenta[b][1,3]oxazolo[5,4-d]pyridine-2,4(3H)-dione | (CD$_3$SO$_2$CD$_3$) δ 2.02(m, 2H), 2.21(s, 3H), 2.64-2.80(m, 4H), 5.42(s, 2H), 7.05-7.33(m, 3H), 11.81(br. s, 1H). |
| 5-(2-chloro-6-ethoxybenzyl)-7-ethyl-3,5-dihydro[1,3]oxazolo[4,5-c]pyridine-2,4-dione | (CD$_3$SO$_2$CD$_3$) δ 1.08(t, J=7.7 Hz, 3H), 1.25(t, J=7.0 Hz, 3H), 2.44(q, J=7.7 Hz, 2H), 4.05(q, J=7.0 Hz, 2H), 5.23(s, 2H), 6.99(s, 1H), 7.05(d, J=8.4 Hz, 1H), 7.09(d, J=8.1 Hz, 1H), 7.36(dd, J=8.4, 8.1 Hz, 1H), 11.93(br. s, 1H). |
| 5-(2-chloro-6-propoxybenzyl)-7-methyl-3,5-dihydro[1,3]oxazolo[4,5-c]pyridine-2,4-dione | (CD$_3$SO$_2$CD$_3$) δ 0.88(t, J=7.3 Hz, 3H), 1.66(m, 2H), 2.01(d, J=1.1 Hz, 3H), 3.95(t, J=6.2 Hz, 2H), 5.24(s, 2H), 6.91(q, J=1.1 Hz, 1H), 7.03(d, J=8.4 Hz, 1H), 7.10(d, J=8.1 Hz, 1H), 7.37(dd, J=8.4, 8.1 Hz, 1H), 11.95(br. s, 1H). |
| 5-(2-chloro-6-isobutoxybenzyl)-7-methyl-3,5-dihydro[1,3]oxazolo[4,5-c]pyridine-2,4-dione | (CD$_3$SO$_2$CD$_3$) δ 0.89(d, J=7.0 Hz, 6H), 1.95(m, 1H), 2.00(s, 3H), 3.79(d, J=6.2 Hz, 2H), 5.25(s, 2H), 6.85(s, 1H), 7.06(d, J=8.4 Hz, 1H), 7.11(d, J=8.1 Hz, 1H), 7.38(dd, J=8.4, 8.1 Hz, 1H), 11.97(br. s, 1H). |
| 5-(2-chloro-6-ethoxybenzyl)-5,6,7,8-tetrahydro-2H-cyclopenta[b][1,3]oxazolo[5,4-d]pyridine-2,4(3H)-dione | (CD$_3$SO$_2$CD$_3$) δ 1.10(t, J=7.0 Hz, 3H), 2.06(m, 2H), 2.70-2.92(m, 4H), 3.90(q, J=7.0 Hz, 2H), 5.33(s, 2H), 6.93(d, J=8.4 Hz, 1H), 7.03(d, J=8.1 Hz, 1H), 7.26(dd, J=8.4, 8.1 Hz, 1H), 11.75(br. s, 1H). |
| 5-(2-chloro-6-isopropoxybenzyl)-7-methyl-3,5-dihydro[1,3]oxazolo[4,5-c]pyridine-2,4-dione | (CD$_3$SO$_2$CD$_3$) δ 1.16(d, J=6.2 Hz, 6H), 2.02(s, 3H), 4.67(m, 1H), 5.21(s, 2H), 6.94(s, 1H), 7.07(d, J=8.0 Hz, 2H), 7.34(t, J=8.0 Hz, 1H), 11.93(br. s, 1H). |
| 5-[2-chloro-6-(2,2,2-trifluoroethoxy)benzyl]-7-methyl-3,5-dihydro[1,3]oxazolo[4,5-c]pyridine-2,4-dione | (CD$_3$SO$_2$CD$_3$) δ 2.01(s, 3H), 4.82(q, J=8.8 Hz, 2H), 5.24(s, 2H), 6.94(s, 1H), 7.19(d, J=8.4 Hz, 1H), 7.22(d, J=8.1 Hz, 1H), 7.43(dd, J=8.4, 8.1 Hz, 1H), 11.92(br. s, 1H). |
| 5-(2-chloro-6-ethoxybenzyl)-7-methyl-3,5-dihydro[1,3]oxazolo[4,5-d]pyridazine-2,4-dione | (CD$_3$SO$_2$CD$_3$) δ 1.19(t, J=7.0 Hz, 3H), 2.19(s, 3H), 3.99(q, J=7.0 Hz, 2H), 5.41(s, 2H), 6.98(d, J=8.4 Hz, 1H), 7.05(d, J=8.0 Hz, 1H), 7.30(dd, J=8.4, 8.0 Hz, 1H), 12.70(br. s, 1H). |
| 5-[2-chloro-6-(2-methoxyethoxy)benzyl]-5,6,7,8-tetrahydro-2H-cyclopenta[b][1,3]oxazolo[5,4-d]pyridine-2,4(3H)-dione | (CD$_3$SO$_2$CD$_3$) δ 2.06(m, 2H), 2.74-2.90(m, 4H), 3.20(s, 3H), 3.47(t, J=4.4 Hz, 2H), 4.01(t, J=4.4 Hz, 2H), 5.33(s, 2H), 6.98(d, J=8.0 Hz, 1H), 7.04(d, J=8.0 Hz, 1H), 7.27(t, J=8.0 Hz, 1H), (br. s, 1H). |
| 5-(2-chloro-6-ethoxybenzyl)-6,7-dimethyl-3,5-dihydro[1,3]oxazolo[4,5-c]pyridine-2,4-dione | (CD$_3$SO$_2$CD$_3$) δ 1.03(t, J=7.0 Hz, 3H), 2.06(s, 3H), 2.22(s, 3H), 3.84(q, J=7.0 Hz, 2H), 5.48(s, 2H), 6.92(d, 8.4 Hz, 1H), 7.03(d, J=8.1 Hz, 1H), 7.24(dd, J=8.4, 8.1 Hz, 1H), 11.76(br.s, 1H). |
| 5-(2-chloro-6-ethoxybenzyl)-7-ethyl-6-methyl-3,5-dihydro[1,3]oxazolo[4,5-c]pyridine-2,4-dione | (CD$_3$SO$_2$CD$_3$) δ 1.06(m, 6H), 2.24(s, 3H), 2.48-2.56(m overlapping DMSO, 2H), 3.85(q, J=7.0 Hz, 2H), 5.48(s, 2H), 6.92(d, 8.4 Hz, 1H), 7.03(d, J=8.1 Hz, 1H), 7.24(dd, J=8.4, 8.1 Hz, 1H), 11.77(br.s, 1H). |

TABLE 1-continued

| Compound | $^1$H NMR (400 MHz) |
|---|---|
| 5-(2-chlorobenzyl)-7-ethyl-3,5-dihydro[1,3]oxazolo[4,5-d]pyridazine-2,4-dione | (CD$_3$SO$_2$CD$_3$) δ 1.18(t, J=7.5 Hz, 3H), 2.70(q, J=7.5 Hz, 2H), 5.38(s, 2H), 7.0-7.6(m, 4H), 12.77(br. s, 1H). |
| 5-(2-chloro-6-ethoxybenzyl)-7-propyl-3,5-dihydro[1,3]oxazolo[4,5-c]pyridine-2,4-dione | (CD$_3$SO$_2$CD$_3$) δ 0.82(t, J=7.3 Hz, 3H), 1.24(t, J=7.0 Hz, 3H), 1.48(m, 2H), 2.37(t, J=7.3 Hz, 2H), 4.05(q, J=7.0 Hz, 2H), 5.23(s, 2H), 6.93(s, 1H), 7.05(d, J=8.4 Hz, 1H), 7.09(d, J=8.1 Hz, 1H), 7.36(dd, J=8.4, 8.1 Hz, 1H), 11.94(br. s, 1H). |
| 5-(2-chloro-6-ethoxybenzyl)-7-cyclopropyl-3,5-dihydro[1,3]oxazolo[4,5-c]pyridine-2,4-dione | (CD$_3$SO$_2$CD$_3$) δ 0.55(m, 2H), 0.81(m, 2H), 1.26(t, J=7.0 Hz, 3H), 1.72(m, 1H), 4.05(q, J=7.0 Hz, 2H), 5.22(s, 2H), 6.95(s, 1H), 7.05(d, J=8.4 Hz, 1H), 7.09(d, J=8.1 Hz, 1H), 7.36(dd, J=8.4, 8.1 Hz, 1H), 11.93(br. s, 1H). |
| 5-(2-chloro-5-propoxybenzyl)-7-methyl-3,5-dihydro[1,3]oxazolo[4,5-c]pyridine-2,4-dione | (CD$_3$SO$_2$CD$_3$) δ 0.92(t, J=7.3 Hz, 3H), 1.66(m, 2H), 2.10(s, 3H), 3.85(m, 2H), 5.17(s, 2H), 6.41(d, J=3.3 Hz, 1H), 6.91(dd, J=8.8, 3.3 Hz, 1H), 7.39(d, J=8.8 Hz, 1H), 7.45(s, 1H), 12.00(br. s, 1H). |
| 5-(2-chloro-5-methoxybenzyl)-7-methyl-3,5-dihydro[1,3]oxazolo[4,5-c]pyridine-2,4-dione | (CD$_3$SO$_2$CD$_3$) δ 2.10(s, 3H), 3.9(s, 3H), 5.18(s, 2H), 6.42(d, J=3.0 Hz, 1H), 6.93(dd, J=8.8, 3.0 Hz, 1H), 7.42(d, J=8.8 Hz, 1H), 7.44(s, 1H), 12.00(br. s, 1H). |
| 5-(2-chloro-6-ethoxybenzyl)-6-methyl-3,5-dihydro[1,3]oxazolo[4,5-c]pyridine-2,4-dione | (CD$_3$SO$_2$CD$_3$) δ 1.07(t, J=7.0 Hz, 3H), 2.32(s, 3H), 3.87(q, J=7.0 Hz, 2H), 5.42(s, 2H), 6.44(s, 1H), 6.92(d, J=8.4 Hz, 1H), 7.03(d, J=8.1 Hz, 1H), 7.24(dd, J=8.4, 8.1 Hz, 1H), 11.74(br. s, 1H). |
| 5-(2-chloro-5-ethoxybenzyl)-7-methyl-3,5-dihydro[1,3]oxazolo[4,5-c]pyridine-2,4-dione | (CD$_3$SO$_2$CD$_3$) δ 1.26(t, J=7.0 Hz, 3H), 2.10(s, 3H), 3.94(q, J=7.0 Hz, 2H), 5.17(s, 2H), 6.38(d, J=2.9 Hz, 1H), 6.91(dd, J=8.8, 2.9 Hz, 1H), 7.39(d, J=8.8 Hz, 1H), 7.44(s, 1H), 11.99(br. s, 1H). |
| 5-[2-chloro-5-(piperidin-1-ylsulfonyl)benzyl]-7-methyl-3,5-dihydro[1,3]oxazolo[4,5-c]pyridine-2,4-dione | (CD$_3$SO$_2$CD$_3$) δ 1.35(m, 2H), 1.47(m, 4H), 2.10(s, 3H), 2.81(m, 4H), 5.30(s, 2H), 7.18(d, J=2.2 Hz, 1H), 7.57(s, 1H), 7.67(dd, J=8.4, 2.2 Hz, 1H), 7.78(d, J=8.4 Hz, 1H), 12.07(br. s, 1H). |
| 5-[2-chloro-5-(pyrrolidin-1-ylsulfonyl)benzyl]-7-methyl-3,5-dihydro[1,3]oxazolo[4,5-c]pyridine-2,4-dione | (CD$_3$SO$_2$CD$_3$) δ 1.62(m, 4H), 2.11(s, 3H), 3.05(m, 4H), 5.30(s, 2H), 7.30(s, 1H), 7.57(s, 1H), 7.75-7.82(m, 2H), 12.08(br. s, 1H). |
| 5-[2-chloro-6-(cyclopentylmethoxy)benzyl]-7-methyl-3,5-dihydro[1,3]oxazolo[4,5-c]pyridine-2,4-dione | (CD$_3$SO$_2$CD$_3$) δ 1.22(m, 2H), 1.51(m, 4H), 1.68(m, 2H), 2.00(s, 3H), 2.20(m, 1H), 3.89(d, J=7.0 Hz, 2H), 5.24(s, 2H), 6.86(s, 1H), 7.07(d, J=8.4 Hz, 1H), 7.11(d, J=8.1 Hz, 1H), 7.37(dd, J=8.4, 8.1 Hz, 1H), 11.97(br. s, 1H). |
| 5-[2-(benzyloxy)-6-chlorobenzyl]-7-methyl-3,5-dihydro[1,3]oxazolo[4,5-c]pyridine-2,4-dione | (CD$_3$SO$_2$CD$_3$) δ 1.90(s, 3H), 5.15(s, 2H), 5.25(s, 2H), 6.84(s, 1H), 7.13(d, J=8.1 Hz, 1H), 7.19(d, J=7.7 Hz, 1H), 7.30-7.37(m, 5H), 7.39(dd, J=8.1, 7.7 Hz, 1H), 11.91(br. s, 1H). |
| 5-(2,3-dichloro-6-ethoxybenzyl)-5,6,7,8-tetrahydro-2H-cyclopenta[b][1,3]oxazolo[5,4-d]pyridine-2,4(3H)-dione | (CD$_3$SO$_2$CD$_3$) δ 1.10(t, J=7.0 Hz, 3H), 2.09(m, 2H) 2.80(m, 2H), 2.89(m, 2H), 3.92(q, J=7.0 Hz, 2H), 5.33(s, 2H), 6.98(d, J=8.8 Hz, 1H), 7.50(d, J=8.8 Hz, 1H), 11.71(br. s, 1H). |
| 5-[2-chloro-5-(trifluoromethyl)benzyl]-7-methyl-3,5-dihydro[1,3]oxazolo[4,5-c]pyridine-2,4-dione | (CD$_3$SO$_2$CD$_3$) δ 2.11(s, 3H), 5.29(s, 2H), 7.34(s, 1H), 7.54(s, 1H), 7.72-7.79(m, 2H), 12.00(br. s, 1H). |
| 5-(2-chloro-5-fluorobenzyl)-7-methyl-3,5-dihydro[1,3]oxazolo[4,5-c]pyridine-2,4-dione | (CD$_3$SO$_2$CD$_3$) δ 2.11(s, 3H), 5.20(s, 2H), 6.71(dd, J=9.4, 2.9 Hz, 1H), 7.22(td, J=8.4, 2.9 Hz, 1H), 7.49(s, 1H), 7.57(dd, J=8.4, 5.2 Hz, 1H), 11.99(br. s, 1H). |

EXAMPLE 42

A procedure in which a 26-amino acid peptide containing the CS1 sequence of fibronectin with an N-terminal Cys (CDELPQLVTLPHPNLHGPEILDVPST) was coupled to maleimide activated ovalbumin was used to determine the efficacy of the compounds synthesized. Bovine serum albumin (BSA) and CS1 conjugated ovalbumin were coated onto 96-well polystyrene plates at 0.5 μg/ml in TBS (50 mM TRIS, pH 7.5; 150 mM NaCl) at 4° C. for 16 hours. The plates were washed three times with TBS and blocked with TBS containing 3% BSA at room temperature for 4 hours. Blocked plates were washed three times in binding buffer (TBS; 1 mM $MgCl_2$; 1 mM $CaCl_2$; 1 mM $MnCl_2$) prior to assay. Ramos cells fluorescently labeled with calcein AM were resuspended in binding buffer (1 cells/ml) and diluted 1:2 with same buffer with or without compound. 100 μM of compound was added. The cells were added immediately to the wells ($2.5 \times 10^5$ cells/well) and incubated for 30 minutes at 37° C. Following three washes with binding buffer, adherent cells were lysed and quantitated using a fluorometer. The results are shown in Tables 2-7. $IC_{50}$ is defined as the dose required to give 50% inhibition, measured in μM for Tables 2 and 4. The lower the $IC_{50}$ value and the greater the percentage of inhibition, the more efficient the compound is at prevention of cell adhesion.

TABLE 2

| Name | $IC_{50}$ | Mass Spectral Data (m/z) |
|---|---|---|
| (3S)-3-(1,3-benzodioxol-5-yl)-3-[({[(3S)-2-oxo-1-(2-thienylmethyl)hexahydro-3-pyridinyl]amino}carbonyl)amino]propanoic acid | 0.2 | Calc'd $(M - H)^- = 444.12$; Found $(M - H)^- = 444.08$ |
| (3S)-3-(1,3-benzodioxol-5-yl)-3-[({[(3S)-2-oxo-1-(2-thienylmethyl)tetrahydro-1H-pyrrol-3-yl]amino}carbonyl)amino]propanoic acid | 15 | Calc'd $(M - H)^- = 430.11$; Found $(M - H)^- = 430.06$ |
| (3S)-3-(1,3-benzodioxol-5-yl)-3-[({[(3R)-2-oxo-1-(2-thienylmethyl)hexahydro-3-pyridinyl]amino}carbonyl)amino]propanoic acid | 2 | Calc'd $(M - H)^- = 444.12$; Found $(M - H)^- = 444.05$ |
| (3S)-3-(1,3-benzodioxol-5-yl)-3-[({[2-oxo-1-(2-thienylmethyl)-1,2-dihydro-3-pyridinyl]amino}carbonyl)amino]propanoic acid | 0.9 | Calc'd $(M - H)^- = 440.09$; Found $(M - H)^- = 439.98$ |
| (3S)-3-(1,3-benzodioxol-5-yl)-3-({[((3S)-2-oxo-1-{4-[(2-toluidinocarbonyl)amino]benzyl}hexahydro-3-pyridinyl)amino]carbonyl}amino)propanoic acid | 0.0003 | Calc'd $(M - H)^- = 586.23$; Found $(M - H)^- = 586.17$ |
| (3S)-3-(1,3-benzodioxol-5-yl)-3-[({[2-oxo-1-{4-[(2-toluidinocarbonyl)amino]benzyl}-1,2-dihydro-3-pyridinyl]amino}carbonyl)amino]propanoic acid | 0.001 | Calc'd $(M - H)^- = 582.20$; Found $(M - H)^- = 582.20$ |
| (3S)-3-(1,3-benzodioxol-5-yl)-3-({[((3S)-1-{4-[(2-methylbenzyl)amino]benzyl}-2-oxohexahydro-pyridinyl)amino]carbonyl}amino)propanoic acid | nd | nd |
| (3S)-3-(1,3-benzodioxol-5-yl)-3-[({butyl[2-oxo-1-(2-thienylmethyl)-1,2-dihydro-3-pyridinyl]amino}carbonyl)amino]propanoic acid | 20 | Calculated $(M - H)^- = 496.15$; Found $(M - H)^- = 496.10$ |
| (3S)-3-(1,3-benzodioxol-5-yl)-3-[({[(3S)-2-oxo-1-(2-thienylmethyl)azepanyl]amino}carbonyl)amino]propanoic acid | 0.015 | Calculated $(M - H)^- = 458.13$; Found $(M - H)^- = 458.09$ |

TABLE 3

| Compound | $IC_{50}$ (nM) | Mass Spectral Data |
|---|---|---|
| (3S)-3-[({[2-methyl-4-(2-methylpropyl)-6-oxo-1-(phenylmethyl)-1,6-dihydro-5-pyrimidinyl]amino}carbonyl)amino]-3-(4-methylphenyl)propanoic acid | 10 | Calculated $(M - H)^- = 475.23$ m/z; Found $(M - H)^- = 475.02$ m/z. |
| (3S)-3-(1,3-benzodioxol-5-yl)-3-[({[2-oxo-1-(phenylmethyl)-4-propyl-1,2-dihydro-3-pyridinyl]amino}carbonyl)amino]propanoic acid | 10 | Calculated $(M - H)^- = 476.18$ m/z; Found $(M - H)^- = 475.99$ m/z. |
| (3S)-3-(1,3-benzodioxol-5-yl)-3-({[9-oxo-8-(phenylmethyl)-2,3,4,5,8,9-hexahydro-1H-pyrido[3,4-b]azepin-1-yl]carbonyl}amino)propanoic acid | 4000 | Calculated $(M - H)^- = 488.18$ m/z; Found $(M - H)^- = 488.19$ m/z. |
| (3S)-3-{[({1-[(2-chlorophenyl)methyl]-4-ethyl-2-oxo-1,2-dihydro-3-pyridinyl}amino)carbonyl]amino}-3-(4-methylphenyl)propanoic acid | 10 | Calculated $(M - H)^- = 466.15$ m/z; Found $(M - H)^- = 465.95$ m/z. |
| (3S)-3-{[({1-[(2-chlorophenyl)methyl]-2-oxo-4-propyl-1,2-dihydro-3-pyridinyl}amino)carbonyl]amino}-3-(4-methylphenyl)propanoic acid | 4 | Calculated $(M - H)^- = 480.17$ m/z; Found $(M - H)^- = 480.00$ m/z. |
| (3S)-3-{[({1-[(2-chlorophenyl)methyl]-4-methyl-2-oxo-1,2-dihydro-3-pyridinyl}amino)carbonyl]amino}-3-(4-methylphenyl)propanoic acid | 5 | Calculated $(M + H)^+ = 454.15$ m/z; Found $(M + H)^+ = 454.09$ m/z. |

TABLE 3-continued

| Compound | IC$_{50}$ (nM) | Mass Spectral Data |
|---|---|---|
| (3S)-3-{[({6-methyl-2-oxo-1-(phenylmethyl)-4-[(phenylmethyl)oxy]-1,2-dihydro-3-pyridinyl}amino)carbonyl]amino}-3-(4-methylphenyl)propanoic acid | 5 | Calculated (M − H)$^-$ = 524.22 m/z; Found (M − H)$^-$ = 524.02 m/z. |
| (3S)-3-{[({1-[(2-chlorophenyl)methyl]-2,4-dimethyl-6-oxo-1,6-dihydro-5-pyrimidinyl}amino)carbonyl]amino}-3-(4-methylphenyl)propanoic acid | 10 | Calculated (M − H)$^-$ = 467.15 m/z; Found (M − H)$^-$ = 467.00 m/z. |
| (3S)-3-{[({1-[(2,4-dichlorophenyl)methyl]-4-methyl-2-oxo-1,2-dihydro-3-pyridinyl}amino)carbonyl]amino}-3-(4-methylphenyl)propanoic acid | 30 | Calculated (M − H)$^-$ = 486.10 m/z; Found (M − H)$^-$ = 485.95 m/z. |
| (3S)-3-{[({4-amino-1-[(2-chlorophenyl)methyl]-6-methyl-2-oxo-1,2-dihydro-3-pyridinyl}amino)carbonyl]amino}-3-(4-methylphenyl)propanoic acid | 10 | Calculated (M − H)$^-$ = 467.15 m/z; Found (M − H)$^-$ = 467.14 m/z. |
| (3S)-3-[({[1-[(2-chlorophenyl)methyl]-4-(methyloxy)-2-oxo-1,2-dihydro-3-pyridinyl]amino}carbonyl)amino]-3-(4-methylphenyl)propanoic acid | 20 | Calculated (M − H)$^-$ = 468.13 m/z; Found (M − H)$^-$ = 467.97 m/z. |
| (3S)-3-{[({4-chloro-1-[(2-chlorophenyl)methyl]-2-oxo-1,2-dihydro-3-pyridinyl}amino)carbonyl]amino}-3-(4-methylphenyl)propanoic acid | 20 | Calculated (M − H)$^-$ = 472.08 m/z; Found (M − H)$^-$ = 471.91 m/z. |
| (3S)-3-{[({1-[(2-chlorophenyl)methyl]-4-methyl-2-oxo-1,2-dihydro-3-pyridinyl}amino)carbonyl]amino}-3-[3-methyl-4-(methyloxy)phenyl]propanoic acid | 15 | Calculated (M − H)$^-$ = 482.15 m/z; Found (M − H)$^-$ = 481.93 m/z. |
| (3S)-3-{[({1-[(2-chlorophenyl)methyl]-4-methyl-2-oxo-1,2-dihydro-3-pyridinyl}amino)carbonyl]amino}-3-[4-(methyloxy)phenyl]propanoic acid | 3 | Calculated (M + H)$^+$ = 470.15 m/z; Found (M + H)$^+$ = 470.01 m/z. |
| (3S)-3-{[({1-[(2-chlorophenyl)methyl]-4-methyl-2-oxo-1,2-dihydro-3-pyridinyl}amino)carbonyl]amino}-3-(3,4-dimethylphenyl)propanoic acid | 10 | Calculated (M + H)$^+$ = 468.17 m/z; Found (M + H)$^+$ = 468.05 m/z. |
| (3S)-3-{[({4-amino-1-[(2-chlorophenyl)methyl]-2-oxo-1,2-dihydro-3-pyridinyl}amino)carbonyl]amino}-3-(4-methylphenyl)propanoic acid | 10 | Calculated (M − H)$^-$ = 453.13 m/z; Found (M − H)$^-$ = 453.01 m/z. |
| (3S)-3-{[({1-[(2-chlorophenyl)methyl]-4-fluoro-2-oxo-1,2-dihydro-3-pyridinyl}amino)carbonyl]amino}-3-(4-methylphenyl)propanoic acid | 15 | Calculated (M − H)$^-$ = 456.12 m/z; Found (M − H)$^-$ = 455.94 m/z. |
| (3S)-3-[({[1-[(2-chlorophenyl)methyl]-2-oxo-4-(phenylamino)-1,2-dihydro-3-pyridinyl]amino}carbonyl)amino]-3-(4-methylphenyl)propanoic acid | 20 | Calculated (M − H)$^-$ = 529.16 m/z; Found (M − H)$^-$ = 529.02 m/z. |
| (3S)-3-[({[1-[(2-chlorophenyl)methyl]-2-oxo-4-(2-pyridinylamino)-1,2-dihydro-3-pyridinyl]amino}carbonyl)amino]-3-(4-methylphenyl)propanoic acid | 15 | Calculated (M − H)$^-$ = 530.16 m/z; Found (M − H)$^-$ = 529.99 m/z. |
| (3S)-3-{[({1-[(2-chlorophenyl)methyl]-4-hydroxy-2-oxo-1,2-dihydro-3-pyridinyl}amino)carbonyl]amino}-3-(4-methylphenyl)propanoic acid | 10 | Calculated (M − H)$^-$ = 454.11 m/z; Found (M − H)$^-$ = 454.05 m/z. |
| (3S)-3-{[({1-[(2-chlorophenyl)methyl]-2-oxo-4-[(2-pyridinylmethyl)amino]-1,2-dihydro-3-pyridinyl}amino)carbonyl]amino}-3-(4-methylphenyl)propanoic acid | 15 | Calculated (M − H)$^-$ = 544.17 m/z; Found (M − H)$^-$ = 544.03 m/z. |
| (3S)-3-{[({1-[(2-chlorophenyl)methyl]-2-oxo-4-[(3-pyridinylmethyl)amino]-1,2-dihydro-3-pyridinyl}amino)carbonyl]amino}-3-(4-methylphenyl)propanoic acid | 20 | Calculated (M − H)$^-$ = 544.17 m/z; Found (M − H)$^-$ = 544.02 m/z. |
| (3S)-3-[({[1-[(2-chlorophenyl)methyl]-4-(1,4-oxazinan-4-yl)-2-oxo-1,2-dihydro-3-pyridinyl]amino}carbonyl)amino]-3-(4-methylphenyl)propanoic acid | 1 | Calculated (M − H)$^-$ = 523.17 m/z; Found (M − H)$^-$ = 523.02 m/z. |
| (3S)-3-[({[1-[(2-chlorophenyl)methyl]-2-oxo-4-(propylamino)-1,2-dihydro-3-pyridinyl]amino}carbonyl)amino]-3-(4-methylphenyl)propanoic acid | 10 | Calculated (M − H)$^-$ = 495.18 m/z; Found (M − H)$^-$ = 495.04 m/z. |
| (3S)-3-{[({1-[(2-fluorophenyl)methyl]-4-methyl-2-oxo-1,2-dihydro-3-pyridinyl}amino)carbonyl]amino}-3-(4-methylphenyl)propanoic acid | 20 | Calculated (M − H)$^-$ = 436.17 m/z; Found (M − H)$^-$ = 435.99 m/z. |

TABLE 3-continued

| Compound | IC$_{50}$ (nM) | Mass Spectral Data |
|---|---|---|
| (3S)-3-{[({1-[(2,6-dichlorophenyl)methyl]-4-methyl-2-oxo-1,2-dihydro-3-pyridinyl}amino)carbonyl]amino}-3-(4-methylphenyl)propanoic acid | 20 | Calculated (M − H)⁻ = 486.10 m/z; Found (M − H)⁻ = 485.95 m/z. |
| (3R)-3-{[({1-[(2-chlorophenyl)methyl]-4-methyl-2-oxo-1,2-dihydro-3-pyridinyl}amino)carbonyl]amino}butanoic acid | 300 | Calculated (M − H)⁻ = 376.11 m/z; Found (M − H)⁻ = 376.00 m/z. |
| (3S)-3-{[({1-[(2-bromophenyl)methyl]-4-methyl-2-oxo-1,2-dihydro-3-pyridinyl}amino)carbonyl]amino}-3-(4-methylphenyl)propanoic acid | 10 | Calculated (M − H)⁻ = 496.09 m/z; Found (M − H)⁻ = 495.87 m/z. |
| (3S)-3-[({[4-methyl-2-oxo-1-(phenylmethyl)-1,2-dihydro-3-pyridinyl]amino}carbonyl)amino]-3-(4-methylphenyl)propanoic acid | 30 | Calculated (M − H)⁻ = 418.17 m/z; Found (M − H)⁻ = 417.96 m/z. |
| (3S)-3-{[({1-[(2-chlorophenyl)methyl]-4-hydroxy-2-oxo-1,2-dihydro-3-pyridinyl}amino)carbonyl]amino}-3-[3-methyl-4-(methyloxy)phenyl]propanoic acid | 8 | Calculated (M − H)⁻ = 484.12 m/z; Found (M − H)⁻ = 484.03 m/z. |
| (3S)-3-{[({1-[(2-chlorophenyl)methyl]-2-oxo-4-phenyl-1,2-dihydro-3-pyridinyl}amino)carbonyl]amino}-3-(4-methylphenyl)propanoic acid | 10 | Calculated (M − H)⁻ = 514.15 m/z; Found (M − H)⁻ = 514.00 m/z. |
| (3S)-3-{[({4-bromo-1-[(2-chlorophenyl)methyl]-2-oxo-1,2-dihydro-3-pyridinyl}amino)carbonyl]amino}-3-(4-methylphenyl)propanoic acid | 20 | Calculated (M − H)⁻ = 516.03 m/z; Found (M − H)⁻ = 515.90 m/z. |
| (3S)-3-(1,3-benzodioxol-5-yl)-3-{[({1-[(2-chlorophenyl)methyl]-4-hydroxy-2-oxo-1,2-dihydro-3-pyridinyl}amino)carbonyl]amino}propanoic acid | 20 | Calculated (M − H)⁻ = 484.09 m/z; Found (M − H)⁻ = 484.03 m/z. |
| (3S)-3-{[({1-[(2-chlorophenyl)methyl]-4-[(2-{[2-(methyloxy)ethyl]oxy}ethyl)oxy]-2-oxo-1,2-dihydro-3-pyridinyl}amino)carbonyl]amino}-3-(4-methylphenyl)propanoic acid | 2 | Calculated (M − H)⁻ = 556.18 m/z; Found (M − H)⁻ = 556.03 m/z. |
| (3S)-3-{[({1-[(2-chlorophenyl)methyl]-4-hydroxy-6-methyl-2-oxo-1,2-dihydro-3-pyridinyl}amino)carbonyl]amino}-3-(4-methylphenyl)propanoic acid | 15 | Calculated (M − H)⁻ = 468.13 m/z; Found (M − H)⁻ = 468.05 m/z. |
| (3S)-3-{[({1-[(2-chlorophenyl)methyl]-4-[(1,1-dimethylethyl)amino]-2-oxo-1,2-dihydro-3-pyridinyl}amino)carbonyl]amino}-3-(4-methylphenyl)propanoic acid | 3 | Calculated (M − H)⁻ = 509.20 m/z; Found (M − H)⁻ = 509.06 m/z. |
| (3S)-3-{[({1-[(2-chlorophenyl)methyl]-4-hydroxy-2-oxo-1,2-dihydro-3-pyridinyl}amino)carbonyl]amino}-3-phenylpropanoic acid | 10 | Calculated (M − H)⁻ = 440.10 m/z; Found (M − H)⁻ = 440.04 m/z. |
| (3S)-3-{[({1-[(2-chlorophenyl)methyl]-4-[4-methyltetrahydro-1(2H)-pyrazinyl]-2-oxo-1,2-dihydro-3-pyridinyl}amino)carbonyl]amino}-3-(4-methylphenyl)propanoic acid | 3 | Calculated (M − H)⁻ = 536.20 m/z; Found (M − H)⁻ = 536.12 m/z. |
| (3S)-3-{[({1-[(2-chlorophenyl)methyl]-4-hydroxy-2-oxo-1,2-dihydro-3-pyridinyl}amino)carbonyl]amino}-3-[4-(methyloxy)phenyl]propanoic acid | 5 | Calculated (M − H)⁻ = 470.11 m/z; Found (M − H)⁻ = 470.05 m/z. |
| (3S)-3-{[({1-[(2-chlorophenyl)methyl]-4-hydroxy-2-oxo-1,2-dihydro-3-pyridinyl}amino)carbonyl]amino}-3-[3,4,5-tris(methyloxy)phenyl]propanoic acid | 20 | Calculated (M − H)⁻ = 530.13 m/z; Found (M − H)⁻ = 530.05 m/z. |
| (3S)-3-{[({1-[(2-chlorophenyl)methyl]-4-hydroxy-2-oxo-1,2-dihydro-3-pyridinyl}amino)carbonyl]amino}-3-(3,5-dimethylphenyl)propanoic acid | 15 | Calculated (M − H)⁻ = 468.13 m/z; Found (M − H)⁻ = 468.08 m/z. |
| (3S)-3-{[({1-[(2-chlorophenyl)methyl]-4-[(3-methyl-5-isoxazolyl)amino]-2-oxo-1,2-dihydro-3-pyridinyl}amino)carbonyl]amino}-3-(4-methylphenyl)propanoic acid | 15 | Calculated (M − H)⁻ = 534.15 m/z; Found (M − H)⁻ = 534.01 m/z. |
| (3S)-3-{[({1-[(2-chlorophenyl)methyl]-4-hydroxy-2-oxo-1,2-dihydro-3-pyridinyl}amino)carbonyl]amino}-3-(3-methylphenyl)propanoic acid | 20 | Calculated (M − H)⁻ = 454.17 m/z; Found (M − H)⁻ = 454.04 m/z. |
| (3S)-3-{[({1-[(2-chlorophenyl)methyl]-4-hydroxy-2-oxo-1,2-dihydro-3-pyridinyl}amino)carbonyl]amino}-3-[3-(methyloxy)phenyl]propanoic acid | 5 | Calculated (M − H)⁻ = 470.11 m/z; Found (M − H)⁻ = 470.03 m/z. |

TABLE 3-continued

| Compound | IC$_{50}$ (nM) | Mass Spectral Data |
| --- | --- | --- |
| (3S)-3-[3,5-bis(methyloxy)phenyl]-3-{[({1-[(2-chlorophenyl)methyl]-4-hydroxy-2-oxo-1,2-dihydro-3-pyridinyl}amino)carbonyl]amino}propanoic acid | 3 | Calculated (M − H)⁻ = 500.12 m/z; Found (M − H)⁻ = 500.07 m/z. |
| (3S)-3-{[({1-[(2-chlorophenyl)methyl]-4-hydroxy-2-oxo-1,2-dihydro-3-quinolinyl}amino)carbonyl]amino}-3-(4-methylphenyl)propanoic acid | 8 | Calculated (M − H)⁻ = 504.13 m/z; Found (M − H)⁻ = 504.06 m/z. |
| (3S)-3-{[({1-[(2-chlorophenyl)methyl]-4-hydroxy-2-oxo-1,2-dihydro-3-pyridinyl}amino)carbonyl]amino}-3-[3-(trifluoromethyl)phenyl]propanoic acid | 20 | Calculated (M − H)⁻ = 508.04 m/z; Found (M − H)⁻ = 508.09 m/z. |
| (3S)-3-{[({1-[(2-chlorophenyl)methyl]-4-[({ethyl[(ethylamino)carbonyl]amino}carbonyl)amino]-2-oxo-1,2-dihydro-3-pyridinyl}amino)carbonyl]amino}-3-(4-methylphenyl)propanoic acid | 2 | Calculated (M − H)⁻ = 595.21 m/z; Found (M − H)⁻ = 594.97 m/z. |
| (3S)-3-{[({4-(1-azetanyl)-1-[(2-chlorophenyl)methyl]-2-oxo-1,2-dihydro-3-pyridinyl}amino)carbonyl]amino}-3-(4-methylphenyl)propanoic acid | 5 | Calculated (M − H)⁻ = 493.16 m/z; Found (M − H)⁻ = 493.05 m/z. |
| (3S)-3-{[({1-[(2-chlorophenyl)methyl]-4-hydroxy-2-oxo-1,2-dihydro-3-pyridinyl}amino)carbonyl]amino}-3-(4-fluorophenyl)propanoic acid | 30 | Calculated (M − H)⁻ = 458.09 m/z; Found (M − H)⁻ = 458.03 m/z. |
| (3S)-3-{[({1-[(2-chlorophenyl)methyl]-4-hydroxy-2-oxo-1,2-dihydro-3-pyridinyl}amino)carbonyl]amino}-3-(3-fluorophenyl)propanoic acid | 40 | Calculated (M − H)⁻ = 458.09 m/z; Found (M − H)⁻ = 458.06 m/z. |
| (3S)-3-[({[1-[(2-chlorophenyl)methyl]-4-({2-[(2-{[2-(methyloxy)ethyl]oxy}ethyl)oxy]ethyl}oxy)-2-oxo-1,2-dihydro-3-pyridinyl]amino}carbonyl)amino]-3-(4-methylphenyl)propanoic acid | 2 | Calculated (M − H)⁻ = 600.21 m/z; Found (M − H)⁻ = 600.10 m/z. |
| (3S)-3-{[({1-[(2-chlorophenyl)methyl]-4-hydroxy-2-oxo-1,2-dihydro-3-pyridinyl}amino)carbonyl]amino}-3-[4-(trifluoromethyl)phenyl]propanoic acid | 25 | Calculated (M − H)⁻ = 508.09 m/z; Found (M − H)⁻ = 508.02 m/z. |
| (3S)-3-{[({1-[(2-fluorophenyl)methyl]-4-hydroxy-2-oxo-1,2-dihydro-3-pyridinyl}amino)carbonyl]amino}-3-(4-methylphenyl)propanoic acid | 30 | Calculated (M − H)⁻ = 438.15 m/z; Found (M − H)⁻ = 438.07 m/z. |
| (3S)-3-{[({1-[(2-chloro-6-fluorophenyl)methyl]-4-hydroxy-2-oxo-1,2-dihydro-3-pyridinyl}amino)carbonyl]amino}-3-(4-methylphenyl)propanoic acid | 10 | Calculated (M − H)⁻ = 472.11 m/z; Found (M − H)⁻ = 472.06 m/z. |
| (3S)-3-{[({1-[(2-chlorophenyl)methyl]-4-hydroxy-2-oxo-1,2-dihydro-3-pyridinyl}amino)carbonyl]amino}-3-[4-(1,1-dimethylethyl)phenyl]propanoic acid | 400 | Calculated (M − H)⁻ = 496.16 m/z; Found (M − H)⁻ = 496.11 m/z. |
| (3S)-3-{[({1-[(2-chlorophenyl)methyl]-5-methyl-2-oxo-1,2-dihydro-3-pyridinyl}amino)carbonyl]amino}-3-(4-methylphenyl)propanoic acid | 70 | Calculated (M − H)⁻ = 452.14 m/z; Found (M − H)⁻ = 451.99 m/z. |
| 3-(4-chlorophenyl)-3-{[({1-[(2-chlorophenyl)methyl]-4-hydroxy-2-oxo-1,2-dihydro-3-pyridinyl}amino)carbonyl]amino}propanoic acid | 30 | Calculated (M − H)⁻ = 474.06 m/z; Found (M − H)⁻ = 474.07 m/z. |
| (3S)-3-[({[2-methyl-6-oxo-1-(phenylmethyl)-4-(2-pyridinyl)-1,6-dihydro-5-pyrimidinyl]amino}carbonyl)amino]-3-(4-methylphenyl)propanoic acid | 25 | Calculated (M + H)⁺ = 498.22 m/z; Found (M + H)⁺ = 498.10 m/z. |
| 3-(3-chlorophenyl)-3-{[({1-[(2-chlorophenyl)methyl]-4-hydroxy-2-oxo-1,2-dihydro-3-pyridinyl}amino)carbonyl]amino}propanoic acid | 30 | Calculated (M − H)⁻ = 474.06 m/z; Found (M − H)⁻ = 474.03 m/z. |
| 3-{[({1-[(2-chlorophenyl)methyl]-4-hydroxy-2-oxo-1,2-dihydro-3-pyridinyl}amino)carbonyl]amino}-3-(3,4-dichlorophenyl)propanoic acid | 40 | Calculated (M − H)⁻ = 508.02 m/z; Found (M − H)⁻ = 507.97 m/z. |

TABLE 4

| Name | IC$_{50}$ | Mass Spectral Data |
|---|---|---|
| (3S)-3-(1,3-benzodioxol-5-yl)-3-[({[2-oxo-1-(phenylmethyl)-3-azepanyl]amino}carbonyl)amino]propanoic acid | 0.015 | Calculated (M − H)⁻ = 452.18 m/z; Found (M − H)⁻ = 452.10 m/z. |
| (3S)-3-(1,3-benzodioxol-5-yl)-3-{[({1-[(3-cyanophenyl)methyl]-2-oxo-3-azepanyl}amino)carbonyl]amino}propanoic acid | 0.04 | Calculated (M − H)⁻ = 477.18 m/z; Found (M − H)⁻ = 477.14 m/z. |
| (3S)-3-(4-methylphenyl)-3-[({[2-oxo-1-(2-thiophenylmethyl)-1,2-dihydro-3-pyridinyl]amino}carbonyl)amino]propanoic acid | 0.6 | Calculated (M − H)⁻ = 410.11 m/z; Found (M − H)⁻ = 410.00 m/z. |
| (3S)-3-(1,3-benzodioxol-5-yl)-3-[({[2-oxo-1-(phenylmethyl)-1,2-dihydro-3-pyridinyl]amino}carbonyl)amino]propanoic acid | 0.5 | Calculated (M − H)⁻ = 434.13 m/z; Found (M − H)⁻ = 434.05 m/z. |
| (3S)-3-(1,3-benzodioxol-5-yl)-3-{[({1-[(4-methylphenyl)methyl]-2-oxo-1,2-dihydro-3-pyridinyl}amino)carbonyl]amino}propanoic acid | 1 | Calculated (M − H)⁻ = 448.14 m/z; Found (M − H)⁻ = 448.02 m/z. |
| (3S)-3-(1,3-benzodioxol-5-yl)-3-({[(1-{[4-(methyloxy)phenyl]methyl}-2-oxo-1,2-dihydro-3-pyridinyl)amino]carbonyl}amino)propanoic acid | 3 | Calculated (M − H)⁻ = 464.14 m/z; Found (M − H)⁻ = 464.03 m/z. |
| (3S)-3-(1,3-benzodioxol-5-yl)-3-{[({1-[(3-methylphenyl)methyl]-2-oxo-1,2-dihydro-3-pyridinyl}amino)carbonyl]amino}propanoic acid | 1.5 | Calculated (M − H)⁻ = 448.15 m/z; Found (M − H)⁻ = 448.04 m/z. |
| (3S)-3-[3,5-bis(methyloxy)phenyl]-3-[({[2-oxo-1-(2-thiophenylmethyl)-1,2-dihydro-3-pyridinyl]amino}carbonyl)amino]propanoic acid | 0.7 | Calculated (M − H)⁻ = 456.12 m/z; Found(M − H)⁻ = 456.00 m/z. |
| (3S)-3-[4-(methyloxy)phenyl]-3-[({[2-oxo-1-(2-thiophenylmethyl)-1,2-dihydro-3-pyridinyl]amino}carbonyl)amino]propanoic acid | 0.8 | Calculated (M − H)⁻ = 426.11 m/z; Found (M − H)⁻ = 426.00 m/z. |
| (3S)-3-[({[2-oxo-1-(2-thiophenylmethyl)-1,2-dihydro-3-pyridinyl]amino}carbonyl)amino]-3-[3-(trifluoromethyl)phenyl]propanoic acid | 2.5 | Calculated (M − H)⁻ = 464.09 m/z; Found (M − H)⁻ = 463.99 m/z. |
| (3S)-3-(1,3-benzodioxol-5-yl)-3-[({[3-(phenyloxy)phenyl]amino}carbonyl)amino] propanoic acid | 50 | Calculated (M − H)⁻ = 419.12 m/z; Found (M − H)⁻ = 418.97 m/z. |
| (3S)-3-(1,3-benzodioxol-5-yl)-3-{[({3-[(2-thiophenylmethyl)amino]phenyl}amino)carbonyl]amino}propanoic acid | 5 | Calculated (M − H)⁻ = 438.11 m/z; Found (M − H)⁻ = 438.00 m/z. |
| (3S)-3-(1,3-benzodioxol-5-yl)-3-{[({1-[(3-chlorophenyl)methyl]-2-oxo-1,2-dihydro-3-pyridinyl}amino)carbonyl]amino}propanoic acid | 0.8 | Calculated (M − H)⁻ = 468.09 m/z; Found (M − H)⁻ = 468.01 m/z. |
| (3S)-3-(1,3-benzodioxol-5-yl)-3-({[(2-oxo-1-{[3-(trifluoromethyl)phenyl]methyl}-1,2-dihydro-3-pyridinyl)amino]carbonyl}amino)propanoic acid | 0.8 | Calculated (M − H)⁻ = 502.12 m/z; Found (M − H)⁻ = 502.03 m/z. |
| (3S)-3-(4-fluorophenyl)-3-[({[2-oxo-1-(2-thiophenylmethyl)-1,2-dihydro-3-pyridinyl]amino}carbonyl)amino]propanoic acid | 1.6 | Calculated (M − H)⁻ = 414.09 m/z; Found (M − H)⁻ = 414.01 m/z. |
| (3S)-3-(1,3-benzodioxol-5-yl)-3-{[({1-[(4-chlorophenyl)methyl]-2-oxo-1,2-dihydro-3-pyridinyl}amino)carbonyl]amino}propanoic acid | 3 | Calculated (M − H)⁻ = 468.09 m/z; Found (M − H)⁻ = 467.99 m/z. |
| (3S)-3-(1,3-benzodioxol-5-yl)-3-({[(1-{[2-(methyloxy)phenyl]methyl}-2-oxo-1,2-dihydro-3-pyridinyl)amino]carbonyl}amino)propanoic acid | 0.5 | Calculated (M − H)⁻ = 464.14 m/z; Found (M − H)⁻ = 464.04 m/z. |
| (3S)-3-[3-(methyloxy)phenyl]-3-[({[2-oxo-1-(2-thiophenylmethyl)-1,2-dihydro-3-pyridinyl]amino}carbonyl)amino]propanoic acid | 1.4 | Calculated (M − H)⁻ = 426.11 m/z; Found (M − H)⁻ = 426.02 m/z. |
| (3S)-3-[({[2-oxo-1-(2-thiophenylmethyl)-1,2-dihydro-3-pyridinyl]amino}carbonyl)amino]-3-phenylpropanoic acid | 1 | Calculated (M − H)⁻ = 396.10 m/z; Found (M − H)⁻ = 396.01 m/z. |
| (3S)-3-[({[2-oxo-1-(2-thiophenylmethyl)-1,2-dihydro-3-pyridinyl]amino}carbonyl)amino]-3-[3,4,5-tris(methyloxy)phenyl]propanoic acid | 0.3 | Calculated (M − H)⁻ = 486.13 m/z; Found (M − H)⁻ = 485.98 m/z. |

TABLE 4-continued

| Name | IC$_{50}$ | Mass Spectral Data |
|---|---|---|
| (3S)-3-(1,3-benzodioxol-5-yl)-3-{[({1-[(2-chlorophenyl)methyl]-2-oxo-1,2-dihydro-3-pyridinyl}amino)carbonyl]amino}propanoic acid | 0.3 | Calculated (M − H)⁻ = 468.08 m/z; Found (M − H)⁻ = 468.03 m/z. |
| (3S)-3-(1,3-benzodioxol-5-yl)-3-{[({1-[(4-fluorophenyl)methyl]-2-oxo-1,2-dihydro-3-pyridinyl}amino)carbonyl]amino}propanoic acid | 2 | Calculated (M − H)⁻ = 452.12 m/z; Found (M − H)⁻ = 452.00 m/z. |
| 3-(1,3-benzodioxol-5-yl)-2,2-difluoro-3-[({[2-oxo-1-(2-thiophenylmethyl)-1,2-dihydro-3-pyridinyl]amino}carbonyl)amino]propanoic acid | >100 | Calculated (M − H)⁻ = 476.07 m/z; Found (M − H)⁻ = 476.00 m/z. |
| (3S)-3-(1,3-benzodioxol-5-yl)-3-{[({2-oxo-1-[3-(phenyloxy)propyl]-1,2-dihydro-3-pyridinyl}amino)carbonyl]amino}propanoic acid | 14 | Calculated (M − H)⁻ = 478.16 m/z; Found (M − H)⁻ = 478.09 m/z. |
| (3S)-3-(1,3-benzodioxol-5-yl)-3-{[({1-[(3,5-dichlorophenyl)methyl]-2-oxo-1,2-dihydro-3-pyridinyl}amino)carbonyl]amino}propanoic acid | 5 | Calculated (M − H)⁻ = 502.05 m/z; Found (M − H)⁻ = 501.94 m/z. |
| (3S)-3-(1,3-benzodioxol-5-yl)-3-[({[1-(cyclopentylmethyl)-2-oxo-1,2-dihydro-3-pyridinyl]amino}carbonyl)amino]propanoic acid | 6 | Calculated (M − H)⁻ = 426.16 m/z; Found (M − H)⁻ = 426.09 m/z. |
| (3S)-3-(1,3-benzodioxol-5-yl)-3-{[({2-oxo-1-[2-(2-thiophenyl)ethyl]-1,2-dihydro-3-pyridinyl}amino)carbonyl]amino}propanoic acid | 15 | Calculated (M − H)⁻ = 454.09 m/z; Found (M − H)⁻ = 453.99 m/z. |
| (3S)-3-{[({1-[(2-chlorophenyl)methyl]-2-oxo-1,2-dihydro-3-pyridinyl}amino)carbonyl]amino}-3-(4-methylphenyl)propanoic acid | 0.1 | Calculated (M + H)⁺ = 440.14 m/z; Found (M + H)⁺ = 440.09 m/z. |
| (3S)-3-(2,3-dihydro-1-benzofuran-5-yl)-3-[({[2-oxo-1-(2-thiophenylmethyl)-1,2-dihydro-3-pyridinyl]amino}carbonyl)amino]propanoic acid | 0.14 | Calculated (M − H)⁻ = 438.11 m/z; Found (M − H)⁻ = 437.99 m/z. |
| (3S)-3-(3-fluorophenyl)-3-[({[2-oxo-1-(2-thiophenylmethyl)-1,2-dihydro-3-pyridinyl]amino}carbonyl)amino]propanoic acid | 3 | Calculated (M − H)⁻ = 414.09 m/z; Found (M − H)⁻ = 413.99 m/z. |
| (3S)-3-[({[2-oxo-1-(2-thiophenylmethyl)-1,2-dihydro-3-pyridinyl]amino}carbonyl)amino]-3-[4-(trifluoromethyl)phenyl]propanoic acid | 1.5 | Calculated (M − H)⁻ = 464.09 m/z; Found (M − H)⁻ = 463.99 m/z. |
| (3S)-3-(1,3-benzodioxol-5-yl)-3-[({[6-oxo-1-(phenylmethyl)-1,6-dihydro-3-pyridinyl]amino}carbonyl)amino]propanoic acid | 0.5 | Calculated (M − H)⁻ = 434.13 m/z; Found (M − H)⁻ = 434.02 m/z. |
| (3S)-3-[4-fluoro-3-(trifluoromethyl)phenyl]-3-[({[2-oxo-1-(2-thiophenylmethyl)-1,2-dihydro-3-pyridinyl]amino}carbonyl)amino]propanoic acid | 0.35 | Calculated (M − H)⁻ = 482.08 m/z; Found (M − H)⁻ = 481.97 m/z. |
| (3S)-3-[4-(1,1-dimethylethyl)phenyl]-3-[({[2-oxo-1-(2-thiophenylmethyl)-1,2-dihydro-3-pyridinyl]amino}carbonyl)amino]propanoic acid | 2 | Calculated (M − H)⁻ = 452.16 m/z; Found (M − H)⁻ = 452.02 m/z. |
| (3S)-3-(1,3-benzodioxol-5-yl)-3-[({butyl[2,5-dioxo-1-(phenylmethyl)tetrahydro-1H-pyrrol-3-yl]amino}carbonyl)amino]propanoic acid | 70 | Calculated (M − H)⁻ = 494.19 m/z; Found (M − H)⁻ = 494.12 m/z. |
| (3S)-3-{[({1-[(2-chlorophenyl)methyl]-2-oxo-1,2-dihydro-3-pyridinyl}amino)carbonyl]amino}-3-[3,4,5-tris(methyloxy)phenyl]propanoic acid | 0.04 | Calculated (M + H)⁺ = 516.16 m/z; Found (M + H)⁺ = 516.02 m/z. |
| (3S)-3-{[({1-[(2,6-dichlorophenyl)methyl]-2-oxo-1,2-dihydro-3-pyridinyl}amino)carbonyl]amino}-3-(4-methylphenyl)propanoic acid | 0.2 | Calculated (M + H)⁺ = 474.10 m/z; Found (M + H)⁺ = 474.04 m/z. |
| (3S)-3-{[({1-[(2-chlorophenyl)methyl]-2-oxo-1,2-dihydro-3-pyridinyl}amino)carbonyl]amino}-3-[4-fluoro-3-(trifluoromethyl)phenyl]propanoic acid | 0.2 | Calculated (M + H)⁺ = 512.10 m/z; Found (M + H)⁺ = 512.04 m/z. |
| (3S)-3-{[({1-[(2-fluorophenyl)methyl]-2-oxo-1,2-dihydro-3-pyridinyl}amino)carbonyl]amino}-3-(4-methylphenyl)propanoic acid | 0.1 | Calculated (M − H)⁻ = 422.15 m/z; Found (M − H)⁻ = 422.01 m/z. |

TABLE 4-continued

| Name | IC$_{50}$ | Mass Spectral Data |
|---|---|---|
| (3S)-3-(4-methylphenyl)-3-{[({1-[(2-methylphenyl)methyl]-2-oxo-1,2-dihydro-3-pyridinyl}amino)carbonyl]amino}propanoic acid | 0.1 | Calculated (M − H)$^-$ = 418.18 m/z; Found (M − H)$^-$ = 418.02 m/z. |
| (3S)-3-{[({1-[(2-bromophenyl)methyl]-2-oxo-1,2-dihydro-3-pyridinyl}amino)carbonyl]amino}-3-(4-methylphenyl)propanoic acid | 0.05 | Calculated (M + H)$^+$ = 484.09 m/z; Found (M + H)$^+$ = 484.03 m/z. |
| (3S)-3-{[({1-[(2,4-dichlorophenyl)methyl]-2-oxo-1,2-dihydro-3-pyridinyl}amino)carbonyl]amino}-3-(4-methylphenyl)propanoic acid | 0.4 | Calculated (M + H)$^+$ = 474.10 m/z; Found (M + H)$^+$ = 474.05 m/z. |
| (3S)-3-{[({1-[(2-chlorophenyl)methyl]-2-oxo-1,2-dihydro-3-pyridinyl}amino)carbonyl]amino}-3-(2,3-dihydro-1-benzofuran-5-yl)propanoic acid | 0.04 | Calculated (M − H)$^-$ = 466.11 m/z; Found (M − H)$^-$ = 466.00 m/z. |
| (3R)-3-(1,3-benzodioxol-5-yl)-3-{[({1-[(2-chlorophenyl)methyl]-2-oxo-1,2-dihydro-3-pyridinyl}amino)carbonyl]amino}propanoic acid | 2 | Calculated (M − H)$^-$ = 468.09 m/z; Found (M − H)$^-$ = 467.97 m/z. |
| (3S)-3-(4-methylphenyl)-3-({[(2-oxo-1-{[2-(trifluoromethyl)phenyl]methyl}-1,2-dihydro-3-pyridinyl)amino]carbonyl}amino)propanoic acid | 1 | Calculated (M + H)$^+$ = 474.10 m/z; Found (M + H)$^+$ = 474.09 m/z. |
| (3S)-3-{[({1-[(2,5-dichlorophenyl)methyl]-2-oxo-1,2-dihydro-3-pyridinyl}amino)carbonyl]amino}-3-(4-methylphenyl)propanoic acid | 0.15 | Calculated (M + H)$^+$ = 474.10 m/z; Found (M + H)$^+$ = 474.04 m/z. |
| (2R)-2-{[({1-[(2-chlorophenyl)methyl]-2-oxo-1,2-dihydro-3-pyridinyl}amino)carbonyl]amino}-3-phenylpropanoic acid | 50 | Calculated (M − H)$^-$ = 424.10 m/z; Found (M − H)$^-$ = 423.99 m/z. |
| (2R)-2-{[({1-[(2-chlorophenyl)methyl]-2-oxo-1,2-dihydro-3-pyridinyl}amino)carbonyl]amino}-2-phenylethanoic acid | 80 | Calculated (M − H)$^-$ = 410.08 m/z; Found (M − H)$^-$ = 409.95 m/z. |
| (3S)-3-{[({1-[(2-chlorophenyl)methyl]-2-oxo-1,2-dihydro-3-pyridinyl}amino)carbonyl]amino}-3-(3,5-dimethylphenyl)propanoic acid | 0.1 | Calculated (M − H)$^-$ = 452.14 m/z; Found (M − H)$^-$ = 451.96 m/z. |
| (3S)-3-{[({1-[(2-chlorophenyl)methyl]-2-oxo-1,2-dihydro-3-pyridinyl}amino)carbonyl]amino}-3-phenylpropanoic acid | 0.1 | Calculated (M − H)$^-$ = 424.10 m/z; Found (M − H)$^-$ = 424.07 m/z. |
| (3S)-3-{[({1-[(2-chlorophenyl)methyl]-2-oxo-1,2-dihydro-3-pyridinyl}amino)carbonyl]amino}-3-[4-(methyloxy)phenyl]propanoic acid | 0.1 | Calculated (M − H)$^-$ = 454.11 m/z; Found (M − H)$^-$ = 454.01 m/z. |
| (3S)-3-{[({1-[(2-chlorophenyl)methyl]-2-oxo-1,2-dihydro-3-pyridinyl}amino)carbonyl]amino}-3-(4-hydroxyphenyl)propanoic acid | 0.1 | Calculated (M − H)$^-$ = 440.10 m/z; Found (M − H)$^-$ = 440.00 m/z. |
| (3S)-3-({[(1-{[3-(methyloxy)phenyl]methyl}-2-oxo-1,2-dihydro-3-pyridinyl)amino]carbonyl}amino)-3-(4-methylphenyl)propanoic acid | 0.2 | Calculated (M − H)$^-$ = 434.17 m/z; Found (M − H)$^-$ = 434.01 m/z. |
| (3S)-3-{[({1-[(2-bromophenyl)methyl]-2-oxo-1,2-dihydro-3-pyridinyl}amino)carbonyl]amino}-3-[3,4,5-tris(methyloxy)phenyl]propanoic acid | 0.08 | Calculated (M − H)$^-$ = 558.09 m/z; Found (M − H)$^-$ = 557.87 m/z. |
| (3S)-3-{[({1-[(2-chlorophenyl)methyl]-2-oxo-1,2-dihydro-3-pyridinyl}amino)carbonyl]amino}-3-(3,4-dimethylphenyl)propanoic acid | 0.09 | Calculated (M + H)$^+$ = 454.15 m/z; Found (M + H)$^+$ = 454.07 m/z. |
| (3S)-3-[({[5-chloro-2-hydroxy-3-(phenylmethyl)phenyl]amino}carbonyl)amino]-3-(4-methylphenyl)propanoic acid | 8 | Calculated (M − H)$^-$ = 437.12 m/z; Found (M − H)$^-$ = 437.06 m/z. |
| (3S)-3-(4-methylphenyl)-3-[({[3-(phenylmethyl)phenyl]amino}carbonyl)amino]propanoic acid | 10 | Calculated (M − H)$^-$ = 387.17 m/z; Found (M − H)$^-$ = 387.00 m/z. |
| (3S)-3-{[({1-[(2-chlorophenyl)methyl]-2-oxo-1,2-dihydro-3-pyridinyl}amino)carbonyl]amino}-3-[3-methyl-4-(methyloxy)phenyl]propanoic acid | 0.04 | Calculated (M − H)$^-$ = 468.13 m/z; Found (M − H)$^-$ = 468.01 m/z. |

TABLE 4-continued

| Name | IC$_{50}$ | Mass Spectral Data |
|---|---|---|
| (3S)-3-{[({1-[(2-chlorophenyl)methyl]-2-oxo-1,2-dihydro-3-pyridinyl}amino)carbonyl]amino}-3-(4-hydroxy-3-methylphenyl)propanoic acid | 0.07 | Calculated (M − H)$^-$ = 454.11 m/z; Found (M − H)$^-$ = 454.00 m/z. |
| (3S)-3-{[({1-[(2,3-dichlorophenyl)methyl]-2-oxo-1,2-dihydro-3-pyridinyl}amino)carbonyl]amino}-3-(4-methylphenyl)propanoic acid | 0.35 | Calculated (M − H)$^-$ = 472.08 m/z; Found (M − H)$^-$ = 471.94 m/z. |
| (3S)-3-[({1-([1,1'-biphenyl]-2-ylmethyl)-2-oxo-1,2-dihydro-3-pyridinyl]amino}carbonyl)amino]-3-(4-methylphenyl)propanoic acid | 2.5 | Calculated (M − H)$^-$ = 480.19 m/z; Found (M − H)$^-$ = 480.05 m/z. |
| (3S)-3-{[({1-[(2-chlorophenyl)methyl]-2-oxo-1,2-dihydro-3-pyridinyl}amino)carbonyl]amino}-3-(3-methylphenyl)propanoic acid | 0.2 | Calculated (M − H)$^-$ = 438.12 m/z; Found (M − H)$^-$ = 438.00 m/z. |
| (3S)-3-{[({1-[(2-chlorophenyl)methyl]-2-oxo-1,2-dihydro-3-pyridinyl}amino)carbonyl]amino}-3-(2-methylphenyl)propanoic acid | 3 | Calculated (M − H)$^-$ = 438.12 m/z; Found (M − H)$^-$ = 437.99 m/z. |
| (3S)-3-{[({1-[(2-chlorophenyl)methyl]-2-oxo-1,2-dihydro-3-pyridinyl}amino)carbonyl]amino}-3-(2,3-dihydro-1H-inden-5-yl)propanoic acid | 0.3 | Calculated (M − H)$^-$ = 464.13 m/z; Found (M − H)$^-$ = 464.03 m/z. |
| (3S)-3-{[({1-{(2-cyanophenyl)methyl]-2-oxo-1,2-dihydro-3-pyridinyl}amino)carbonyl]amino}-3-(4-methylphenyl)propanoic acid | 0.1 | Calculated (M + H)$^+$ = 431.18 m/z; Found (M + H)$^+$ = 431.09 m/z. |
| (3S)-3-[2,6-bis(methyloxy)phenyl]-3-{[({1-[(2-chlorophenyl)methyl]-2-oxo-1,2-dihydro-3-pyridinyl}amino)carbonyl]amino}propanoic acid | 6 | Calculated (M − H)$^-$ = 484.14 m/z; Found (M − H)$^-$ = 483.96 m/z. |
| (3S)-3-{[({1-[(3-hydroxyphenyl)methyl]-2-oxo-1,2-dihydro-3-pyridinyl}amino)carbonyl]amino}-3-(4-methylphenyl)propanoic acid | 0.2 | Calculated (M + H)$^+$ = 420.18 m/z; Found (M + H)$^+$ = 422.05 m/z. |
| (3S)-3-[({[2-methyl-6-oxo-1-(phenylmethyl)-1,6-dihydro-5-pyrimidinyl]amino}carbonyl)amino]-3-(4-methylphenyl)propanoic acid | 0.1 | Calculated (M − H)$^-$ = 419.17 m/z; Found (M − H)$^-$ = 419.03 m/z. |
| (3S)-3-[({1-[(2-chlorophenyl)methyl]-4-oxo-1,4-dihydro-3-pyridinyl}amino)carbonyl]amino}-3-(4-methylphenyl)propanoic acid | 0.1 | Calculated (M − H)$^-$ = 438.12 m/z; Found (M − H)$^-$ = 438.10 m/z. |
| (3S)-3-(4-methylphenyl)-3-{[({1-[(2-nitrophenyl)methyl]-2-oxo-1,2-dihydro-3-pyridinyl}amino)carbonyl]amino}propanoic acid | 1 | Calculated (M + H)$^+$ = 451.17 m/z; Found (M + H)$^+$ = 451.07 m/z. |
| (3S)-3-(4-methylphenyl)-3-{[({1-[(4-nitrophenyl)methyl]-2-oxo-1,2-dihydro-3-pyridinyl}amino)carbonyl]amino}propanoic acid | 1 | Calculated (M + H)$^+$ = 451.17 m/z; Found (M + H)$^+$ = 451.09 m/z. |
| (3S)-3-{[({1-[(2-chlorophenyl)methyl]-2-oxo-1,2-dihydro-3-pyridinyl}amino)carbonyl]amino}-3-(2,6-dihydroxyphenyl)propanoic acid | 3 | Calculated (M − H)$^-$ = 456.10 m/z; Found (M − H)$^-$ = 456.04 m/z. |
| (3S)-3-{[({1-[(2,6-difluorophenyl)methyl]-2-oxo-1,2-dihydro-3-pyridinyl}amino)carbonyl]amino}-3-(4-methylphenyl)propanoic acid | 0.3 | Calculated (M − H)$^-$ = 440.14 m/z; Found (M − H)$^-$ = 440.00 m/z. |
| (3S)-3-{[({1-[(2,4-difluorophenyl)methyl]-2-oxo-1,2-dihydro-3-pyridinyl}amino)carbonyl]amino}-3-(4-methylphenyl)propanoic acid | 1.3 | Calculated (M − H)$^-$ = 440.14 m/z; Found (M − H)$^-$ = 439.96 m/z. |
| (3S)-3-{[({1-[(2,5-difluorophenyl)methyl]-2-oxo-1,2-dihydro-3-pyridinyl}amino)carbonyl]amino}-3-(4-methylphenyl)propanoic acid | 0.8 | Calculated (M − H)$^-$ = 440.14 m/z; Found (M − H)$^-$ = 439.96 m/z. |
| (3S)-3-{[({1-[(2-chlorophenyl)methyl]-2-methyl-6-oxo-1,6-dihydro-5-pyrimidinyl}amino)carbonyl]amino}-3-(4-methylphenyl)propanoic acid | 0.09 | Calculated (M − H)$^-$ = 453.13 m/z; Found (M − H)$^-$ = 453.00 m/z. |
| (3S)-3-{[({1-[(2-chloro-6-fluorophenyl)methyl]-2-oxo-1,2-dihydro-3-pyridinyl}amino)carbonyl]amino}-3-(4-methylphenyl)propanoic acid | 0.1 | Calculated (M − H)$^-$ = 456.11 m/z; Found (M − H)$^-$ = 455.94 m/z. |

TABLE 4-continued

| Name | IC$_{50}$ | Mass Spectral Data |
| --- | --- | --- |
| (3S)-3-{[({1-[(2-bromo-5-fluorophenyl)methyl]-2-oxo-1,2-dihydro-3-pyridinyl}amino)carbonyl]amino}-3-(4-methylphenyl)propanoic acid | 0.5 | Calculated (M − H)$^-$ = 500.06 m/z; Found (M − H)$^-$ = 499.91 m/z. |
| (3S)-3-{[({1-[(2-chloro-4-fluorophenyl)methyl]-2-oxo-1,2-dihydro-3-pyridinyl}amino)carbonyl]amino}-3-(4-methylphenyl)propanoic acid | 0.35 | Calculated (M − H)$^-$ = 456.11 m/z; Found (M − H)$^-$ = 455.93 m/z; |
| (3S)-3-{[({1-[(2-bromophenyl)methyl]-2-oxo-1,2-dihydro-3-pyridinyl}amino)carbonyl]amino}-3-[3-methyl-4-(methyloxy)phenyl]propanoic acid | 0.2 | Calculated (M − H)$^-$ = 512.08 m/z; Found (M − H)$^-$ = 511.96 m/z. |
| (3S)-3-{[({1-[(3,5-dimethyl-4-isoxazolyl)methyl]-2-oxo-1,2-dihydro-3-pyridinyl}amino)carbonyl]amino}-3-(4-methylphenyl)propanoic acid | 3 | Calculated (M − H)$^-$ = 423.17 m/z; Found (M − H)$^-$ = 423.02 m/z. |
| (3S)-3-(4-methylphenyl)-3-{[({2-oxo-1-[(2,4,6-trimethylphenyl)methyl]-1,2-dihydro-3-pyridinyl}amino)carbonyl]amino}propanoic acid | 2.5 | Calculated (M − H)$^-$ = 446.21 m/z; Found (M − H)$^-$ = 446.08 m/z. |
| (3S)-3-(4-methylphenyl)-3-{[({1-[(2-methyl-1,3-thiazol-4-yl)methyl]-2-oxo-1,2-dihydro-3-pyridinyl}amino)carbonyl]amino}propanoic acid | 1 | Calculated (M − H)$^-$ = 425.13 m/z; Found (M − H)$^-$ = 424.99 m/z. |
| (3S)-3-({[(1-{[4-(1,1-dimethylethyl)phenyl]methyl}-2-oxo-1,2-dihydro-3-pyridinyl)amino]carbonyl}amino)-3-(4-methylphenyl)propanoic acid | 6 | Calculated (M − H)$^-$ = 460.22 m/z; Found (M − H)$^-$ = 460.07 m/z. |
| (3S)-3-[({[1-(1,3-benzoxazol-2-ylmethyl)-2-oxo-1,2-dihydro-3-pyridinyl]amino}carbonyl)amino]-3-(4-methylphenyl)propanoic acid | >10 | Calculated (M − H)$^-$ = 445.15 m/z; Found (M − H)$^-$ = 445.01 m/z. |
| (3S)-3-({[(1-{2-[(2-hydroxyphenyl)amino]-2-oxoethyl}-2-oxo-1,2-dihydro-3-pyridinyl)amino]carbonyl}amino)-3-(4-methylphenyl)propanoic acid | >10 | Calculated (M − H)$^-$ = 463.16 m/z; Found (M − H)$^-$ = 463.06 m/z. |
| (3S)-3-{[({1-[(2-chloro-6-nitrophenyl)methyl]-2-oxo-1,2-dihydro-3-pyridinyl}amino)carbonyl]amino}-3-(4-methylphenyl)propanoic acid | 4 | Calculated (M − H)$^-$ = 483.11 m/z; Found (M − H)$^-$ = 483.01 m/z. |
| (3S)-3-{[({1-[(5-chloro-2-fluorophenyl)methyl]-2-oxo-1,2-dihydro-3-pyridinyl}amino)carbonyl]amino}-3-(4-methylphenyl)propanoic acid | 2.5 | Calculated (M − H)$^-$ = 456.11 m/z; Found (M − H)$^-$ = 456.00 m/z. |
| (3S)-3-{[({1-[(2-amino-6-chlorophenyl)methyl]-2-oxo-1,2-dihydro-3-pyridinyl}amino)carbonyl]amino}-3-(4-methylphenyl)propanoic acid | 2 | Calculated (M − H)$^-$ = 453.13 m/z; Found (M − H)$^-$ = 453.02 m/z. |
| (3S)-3-({[(1-{[2-fluoro-4-(trifluoromethyl)phenyl]methyl}-2-oxo-1,2-dihydro-3-pyridinyl)amino]carbonyl}amino)-3-(4-methylphenyl)propanoic acid | 3 | Calculated (M − H)$^-$ = 490.14 m/z; Found (M − H)$^-$ = 489.99 m/z. |
| (3S)-3-{[({1-[(5-chloro-2-thiophenyl)methyl]-2-oxo-1,2-dihydro-3-pyridinyl}amino)carbonyl]amino}-3-(4-methylphenyl)propanoic acid | 1.3 | Calculated (M − H)$^-$ = 444.08 m/z; Found (M − H)$^-$ = 443.97 m/z. |
| (3S)-3-{[({1-[(2-bromo-5-nitrophenyl)methyl]-2-oxo-1,2-dihydro-3-pyridinyl}amino)carbonyl]amino}-3-(4-methylphenyl)propanoic acid | 2 | Calculated (M − H)$^-$ = 527.06 m/z; Found (M − H)$^-$ = 526.95 m/z. |
| 3-(4-chlorophenyl)-3-{[({1-[(2-chlorophenyl)methyl]-4-hydroxy-2-oxo-1,2-dihydro-3-pyridinyl}amino)carbonyl]amino}propanoic acid | 0.03 | Calculated (M − H)$^-$ = 474.06 m/z; Found (M − H)$^-$ = 474.07 m/z. |
| (3S)-3-[({[2-methyl-6-oxo-1-(phenylmethyl)-4-(2-pyridinyl)-1,6-dihydro-5-pyrimidinyl]amino}carbonyl)amino]-3-(4-methylphenyl)propanoic acid | 0.025 | Calculated (M + H)$^+$ = 498.22 m/z; Found (M + H)$^+$ = 498.10 m/z. |
| (3S)-3-{[({1-[(5-amino-2-bromophenyl)methyl]-2-oxo-1,2-dihydro-3-pyridinyl}amino)carbonyl]amino}-3-(4-methylphenyl)propanoic acid | 0.08 | Calculated (M − H)$^-$ = 497.08 m/z; Found (M − H)$^-$ = 497.02 m/z. |
| (3S)-3-{[({1-[(2,5-dimethylphenyl)methyl]-2-oxo-1,2-dihydro-3-pyridinyl}amino)carbonyl]amino}-3-(4-methylphenyl)propanoic acid | 0.15 | Calculated (M − H)$^-$ = 432.19 m/z; Found (M − H)$^-$ = 432.04 m/z. |

TABLE 4-continued

| Name | IC$_{50}$ | Mass Spectral Data |
| --- | --- | --- |
| 3-(3-chlorophenyl)-3-{[({1-[(2-chlorophenyl)methyl]-4-hydroxy-2-oxo-1,2-dihydro-3-pyridinyl}amino)carbonyl]amino}propanoic acid | 0.03 | Calculated (M − H)$^-$ = 474.06 m/z; Found (M − H)$^-$ = 474.03 m/z. |
| 3-{[({1-[(2-chlorophenyl)methyl]-4-hydroxy-2-oxo-1,2-dihydro-3-pyridinyl}amino)carbonyl]amino}-3-(3,4-dichlorophenyl)propanoic acid | 0.04 | Calculated (M − H)$^-$ = 508.02 m/z; Found (M − H)$^-$ = 507.97 m/z. |
| (3S)-3-({[(1-{[5-(acetylamino)-2-bromophenyl]methyl}-2-oxo-1,2-dihydro-3-pyridinyl]amino]carbonyl}amino)-3-(4-methylphenyl)propanoic acid | 0.2 | Calculated (M − H)$^-$ = 539.09 m/z; Found (M − H)$^-$ = 539.02 m/z. |
| (3S)-3-[({1-({2-bromo-5-[(methylsulfonyl)amino]phenyl}methyl)-2-oxo-1,2-dihydro-3-pyridinyl]amino}carbonyl)amino]-3-(4-methylphenyl)propanoic acid | 0.25 | Calculated (M − H)$^-$ = 575.06 m/z; Found (M − H)$^-$ = 575.01 m/z. |
| 3-(4-chlorophenyl)-3-{[({1-[(2-chlorophenyl)methyl]-2-oxo-1,2-dihydro-3-pyridinyl}amino)carbonyl]amino}propanoic acid | 0.4 | Calculated (M − H)$^-$ = 458.07 m/z; Found (M − H)$^-$ = 457.96 m/z. |
| 3-(3-chlorophenyl)-3-{[({1-[(2-chlorophenyl)methyl]-2-oxo-1,2-dihydro-3-pyridinyl}amino)carbonyl]amino}propanoic acid | 1 | Calculated (M − H)$^-$ = 458.07 m/z; Found (M − H)$^-$ = 457.93 m/z. |
| 3-{[({1-[(2-chlorophenyl)methyl]-2-oxo-1,2-dihydro-3-pyridinyl}amino)carbonyl]amino}-3-(3,4-dichlorophenyl)propanoic acid | 1 | Calculated (M − H)$^-$ = 492.03 m/z; Found (M − H)$^-$ = 491.85 m/z. |
| (3S)-3-{[({1-[(2-bromo-4-chlorophenyl)methyl]-2-oxo-1,2-dihydro-3-pyridinyl}amino)carbonyl]amino}-3-(4-methylphenyl)propanoic acid | 1 | Calculated (M − H)$^-$ = 516.03 m/z; Found (M − H)$^-$ = 515.91 m/z. |
| (3S)-3-{[({1-[(4-chlorophenyl)methyl]-2-oxo-1,2-dihydro-3-pyridinyl}amino)carbonyl]amino}-3-(4-methylphenyl)propanoic acid | 2 | Calculated (M − H)$^-$ = 438.12 m/z; Found (M − H)$^-$ = 437.88 m/z. |
| (3S)-3-{[({1-[(2-chlorophenyl)methyl]-4-hydroxy-2-oxo-1,2-dihydro-3-pyridinyl}amino)carbonyl]amino}-3-[2,3-dimethyl-4-(methyloxy)phenyl]propanoic acid | 0.035 | Calculated (M − H)$^-$ = 498.14 m/z; Found (M − H)$^-$ = 498.05 m/z. |
| (3S)-3-{[({1-[(2-chlorophenyl)methyl]-4-hydroxy-2-oxo-1,2-dihydro-3-pyridinyl}amino)carbonyl]amino}-3-{4-[(trifluoromethyl)oxy]phenyl}propanoic acid | 0.015 | Calculated (M − H)$^-$ = 524.08 m/z; Found (M − H)$^-$ = 524.03 m/z. |
| (3R)-3-[({[1-[(2-chlorophenyl)methyl]-4-(1,4-oxazinan-4-yl)-2-oxo-1,2-dihydro-3-pyridinyl}amino}carbonyl)amino]-5-methylhexanoic acid | 0.1 | Calculated (M − H)$^-$ = 489.19 m/z; Found (M − H)$^-$ = 489.13 m/z. |
| (3S)-3-[({[4-hydroxy-6-methyl-2-oxo-1-(phenylmethyl)-1,2-dihydro-3-pyridinyl]amino}carbonyl)amino]-3-(4-methylphenyl)propanoic acid | 0.035 | Calculated (M − H)$^-$ = 434.17 m/z; Found (M − H)$^-$ = 434.08 m/z. |
| (3S)-3-{[({1-[(2-chlorophenyl)methyl]-2-oxo-4-[(propylsulfonyl)amino]-1,2-dihydro-3-pyridinyl}amino)carbonyl]amino}-3-(4-methylphenyl)propanoic acid | 0.030 | Calculated (M − H)$^-$ = 559.14 m/z; Found (M − H)$^-$ = 559.04 m/z. |
| (3S)-3-{[({1-[(2-chlorophenyl)methyl]-4-hydroxy-2-oxo-1,2-dihydro-3-pyridinyl}amino)carbonyl]amino}-3-(4-ethylphenyl)propanoic acid | 0.025 | Calculated (M − H)$^-$ = 468.13 m/z; Found (M − H)$^-$ = 468.06 m/z. |
| (3S)-3-{[({1-[(2-chlorophenyl)methyl]-4-hydroxy-2-oxo-1,2-dihydro-3-pyridinyl}amino)carbonyl]amino}-3-[4-(ethyloxy)phenyl]propanoic acid | 0.02 | Calculated (M − H)$^-$ = 484.13 m/z; Found (M − H)$^-$ = 484.06 m/z. |
| (3S)-3-[({[4-hydroxy-2-oxo-1-(phenylmethyl)-1,2-dihydro-3-pyridinyl]amino}carbonyl)amino]-3-(4-methylphenyl)propanoic acid | 0.030 | Calculated (M − H)$^-$ = 420.16 m/z; Found (M − H)$^-$ = 420.08 m/z. |

TABLE 5

| Name | IC$_{50}$ (μM) | Mass Spectral Data |
| --- | --- | --- |
| (3S)-3-[({[1-(3-tert-butyl-2-methoxybenzyl)-2-oxo-1,2-dihydropyridin-3-yl]amino}carbonyl)amino]-3-(4-methylphenyl)propanoic acid | 2.5 | Calculated (M − H)$^-$ = 490.23 m/z; Found (M − H)$^-$ = 490.11 m/z. |
| (3S)-3-[({[1-(4-fluorobenzyl)-2-oxo-1,2-dihydropyridin-3-yl]amino}carbonyl)amino]-3-(4-methylphenyl)propanoic acid | 2 | Calculated (M − H)$^-$ = 422.12 m/z; Found (M − H)$^-$ = 422.00 m/z. |
| (3S)-3-[({[1-(2-chlorobenzyl)-4-hydroxy-2-oxo-1,2-dihydropyridin-3-yl]amino}carbonyl)amino]-3-[4-fluoro-3-(trifluoromethyl)phenyl]propanoic acid | 0.025 | Calculated (M − H)$^-$ = 526.08 m/z; Found (M − H)$^-$ = 526.01 m/z. |
| (3S)-3-[({[1-(2,5-dimethylbenzyl)-4-hydroxy-2-oxo-1,2-dihydropyridin-3-yl]amino}carbonyl)amino]-3-(4-methylphenyl)propanoic acid | 0.02 | Calculated (M − H)$^-$ = 448.19 m/z; Found (M − H)$^-$ = 448.00 m/z. |
| (3S)-3-[({[4-hydroxy-1-(2-methylbenzyl)-2-oxo-1,2-dihydropyridin-3-yl]amino}carbonyl)amino]-3-(4-methylphenyl)propanoic acid | 0.02 | Calculated (M − H)$^-$ = 434.17 m/z; Found (M − H)$^-$ = 434.05 m/z. |
| (3S)-3-[({[1-(2-hydroxybenzyl)-2-oxo-1,2-dihydropyridin-3-yl]amino}carbonyl)amino]-3-(4-methylphenyl)propanoic acid | 0.2 | Calculated (M − H)$^-$ = 420.16 m/z; Found (M − H)$^-$ = 420.09 m/z. |
| (3S)-3-[({[1-(3-chlorobenzyl)-2-oxo-1,2-dihydropyridin-3-yl]amino}carbonyl)amino]-3-(4-methylphenyl)propanoic acid | 0.5 | Calculated (M − H)$^-$ = 438.12 m/z; Found (M − H)$^-$ = 438.01 m/z. |
| (3S)-3-[({[1-(2-chloro-6-methoxybenzyl)-2-oxo-1,2-dihydropyridin-3-yl]amino}carbonyl)amino]-3-(4-methylphenyl)propanoic acid | 0.1 | Calculated (M − H)$^-$ = 468.13 m/z; Found (M − H)$^-$ = 468.08 m/z. |
| (3S)-3-[({[1-(2-chlorobenzyl)-4-hydroxy-2-oxo-1,2-dihydropyridin-3-yl]amino}carbonyl)amino]-3-(4-methoxy-3,5-dimethylphenyl)propanoic acid | 0.035 | Calculated (M − H)$^-$ = 498.14 m/z; Found (M − H)$^-$ = 497.94 m/z. |
| 4-{3-[({[(1S)-2-carboxy-1-(4-methylphenyl)ethyl]amino}carbonyl)amino]-1-(2-chlorobenzyl)-2-oxo-1,2-dihydropyridin-4-yl]amino}benzoic acid | 0.004 | Calculated (M − H)$^-$ = 573.15 m/z; Found (M − H)$^-$ = 572.92 m/z. |
| (3S)-3-{[({1-(2-chlorobenzyl)-4-[(2,2-dimethylpropanoyl)amino]-2-oxo-1,2-dihydropyridin-3-yl}amino)carbonyl]amino}-3-(4-methylphenyl)propanoic acid | 0.01 | Calculated (M − H)$^-$ = 537.19 m/z; Found (M − H)$^-$ = 536.88 m/z. |
| (3S)-3-[({[1-(2-chloro-5-methoxybenzyl)-2-oxo-1,2-dihydropyridin-3-yl]amino}carbonyl)amino]-3-(4-methylphenyl)propanoic acid | 0.09 | Calculated (M − H)$^-$ = 468.13 m/z; Found (M − H)$^-$ = 467.99 m/z. |
| (3R)-3-[({[1-(2-chlorobenzyl)-4-hydroxy-2-oxo-1,2-dihydropyridin-3-yl]amino}carbonyl)amino]butanoic acid | 0.19 | Calculated (M − H)$^-$ = 378.09 m/z; Found (M − H)$^-$ = 378.01 m/z. |
| (3S)-3-[({[4-{[(tert-butylamino)carbonyl]amino}-1-(2-chlorobenzyl)-2-oxo-1,2-dihydropyridin-3-yl]amino}carbonyl)amino]-3-(4-methylphenyl)propanoic acid | 0.01 | Calculated (M − H)$^-$ = 552.20 m/z; Found (M − H)$^-$ = 551.89 m/z. |
| (3S)-3-[({[1-(2-chloro-5-hydroxybenzyl)-2-oxo-1,2-dihydropyridin-3-yl]amino}carbonyl)amino]-3-(4-methylphenyl)propanoic acid | 0.25 | Calculated (M − H)$^-$ = 454.12 m/z; Found (M − H)$^-$ = 454.03 m/z. |
| (3S)-3-[({[1-(2-cyanobenzyl)-4-hydroxy-2-oxo-1,2-dihydropyridin-3-yl]amino}carbonyl)amino]-3-(4-methylphenyl)propanoic acid | 0.009 | Calculated (M − H)$^-$ = 445.15 m/z; Found (M − H)$^-$ = 445.01 m/z. |
| (3S)-3-[({[1-(2,4-dichlorobenzyl)-4-hydroxy-2-oxo-1,2-dihydropyridin-3-yl]amino}carbonyl)amino]-3-(4-methylphenyl)propanoic acid | 0.06 | Calculated (M − H)$^-$ = 488.08 m/z; Found (M − H)$^-$ = 487.96 m/z. |
| (3S)-3-[({[4-hydroxy-1-(2-methoxybenzyl)-2-oxo-1,2-dihydropyridin-3-yl]amino}carbonyl)amino]-3-(4-methylphenyl)propanoic acid | 0.08 | Calculated (M − H)$^-$ = 450.17 m/z; Found (M − H)$^-$ = 450.02 m/z. |
| (3S)-3-[({[1-(2-chlorobenzyl)-4-hydroxy-2-oxo-1,2-dihydropyridin-3-yl]amino}carbonyl)amino]-3-(4-methoxy-2,5-dimethylphenyl)propanoic acid | 0.08 | Calculated (M − H)$^-$ = 498.14 m/z; Found (M − H)$^-$ = 497.95 m/z. |
| (3S)-3-[({[1-(2-chloro-6-hydroxybenzyl)-2-oxo-1,2-dihydropyridin-3-yl]amino}carbonyl)amino]-3-(4-methylphenyl)propanoic acid | 0.1 | Calculated (M − H)$^-$ = 454.12 m/z; Found (M − H)$^-$ = 454.05 m/z. |
| (3S)-3-[({[1-(3-tert-butyl-2-hydroxybenzyl)-2-oxo-1,2-dihydropyridin-3-yl]amino}carbonyl)amino]-3-(4-methylphenyl)propanoic acid | 4 | Calculated (M − H)$^-$ = 476.02 m/z; Found (M − H)$^-$ = 476.00 m/z. |
| (3R)-3-[({[1-(2-chlorobenzyl)-4-hydroxy-2-oxo-1,2-dihydropyridin-3-yl]amino}carbonyl)amino]-3-(4-methylphenyl)propanoic acid | 0.3 | Calculated (M − H)$^-$ = 454.17 m/z; Found (M − H)$^-$ = 454.05 m/z. |
| (3S)-3-[({[1-(2-chlorobenzyl)-4-hydroxy-2-oxo-1,2-dihydropyridin-3-yl]amino}carbonyl)amino]-3-(3-ethylphenyl)propanoic acid | 0.015 | Calculated (M − H)$^-$ = 468.13 m/z; Found (M − H)$^-$ = 467.95 m/z. |
| (3S)-3-[({[1-(2-chlorobenzyl)-4-hydroxy-2-oxo-1,2-dihydropyridin-3-yl]amino}carbonyl)amino]-3-(2,3-dihydro-1,4-benzodioxin-6-yl)propanoic acid | 0.01 | Calculated (M − H)$^-$ = 498.10 m/z; Found (M − H)$^-$ = 497.85 m/z. |

TABLE 5-continued

| Name | IC$_{50}$ (μM) | Mass Spectral Data |
| --- | --- | --- |
| (3S)-3-[({[1-(2,5-difluorobenzyl)-4-hydroxy-2-oxo-1,2-dihydropyridin-3-yl]amino}carbonyl)amino]-3-(4-methylphenyl)propanoic acid | 0.015 | Calculated (M − H)⁻ = 456.14 m/z; Found (M − H)⁻ = 455.96 m/z. |
| (3S)-3-[({[1-(2-chlorobenzyl)-4-hydroxy-2-oxo-1,2-dihydropyridin-3-yl]amino}carbonyl)amino]-4-(4-methylphenyl)butanoic acid | 30 | Calculated (M − H)⁻ = 468.13 m/z; Found (M − H)⁻ = 467.87 m/z. |
| (3S)-3-{[({1-[2-chloro-5-(methylthio)benzyl]-4-hydroxy-2-oxo-1,2-dihydropyridin-3-yl}amino)carbonyl]amino}-3-(4-methylphenyl)propanoic acid | 0.015 | Calculated (M − H)⁻ = 500.10 m/z; Found (M − H)⁻ = 499.92 m/z. |
| (3S)-3-[({[1-(2-chlorobenzyl)-4-hydroxy-2-oxo-1,2-dihydropyridin-3-yl]amino}carbonyl)amino]-3-(7-methoxy-1,3-benzodioxol-5-yl)propanoic acid | 0.005 | Calculated (M − H)⁻ = 514.10 m/z; Found (M − H)⁻ = 513.86 m/z. |
| (3S)-3-[({[1-(2-chlorobenzyl)-4-hydroxy-2-oxo-1,2-dihydropyridin-3-yl]amino}carbonyl)amino]-3-(3-ethoxy-4-methoxyphenyl)propanoic acid | 0.002 | Calculated (M − H)⁻ = 514.13 m/z; Found (M − H)⁻ = 513.90 m/z. |
| (3S)-3-[({[1-(2-chlorobenzyl)-4-hydroxy-2-oxo-1,2-dihydropyridin-3-yl]amino}carbonyl)amino]-3-(3-fluoro-4-methoxyphenyl)propanoic acid | 0.015 | Calculated (M − H)⁻ = 488.10 m/z; Found (M − H)⁻ = 487.92 m/z. |
| (3S)-3-[({[1-(2-chlorobenzyl)-4-hydroxy-2-oxo-1,2-dihydropyridin-3-yl]amino}carbonyl)amino]-3-(3,4-dimethoxyphenyl)propanoic acid | 0.002 | Calculated (M − H)⁻ = 500.12 m/z; Found (M − H)⁻ = 500.01 m/z. |
| (3S)-3-[({[1-(4-fluorobenzyl)-4-hydroxy-2-oxo-1,2-dihydropyridin-3-yl]amino}carbonyl)amino]-3-(4-methylphenyl)propanoic acid | 0.022 | Calculated (M − H)⁻ = 438.18 m/z; Found (M − H)⁻ = 438.00 m/z. |
| (3S)-3-[({[1-(2-methoxybenzyl)-2-oxo-1,2-dihydropyridin-3-yl]amino}carbonyl)amino]-3-(4-methylphenyl)propanoic acid | 0.25 | Calculated (M − H)⁻ = 434.17 m/z; Found (M − H)⁻ = 433.95 m/z. |
| (3S)-3-[({[1-(2-chlorobenzyl)-4-hydroxy-2-oxo-1,2-dihydropyridin-3-yl]amino}carbonyl)amino]-3-(2,5-dimethylphenyl)propanoic acid | 0.05 | Calculated (M − H)⁻ = 468.13 m/z; Found (M − H)⁻ = 467.94 m/z. |
| (3S)-3-[({[1-(2-chloro-5-methoxybenzyl)-4-hydroxy-2-oxo-1,2-dihydropyridin-3-yl]amino}carbonyl)amino]-3-(4-methylphenyl)propanoic acid | 0.012 | Calculated (M − H)⁻ = 484.13 m/z; Found (M − H)⁻ = 484.03 m/z. |
| (3S)-3-{[({1-[3,5-bis(trifluoromethyl)benzyl]-4-hydroxy-2-oxo-1,2-dihydropyridin-3-yl}amino)carbonyl]amino}-3-(4-methylphenyl)propanoic acid | 0.3 | Calculated (M − H)⁻ = 556.13 m/z; Found (M − H)⁻ = 555.95 m/z. |
| (3S)-3-[({[1-(4-tert-butylbenzyl)-4-hydroxy-2-oxo-1,2-dihydropyridin-3-yl]amino}carbonyl)amino]-3-(4-methylphenyl)propanoic acid | 0.03 | Calculated (M − H)⁻ = 476.22 m/z; Found (M − H)⁻ = 476.05 m/z. |
| (3S)-3-[({[1-(3-chlorobenzyl)-4-hydroxy-2-oxo-1,2-dihydropyridin-3-yl]amino}carbonyl)amino]-3-(4-methylphenyl)propanoic acid | 0.015 | Calculated (M − H)⁻ = 454.12 m/z; Found (M − H)⁻ = 453.99 m/z. |
| (3S)-3-[({[1-(4-chlorobenzyl)-4-hydroxy-2-oxo-1,2-dihydropyridin-3-yl]amino}carbonyl)amino]-3-(4-methylphenyl)propanoic acid | 0.007 | Calculated (M − H)⁻ = 454.12 m/z; Found (M − H)⁻ = 454.00 m/z. |
| (3S)-3-{[({4-hydroxy-2-oxo-1-[3-(trifluoromethyl)benzyl]-1,2-dihydropyridin-3-yl}amino)carbonyl]amino}-3-(4-methylphenyl)propanoic acid | 0.017 | Calculated (M − H)⁻ = 488.14 m/z; Found (M − H)⁻ = 487.99 m/z. |
| (3S)-3-[({[1-(2-bromobenzyl)-4-hydroxy-2-oxo-1,2-dihydropyridin-3-yl]amino}carbonyl)amino]-3-(4-methylphenyl)propanoic acid | 0.015 | Calculated (M − H)⁻ = 498.07 m/z; Found (M − H)⁻ = 497.97 m/z. |
| (3S)-3-[({[1-(3,4-dichlorobenzyl)-4-hydroxy-2-oxo-1,2-dihydropyridin-3-yl]amino}carbonyl)amino]-3-(4-methylphenyl)propanoic acid | 0.045 | Calculated (M − H)⁻ = 488.08 m/z; Found (M − H)⁻ = 487.96 m/z. |
| (3S)-3-[({[4-hydroxy-1-(4-methylbenzyl)-2-oxo-1,2-dihydropyridin-3-yl]amino}carbonyl)amino]-3-(4-methylphenyl)propanoic acid | 0.025 | Calculated (M − H)⁻ = 434.17 m/z; Found (M − H)⁻ = 434.05 m/z. |
| (3S)-3-[({[1-(2-chloro-6-methoxybenzyl)-4-hydroxy-2-oxo-1,2-dihydropyridin-3-yl]amino}carbonyl)amino]-3-(4-methylphenyl)propanoic acid | 0.003 | Calculated (M − H)⁻ = 484.13 m/z; Found (M − H)⁻ = 484.02 m/z. |
| (3S)-3-{[({4-hydroxy-2-oxo-1-[4-(trifluoromethyl)benzyl]-1,2-dihydropyridin-3-yl}amino)carbonyl]amino}-3-(4-methylphenyl)propanoic acid | 0.02 | Calculated (M − H)⁻ = 488.14 m/z; Found (M − H)⁻ = 487.99 m/z. |
| (3S)-3-[({[1-(2-chlorobenzyl)-4-hydroxy-2-oxo-1,2-dihydropyridin-3-yl]amino}carbonyl)amino]-3-[3-(trifluoromethoxy)phenyl]propanoic acid | 0.02 | Calculated (M − H)⁻ = 524.08 m/z; Found (M − H)⁻ = 523.91 m/z. |
| (3S)-3-[({[4-hydroxy-1-(3-methylbenzyl)-2-oxo-1,2-dihydropyridin-3-yl]amino}carbonyl)amino]-3-(4-methylphenyl)propanoic acid | 0.055 | Calculated (M − H)⁻ = 434.17 m/z; Found (M − H)⁻ = 433.99 m/z. |

TABLE 5-continued

| Name | IC$_{50}$ (µM) | Mass Spectral Data |
|---|---|---|
| (3S)-3-[({[4-hydroxy-2-oxo-1-(pyridin-2-ylmethyl)-1,2-dihydropyridin-3-yl]amino}carbonyl)amino]-3-(4-methylphenyl)propanoic acid | 0.045 | Calculated (M − H)⁻ = 421.15 m/z; Found (M − H)⁻ = 421.06 m/z. |
| (3S)-3-[({[1-(2-chlorobenzyl)-4-hydroxy-5-methyl-2-oxo-1,2-dihydropyridin-3-yl]amino}carbonyl)amino]-3-(4-methylphenyl)propanoic acid | 0.005 | Calculated (M − H)⁻ = 468.13 m/z; Found (M − H)⁻ = 467.99 m/z. |
| (3S)-3-[({[1-(2,4-difluorobenzyl)-4-hydroxy-2-oxo-1,2-dihydropyridin-3-yl]amino}carbonyl)amino]-3-(4-methylphenyl)propanoic acid | 0.03 | Calculated (M − H)⁻ = 456.14 m/z; Found (M − H)⁻ = 456.01 m/z. |
| (3S)-3-[({[1-(2,6-difluorobenzyl)-4-hydroxy-2-oxo-1,2-dihydropyridin-3-yl]amino}carbonyl)amino]-3-(4-methylphenyl)propanoic acid | 0.008 | Calculated (M − H)⁻ = 456.14 m/z; Found (M − H)⁻ = 456.01 m/z. |
| (3S)-3-{[({4-hydroxy-2-oxo-1-[3-(trifluoromethoxy)benzyl]-1,2-dihydropyridin-3-yl}amino)carbonyl]amino}-3-(4-methylphenyl)propanoic acid | 0.045 | Calculated (M − H)⁻ = 504.14 m/z; Found (M − H)⁻ = 503.98 m/z. |
| (3S)-3-{[({4-hydroxy-2-oxo-1-[4-(trifluoromethoxy)benzyl]-1,2-dihydropyridin-3-yl}amino)carbonyl]amino}-3-(4-methylphenyl)propanoic acid | 0.025 | Calculated (M − H)⁻ = 504.14 m/z; Found (M − H)⁻ = 503.98 m/z. |
| (3S)-3-[({[1-(2-chloro-6-methoxybenzyl)-4-hydroxy-2-oxo-1,2-dihydropyridin-3-yl]amino}carbonyl)amino]-3-(3,5-dimethoxyphenyl)propanoic acid | 0.0015 | Calculated (M − H)⁻ = 530.13 m/z; Found (M − H)⁻ = 529.91 m/z. |
| 3-[({[1-(2-chlorobenzyl)-4-hydroxy-2-oxo-1,2-dihydropyridin-3-yl]amino}carbonyl)amino]-3-(2-furyl)propanoic acid | 0.05 | Calculated (M − H)⁻ = 430.08 m/z; Found (M − H)⁻ = 429.94 m/z. |
| (3S)-3-{[({4-hydroxy-2-oxo-1-[2-(trifluoromethyl)benzyl]-1,2-dihydropyridin-3-yl}amino)carbonyl]amino}-3-(4-methylphenyl)propanoic acid | 0.02 | Calculated (M − H)⁻ = 488.14 m/z; Found (M − H)⁻ = 487.96 m/z. |
| (3R)-3-[({[1-(2-chlorobenzyl)-4-hydroxy-2-oxo-1,2-dihydropyridin-3-yl]amino}carbonyl)amino]-4-(4-methylphenyl)butanoic acid | 0.15 | Calculated (M − H)⁻ = 468.13 m/z; Found (M − H)⁻ = 467.99 m/z. |
| (3S)-3-[({[1-(2-chlorobenzyl)-4-hydroxy-2-oxo-1,2-dihydropyridin-3-yl]amino}carbonyl)amino]-3-(3,4-diethoxyphenyl)propanoic acid | 0.0008 | Calculated (M − H)⁻ = 528.15 m/z; Found (M − H)⁻ = 527.96 m/z. |
| (3S)-3-[({[1-(2-chlorobenzyl)-4-hydroxy-2-oxo-1,2-dihydropyridin-3-yl]amino}carbonyl)amino]-3-(3-ethoxyphenyl)propanoic acid | 0.003 | Calculated (M − H)⁻ = 484.12 m/z; Found (M − H)⁻ = 483.94 m/z. |
| (3S)-3-[({[4-hydroxy-1-(3-methoxybenzyl)-2-oxo-1,2-dihydropyridin-3-yl]amino}carbonyl)amino]-3-(4-methylphenyl)propanoic acid | 0.04 | Calculated (M − H)⁻ = 450.17 m/z; Found (M − H)⁻ = 450.00 m/z. |
| (3S)-3-[({[1-(2,3-dichlorobenzyl)-4-hydroxy-2-oxo-1,2-dihydropyridin-3-yl]amino}carbonyl)amino]-3-(4-methylphenyl)propanoic acid | 0.13 | Calculated (M − H)⁻ = 488.08 m/z; Found (M − H)⁻ = 487.92 m/z. |
| (3S)-3-[({[1-benzyl-2-oxo-5-(trifluoromethyl)-1,2-dihydropyridin-3-yl]amino}carbonyl)amino]-3-(4-methylphenyl)propanoic acid | 1.5 | Calculated (M − H)⁻ = 472.15 m/z; Found (M − H)⁻ = 471.89 m/z. |
| (3S)-3-[({[1-(3,5-dimethylbenzyl)-4-hydroxy-2-oxo-1,2-dihydropyridin-3-yl]amino}carbonyl)amino]-3-(4-methylphenyl)propanoic acid | 0.06 | Calculated (M − H)⁻ = 448.19 m/z; Found (M − H)⁻ = 448.02 m/z. |
| (3S)-3-[({[1-(2-chloro-6-methoxybenzyl)-4-hydroxy-2-oxo-1,2-dihydropyridin-3-yl]amino}carbonyl)amino]-3-[4-(trifluoromethoxy)phenyl]propanoic acid | 0.04 | Calculated (M − H)⁻ = 554.09 m/z; Found (M − H)⁻ = 553.98 m/z. |
| (3S)-3-[({[1-(2-chlorobenzyl)-4-hydroxy-2-oxo-1,2-dihydropyridin-3-yl]amino}carbonyl)amino]-3-(3-methoxy-4-methylphenyl)propanoic acid | 0.003 | Calculated (M − H)⁻ = 484.13 m/z; Found (M − H)⁻ = 483.95 m/z. |
| (3S)-3-[({[1-(2-chlorobenzyl)-4-hydroxy-2-oxo-1,2-dihydropyridin-3-yl]amino}carbonyl)amino]-3-(3,5-dimethoxy-4-methylphenyl)propanoic acid | 0.003 | Calculated (M − H)⁻ = 514.14 m/z; Found (M − H)⁻ = 513.95 m/z. |
| (3S)-3-[({[1-(2-chlorobenzyl)-4-hydroxy-2-oxo-5-pentyl-1,2-dihydropyridin-3-yl]amino}carbonyl)amino]-3-(4-methylphenyl)propanoic acid | 0.04 | Calculated (M − H)⁻ = 524.20 m/z; Found (M − H)⁻ = 523.98 m/z. |
| (3S)-3-[({[1-(2-chlorobenzyl)-4-hydroxy-2-oxo-1,2-dihydropyridin-3-yl]amino}carbonyl)amino]-3-(3,4-dimethylphenyl)propanoic acid | 0.005 | Calculated (M + H) = 468.13 m/z; Found (M + H)⁺ = 467.99 m/z. |
| (3S)-3-[({[1-(2,4-dichlorobenzyl)-4-hydroxy-5-methyl-2-oxo-1,2-dihydropyridin-3-yl]amino}carbonyl)amino]-3-(4-methylphenyl)propanoic acid | 0.02 | Calculated (M − H)⁻ = 502.09 m/z; Found (M − H)⁻ = 501.89 m/z. |

TABLE 5-continued

| Name | IC$_{50}$ (μM) | Mass Spectral Data |
|---|---|---|
| [2-({[1-(2-chlorobenzyl)-4-hydroxy-2-oxo-1,2-dihydropyridin-3-yl]amino}carbonyl)-1-(4-methylphenyl)hydrazino]acetic acid | >10 | Calculated (M − H)⁻ = 455.11 m/z; Found (M − H)⁻ = 454.97 m/z. |
| (3S)-3-[({[1-(2-chlorobenzyl)-5-ethyl-4-hydroxy-2-oxo-1,2-dihydropyridin-3-yl]amino}carbonyl)amino]-3-(4-methylphenyl)propanoic acid | 0.01 | Calculated (M − H)⁻ = 482.15 m/z; Found (M − H)⁻ = 482.00 m/z. |
| 3-[({[1-(2-chlorobenzyl)-4-hydroxy-2-oxo-1,2-dihydropyridin-3-yl]amino}carbonyl)amino]-3-pyridin-3-ylpropanoic acid | 0.05 | Calculated (M − H)⁻ = 441.09 m/z; Found (M − H)⁻ = 441.00 m/z. |
| (3S)-3-[({[5-butyl-1-(2-chlorobenzyl)-4-hydroxy-2-oxo-1,2-dihydropyridin-3-yl]amino}carbonyl)amino]-3-(4-methylphenyl)propanoic acid | 0.025 | Calculated (M − H)⁻ = 510.18 m/z; Found (M − H)⁻ = 509.98 m/z. |
| (3S)-3-{[({1-[2-chloro-5-(trifluoromethyl)benzyl]-4-hydroxy-2-oxo-1,2-dihydropyridin-3-yl}amino)carbonyl]amino}-3-(4-methylphenyl)propanoic acid | 0.01 | Calculated (M − H)⁻ = 522.10 m/z; Found (M − H)⁻ = 521.97 m/z. |
| (3S)-3-[({[1-(2-chloro-6-methoxybenzyl)-4-hydroxy-2-oxo-1,2-dihydropyridin-3-yl]amino}carbonyl)amino]-3-(3-methylphenyl)propanoic acid | 0.005 | Calculated (M − H)⁻ = 484.13 m/z; Found (M − H)⁻ = 484.00 m/z. |
| (3S)-3-[({[1-(2,6-dichlorobenzyl)-4-hydroxy-2-oxo-1,2-dihydropyridin-3-yl]amino}carbonyl)amino]-3-(4-methylphenyl)propanoic acid | 0.013 | Calculated (M − H)⁻ = 488.08 m/z; Found (M − H)⁻ = 487.91 m/z. |
| (3S)-3-[({[1-(2-chloro-5-fluorobenzyl)-4-hydroxy-2-oxo-1,2-dihydropyridin-3-yl]amino}carbonyl)amino]-3-(4-methylphenyl)propanoic acid | 0.014 | Calculated (M − H)⁻ = 472.11 m/z; Found (M − H)⁻ = 471.96 m/z. |
| (3S)-3-[({[1-(2-chloro-6-methylbenzyl)-4-hydroxy-5-methyl-2-oxo-1,2-dihydropyridin-3-yl]amino}carbonyl)amino]-3-(4-methylphenyl)propanoic acid | 0.01 | Calculated (M − H)⁻ = 482.15 m/z; Found (M − H)⁻ = 481.98 m/z. |
| (3S)-3-[({[1-(4-chlorobenzyl)-4-hydroxy-5-methyl-2-oxo-1,2-dihydropyridin-3-yl]amino}carbonyl)amino]-3-(4-methylphenyl)propanoic acid | 0.02 | Calculated (M − H)⁻ = 468.13 m/z; Found (M − H)⁻ = 467.94 m/z. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-methylphenyl)propanoic acid | 0.003 | Calculated (M + H)⁺ = 496.16 m/z; Found (M + H)⁺ = 495.99 m/z. |
| (3S)-3-{[({4-hydroxy-5-methyl-1-[4-(methylsulfonyl)benzyl]-2-oxo-1,2-dihydropyridin-3-yl}amino)carbonyl]amino}-3-(4-methylphenyl)propanoic acid | 0.02 | Calculated (M − H)⁻ = 512.15 m/z; Found (M − H)⁻ = 511.96 m/z. |
| (3S)-3-[({[4-hydroxy-1-(4-methoxybenzyl)-2-oxo-1,2-dihydropyridin-3-yl]amino}carbonyl)amino]-3-(4-methylphenyl)propanoic acid | 0.02 | Calculated (M − H)⁻ = 450.17 m/z; Found (M − H)⁻ = 449.99 m/z. |
| (3S)-3-[({[1-(2-chlorobenzyl)-4-hydroxy-2-oxo-5-propyl-1,2-dihydropyridin-3-yl]amino}carbonyl)amino]-3-(4-methylphenyl)propanoic acid | 0.02 | Calculated (M − H)⁻ = 496.16 m/z; Found (M − H)⁻ = 495.94 m/z. |
| (3S)-3-({[(1-{4-[(dimethylamino)sulfonyl]benzyl}-4-hydroxy-2-oxo-1,2-dihydropyridin-3-yl)amino]carbonyl}amino)-3-(4-methylphenyl)propanoic acid | 0.035 | Calculated (M − H)⁻ = 527.16 m/z; Found (M − H)⁻ = 526.96 m/z. |
| (3S)-3-[({[4-hydroxy-1-(mesitylmethyl)-2-oxo-1,2-dihydropyridin-3-yl]amino}carbonyl)amino]-3-(4-methylphenyl)propanoic acid | 0.06 | Calculated (M − H)⁻ = 462.20 m/z; Found (M − H)⁻ = 462.02 m/z. |
| (3S)-3-[({[1-(2-chlorobenzyl)-4-hydroxy-2-oxo-1,2,5,6,7,8-hexahydroquinolin-3-yl]amino}carbonyl)amino]-3-(4-methylphenyl)propanoic acid | 0.02 | Calculated (M − H)⁻ = 508.16 m/z; Found (M − H)⁻ = 507.96 m/z. |
| (3S)-3-[({[1-(2-chlorobenzyl)-5-ethyl-4-hydroxy-6-methyl-2-oxo-1,2-dihydropyridin-3-yl]amino}carbonyl)amino]-3-(4-methylphenyl)propanoic acid | 0.025 | Calculated (M − H)⁻ = 496.16 m/z; Found (M − H)⁻ = 495.96 m/z. |
| (3S)-3-[({[1-(2-chlorobenzyl)-4-hydroxy-2-oxo-1,2-dihydropyridin-3-yl]amino}carbonyl)(methyl)amino]-3-(4-methylphenyl)propanoic acid | 0.4 | Calculated (M − H)⁻ = 468.13 m/z; Found (M − H)⁻ = 467.85 m/z. |
| (3S)-3-{[({4-hydroxy-1-[2-(methylthio)benzyl]-2-oxo-1,2-dihydropyridin-3-yl}amino)carbonyl]amino}-3-(4-methylphenyl)propanoic acid | 0.02 | Calculated (M − H)⁻ = 466.14 m/z; Found (M − H)⁻ = 465.97 m/z. |

TABLE 5-continued

| Name | IC$_{50}$ (μM) | Mass Spectral Data |
|---|---|---|
| (3S)-3-({[(1-{2-[(dimethylamino)sulfonyl]benzyl}-4-hydroxy-2-oxo-1,2-dihydropyridin-3-yl)amino]carbonyl}amino)-3-(4-methylphenyl)propanoic acid | 0.03 | Calculated (M − H)$^-$ = 527.16 m/z; Found (M − H)$^-$ = 526.97 m/z. |
| (3S)-3-[({[1-(2,6-dimethoxybenzyl)-4-hydroxy-2-oxo-1,2-dihydropyridin-3-yl]amino}carbonyl)amino]-3-(4-methylphenyl)propanoic acid | 0.01 | Calculated (M − H)$^-$ = 480.18 m/z; Found (M − H)$^-$ = 480.00 m/z. |
| (3S)-3-{[({4-hydroxy-2-oxo-1-[2-(trifluoromethoxy)benzyl]-1,2-dihydropyridin-3-yl}amino)carbonyl]amino}-3-(4-methylphenyl)propanoic acid | 0.025 | Calculated (M − H)$^-$ = 504.14 m/z; Found (M − H)$^-$ = 503.96 m/z. |
| (3R)-3-[({[1-(2-chlorobenzyl)-4-hydroxy-2-oxo-1,2-dihydropyridin-3-yl]amino}carbonyl)amino]-4-[3-(trifluoromethyl)phenyl]butanoic acid | 0.35 | Calculated (M − H)$^-$ = 522.10 m/z; Found (M − H)$^-$ = 521.95 m/z. |
| (3S)-3-[({[1-(2-chlorobenzyl)-4-hydroxy-2-oxo-1,2-dihydropyridin-3-yl]amino}carbonyl)amino]-3-(3-propoxyphenyl)propanoic acid | 0.003 | Calculated (M − H)$^-$ = 498.14 m/z; Found (M − H)$^-$ = 497.97 m/z. |
| (3S)-3-[({[1-(2-chlorobenzyl)-4-hydroxy-2-oxo-5-propyl-1,2-dihydropyridin-3-yl]amino}carbonyl)amino]-3-(3-ethoxyphenyl)propanoic acid | 0.003 | Calculated (M + H)$^+$ = 528.19 m/z; Found (M + H)$^+$ = 528.02 m/z. |
| (3S)-3-[({[1-(2-chlorobenzyl)-4-hydroxy-5,6-dimethyl-2-oxo-1,2-dihydropyridin-3-yl]amino}carbonyl)amino]-3-(4-methylphenyl)propanoic acid | 0.006 | Calculated (M − H)$^-$ = 482.15 m/z; Found (M − H)$^-$ = 481.95 m/z. |
| (3S)-3-[({[1-(2-chlorobenzyl)-4-hydroxy-2-oxo-5-propyl-1,2-dihydropyridin-3-yl]amino}carbonyl)amino]-3-(3,4-diethoxyphenyl)propanoic acid | 0.005 | Calculated (M − H)$^-$ = 570.20 m/z; Found (M − H)$^-$ = 569.98 m/z. |
| (3S)-3-(3-butoxyphenyl)-3-[({[1-(2-chlorobenzyl)-4-hydroxy-2-oxo-1,2-dihydropyridin-3-yl]amino}carbonyl)amino]propanoic acid | 0.005 | Calculated (M + H)$^+$ = 514.17 m/z; Found (M + H)$^+$ = 514.00 m/z. |
| (3S)-3-{[({1-[2-chloro-5-(methylsulfonyl)benzyl]-4-hydroxy-2-oxo-1,2-dihydropyridin-3-yl}amino)carbonyl]amino}-3-(4-methylphenyl)propanoic acid | 0.003 | Calculated (M − H)$^-$ = 532.10 m/z; Found (M − H)$^-$ = 531.94 m/z. |
| (3R)-3-[({[1-(2-chlorobenzyl)-4-hydroxy-2-oxo-1,2-dihydropyridin-3-yl]amino}carbonyl)amino]-4-(2-methylphenyl)butanoic acid | 0.08 | Calculated (M − H)$^-$ = 468.13 m/z; Found (M − H)$^-$ = 468.03 m/z. |
| (3S)-3-[({[1-(2-chlorobenzyl)-4-hydroxy-2-oxo-1,2-dihydropyridin-3-yl]amino}carbonyl)amino]-3-[3-(2-methoxyethoxy)phenyl]propanoic acid | 0.003 | Calculated (M − H)$^-$ = 514.14 m/z; Found (M − H)$^-$ = 513.95 m/z. |
| (3S)-3-[({[1-(4-chloro-2-methoxybenzyl)-4-hydroxy-2-oxo-1,2-dihydropyridin-3-yl]amino}carbonyl)amino]-3-(4-methylphenyl)propanoic acid | 0.025 | Calculated (M − H)$^-$ = 484.13 m/z; Found (M − H)$^-$ = 483.93 m/z. |
| (3S)-3-[({[1-(2-chlorobenzyl)-4-hydroxy-2-oxo-1,2-dihydropyridin-3-yl]amino}carbonyl)amino]-3-(3,4-dipropoxyphenyl)propanoic acid | 0.003 | Calculated (M − H)$^-$ = 556.18 m/z; Found (M − H)$^-$ = 555.94 m/z. |
| (3S)-3-[({[1-(2-chlorobenzyl)-4-hydroxy-2-oxo-2,5,6,7,8,9-hexahydro-1H-cyclohepta[b]pyridin-3-yl]amino}carbonyl)amino]-3-(4-methylphenyl)propanoic acid | 0.12 | Calculated (M − H)$^-$ = 522.18 m/z; Found (M − H)$^-$ = 521.98 m/z. |
| (3S)-3-[({[1-(2-chlorobenzyl)-4-hydroxy-2-oxo-1,2-dihydropyridin-3-yl]amino}carbonyl)amino]-4,4-diphenylbutanoic acid | 12 | Calculated (M − H)$^-$ = 530.15 m/z; Found (M − H)$^-$ = 529.92 m/z. |
| (3S)-3-{[({1-[2-(difluoromethoxy)benzyl]-4-hydroxy-2-oxo-1,2-dihydropyridin-3-yl}amino)carbonyl]amino}-3-(4-methylphenyl)propanoic acid | 0.075 | Calculated (M − H)$^-$ = 486.15 m/z; Found (M − H)$^-$ = 486.00 m/z. |
| (3S)-3-{[({4-hydroxy-5-methyl-2-oxo-1-[(1R)-1-phenylethyl]-1,2-dihydropyridin-3-yl}amino)carbonyl]amino}-3-(4-methylphenyl)propanoic acid | 4 | Calculated (M − H)$^-$ = 448.19 m/z; Found (M − H)$^-$ = 447.99 m/z. |
| (3S)-3-[({[1-(4-chlorobenzyl)-4-hydroxy-2-oxo-5-propyl-1,2-dihydropyridin-3-yl]amino}carbonyl)amino]-3-(4-methylphenyl)propanoic acid | 0.03 | Calculated (M − H)$^-$ = 496.16 m/z; Found (M − H)$^-$ = 495.96 m/z. |
| (3S)-3-[({[1-(2-chlorobenzyl)-4-hydroxy-2-oxo-1,2-dihydropyridin-3-yl]amino}carbonyl)amino]-3-(3,4-diethylphenyl)propanoic acid | 0.05 | Calculated (M − H)$^-$ = 496.16 m/z; Found (M − H)$^-$ = 495.98 m/z. |
| (3S)-3-[({[1-(2-chlorobenzyl)-4-hydroxy-2-oxo-1,2-dihydropyridin-3-yl]amino}carbonyl)amino]-3-(3,5-difluorophenyl)propanoic acid | 0.05 | Calculated (M − H)$^-$ = 476.08 m/z; Found (M − H)$^-$ = 475.93 m/z. |

TABLE 5-continued

| Name | IC$_{50}$ (μM) | Mass Spectral Data |
| --- | --- | --- |
| 3-[({[1-(2-chlorobenzyl)-4-hydroxy-2-oxo-1,2-dihydropyridin-3-yl]amino}carbonyl)amino]-3-(2-naphthyl)propanoic acid | 0.02 | Calculated (M − H)$^-$ = 490.12 m/z; Found (M − H)$^-$ = 489.97 m/z. |
| 3-[({[1-(2-chlorobenzyl)-4-hydroxy-2-oxo-1,2-dihydropyridin-3-yl]amino}carbonyl)amino]-3-(5-methyl-2-furyl)propanoic acid | 0.025 | Calculated (M + H)$^+$ = 446.11 m/z; Found (M + H)$^+$ = 446.08 m/z. |
| (3S)-3-[({[1-(2-chlorobenzyl)-4-hydroxy-2-oxo-1,2-dihydropyridin-3-yl]amino}carbonyl)amino]-3-(3,4-dibutoxyphenyl)propanoic acid | 0.025 | Calculated (M − H)$^-$ = 584.21 m/z; Found (M − H)$^-$ = 583.98 m/z. |
| (3S)-3-{[({4-hydroxy-1-[2-(methylsulfonyl)benzyl]-2-oxo-1,2-dihydropyridin-3-yl}amino)carbonyl]amino}-3-(4-methylphenyl)propanoic acid | 0.035 | Calculated (M + H)$^+$ = 500.15 m/z; Found (M + H)$^+$ = 500.01 m/z. |
| 3-[({[1-(2-chlorobenzyl)-4-hydroxy-2-oxo-1,2-dihydropyridin-3-yl]amino}carbonyl)amino]-3-(1-naphthyl)propanoic acid | 0.2 | Calculated (M − H)$^-$ = 490.12 m/z; Found (M − H)$^-$ = 489.91 m/z. |
| (3S)-3-[({[1-(4-chlorobenzyl)-4-hydroxy-2-oxo-5-propyl-1,2-dihydropyridin-3-yl]amino}carbonyl)amino]-3-(3-ethoxyphenyl)propanoic acid | 0.03 | Calculated (M − H)$^-$ = 526.17 m/z; Found (M − H)$^-$ = 525.95 m/z. |
| (3S)-3-[({[1-(4-chlorobenzyl)-4-hydroxy-2-oxo-5-propyl-1,2-dihydropyridin-3-yl]amino}carbonyl)amino]-3-(3,4-diethoxyphenyl)propanoic acid | 0.015 | Calculated (M − H)$^-$ = 570.20 m/z; Found (M − H)$^-$ = 569.97 m/z. |
| (3S)-3-[({[1-(2,6-dimethylbenzyl)-4-hydroxy-2-oxo-1,2-dihydropyridin-3-yl]amino}carbonyl)amino]-3-(4-methylphenyl)propanoic acid | 0.035 | Calculated (M − H)$^-$ = 448.19 m/z; Found (M − H)$^-$ = 448.02 m/z. |
| (3S)-3-[3,5-bis(trifluoromethyl)phenyl]-3-[({[1-(2-chlorobenzyl)-4-hydroxy-2-oxo-1,2-dihydropyridin-3-yl]amino}carbonyl)amino]propanoic acid | 0.22 | Calculated (M − H)$^-$ = 576.08 m/z; Found (M − H)$^-$ = 575.91 m/z. |
| (3S)-3-[({[1-(2-chlorobenzyl)-4-hydroxy-2-oxo-1,2-dihydropyridin-3-yl]amino}carbonyl)amino]-3-[3-(difluoromethoxy)phenyl]propanoic acid | 0.006 | Calculated (M − H)$^-$ = 506.09 m/z; Found (M − H)$^-$ = 505.93 m/z. |
| (3R)-3-[({[1-(2-chlorobenzyl)-4-hydroxy-2-oxo-1,2-dihydropyridin-3-yl]amino}carbonyl)amino]-4-pyridin-2-ylbutanoic acid | 0.225 | Calculated (M − H)$^-$ = 455.11 m/z; Found (M − H)$^-$ = 455.09 m/z. |
| (3S)-3-[({[1-(2-chlorobenzyl)-4-hydroxy-5-methyl-2-oxo-1,2-dihydropyridin-3-yl]amino}carbonyl)amino]-3-(3,4-diethoxyphenyl)propanoic acid | 0.0006 | Calculated (M − H)$^-$ = 542.17 m/z; Found (M − H)$^-$ = 542.06 m/z. |
| (3S)-3-[({[1-(2-chlorobenzyl)-4-hydroxy-5-methyl-2-oxo-1,2-dihydropyridin-3-yl]amino}carbonyl)amino]-3-(3-ethoxyphenyl)propanoic acid | 0.002 | Calculated (M − H)$^-$ = 499.15 m/z; Found (M − H)$^-$ = 498.07 m/z. |
| (3S)-3-[({[1-(2-chlorobenzyl)-4-hydroxy-5-methyl-2-oxo-1,2-dihydropyridin-3-yl]amino}carbonyl)amino]-3-(3-methoxy-4-methylphenyl)propanoic acid | 0.020 | Calculated (M + H)$^+$ = 500.16 m/z; Found (M + H)$^+$ = 500.02 m/z. |
| 3-[({[1-(2-chlorobenzyl)-4-hydroxy-5-methyl-2-oxo-1,2-dihydropyridin-3-yl]amino}carbonyl)amino]-3-(2-naphthyl)propanoic acid | 0.030 | Calculated (M − H)$^-$ = 504.13 m/z; Found (M − H)$^-$ = 504.04 m/z. |
| (3S)-3-[({[1-(2-chloro-6-methylbenzyl)-4-hydroxy-5,6-dimethyl-2-oxo-1,2-dihydropyridin-3-yl]amino}carbonyl)amino]-3-(3-ethoxyphenyl)propanoic acid | 0.015 | Calculated (M − H)$^-$ = 526.17 m/z; Found (M − H)$^-$ = 525.95 m/z. |
| (3S)-3-[({[1-(2-chloro-6-methylbenzyl)-4-hydroxy-5,6-dimethyl-2-oxo-1,2-dihydropyridin-3-yl]amino}carbonyl)amino]-3-(3-methoxy-4-methylphenyl)propanoic acid | 0.025 | Calculated (M − H)$^-$ = 526.17 m/z; Found (M − H)$^-$ = 525.97 m/z. |
| (3S)-3-[({[1-(2-chloro-6-methylbenzyl)-4-hydroxy-5,6-dimethyl-2-oxo-1,2-dihydropyridin-3-yl]amino}carbonyl)amino]-3-(3,4-diethoxyphenyl)propanoic acid | 0.004 | Calculated (M − H)$^-$ = 570.20 m/z; Found (M − H)$^-$ = 570.00 m/z. |
| (3S)-3-[({[1-(2-chloro-6-cyanobenzyl)-4-hydroxy-2-oxo-1,2-dihydropyridin-3-yl]amino}carbonyl)amino]-3-(4-methylphenyl)propanoic acid | 0.007 | Calculated (M − H)$^-$ = 479.11 m/z; Found (M − H)$^-$ = 478.90 m/z. |
| (3S)-3-[({[1-(2-chloro-6-methylbenzyl)-4-hydroxy-5,6-dimethyl-2-oxo-1,2-dihydropyridin-3-yl]amino}carbonyl)amino]-3-(4-methylphenyl)propanoic acid | 0.03 | Calculated (M − H)$^-$ = 496.16 m/z; Found (M − H)$^-$ = 495.97 m/z. |
| (3S)-3-[({[1-(2-chlorobenzyl)-4-hydroxy-5,6-dimethyl-2-oxo-1,2-dihydropyridin-3-yl]amino}carbonyl)amino]-3-(3-methoxy-4-methylphenyl)propanoic acid | 0.015 | Calculated (M − H)$^-$ = 512.16 m/z; Found (M − H)$^-$ = 511.95 m/z. |

TABLE 5-continued

| Name | IC$_{50}$ (µM) | Mass Spectral Data |
|---|---|---|
| (3S)-3-[({[1-(2-chlorobenzyl)-4-hydroxy-5,6-dimethyl-2-oxo-1,2-dihydropyridin-3-yl]amino}carbonyl)amino]-3-(3,4-diethoxyphenyl)propanoic acid | 0.003 | Calculated (M − H)$^-$ = 556.18 m/z; Found (M − H)$^-$ = 555.99 m/z. |

TABLE 6

| Compound | IC$_{50}$ (nM) | Mass Spectral Data (m/z) |
|---|---|---|
| (3R)-3-[({[1-(2-chlorobenzyl)-4-hydroxy-2-oxo-1,2-dihydropyridin-3-yl]amino}carbonyl)amino]-4-(1-naphthyl)butanoic acid | 2500 | Calculated (M − H)$^-$ = 504.13; Found (M − H)$^-$ = 503.97. |
| (3S)-3-[({[1-(2-chlorobenzyl)-4-hydroxy-5,6-dimethyl-2-oxo-1,2-dihydropyridin-3-yl]amino}carbonyl)amino]-3-(3-ethoxyphenyl)propanoic acid | 30 | Calculated (M − H)$^-$ = 512.16; Found (M − H)$^-$ = 511.99. |
| (3S)-3-[({[1-(2-chlorobenzyl)-4-hydroxy-5,6-dimethyl-2-oxo-1,2-dihydropyridin-3-yl]amino}carbonyl)amino]-3-(3,4-dimethylphenyl)propanoic acid | 40 | Calculated (M − H)$^-$ = 496.16; Found (M − H)$^-$ = 496.05. |
| (3S)-3-[({[1-(2-chloro-6-methoxybenzyl)-4-hydroxy-5-methyl-2-oxo-1,2-dihydropyridin-3-yl]amino}carbonyl)amino]-3-(4-methylphenyl)propanoic acid | 5 | Calculated (M − H)$^-$ = 498.15; Found (M − H)$^-$ = 497.91. |
| (3S)-3-[({[1-(2-chloro-6-methoxybenzyl)-4-hydroxy-5-methyl-2-oxo-1,2-dihydropyridin-3-yl]amino}carbonyl)amino]-3-(3,4-diethoxyphenyl)propanoic acid | 2 | Calculated (M − H)$^-$ = 572.18. Found (M − H)$^-$ = 571.96. |
| (3S)-3-[({[1-(2-chloro-6-methoxybenzyl)-4-hydroxy-5-methyl-2-oxo-1,2-dihydropyridin-3-yl]amino}carbonyl)amino]-3-(3-methoxy-4-methylphenyl)propanoic acid | 6 | Calculated (M − H)$^-$ = 528.15; Found (M − H)$^-$ = 527.95. |
| (3S)-3-[({[1-(2-chloro-6-methoxybenzyl)-4-hydroxy-5-methyl-2-oxo-1,2-dihydropyridin-3-yl]amino}carbonyl)amino]-3-(3-ethoxyphenyl)propanoic acid | 3 | Calculated (M − H)$^-$ = 528.15; Found (M − H)$^-$ = 527.99. |
| (3S)-3-[({[1-(2-chlorobenzyl)-4-hydroxy-2-oxo-1,2-dihydropyridin-3-yl]amino}carbonyl)amino]-3-[3-(1,1,2,2-tetrafluoroethoxy)phenyl]propanoic acid | 15 | Calculated (M − H)$^-$ = 556.09; Found (M − H)$^-$ = 555.97. |
| (3R)-3-[({[1-(2-chlorobenzyl)-4-hydroxy-2-oxo-1,2-dihydropyridin-3-yl]amino}carbonyl)amino]-4-(2-chlorophenyl)butanoic acid | 700 | Calculated (M − H)$^-$ = 488.08; Found (M − H)$^-$ = 487.96. |
| (3S)-3-{[({4-hydroxy-1-[3-(methylthio)benzyl]-2-oxo-1,2-dihydropyridin-3-yl}amino)carbonyl]amino}-3-(4-methylphenyl)propanoic acid | 20 | Calculated (M − H)$^-$ = 466.14; Found (M − H)$^-$ = 466.04. |
| (3S)-3-[({[1-(2-chlorobenzyl)-4-hydroxy-5-methyl-2-oxo-1,2-dihydropyridin-3-yl]amino}carbonyl)amino]-3-(3,4-dimethylphenyl)propanoic acid | 15 | Calculated (M − H)$^-$ = 482.15; Found (M − H)$^-$ = 482.02. |
| (3S)-3-[({[1-(2-chloro-6-methoxybenzyl)-4-hydroxy-5-methyl-2-oxo-1,2-dihydropyridin-3-yl]amino}carbonyl)amino]-3-(3,4-dimethylphenyl)propanoic acid | 3 | Calculated (M − H)$^-$ = 512.16; Found (M − H)$^-$ = 512.03. |
| (3S)-3-[({[1-(2-chlorobenzyl)-5-cyclopropyl-4-hydroxy-2-oxo-1,2-dihydropyridin-3-yl]amino}carbonyl)amino]-3-(4-methylphenyl)propanoic acid | 20 | Calculated (M + H)$^+$ = 496.16; Found (M + H)$^+$ = 496.05. |
| (3S)-3-[({[1-(4-chlorobenzyl)-4-hydroxy-2-oxo-2,5,6,7-tetrahydro-1H-cyclopenta[b]pyridin-3-yl]amino}carbonyl)amino]-3-(4-methylphenyl)propanoic acid | 50 | Calculated (M − H)$^-$ = 494.15; Found (M − H)$^-$ = 494.02. |
| (3S)-3-[({[1-(3-chlorobenzyl)-4-hydroxy-5-methyl-2-oxo-1,2-dihydropyridin-3-yl]amino}carbonyl)amino]-3-(4-methylphenyl)propanoic acid | 20 | Calculated (M − H)$^-$ = 468.13; Found (M − H)$^-$ = 468.02. |
| (3S)-3-[({[1-(2,6-dichlorobenzyl)-4-hydroxy-5-methyl-2-oxo-1,2-dihydropyridin-3-yl]amino}carbonyl)amino]-3-(4-methylphenyl)propanoic acid | 20 | Calculated (M − H)$^-$ = 502.09; Found (M − H)$^-$ = 501.92. |

TABLE 6-continued

| Compound | IC$_{50}$ (nM) | Mass Spectral Data (m/z) |
|---|---|---|
| (3S)-3-[({[4-hydroxy-5-methyl-1-(4-methylbenzyl)-2-oxo-1,2-dihydropyridin-3-yl]amino}carbonyl)amino]-3-(4-methylphenyl)propanoic acid | 150 | Calculated (M − H)⁻ = 448.19; Found (M − H)⁻ = 448.05. |
| 3-(1-benzofuran-2-yl)-3-[({[1-(2-chlorobenzyl)-4-hydroxy-2-oxo-1,2-dihydropyridin-3-yl]amino}carbonyl)amino]propanoic acid | 140 | Calculated (M − H)⁻ = 480.10; Found (M−−H)⁻ = 479.96. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid | 3 | Calculated (M − H)⁻ = 524.16; Found (M − H)⁻ = 523.95. |
| 3-[({[1-(2-chlorobenzyl)-4-hydroxy-2-oxo-1,2-dihydropyridin-3-yl]amino}carbonyl)amino]-3-(6-methoxy-2-naphthyl)propanoic acid | 15 | Calculated (M − H)⁻ = 520.13; Found (M − H)⁻ = 520.00. |
| (3S)-3-[({[1-(3,5-dimethoxybenzyl)-4-hydroxy-5-methyl-2-oxo-1,2-dihydropyridin-3-yl]amino}carbonyl)amino]-3-(4-methylphenyl)propanoic acid | 70 | Calculated (M − H)⁻ = 494.19; Found (M − H)⁻ = 494.04. |
| (3S)-3-[({[1-(2,6-difluorobenzyl)-4-hydroxy-5-methyl-2-oxo-1,2-dihydropyridin-3-yl]amino}carbonyl)amino]-3-(4-methylphenyl)propanoic acid | 25 | Calculated (M − H)⁻ = 470.15; Found (M − H)⁻ = 470.03. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3,4-diethoxyphenyl)propanoic acid | 3 | Calculated (M + H)⁺ = 570.20; Found (M + H)⁺ = 570.00. |
| (3S)-3-{[({4-hydroxy-1-[3-(methylsulfonyl)benzyl]-2-oxo-1,2-dihydropyridin-3-yl}amino)carbonyl]amino}-3-(4-methylphenyl)propanoic acid | 25 | Calculated (M − H)⁻ = 498.13; Found (M − H)⁻ = 498.01. |
| (3S)-3-[({[1-(2-chloro-6-methylbenzyl)-4-hydroxy-5-methyl-2-oxo-1,2-dihydropyridin-3-yl]amino}carbonyl)amino]-3-(3,4-diethoxyphenyl)propanoic acid | 3 | Calculated (M − H)⁻ = 556.19; Found (M − H)⁻ = 556.02. |
| (3S)-3-[({[1-(2-chloro-6-methylbenzyl)-4-hydroxy-5-methyl-2-oxo-1,2-dihydropyridin-3-yl]amino}carbonyl)amino]-3-(3-ethoxyphenyl)propanoic acid | 4 | Calculated (M − H)⁻ = 512.16; Found (M − H)⁻ = 512.02. |
| (3S)-3-[({[1-(2-chloro-6-methylbenzyl)-4-hydroxy-5-methyl-2-oxo-1,2-dihydropyridin-3-yl]amino}carbonyl)amino]-3-(3,4-dimethylphenyl)propanoic acid | 45 | Calculated (M − H)⁻ = 496.16; Found (M − H)⁻ = 496.01. |
| (3S)-3-[({[1-(2-chloro-6-methylbenzyl)-4-hydroxy-5-methyl-2-oxo-1,2-dihydropyridin-3-yl]amino}carbonyl)amino]-3-(3-methoxy-4-methylphenyl)propanoic acid | 25 | Calculated (M − H)⁻ = 512.16; Found (M − H)⁻ = 511.97. |
| 3-[({[1-(2-chlorobenzyl)-4-hydroxy-2-oxo-1,2-dihydropyridin-3-yl]amino}carbonyl)amino]-3-(4,5-dimethyl-2-furyl)propanoic acid | 115 | Calculated (M − H)⁻ = 458.11; Found (M − H)⁻ = 457.99. |
| 3-[({[1-(2-chlorobenzyl)-4-hydroxy-2-oxo-1,2-dihydropyridin-3-yl]amino}carbonyl)amino]-3-(4-methoxy-1-naphthyl)propanoic acid | 160 | Calculated (M − H)⁻ = 520.13; Found (M − H)⁻ = 519.97. |
| (3R)-3-[({[1-(2-chlorobenzyl)-4-hydroxy-2-oxo-1,2-dihydropyridin-3-yl]amino}carbonyl)amino]-5-phenylpentanoic acid | 115 | Calculated (M − H)⁻ = 468.13; Found (M − H)⁻ = 467.98. |
| (3S)-3-[({[1-(2-chlorobenzyl)-4-hydroxy-2-oxo-1,2-dihydroquinolin-3-yl]amino}carbonyl)amino]-3-(3-ethoxyphenyl)propanoic acid | 12 | Calculated (M − H)⁻ = 534.14; Found (M − H)⁻ = 533.94. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3,4-dimethylphenyl)propanoic acid | 18 | Calculated (M + H)⁺ = 510.18; Found (M + H)⁺ = 510.06. |
| (3S)-3-[({[1-(2-chloro-6-ethoxybenzyl)-4-hydroxy-2-oxo-1,2-dihydropyridin-3-yl]amino}carbonyl)amino]-3-(4-methylphenyl)propanoic acid | 7 | Calculated (M + H)⁺ = 500.16; Found (M + H)⁺ = 500.06. |
| (3S)-3-[({[1-(2-chloro-6-ethoxybenzyl)-4-hydroxy-5-methyl-2-oxo-1,2-dihydropyridin-3-yl]amino}carbonyl)amino]-3-(4-methylphenyl)propanoic acid | 3 | Calculated (M − H)⁻ = 512.16; Found (M − H)⁻ = 512.03. |
| (3S)-3-[({[1-(2-chlorobenzyl)-5-cyclopropyl-4-hydroxy-2-oxo-1,2-dihydropyridin-3-yl]amino}carbonyl)amino]-3-(3-ethoxyphenyl)propanoic acid | 14 | Calculated (M + H)⁺ = 526.17; Found (M + H)⁺ = 526.01. |

TABLE 6-continued

| Compound | IC$_{50}$ (nM) | Mass Spectral Data (m/z) |
|---|---|---|
| (3S)-3-[({[1-(2-chlorobenzyl)-5-cyclopropyl-4-hydroxy-2-oxo-1,2-dihydropyridin-3-yl]amino}carbonyl)amino]-3-(3,4-diethoxyphenyl)propanoic acid | 6 | Calculated (M + H)$^+$ = 570.20; Found (M + H)$^+$ = 570.04. |
| (3S)-3-[({[1-(2-chlorobenzyl)-4-hydroxy-2-oxo-1,2-dihydropyridin-3-yl]amino}carbonyl)amino]-3-[4-(difluoromethoxy)phenyl]propanoic acid | 30 | Calculated (M − H)$^−$ = 506.09; Found (M − H)$^−$ = 505.96. |
| 3-[({[1-(2-chlorobenzyl)-4-hydroxy-2-oxo-1,2-dihydropyridin-3-yl]amino}carbonyl)amino]-3-quinolin-2-ylpropanoic acid | 105 | Calculated (M − H)$^−$ = 491.11; Found (M − H)$^−$ = 490.96. |
| (3S)-3-[({[1-(2-fluoro-6-methoxybenzyl)-4-hydroxy-5-methyl-2-oxo-1,2-dihydropyridin-3-yl]amino}carbonyl)amino]-3-(4-methylphenyl)propanoic acid | 10 | Calculated (M − H)$^−$ = 482.17; Found (M − H)$^−$ = 482.02. |
| (3S)-3-[({[1-(2-chloro-6-methoxybenzyl)-4-hydroxy-2-oxo-5-propyl-1,2-dihydropyridin-3-yl]amino}carbonyl)amino]-3-(4-methylphenyl)propanoic acid | 15 | Calculated (M + H)$^+$ = 528.19; Found (M + H)$^+$ = 528.04. |
| (3S)-3-[({[1-(2-chloro-6-methoxybenzyl)-4-hydroxy-2-oxo-5-propyl-1,2-dihydropyridin-3-yl]amino}carbonyl)amino]-3-(3-ethoxyphenyl)propanoic acid | 7 | Calculated (M + H)$^+$ = 558.20; Found (M + H)$^+$ = 558.07. |
| (3S)-3-[({[1-(5-chloro-2-fluorobenzyl)-4-hydroxy-5-methyl-2-oxo-1,2-dihydropyridin-3-yl]amino}carbonyl)amino]-3-(4-methylphenyl)propanoic acid | 15 | Calculated (M − H)$^−$ = 486.12; Found (M − H)$^−$ = 486.00. |
| (3S)-3-[({[1-(2-chlorobenzyl)-4-hydroxy-2-oxo-1,2-dihydroquinolin-3-yl]amino}carbonyl)amino]-3-(3-methoxy-4-methylphenyl)propanoic acid | 14 | Calculated (M − H)$^−$ = 534.14; Found (M − H)$^−$ = 533.95. |
| (3S)-3-[({[1-(2-chlorobenzyl)-4-hydroxy-2-oxo-1,2-dihydroquinolin-3-yl]amino}carbonyl)amino]-3-(3,4-diethoxyphenyl)propanoic acid | 4 | Calculated (M − H)$^−$ = 578.17; Found (M − H)$^−$ = 577.99. |
| (3S)-3-[({[1-(2-chlorobenzyl)-4-hydroxy-2-oxo-1,2-dihydroquinolin-3-yl]amino}carbonyl)amino]-3-(3,4-dimethylphenyl)propanoic acid | 25 | Calculated (M − H)$^−$ = 518.15; Found (M − H)$^−$ = 517.96. |
| (3S)-3-[({[1-(2-chlorobenzyl)-4-hydroxy-2-oxo-1,2-dihydropyridin-3-yl]amino}carbonyl)amino]-3-pyridin-2-ylpropanoic acid | 150 | Calculated (M + H)$^+$ = 443.11; Found (M + H)$^+$ = 443.03. |
| (3S)-3-[({[1-(2-chlorobenzyl)-4-hydroxy-2-oxo-1,2-dihydropyridin-3-yl]amino}carbonyl)amino]-3-(3-isopropoxyphenyl)propanoic acid | 3 | Calculated (M − H)$^−$ = 498.14; Found (M − H)$^−$ = 498.04. |
| (3S)-3-[({[1-(2-chlorobenzyl)-4-hydroxy-2-oxo-1,2-dihydropyridin-3-yl]amino}carbonyl)amino]-3-(3,5-diethoxyphenyl)propanoic acid | 7 | Calculated (M − H)$^−$ = 528.15; Found (M − H)$^−$ = 528.02. |
| (3S)-3-[({[1-(2-chlorobenzyl)-4-hydroxy-5-isopropyl-2-oxo-1,2-dihydropyridin-3-yl]amino}carbonyl)amino]-3-(4-methylphenyl)propanoic acid | 60 | Calculated (M + H)$^+$ = 498.18; Found (M + H)$^+$ = 498.05. |
| (3S)-3-[({[1-(5-fluoro-2-methylbenzyl)-4-hydroxy-5-methyl-2-oxo-1,2-dihydropyridin-3-yl]amino}carbonyl)amino]-3-(4-methylphenyl)propanoic acid | 20 | Calculated (M + H)$^+$ = 468.19; Found (M + H)$^+$ = 468.07. |
| (3S)-3-{[({4-hydroxy-5-methyl-2-oxo-1-[(1S)-1-phenylethyl]-1,2-dihydropyridin-3-yl}amino)carbonyl]amino}-3-(4-methylphenyl)propanoic acid | 1500 | Calculated (M + H)$^+$ = 450.20; Found (M + H)$^+$ = 450.07. |
| (3S)-3-[({[1-(2-chloro-6-methoxybenzyl)-4-hydroxy-2-oxo-5-propyl-1,2-dihydropyridin-3-yl]amino}carbonyl)amino]-3-(3,4-diethoxyphenyl)propanoic acid | 3 | Calculated (M + H)$^+$ = 602.23; Found (M + H)$^+$ = 602.04. |
| (3S)-3-[({[1-(2-chloro-5-isopropoxybenzyl)-4-hydroxy-5-methyl-2-oxo-1,2-dihydropyridin-3-yl]amino}carbonyl)amino]-3-(4-methylphenyl)propanoic acid | 7 | Calculated (M − H)$^−$ = 526.17; Found (M − H)$^−$ = 526.04. |
| (3S)-3-[({[1-(2-chloro-6-methoxybenzyl)-4-hydroxy-2-oxo-5-propyl-1,2-dihydropyridin-3-yl]amino}carbonyl)amino]-3-(3-methoxy-4-methylphenyl)propanoic acid | 15 | Calculated (M + H)$^+$ = 558.20; Found (M + H)$^+$ = 588.05. |
| (3S)-3-[({[1-(2-chloro-6-ethoxybenzyl)-4-hydroxy-5-methyl-2-oxo-1,2-dihydropyridin-3-yl]amino}carbonyl)amino]-3-(3-ethoxyphenyl)propanoic acid | 2 | Calculated (M + H)$^+$ = 544.19; Found (M + H)$^+$ = 544.04. |
| (3S)-3-[({[1-(5-acetyl-2-methoxybenzyl)-4-hydroxy-2-oxo-1,2-dihydropyridin-3-yl]amino}carbonyl)amino]-3-(4-methylphenyl)propanoic acid | 33 | Calculated (M − H)$^−$ = 492.18; Found (M − H)$^−$ = 492.04. |

TABLE 6-continued

| Compound | IC$_{50}$ (nM) | Mass Spectral Data (m/z) |
|---|---|---|
| 3-[({[1-(2-chloro-6-methylbenzyl)-4-hydroxy-5-methyl-2-oxo-1,2-dihydropyridin-3-yl]amino}carbonyl)amino]-3-(6-methoxy-2-naphthyl)propanoic acid | 35 | Calculated (M − H)$^-$ = 548.16; Found (M − H)$^-$ = 548.01. |
| (3S)-3-[({[1-(2-chloro-6-methoxybenzyl)-4-hydroxy-2-oxo-5-propyl-1,2-dihydropyridin-3-yl]amino}carbonyl)amino]-3-(3,4-dimethylphenyl)propanoic acid | 17 | Calculated (M + H)$^+$ = 542.21; Found (M + H)$^+$ = 542.05. |
| (3S)-3-[({[1-(2-chlorobenzyl)-4-hydroxy-2-oxo-1,2-dihydropyridin-3-yl]amino}carbonyl)amino]-3-(1-methyl-1H-indol-5-yl)propanoic acid | 3 | Calculated (M − H)$^-$ = 493.13; Found (M − H)$^-$ = 492.95. |
| (3S)-3-[({[2-(2-chlorobenzyl)-5-hydroxy-6-methyl-3-oxo-2,3-dihydropyridazin-4-yl]amino}carbonyl)amino]-3-(4-methylphenyl)propanoic acid | 18 | Calculated (M + H)$^+$ = 471.14; Found (M + H)$^+$ = 471.00. |
| (3S)-3-[({[1-(2-chlorobenzyl)-4-hydroxy-5-methyl-2-oxo-1,2-dihydropyridin-3-yl]amino}carbonyl)amino]-3-(6-methoxy-2-naphthyl)propanoic acid | 5 | Calculated (M − H)$^-$ = 534.14; Found (M − H)$^-$ = 533.91. |
| (3S)-3-[({[2-(2-chlorobenzyl)-5-hydroxy-6-methyl-3-oxo-2,3-dihydropyridazin-4-yl]amino}carbonyl)amino]-3-(3-ethoxyphenyl)propanoic acid | 5 | Calculated (M + H)$^+$ = 501.15; Found (M + H)$^+$ = 501.01. |
| 3-[({[1-(2-chlorobenzyl)-4-hydroxy-2-oxo-1,2-dihydropyridin-3-yl]amino}carbonyl)amino]-3-thien-2-ylpropanoic acid | 30 | Calculated (M + H)$^+$ = 448.07; Found (M + H)$^+$ = 447.97. |
| (3S)-3-[({[5-chloro-1-(2-chlorobenzyl)-4-hydroxy-2-oxo-1,2-dihydropyridin-3-yl]amino}carbonyl)amino]-3-(4-methylphenyl)propanoic acid | 6 | Calculated (M − H)$^-$ = 488.08; Found (M − H)$^-$ = 487.97. |
| (3S)-3-(3-butoxyphenyl)-3-[({[1-(2-chlorobenzyl)-4-hydroxy-2-oxo-2,5,6,7-tetrahydro-1H-cyclopenta[b]pyridin-3-yl]amino}carbonyl)amino]propanoic acid | 20 | Calculated (M − H)$^-$ = 552.19; Found (M − H)$^-$ = 552.01. |
| (3S)-3-[({[1-(2-chlorobenzyl)-4-hydroxy-2-oxo-1,2-dihydropyridin-3-yl]amino}carbonyl)amino]-3-[3-(cyclopentyloxy)phenyl]propanoic acid | 5 | Calculated (M − H)$^-$ = 524.16; Found (M − H)$^-$ = 524.00. |
| (3S)-3-[({[2-(2-chlorobenzyl)-5-hydroxy-6-methyl-3-oxo-2,3-dihydropyridazin-4-yl]amino}carbonyl)amino]-3-(3,4-diethoxyphenyl)propanoic acid | 3 | Calculated (M + H)$^+$ = 545.18; Found (M + H)$^+$ = 544.98. |
| (3S)-3-[({[1-(2-chlorobenzyl)-4-hydroxy-5-methyl-2-oxo-1,2-dihydropyridin-3-yl]amino}carbonyl)amino]-3-(1-methyl-1H-indol-5-yl)propanoic acid | 3 | Calculated (M − H)$^-$ = 507.14; Found (M − H)$^-$ = 506.94. |
| (3S)-3-[({[2-(2-chlorobenzyl)-5-hydroxy-6-methyl-3-oxo-2,3-dihydropyridazin-4-yl]amino}carbonyl)amino]-3-(3,5-diethoxyphenyl)propanoic acid | 10 | Calculated (M + H)$^+$ = 545.18; Found (M + H)$^+$ = 545.01. |
| (3S)-3-[({[1-(2-chlorobenzyl)-4-hydroxy-5-methyl-2-oxo-1,2-dihydropyridin-3-yl]amino}carbonyl)amino]-3-[4-(trifluoromethoxy)phenyl]propanoic acid | 70 | Calculated (M − H)$^-$ = 538.10; Found (M − H)$^-$ = 537.95. |
| (3S)-3-[({[1-(2-chlorobenzyl)-4-hydroxy-5-methyl-2-oxo-1,2-dihydropyridin-3-yl]amino}carbonyl)amino]-3-[3-(trifluoromethoxy)phenyl]propanoic acid | 10 | Calculated (M − H)$^-$ = 538.10; Found (M − H)$^-$ = 537.95. |
| (3S)-3-[({[1-(2-chlorobenzyl)-4-hydroxy-5-methyl-2-oxo-1,2-dihydropyridin-3-yl]amino}carbonyl)amino]-3-(4-methoxyphenyl)propanoic acid | 4 | Calculated (M + H)$^+$ = 486.14; Found (M + H)$^+$ = 486.04. |
| (3S)-3-[({[1-(2-chlorobenzyl)-4-hydroxy-2-oxo-1,2-dihydropyridin-3-yl]amino}carbonyl)amino]-3-(6-methoxy-2-naphthyl)propanoic acid | 15 | Calculated (M − H)$^-$ = 520.13; Found (M − H)$^-$ = 520.03. |
| (3S)-3-{[({1-[2-fluoro-6-(trifluoromethyl)benzyl]-4-hydroxy-5-methyl-2-oxo-1,2-dihydropyridin-3-yl}amino)carbonyl]amino}-3-(4-methylphenyl)propanoic acid | 100 | Calculated (M − H)$^-$ = 520.15; Found (M − H)$^-$ = 519.97. |
| (3S)-3-[({[1-(2-chlorobenzyl)-4-hydroxy-5-methyl-2-oxo-1,2-dihydropyridin-3-yl]amino}carbonyl)amino]-3-[3-(trifluoromethyl)phenyl]propanoic acid | 10 | Calculated (M − H)$^-$ = 522.10; Found (M − H)$^-$ = 521.96. |
| (3S)-3-[({[1-(2-chlorobenzyl)-4-hydroxy-5-methyl-2-oxo-1,2-dihydropyridin-3-yl]amino}carbonyl)amino]-3-(3-methoxyphenyl)propanoic acid | 3 | Calculated (M − H)$^-$ = 484.13; Found (M − H)$^-$ = 484.00. |

TABLE 6-continued

| Compound | IC$_{50}$ (nM) | Mass Spectral Data (m/z) |
|---|---|---|
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(4-methylphenyl)propanoic acid | 20 | Calculated (M + H)$^+$ = 510.18; Found (M + H)$^+$ = 510.05. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid | 4 | Calculated (M + H)$^+$ = 540.19; Found (M + H)$^+$ = 540.10. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid | 3 | Calculated (M + H)$^+$ = 540.19; Found (M + H)$^+$ = 540.09. |
| (3S)-3-[({[1-(2-chlorobenzyl)-4-hydroxy-5-methyl-2-oxo-1,2-dihydropyridin-3-yl]amino}carbonyl)amino]-3-(3,5-diethoxyphenyl)propanoic acid | 3 | Calculated (M − H)$^-$ = 542.17; Found (M − H)$^-$ = 542.00. |
| (3S)-3-[({[1-(2-chloro-6-ethoxybenzyl)-5-ethyl-4-hydroxy-2-oxo-1,2-dihydropyridin-3-yl]amino}carbonyl)amino]-3-(3-ethoxyphenyl)propanoic acid | 4 | Calculated (M − H)$^-$ = 556.19; Found (M − H)$^-$ = 556.01. |
| (3S)-3-[({[1-(2-chloro-6-ethoxybenzyl)-4-hydroxy-2-oxo-1,2-dihydropyridin-3-yl]amino}carbonyl)amino]-3-(3-ethoxyphenyl)propanoic acid | 3 | Calculated (M + H)$^+$ = 530.17; Found (M + H)$^+$ = 530.04. |
| (3S)-3-[({[1-(2-chlorobenzyl)-4-hydroxy-5-methyl-2-oxo-1,2-dihydropyridin-3-yl]amino}carbonyl)amino]-3-[3-(cyclopentyloxy)phenyl]propanoic acid | 15 | Calculated (M − H)$^-$ = 530.17; Found (M − H)$^-$ = 538.03. |
| 3-(1,1'-biphenyl-4-yl)-3-[({[1-(2-chlorobenzyl)-4-hydroxy-5-methyl-2-oxo-1,2-dihydropyridin-3-yl]amino}carbonyl)amino]propanoic acid | 130 | Calculated (M − H)$^-$ = 530.15; Found (M − H)$^-$ = 529.96. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(2,2,2-trifluoroethoxy)phenyl]propanoic acid | 30 | Calculated (M + H)$^+$ = 580.15; Found (M + H)$^+$ = 580.02. |
| (3S)-3-[({[1-(2-chlorobenzyl)-4-hydroxy-5-methyl-2-oxo-1,2-dihydropyridin-3-yl]amino}carbonyl)amino]-3-[3-(2,2,2-trifluoroethoxy)phenyl]propanoic acid | 15 | Calculated (M + H)$^+$ = 554.13; Found (M + H)$^+$ = 554.00. |
| (3S)-3-[({[1-(2-chlorobenzyl)-4-hydroxy-5-methyl-2-oxo-1,2-dihydropyridin-3-yl]amino}carbonyl)amino]-3-(3-isopropoxyphenyl)propanoic acid | 3 | Calculated (M + H)$^+$ = 514.17; Found (M + H)$^+$ = 514.05. |
| (3S)-3-[({[1-(2-chloro-6-ethoxybenzyl)-4-hydroxy-5-methyl-2-oxo-1,2-dihydropyridin-3-yl]amino}carbonyl)amino]-3-(3-isopropoxyphenyl)propanoic acid | 4 | Calculated (M + H)$^+$ = 558.20; Found (M + H)$^+$ = 558.05. |

TABLE 7

| Compound | IC$_{50}$ (nM) | Mass Spectral Data (m/z) |
|---|---|---|
| (3S)-3-[({[1-(2-chlorobenzyl)-4-hydroxy-5-methyl-2-oxo-1,2-dihydropyridin-3-yl]amino}carbonyl)amino]-3-(4-methoxy-3-methylphenyl)propanoic acid | 9 | Calculated (M + H)$^+$ = 500.16; Found (M + H)$^+$ = 500.01. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid | 10 | Calculated (M + H)$^+$ = 554.21; Found (M + H)$^+$ = 554.06. |
| (3S)-3-[({[1-(2-chloro-6-ethoxybenzyl)-4-hydroxy-5-methyl-2-oxo-1,2-dihydropyridin-3-yl]amino}carbonyl)amino]-3-(6-methoxy-2-naphthyl)propanoic acid | 3 | Calculated (M + H)$^+$ = 580.19; Found (M + H)$^+$ = 580.07. |
| (3S)-3-[({[1-(2-chlorobenzyl)-4-hydroxy-5-methyl-2-oxo-1,2-dihydropyridin-3-yl]amino}carbonyl)amino]-3-(3,5-dimethoxy-4-methylphenyl)propanoic acid | 12 | Calculated (M + H)$^+$ = 530.17; Found (M + H)$^+$ = 530.00. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(3-propoxyphenyl)propanoic acid | 12 | Calculated (M + H)$^+$ = 554.21; Found (M + H)$^+$ = 554.05. |

TABLE 7-continued

| Compound | IC$_{50}$ (nM) | Mass Spectral Data (m/z) |
| --- | --- | --- |
| (3S)-3-[({[1-(2-chloro-6-propoxybenzyl)-4-hydroxy-5-methyl-2-oxo-1,2-dihydropyridin-3-yl]amino}carbonyl)amino]-3-(4-methylphenyl)propanoic acid | 10 | Calculated (M + H)$^+$ = 528.19; Found (M + H)$^+$ = 528.06. |
| (3S)-3-[({[1-(2-chloro-6-isobutoxybenzyl)-4-hydroxy-5-methyl-2-oxo-1,2-dihydropyridin-3-yl]amino}carbonyl)amino]-3-(4-methylphenyl)propanoic acid | 22 | Calculated (M + H)$^+$ = 542.21; Found (M + H)$^+$ = 542.06. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-propoxyphenyl)propanoic acid | 15 | Calculated (M + H)$^+$ = 540.19; Found (M + H)$^+$ = 540.07. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(4-methylphenyl)propanoic acid | 3 | Calculated (M + H)$^+$ = 540.19; Found (M + H)$^+$ = 540.04. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid | 4 | Calculated (M + H)$^+$ = 584.22; Found (M + H)$^+$ = 584.05. |
| (3S)-3-[({[1-(2-chlorobenzyl)-4-hydroxy-5-methyl-2-oxo-1,2-dihydropyridin-3-yl]amino}carbonyl)amino]-3-(2',6'-dimethoxy-1,1'-biphenyl-4-yl)propanoic acid | 40 | Calculated (M + H)$^+$ = 592.19; Found (M + H)$^+$ = 592.04. |
| (3S)-3-[({[1-(2-chlorobenzyl)-4-hydroxy-5-methyl-2-oxo-1,2-dihydropyridin-3-yl]amino}carbonyl)amino]-3-(1-methyl-1H-indol-7-yl)propanoic acid | 30 | Calculated (M + H)$^+$ = 509.16; Found (M + H)$^+$ = 509.03. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid | 2 | Calculated (M + H)$^+$ = 570.20; Found (M + H)$^+$ = 570.09. |
| (3S)-3-[({[1-(2-chloro-6-propoxybenzyl)-4-hydroxy-5-methyl-2-oxo-1,2-dihydropyridin-3-yl]amino}carbonyl)amino]-3-(3-ethoxyphenyl)propanoic acid | 5 | Calculated (M + H)$^+$ = 558.20; Found (M + H)$^+$ = 558.03. |
| (3S)-3-[({[1-(2-chloro-6-isobutoxybenzyl)-4-hydroxy-5-methyl-2-oxo-1,2-dihydropyridin-3-yl]amino}carbonyl)amino]-3-(3-ethoxyphenyl)propanoic acid | 14 | Calculated (M + H)$^+$ = 572.22; Found (M + H)$^+$ = 572.05. |
| (3S)-3-[({[1-(2-chloro-6-isopropoxybenzyl)-4-hydroxy-5-methyl-2-oxo-1,2-dihydropyridin-3-yl]amino}carbonyl)amino]-3-(3-ethoxyphenyl)propanoic acid | 7 | Calculated (M + H)$^+$ = 558.20; Found (M + H)$^+$ = 558.03. |
| (3S)-3-{[({1-[2-chloro-6-(2,2,2-trifluoroethoxy)benzyl]-4-hydroxy-5-methyl-2-oxo-1,2-dihydropyridin-3-yl}amino)carbonyl]amino}-3-(3-ethoxyphenyl)propanoic acid | 4 | Calculated (M + H)$^+$ = 598.16; Found (M + H)$^+$ = 597.99. |
| 3-[({[1-(2-chlorobenzyl)-4-hydroxy-5-methyl-2-oxo-1,2-dihydropyridin-3-yl]amino}carbonyl)amino]-3-[4-(methylthio)phenyl]propanoic acid | 15 | Calculated (M + H)$^+$ = 502.12; Found (M + H)$^+$ = 501.98. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(6-methoxy-2-naphthyl)propanoic acid | 2 | Calculated (M + H)$^+$ = 606.20; Found (M + H)$^+$ = 606.04. |
| (3S)-3-[({[1-(2-chlorobenzyl)-4-hydroxy-5-methyl-2-oxo-1,2-dihydropyridin-3-yl]amino}carbonyl)amino]-3-(2,3-dihydro-1-benzofuran-5-yl)propanoic acid | 6 | Calculated (M + H)$^+$ = 498.14; Found (M + H)$^+$ = 498.02. |
| (3S)-3-[({[1-(2-chloro-6-ethoxybenzyl)-4-hydroxy-5-methyl-2-oxo-1,2-dihydropyridin-3-yl]amino}carbonyl)amino]-3-(1-methyl-1H-indol-5-yl)propanoic acid | 3 | Calculated (M + H)$^+$ = 553.19; Found (M + H)$^+$ = 553.05. |
| (3S)-3-[({[1-(2-chloro-6-ethoxybenzyl)-4-hydroxy-5-methyl-2-oxo-1,2-dihydropyridin-3-yl]amino}carbonyl)amino]-3-(2,3-dihydro-1-benzofuran-5-yl)propanoic acid | 2 | Calculated (M + H)$^+$ = 542.17; Found (M + H)$^+$ = 542.06. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3,5-diethoxyphenyl)propanoic acid | 3 | Calculated (M + H)$^+$ = 614.22; Found (M + H)$^+$ = 614.11. |
| (3S)-3-[({[1-(2-chloro-6-isopropoxybenzyl)-4-hydroxy-5-methyl-2-oxo-1,2-dihydropyridin-3-yl]amino}carbonyl)amino]-3-(3-ethoxyphenyl)propanoic acid | 4 | Calculated (M + H)$^+$ = 558.20; Found (M + H)$^+$ = 558.02. |
| (3S)-3-[({[1-(2-chloro-6-ethoxybenzyl)-4-hydroxy-5-methyl-2-oxo-1,2-dihydropyridin-3-yl]amino}carbonyl)amino]-3-(3-propoxyphenyl)propanoic acid | 3 | Calculated (M + H)$^+$ = 558.20; Found (M + H)$^+$ = 558.07. |

TABLE 7-continued

| Compound | IC$_{50}$ (nM) | Mass Spectral Data (m/z) |
|---|---|---|
| (3S)-3-(3-butoxyphenyl)-3-[({[1-(2-chloro-6-ethoxybenzyl)-4-hydroxy-5-methyl-2-oxo-1,2-dihydropyridin-3-yl]amino}carbonyl)amino]propanoic acid | 4 | Calculated (M + H)$^+$ = 572.22; Found (M + H)$^+$ = 572.04. |
| (3S)-3-[({[5-chloro-1-(2-chloro-6-ethoxybenzyl)-4-hydroxy-2-oxo-1,2-dihydropyridin-3-yl]amino}carbonyl)amino]-3-(3-ethoxyphenyl)propanoic acid | 3 | Calculated (M + H)$^+$ = 564.13; Found (M + H)$^+$ = 563.99. |
| (3S)-3-[({[1-(2-chloro-6-ethoxybenzyl)-4-hydroxy-2-oxo-1,2-dihydropyridin-3-yl]amino}carbonyl)amino]-3-(3-isopropoxyphenyl)propanoic acid | 3 | Calculated (M + H)$^+$ = 544.19; Found (M + H)$^+$ = 544.06. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(2,3-dihydro-1-benzofuran-5-yl)propanoic acid | 2 | Calculated (M + H)$^+$ = 524.16; Found (M + H)$^+$ = 524.03. |
| (3S)-3-[({[2-(2-chloro-6-ethoxybenzyl)-5-hydroxy-6-methyl-3-oxo-2,3-dihydropyridazin-4-yl]amino}carbonyl)amino]-3-(4-methylphenyl)propanoic acid | 7 | Calculated (M + H)$^+$ = 515.19; Found (M + H)$^+$ = 515.05. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-propoxyphenyl)propanoic acid | 3 | Calculated (M + H)$^+$ = 584.21; Found (M + H)$^+$ = 584.10. |
| (3S)-3-[({[2-(2-chloro-6-ethoxybenzyl)-5-hydroxy-6-methyl-3-oxo-2,3-dihydropyridazin-4-yl]amino}carbonyl)amino]-3-(3-ethoxyphenyl)propanoic acid | 3 | Calculated (M + H)$^+$ = 545.18; Found (M + H)$^+$ = 545.05. |
| (3S)-3-[({[2-(2-chloro-6-ethoxybenzyl)-5-hydroxy-6-methyl-3-oxo-2,3-dihydropyridazin-4-yl]amino}carbonyl)amino]-3-(3-isopropoxyphenyl)propanoic acid | 2 | Calculated (M + H)$^+$ = 559.20; Found (M + H)$^+$ = 559.04. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopentyloxy)phenyl]propanoic acid | 6 | Calculated (M + H)$^+$ = 610.23; Found (M + H)$^+$ = 610.14. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(cyclopentyloxy)phenyl]propanoic acid | 7 | Calculated (M + H)$^+$ = 566.21; Found (M + H)$^+$ = 566.09. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-phenylpropanoic acid | 2 | Calculated (M + H)$^+$ = 526.17; Found (M + H)$^+$ = 526.07. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-phenylpropanoic acid | 8 | Calculated (M + H)$^+$ = 482.15; Found (M + H)$^+$ = 482.07. |
| (3S)-3-[({[1-(2-chloro-6-methylbenzyl)-4-hydroxy-5-methyl-2-oxo-1,2-dihydropyridin-3-yl]amino}carbonyl)amino]-3-(2,3-dihydro-1-benzofuran-5-yl)propanoic acid | 5 | Calculated (M + H)$^+$ = 512.16; Found (M + H)$^+$ = 512.03. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1,3-diethyl-2-oxo-2,3-dihydro-1H-benzimidazol-5-yl)propanoic acid | 4 | Calculated (M + H)$^+$ = 594.21; Found (M + H)$^+$ = 594.05. |
| (3S)-3-[({[1-(2-chloro-6-ethoxybenzyl)-4-hydroxy-5-methyl-2-oxo-1,2-dihydropyridin-3-yl]amino}carbonyl)amino]-3-[3-(trifluoromethyl)phenyl]propanoic acid | 3 | Calculated (M + H)$^+$ = 568.15; Found (M + H)$^+$ = 568.00. |
| (3S)-3-[({[1-(2-chloro-6-ethoxybenzyl)-4-hydroxy-5-methyl-2-oxo-1,2-dihydropyridin-3-yl]amino}carbonyl)amino]-3-[3-(trifluoromethoxy)phenyl]propanoic acid | 4 | Calculated (M + H)$^+$ = 584.14; Found (M + H)$^+$ = 584.01. |
| (3S)-3-{[({1-[2-chloro-6-(2-methoxyethoxy)benzyl]-4-hydroxy-2-oxo-2,5,6,7-tetrahydro-1H-cyclopenta[b]pyridin-3-yl}amino)carbonyl]amino}-3-(4-methylphenyl)propanoic acid | 6 | Calculated (M − H)$^-$ = 568.18; Found (M − H)$^-$ = 568.03. |
| (3S)-3-{[({1-[2-chloro-6-(2-methoxyethoxy)benzyl]-4-hydroxy-2-oxo-2,5,6,7-tetrahydro-1H-cyclopenta[b]pyridin-3-yl}amino)carbonyl]amino}-3-(3-ethoxyphenyl)propanoic acid | 4 | Calculated (M − H)$^-$ = 598.19; Found (M − H)$^-$ = 598.01. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(cyclopropyloxy)phenyl]propanoic acid | 4 | Calculated (M + H)$^+$ = 538.17; Found (M + H)$^+$ = 538.09. |

TABLE 7-continued

| Compound | IC$_{50}$ (nM) | Mass Spectral Data (m/z) |
|---|---|---|
| (3S)-3-[({[1-(2-chloro-6-ethoxybenzyl)-4-hydroxy-5,6-dimethyl-2-oxo-1,2-dihydropyridin-3-yl]amino}carbonyl)amino]-3-(3-ethoxyphenyl)propanoic acid | 4 | Calculated (M − H)$^-$ = 556.19; Found (M − H)$^-$ = 556.02. |
| (3S)-3-[({[1-(2-chloro-6-ethoxybenzyl)-4-hydroxy-5,6-dimethyl-2-oxo-1,2-dihydropyridin-3-yl]amino}carbonyl)amino]-3-(4-methylphenyl)propanoic acid | 4 | Calculated (M − H)$^-$ = 526.17; Found (M − H)$^-$ = 526.02. |
| (3S)-3-[({[1-(2-chloro-6-ethoxybenzyl)-5-ethyl-4-hydroxy-6-methyl-2-oxo-1,2-dihydropyridin-3-yl]amino}carbonyl)amino]-3-(3-ethoxyphenyl)propanoic acid | 4 | Calculated (M − H)$^-$ = 570.20; Found (M − H)$^-$ = 570.04. |
| (3S)-3-[({[1-(2-chloro-6-ethoxybenzyl)-5-ethyl-4-hydroxy-6-methyl-2-oxo-1,2-dihydropyridin-3-yl]amino}carbonyl)amino]-3-(4-methylphenyl)propanoic acid | 4 | Calculated (M − H)$^-$ = 540.19; Found (M − H)$^-$ = 540.05. |
| (3S)-3-[({[1-(2-chlorobenzyl)-4-hydroxy-5-methyl-2-oxo-1,2-dihydropyridin-3-yl]amino}carbonyl)amino]-3-(2'-methoxy-1,1'-biphenyl-4-yl)propanoic acid | 25 | Calculated (M + H)$^+$ = 562.09; Found (M + H)$^+$ = 562.17. |
| (3S)-3-[({[1-(2-chloro-6-ethoxybenzyl)-4-hydroxy-5,6-dimethyl-2-oxo-1,2-dihydropyridin-3-yl]amino}carbonyl)amino]-3-(3-isopropoxyphenyl)propanoic acid | 3 | Calculated (M − H)$^-$ = 570.20; Found (M − H)$^-$ = 570.00. |
| (3S)-3-[({[1-(2-chloro-6-ethoxybenzyl)-4-hydroxy-5,6-dimethyl-2-oxo-1,2-dihydropyridin-3-yl]amino}carbonyl)amino]-3-phenylpropanoic acid | 4 | Calculated (M − H)$^-$ = 512.16; Found (M − H)$^-$ = 512.01. |
| (3S)-3-[({[1-(2-chloro-6-ethoxybenzyl)-5-ethyl-4-hydroxy-6-methyl-2-oxo-1,2-dihydropyridin-3-yl]amino}carbonyl)amino]-3-(3-isopropoxyphenyl)propanoic acid | 5 | Calculated (M − H)$^-$ = 584.22; Found (M − H)$^-$ = 584.03. |
| (3S)-3-[({[1-(2-chloro-6-ethoxybenzyl)-5-ethyl-4-hydroxy-6-methyl-2-oxo-1,2-dihydropyridin-3-yl]amino}carbonyl)amino]-3-phenylpropanoic acid | 4 | Calculated (M − H)$^-$ = 526.17; Found (M − H)$^-$ = 526.00. |
| (3S)-3-[({[1-(2-chloro-6-ethoxybenzyl)-4-hydroxy-5-methyl-2-oxo-1,2-dihydropyridin-3-yl]amino}carbonyl)amino]-3-(6-ethoxy-2-naphthyl)propanoic acid | 6 | Calculated (M − H)$^-$ = 592.19; Found (M − H)$^-$ = 592.00. |
| (3S)-3-[({[2-(2-chlorobenzyl)-6-ethyl-5-hydroxy-3-oxo-2,3-dihydropyridazin-4-yl]amino}carbonyl)amino]-3-(4-methylphenyl)propanoic acid | 22 | Calculated (M − H)$^-$ = 483.14; Found (M − H)$^-$ = 483.03. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-isobutylphenyl)propanoic acid | 15 | Calculated (M − H)$^-$ = 536.20; Found (M − H)$^-$ = 535.99. |
| (3S)-3-[({[1-(2-chlorobenzyl)-4-hydroxy-5-methyl-2-oxo-1,2-dihydropyridin-3-yl]amino}carbonyl)amino]-3-(1-methyl-1H-indol-6-yl)propanoic acid | 4 | Calculated (M + H)$^+$ = 509.16; Found (M + H)$^+$ = 509.05. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-[3-(cyclopropyloxy)phenyl]propanoic acid | 4 | Calculated (M − H)$^-$ = 550.17; Found (M − H)$^-$ = 550.01. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(6-ethoxy-2-naphthyl)propanoic acid | 15 | Calculated (M − H)$^-$ = 574.17; Found (M − H)$^-$ = 574.02. |
| (3S)-3-[({[1-(2-chloro-6-ethoxybenzyl)-4-hydroxy-2-oxo-5-propyl-1,2-dihydropyridin-3-yl]amino}carbonyl)amino]-3-phenylpropanoic acid | 23 | Calculated (M − H)$^-$ = 526.17; Found (M − H)$^-$ = 526.04. |
| (3S)-3-[({[1-(2-chloro-6-ethoxybenzyl)-4-hydroxy-2-oxo-5-propyl-1,2-dihydropyridin-3-yl]amino}carbonyl)amino]-3-(3-isopropoxyphenyl)propanoic acid | 22 | Calculated (M − H)$^-$ = 584.22; Found (M − H)$^-$ = 584.09. |
| (3S)-3-[({[1-(2-chloro-6-ethoxybenzyl)-4-hydroxy-2-oxo-5-propyl-1,2-dihydropyridin-3-yl]amino}carbonyl)amino]-3-(4-methylphenyl)propanoic acid | 20 | Calculated (M − H)$^-$ = 540.19; Found (M − H)$^-$ = 540.05. |
| (3S)-3-[({[1-(2-chloro-6-ethoxybenzyl)-4-hydroxy-2-oxo-5-propyl-1,2-dihydropyridin-3-yl]amino}carbonyl)amino]-3-(3-ethoxyphenyl)propanoic acid | 6 | Calculated (M − H)$^-$ = 570.20; Found (M − H)$^-$ = 570.04. |
| (3S)-3-[({[1-(2-chlorobenzyl)-4-hydroxy-2-oxo-1,2-dihydropyridin-3-yl]amino}carbonyl)amino]-3-(4'-methyl-1,1'-biphenyl-4-yl)propanoic acid | 40 | Calculated (M − H)$^-$ = 530.15; Found (M − H)$^-$ = 530.02. |

TABLE 7-continued

| Compound | IC$_{50}$ (nM) | Mass Spectral Data (m/z) |
|---|---|---|
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1-methyl-1H-indol-5-yl)propanoic acid | 4 | Calculated (M − H)$^-$ = 533.16; Found (M − H)$^-$ = 533.00. |
| (3S)-3-[({[1-(2-chloro-6-ethoxybenzyl)-5-cyclopropyl-4-hydroxy-2-oxo-1,2-dihydropyridin-3-yl]amino}carbonyl)amino]-3-(3-isopropoxyphenyl)propanoic acid | 3 | Calculated (M − H)$^-$ = 582.20; Found (M − H)$^-$ = 582.07. |
| (3S)-3-[({[1-(2-chloro-6-ethoxybenzyl)-5-cyclopropyl-4-hydroxy-2-oxo-1,2-dihydropyridin-3-yl]amino}carbonyl)amino]-3-(4-methylphenyl)propanoic acid | 3 | Calculated (M − H)$^-$ = 538.17; Found (M − H)$^-$ = 538.06. |
| (3S)-3-[({[1-(2-chloro-5-propoxybenzyl)-4-hydroxy-5-methyl-2-oxo-1,2-dihydropyridin-3-yl]amino}carbonyl)amino]-3-(4-methylphenyl)propanoic acid | 6 | Calculated (M − H)$^-$ = 526.17; Found (M − H)$^-$ = 526.05. |
| (3S)-3-[({[1-(2-chloro-5-methoxybenzyl)-4-hydroxy-5-methyl-2-oxo-1,2-dihydropyridin-3-yl]amino}carbonyl)amino]-3-(4-methylphenyl)propanoic acid | 3 | Calculated (M − H)$^-$ = 498.14; Found (M − H)$^-$ = 498.01. |
| 3-[({[1-(2-chloro-6-ethoxybenzyl)-4-hydroxy-5-methyl-2-oxo-1,2-dihydropyridin-3-yl]amino}carbonyl)amino]-3-(2-naphthyl)propanoic acid | 13 | Calculated (M − H)$^-$ = 548.16; Found (M − H)$^-$ = 548.01. |
| 3-[({[1-(2-chloro-6-ethoxybenzyl)-4-hydroxy-5-methyl-2-oxo-1,2-dihydropyridin-3-yl]amino}carbonyl)amino]-3-[4-(methylsulfonyl)phenyl]propanoic acid | 8 | Calculated (M − H)$^-$ = 576.12; Found (M − H)$^-$ = 576.00. |
| (3S)-3-[({[1-(2-chlorobenzyl)-4-hydroxy-2-oxo-1,2-dihydropyridin-3-yl]amino}carbonyl)amino]-3-(3'-ethoxy-1,1'-biphenyl-4-yl)propanoic acid | 27 | Calculated (M − H)$^-$ = 560.16; Found (M − H)$^-$ = 560.04. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-[3-(cyclobutyloxy)phenyl]propanoic acid | 20 | Calculated (M − H)$^-$ = 564.19; Found (M − H)$^-$ = 564.00. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(cyclobutyloxy)phenyl]propanoic acid | 17 | Calculated (M − H)$^-$ = 550.17; Found (M − H)$^-$ = 550.02. |
| (3S)-3-[({[1-(2-chloro-6-ethoxybenzyl)-4-hydroxy-6-methyl-2-oxo-1,2-dihydropyridin-3-yl]amino}carbonyl)amino]-3-(3-isopropoxyphenyl)propanoic acid | 3 | Calculated (M − H)$^-$ = 556.19; Found (M − H)$^-$ = 556.05. |
| 3-[({[1-(2-chlorobenzyl)-4-hydroxy-5-methyl-2-oxo-1,2-dihydropyridin-3-yl]amino}carbonyl)amino]-3-(3-pyrrolidin-1-ylphenyl)propanoic acid | 10 | Calculated (M − H)$^-$ = 523.17; Found (M − H)$^-$ = 522.99. |
| 3-[({[1-(2-chlorobenzyl)-4-hydroxy-5-methyl-2-oxo-1,2-dihydropyridin-3-yl]amino}carbonyl)amino]-3-(3-piperidin-1-ylphenyl)propanoic acid | 22 | Calculated (M − H)$^-$ = 537.19; Found (M − H)$^-$ = 537.08. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-[3-(1-ethylpropoxy)phenyl]propanoic acid | 22 | Calculated (M − H)$^-$ = 580.22; Found (M − H)$^-$ = 580.04. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(1-ethylpropoxy)phenyl]propanoic acid | 20 | Calculated (M − H)$^-$ = 566.20; Found (M − H)$^-$ = 566.01. |
| (3S)-3-(4-chloro-3-isopropoxyphenyl)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]propanoic acid | 23 | Calculated (M − H)$^-$ = 586.15; Found (M − H)$^-$ = 585.92. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-chloro-3-isopropoxyphenyl)propanoic acid | 38 | Calculated (M − H)$^-$ = 572.14; Found (M − H)$^-$ = 572.00. |
| (3S)-3-[({[1-(2-chlorobenzyl)-4-hydroxy-2-oxo-1,2-dihydropyridin-3-yl]amino}carbonyl)amino]-3-(3'-methyl-1,1'-biphenyl-4-yl)propanoic acid | 30 | Calculated (M − H)$^-$ = 530.15; Found (M − H)$^-$ = 530.02. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1-methyl-1H-indol-6-yl)propanoic acid | 3 | Calculated (M − H)$^-$ = 533.16; Found (M − H)$^-$ = 532.97. |
| (3S)-3-[({[1-(2-chloro-6-ethoxybenzyl)-4-hydroxy-5-methyl-2-oxo-1,2-dihydropyridin-3-yl]amino}carbonyl)amino]-3-(1-methyl-1H-indol-6-yl)propanoic acid | 3 | Calculated (M − H)$^-$ = 551.17; Found (M − H)$^-$ = 551.02. |

TABLE 7-continued

| Compound | IC$_{50}$ (nM) | Mass Spectral Data (m/z) |
|---|---|---|
| (3S)-3-[({[1-(2-chlorobenzyl)-4-hydroxy-5-methyl-2-oxo-1,2-dihydropyridin-3-yl]amino}carbonyl)amino]-3-(4'-methoxy-1,1'-biphenyl-4-yl)propanoic acid | 23 | Calculated (M − H)$^-$ = 560.16; Found (M − H)$^-$ = 560.01. |
| (3S)-3-[({[1-(2-chlorobenzyl)-4-hydroxy-5-methyl-2-oxo-1,2-dihydropyridin-3-yl]amino}carbonyl)amino]-3-(2'-methyl-1,1'-biphenyl-4-yl)propanoic acid | 55 | Calculated (M + H)$^+$ = 546.18; Found (M + H)$^+$ = 546.11. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(6-methoxy-2-naphthyl)propanoic acid | 3 | Calculated (M − H)$^-$ = 560.16; Found (M − H)$^-$ = 560.00. |
| (3S)-3-(4-chloro-3-ethoxyphenyl)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]propanoic acid | 25 | Calculated (M − H)$^-$ = 572.14; Found (M − H)$^-$ = 571.94. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-chloro-3-ethoxyphenyl)propanoic acid | 30 | Calculated (M − H)$^-$ = 558.12; Found (M − H)$^-$ = 557.77. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-isobutylphenyl)propanoic acid | 4 | Calculated (M + H)$^+$ = 582.24; Found (M + H)$^+$ = 582.10. |
| (3S)-3-[({[1-(2-chloro-5-ethoxybenzyl)-4-hydroxy-5-methyl-2-oxo-1,2-dihydropyridin-3-yl]amino}carbonyl)amino]-3-(4-methylphenyl)propanoic acid | 4 | Calculated (M + H)$^+$ = 514.17; Found (M + H)$^+$ = 514.08. |
| 3-[({[1-(2-chlorobenzyl)-4-hydroxy-5-methyl-2-oxo-1,2-dihydropyridin-3-yl]amino}carbonyl)amino]-3-[4-(methylsulfonyl)phenyl]propanoic acid | 134 | Calculated (M + H)$^+$ = 534.11; Found (M + H)$^+$ = 534.07. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(2,4-dichloro-3-ethoxyphenyl)propanoic acid | 225 | Calculated (M + H)$^+$ = 594.09; Found (M + H)$^+$ = 593.98. |
| (3S)-3-{[({1-[2-chloro-5-(piperidin-1-ylsulfonyl)benzyl]-4-hydroxy-5-methyl-2-oxo-1,2-dihydropyridin-3-yl}amino)carbonyl]amino}-3-(4-methylphenyl)propanoic acid | 27 | Calculated (M − H)$^-$ = 615.17; Found (M − H)$^-$ = 615.04. |
| (3S)-3-{[({1-[2-chloro-5-(pyrrolidin-1-ylsulfonyl)benzyl]-4-hydroxy-5-methyl-2-oxo-1,2-dihydropyridin-3-yl}amino)carbonyl]amino}-3-(4-methylphenyl)propanoic acid | 15 | Calculated (M − H)$^-$ = 601.15; Found (M − H)$^-$ = 601.03. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopropyloxy)phenyl]propanoic acid | 2 | Calculated (M + H)$^+$ = 582.20; Found (M + H)$^+$ = 582.10. |
| (3S)-3-{[({1-[2-chloro-6-(cyclopentylmethoxy)benzyl]-4-hydroxy-5-methyl-2-oxo-1,2-dihydropyridin-3-yl}amino)carbonyl]amino}-3-(4-methylphenyl)propanoic acid | 20 | Calculated (M − H)$^-$ = 566.20; Found (M − H)$^-$ = 566.09. |
| (3S)-3-{[({1-[2-(benzyloxy)-6-chlorobenzyl]-4-hydroxy-5-methyl-2-oxo-1,2-dihydropyridin-3-yl}amino)carbonyl]amino}-3-(4-methylphenyl)propanoic acid | 10 | Calculated (M − H)$^-$ = 574.17; Found (M − H)$^-$ = 574.01. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-chloro-4,5-diethoxyphenyl)propanoic acid | 3 | Calculated (M + H)$^+$ = 604.16; Found (M + H)$^+$ = 604.02. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(2,4-dichloro-3,5-diethoxyphenyl)propanoic acid | 500 | Calculated (M + H)$^+$ = 652.14; Found (M + H)$^+$ = 651.98. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(2,4-dichloro-3,5-diethoxyphenyl)propanoic acid | 450 | Calculated (M + H)$^+$ = 638.12; Found (M + H)$^+$ = 637.97. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid | 9 | Calculated (M + H)$^+$ = 552.19; Found (M + H)$^+$ = 552.10. |
| (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid | 4 | Calculated (M + H)$^+$ = 596.21; Found (M + H)$^+$ = 596.11. |

TABLE 7-continued

| Compound | IC$_{50}$ (nM) | Mass Spectral Data (m/z) |
|---|---|---|
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid | 10 | Calculated (M + H)$^+$ = 566.20; Found (M + H)$^+$ = 566.12. |
| (3S)-3-[({[1-(2-chlorobenzyl)-4-hydroxy-5-methyl-2-oxo-1,2-dihydropyridin-3-yl]amino}carbonyl)amino]-3-(2,4-diethoxypyrimidin-5-yl)propanoic acid | 13 | Calculated (M − H)$^-$ = 544.16; Found (M − H)$^-$ = 544.00. |
| (3S)-3-[({[1-(2,3-dichloro-6-ethoxybenzyl)-4-hydroxy-2-oxo-2,5,6,7-tetrahydro-1H-cyclopenta[b]pyridin-3-yl]amino}carbonyl)amino]-3-(4-methylphenyl)propanoic acid | 5 | Calculated (M − H)$^-$ = 572.13; Found (M − H)$^-$ = 571.97. |
| (3S)-3-[3-(cyclopropylmethoxy)phenyl]-3-[({[1-(2,3-dichloro-6-ethoxybenzyl)-4-hydroxy-2-oxo-2,5,6,7-tetrahydro-1H-cyclopenta[b]pyridin-3-yl]amino}carbonyl)amino]propanoic acid | 7 | Calculated (M − H)$^-$ = 628.16; Found (M − H)$^-$ = 627.98. |
| (3S)-3-[({[1-(2,3-dichloro-6-ethoxybenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid | 3 | Calculated (M − H)$^-$ = 602.15; Found (M − H)$^-$ = 601.99. |
| (3S)-3-[({[1-(2,3-dichloro-6-ethoxybenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid | 5 | Calculated (M − H)$^-$ = 616.16; Found (M − H)$^-$ = 616.01. |
| (3S)-3-({[[1-(2-chlorobenzyl)-4-methoxy-2-oxo-1,2-dihydropyridin-3-yl](methyl)amino]carbonyl}amino)-3-(4-methylphenyl)propanoic acid | 2000 | Calculated (M − H)$^-$ = 482.14; Found (M − H)$^-$ = 482.07. |
| (3S)-3-[({[1-(2-chlorobenzyl)-4-hydroxy-5-methyl-2-oxo-1,2-dihydropyridin-3-yl]amino}carbonyl)amino]-3-(2'-methoxy-1,1'-biphenyl-3-yl)propanoic acid | 15 | Calculated (M − H)$^-$ = 560.16; Found (M − H)$^-$ = 559.98. |
| 3-[({[1-(2-chlorobenzyl)-4-hydroxy-5-methyl-2-oxo-1,2-dihydropyridin-3-yl]amino}carbonyl)amino]-3-(5-methyl-2-furyl)propanoic acid | 20 | Calculated (M − H)$^-$ = 458.11; Found (M − H)$^-$ = 457.99. |
| 3-[({[1-(2-chloro-6-methylbenzyl)-4-hydroxy-5-methyl-2-oxo-1,2-dihydropyridin-3-yl]amino}carbonyl)amino]-3-[4-(methylsulfonyl)phenyl]propanoic acid | 43 | Calculated (M + H)$^+$ = 548.13; Found (M + H)$^+$ = 548.07. |
| 3-[({[1-(2-chlorobenzyl)-4-hydroxy-2-oxo-2,5,6,7-tetrahydro-1H-cyclopenta[b]pyridin-3-yl]amino}carbonyl)amino]-3-(2-furyl)propanoic acid | 5 | Calculated (M − H)$^-$ = 470.11; Found (M − H)$^-$ = 469.96. |
| 3-[({[1-(2-chlorobenzyl)-4-hydroxy-5-methyl-2-oxo-1,2-dihydropyridin-3-yl]amino}carbonyl)amino]-3-(2-furyl)propanoic acid | 4 | Calculated (M − H)$^-$ = 444.10; Found (M − H)$^-$ = 443.91. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[4-(trifluoromethyl)phenyl]propanoic acid | 18 | Calculated (M − H)$^-$ = 548.12; Found (M − H)$^-$ = 548.00. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-methylphenyl)propanoic acid | 5 | Calculated (M − H)$^-$ = 494.15; Found (M − H)$^-$ = 494.02. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-trifluoromethyl)phenyl]propanoic acid | 10 | Calculated (M − H)$^-$ = 548.12; Found (M − H)$^-$ = 547.99. |
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3,5-dimethylphenyl)propanoic acid | 9 | Calculated (M − H)$^-$ = 508.16; Found (M − H)$^-$ = 508.02. |
| (3S)-3-[3,5-bis(trifluoromethyl)phenyl]-3-[({[1-(2-chlorobenzyl)-4-hydroxy-2-oxo-2,5,6,7-tetrahydro-1H-cyclopenta[b]pyridin-3-yl]amino}carbonyl)amino]propanoic acid | 130 | Calculated (M − H)$^-$ = 615.11; Found (M − H)$^-$ = 615.99. |
| (3S)-3-{[({1-[2-chloro-5-(trifluoromethyl)benzyl]-4-hydroxy-5-methyl-2-oxo-1,2-dihydropyridin-3-yl}amino)carbonyl]amino}-3-(4-methylphenyl)propanoic acid | 6 | Calculated (M − H)$^-$ = 536.12; Found (M − H)$^-$ = 535.99. |
| (3S)-3-[({[1-(2-chloro-5-fluorobenzyl)-4-hydroxy-5-methyl-2-oxo-1,2-dihydropyridin-3-yl]amino}carbonyl)amino]-3-(4-methylphenyl)propanoic acid | 5 | Calculated (M − H)$^-$ = 486.12; Found (M − H)$^-$ = 485.97. |
| (3S)-3-[({[1-(2-chlorobenzyl)-4-hydroxy-5-methyl-2-oxo-1,2-dihydropyridin-3-yl]amino}carbonyl)amino]-3-[3-(diethylamino)phenyl]propanoic acid | 2 | Calculated (M − H)$^-$ = 525.19; Found (M − H)$^-$ = 525.00. |
| 3-(1,1'-biphenyl-4-yl)-3-[({[1-(2-chlorobenzyl)-4-hydroxy-2-oxo-2,5,6,7-tetrahydro-1H-cyclopenta[b]pyridin-3-yl]amino}carbonyl)amino]propanoic acid | 30 | Calculated (M − H)$^-$ = 556.16; Found (M − H)$^-$ = 555.99. |

TABLE 7-continued

| Compound | IC$_{50}$ (nM) | Mass Spectral Data (m/z) |
|---|---|---|
| (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(2,3-dihydro-1H-inden-5-yl)propanoic acid | 8 | Calculated (M + H)$^+$ = 522.17; Found (M + H)$^+$ = 522.03. |
| (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(2,3-dihydro-1H-inden-5-yl)propanoic acid | 10 | Calculated (M + H)$^+$ = 536.19; Found (M + H)$^+$ = 536.08. |
| N-{1-[(2-chlorophenyl)methyl]-4-hydroxy-5-methyl-2-oxo-1,2-dihydro-3-pyridinyl}-N'-[(1S)-1-(4-methylphenyl)-2-(1H-1,2,3,4-tetraazol-5-yl)ethyl]urea | 6000 | Calculated (M + H)$^+$ = 494.17; Found (M + H)$^+$ = 494.01. |
| (3S)-3-[1,1'-biphenyl]-3-yl-3-{[({1-[(2-chlorophenyl)methyl]-4-hydroxy-2-oxo-2,5,6,7-tetrahydro-1H-cyclopenta[b]pyridin-3-yl}amino)carbonyl]amino}propanoic acid | 17 | Calculated (M − H)$^-$ = 556.16; Found (M − H)$^-$ = 556.01. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{4-[(trifluoromethyl)oxy]phenyl}propanoic acid | 13 | Calculated (M − H)$^-$ = 564.11; Found (M − H)$^-$ = 564.01. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{4-[(difluoromethyl)oxy]phenyl}propanoic acid | 13 | Calculated (M − H)$^-$ = 546.12; Found (M − H)$^-$ = 545.97. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(trifluoromethyl)oxy]phenyl}propanoic acid | 10 | Calculated (M − H)$^-$ = 564.11; Found (M − H)$^-$ = 563.98. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(difluoromethyl)oxy]phenyl}propanoic acid | 5 | Calculated (M − H)$^-$ = 546.12; Found (M − H)$^-$ = 546.01. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(1,1,2,2-tetrafluoroethyl)oxy]phenyl}propanoic acid | 4 | Calculated (M − H)$^-$ = 596.12; Found (M − H)$^-$ = 596.02. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[3,5-dimethyl-4-(methyloxy)phenyl]propanoic acid | 11 | Calculated (M − H)$^-$ = 538.17; Found (M − H)$^-$ = 538.04. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(1-ethyl-1H-indol-5-yl)propanoic acid | 5 | Calculated (M + H)$^+$ = 549.19; Found (M + H)$^+$ = 549.02. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(3,5-difluorophenyl)propanoic acid | 7 | Calculated (M − H)$^-$ = 516.11; Found (M − H)$^-$ = 516.01. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[3-fluoro-4-(methyloxy)phenyl]propanoic acid | 3 | Calculated (M − H)$^-$ = 528.13; Found (M − H)$^-$ = 528.00. |
| (3S)-3-{[({1-[(2-chlorophenyl)methyl]-4-hydroxy-2-oxo-2,5,6,7-tetrahydro-1H-cyclopenta[b]Pyridin-3-yl}amino)carbonyl]amino}-3-(4-propylphenyl)propanoic acid | 17 | Calculated (M − H)$^-$ = 522.18; Found (M − H)$^-$ = 522.04. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(4-propylphenyl)propanoic acid | 20 | Calculated (M − H)$^-$ = 536.20; Found (M − H)$^-$ = 536.06. |
| (3S)-3-{[({1-[(2-chlorophenyl)methyl]-4-hydroxy-5-methyl-2-oxo-1,2-dihydro-3-pyridinyl}amino)carbonyl]amino}-3-(2-methylphenyl)propanoic acid | 267 | Calculated (M − H)$^-$ = 468.13; Found (M − H)$^-$ = 468.00. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(4-cyclopropylphenyl)propanoic acid | 25 | Calculated (M + H)$^+$ = 522.18; Found (M + H)$^+$ = 522.04. |
| (3S)-3-{[({1-[(2-chlorophenyl)methyl]-4-hydroxy-5-methyl-2-oxo-1,2-dihydro-3-pyridinyl}amino)carbonyl]amino}-3-(3-quinolinyl)propanoic acid | 22 | Calculated (M − H)$^-$ = 505.13; Found (M − H)$^-$ = 504.98. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(3-quinolinyl)propanoic acid | 22 | Calculated (M − H)$^-$ = 531.14; Found (M − H)$^-$ = 530.99. |

TABLE 7-continued

| Compound | IC$_{50}$ (nM) | Mass Spectral Data (m/z) |
|---|---|---|
| 3-({[(1-{[2-chloro-6-(ethyloxy)phenyl]methyl}-4-hydroxy-5-methyl-2-oxo-1,2-dihydro-3-pyridinyl)amino]carbonyl}amino)-3-(2-furanyl)propanoic acid | 8 | Calculated (M − H)$^-$ = 488.12; Found (M − H)$^-$ = 487.98. |
| (3S)-3-[2,4-bis(ethyloxy)-5-pyrimidinyl]-3-{[({1-[(2-chlorophenyl)methyl]-4-hydroxy-2-oxo-2,5,6,7-tetrahydro-1H-cyclopenta[b]pyridin-3-yl}amino)carbonyl]amino}propanoic acid | 15 | Calculated (M − H)$^-$ = 570.18; Found (M − H)$^-$ = 570.14. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(4-cyclopropylphenyl)propanoic acid | 19 | Calculated (M + H)$^+$ = 536.20; Found (M + H)$^+$ = 536.07. |
| (3R)-3-{[({1-[(2-chlorophenyl)methyl]-4-hydroxy-2-oxo-2,5,6,7-tetrahydro-1H-cyclopenta[b]pyridin-3-yl}amino)carbonyl]amino}butanoic acid | 15 | Calculated (M − H)$^-$ = 418.12; Found (M − H)$^-$ = 418.00. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(4-ethylphenyl)propanoic acid | 8 | Calculated (M − H)$^-$ = 508.16; Found (M − H)$^-$ = 508.06. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[4-(1-methylethyl)phenyl]propanoic acid | 17 | Calculated (M − H)$^-$ = 522.17; Found (M − H)$^-$ = 522.06. |
| (3S)-3-{[({1-[(2-chlorophenyl)methyl]-4-hydroxy-5-methyl-2-oxo-1,2-dihydro-3-pyridinyl}amino)carbonyl]amino}-3-(4-ethylphenyl)propanoic acid | 30 | Calculated (M − H)$^-$ = 482.14; Found (M − H)$^-$ = 482.00. |
| (3S)-3-{[({1-[(2-chlorophenyl)methyl]-4-hydroxy-5-methyl-2-oxo-1,2-dihydro-3-pyridinyl}amino)carbonyl]amino}-3-[4-(1-methylethyl)phenyl]propanoic acid | 175 | Calculated (M − H)$^-$ = 496.16; Found (M − H)$^-$ = 496.01. |
| (3S)-3-{[({1-[(2-chlorophenyl)methyl]-4-hydroxy-5-methyl-2-oxo-1,2-dihydro-3-pyridinyl}amino)carbonyl]amino}-3-[4-(cyclopropyloxy)phenyl]propanoic acid | 6 | Calculated (M − H)$^-$ = 510.14; Found (M − H)$^-$ = 510.00. |
| (3S)-3-{[({1-[(2-chlorophenyl)methyl]-4-hydroxy-5-methyl-2-oxo-1,2-dihydro-3-pyridinyl}amino)carbonyl]amino}-3-(4-propylphenyl)propanoic acid | 12 | Calculated (M − H)$^-$ = 496.16; Found (M − H)$^-$ = 495.99. |
| 3-{[({1-[(2-chlorophenyl)methyl]-4-hydroxy-5-methyl-2-oxo-1,2-dihydro-3-pyridinyl}amino)carbonyl]amino}-3-(4-cyclopropylphenyl)propanoic acid | 35 | Calculated (M − H)$^-$ = 494.15; Found (M − H)$^-$ = 494.01. |
| (3S)-3-{[({1-[(2-chlorophenyl)methyl]-4-hydroxy-5-methyl-2-oxo-1,2-dihydro-3-pyridinyl}amino)carbonyl]amino}-3-(2,3-dihydro-1H-inden-5-yl)propanoic acid | 18 | Calculated (M − H)$^-$ = 494.15; Found (M − H)$^-$ = 494.02. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(9-ethyl-9H-carbazol-3-yl)propanoic acid | 13 | Calculated (M − H)$^-$ = 597.19; Found (M − H)$^-$ = 597.01. |
| (3S)-3-{[({1-[(2-chlorophenyl)methyl]-4-hydroxy-5-methyl-2-oxo-1,2-dihydro-3-pyridinyl}amino)carbonyl]amino}-3-(9-ethyl-9H-carbazol-3-yl)propanoic acid | 23 | Calculated (M − H)$^-$ = 571.17; Found (M − H)$^-$ = 570.99. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(1-methyl-1H-indol-5-yl)propanoic acid | 3 | Calculated (M − H)$^-$ = 547.17; Found (M − H)$^-$ = 547.04. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[(difluoromethyl)oxy]phenyl}propanoic acid | 3 | Calculated (M − H)$^-$ = 560.14; Found (M − H)$^-$ = 560.03. |
| (3S)-3-{[({1-[(2-chlorophenyl)methyl]-4-hydroxy-5-methyl-2-oxo-1,2-dihydro-3-pyridinyl}amino)carbonyl]amino}-3-[2-(ethyloxy)[1,1'-biphenyl]-4-yl]propanoic acid | 25 | Calculated (M − H)$^-$ = 574.17; Found (M − H)$^-$ = 574.00. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[2-(ethyloxy)[1,1'-biphenyl]-4-yl]propanoic acid | 20 | Calculated (M − H)$^-$ = 600.19; Found (M − H)$^-$ = 600.01. |
| (3S)-3-{[({1-[(2-chlorophenyl)methyl]-4-hydroxy-5-methyl-2-oxo-1,2-dihydro-3-pyridinyl}amino)carbonyl]amino}-3-(2'-methyl[1,1'-biphenyl]-3-yl)propanoic acid | 20 | Calculated (M − H)$^-$ = 544.16; Found (M − H)$^-$ = 544.04. |

TABLE 7-continued

| Compound | IC$_{50}$ (nM) | Mass Spectral Data (m/z) |
| --- | --- | --- |
| (3S)-3-{[({1-[(2-chlorophenyl)methyl]-4-hydroxy-5-methyl-2-oxo-1,2-dihydro-3-pyridinyl}amino)carbonyl]amino}-3-(3'-methyl[1,1'-biphenyl]-3-yl)propanoic acid | 18 | Calculated (M − H)$^-$ = 544.16; Found (M − H)$^-$ = 544.00. |
| (3S)-3-({[(1-{[2-chloro-6-tetrahydro-1(2H)-pyridinylphenyl]methyl}-4-hydroxy-5-methyl-2-oxo-1,2-dihydro-3-pyridinyl)amino]carbonyl}amino)-3-(4-methylphenyl)propanoic acid | 90 | Calculated (M − H)$^-$ = 551.21; Found (M − H)$^-$ = 551.06. |
| (3S)-3-{[({1-[(2-chlorophenyl)methyl]-4-hydroxy-5-methyl-2-oxo-1,2-dihydro-3-pyridinyl}amino)carbonyl]amino}-3-(4'-methyl[1,1'-biphenyl]-3-yl)propanoic acid | 23 | Calculated (M − H)$^-$ = 544.16; Found (M − H)$^-$ = 543.99. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[3-(diethylamino)phenyl]propanoic acid | 3 | Calculated (M − H)$^-$ = 551.21; Found (M − H)$^-$ = 551.05. |
| (3S)-3-{[({1-[(2-chlorophenyl)methyl]-4-hydroxy-5-methyl-2-oxo-1,2-dihydro-3-pyridinyl}amino)carbonyl]amino}-3-[3-(difluoromethyl)phenyl]propanoic acid | 20 | Calculated (M − H)$^-$ = 504.11; Found (M − H)$^-$ = 503.96. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(3-fluorophenyl)propanoic acid | 16 | Calculated (M − H)$^-$ = 498.12; Found (M − H)$^-$ = 498.02. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(4-fluorophenyl)propanoic acid | 9 | Calculated (M − H)$^-$ = 498.12; Found (M − H)$^-$ = 498.01. |
| N-{1-[(2-chlorophenyl)methyl]-4-hydroxy-5-methyl-2-oxo-1,2-dihydro-3-pyridinyl}-N'-[(R)-phenyl(1H-1,2,3,4-tetraazol-5-yl)methyl]urea | >10000 | Calculated (M − H)$^-$ = 464.12; Found (M − H)$^-$ = 464.01. |
| (3S)-3-{[({1-[(2-chloro-6-methylphenyl)methyl]-4-hydroxy-5-methyl-2-oxo-1,2-dihydro-3-pyridinyl}amino)carbonyl]amino}-3-(1-methyl-1H-indol-5-yl)propanoic acid | 4 | Calculated (M − H)$^-$ = 521.16; Found (M − H)$^-$ = 521.00. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-[3-(diethylamino)phenyl]propanoic acid | 10 | Calculated (M − H)$^-$ = 565.14; Found (M − H)$^-$ = 565.04. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(3-methylphenyl)propanoic acid | 4 | Calculated (M − H)$^-$ = 508.16; Found (M − H)$^-$ = 508.03. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-phenylpropanoic acid | 17 | Calculated (M − H)$^-$ = 494.15; Found (M − H)$^-$ = 494.09. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(3-hydroxyphenyl)propanoic acid | 8 | Calculated (M − H)$^-$ = 496.13; Found (M − H)$^-$ = 495.99. |
| (3S)-3-{[({1-[(2-chlorophenyl)methyl]-4-hydroxy-5-methyl-2-oxo-1,2-dihydro-3-pyridinyl}amino)carbonyl]amino}-3-(3-hydroxyphenyl)propanoic acid | 9 | Calculated (M − H)$^-$ = 470.11; Found (M − H)$^-$ = 469.98. |
| (3S)-3-{[({1-[(2-chlorophenyl)methyl]-4-hydroxy-5-methyl-2-oxo-1,2-dihydro-3-pyridinyl}amino)carbonyl]amino}-3-(3',5'-dimethyl[1,1'-biphenyl]-3-yl)propanoic acid | 50 | Calculated (M − H)$^-$ = 558.18; Found (M − H)$^-$ = 558.00. |
| (3S)-3-{[({1-[(2-chlorophenyl)methyl]-4-hydroxy-5-methyl-2-oxo-1,2-dihydro-3-pyridinyl}amino)carbonyl]amino}-3-phenylpropanoic acid | 15 | Calculated (M − H)$^-$ = 455.12; Found (M − H)$^-$ = 454.00. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(methylsulfonyl)amino]phenyl}propanoic acid | 3 | Calculated (M − H)$^-$ = 573.12; Found (M − H)$^-$ = 572.98. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[(methylsulfonyl)amino]phenyl}propanoic acid | 3 | Calculated (M − H)$^-$ = 587.14; Found (M − H)$^-$ = 586.98. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[3-(difluoromethyl)phenyl]propanoic acid | 4 | Calculated (M − H)$^-$ = 530.13; Found (M − H)$^-$ = 530.03. |

TABLE 7-continued

| Compound | IC$_{50}$ (nM) | Mass Spectral Data (m/z) |
|---|---|---|
| (2S,3S)-3-{[({1-[(2-chlorophenyl)methyl]-4-hydroxy-5-methyl-2-oxo-1,2-dihydro-3-pyridinyl}amino)carbonyl]amino}-2-methyl-3-(4-methylphenyl)propanoic acid | 1500 | Calculated (M − H)$^-$ = 482.15; Found (M − H)$^-$ = 481.99. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(4-ethylphenyl)propanoic acid | 15 | Calculated (M − H)$^-$ = 522.18; Found (M − H)$^-$ = 522.04. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-(2,2-dimethyl-2,3-dihydro-1-benzofuran-5-yl)propanoic acid | 3 | Calculated (M − H)$^-$ = 550.17; Found (M − H)− = 550.05. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-[3-fluoro-4-(methyloxy)phenyl]propanoic acid | 3 | Calculated (M − H)$^-$ = 542.15; Found (M − H)− = 542.00. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[(trifluoromethyl)oxy]phenyl}propanoic acid | 11 | Calculated (M − H)$^-$ = 578.13; Found (M − H)− = 578.02. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[methyl(methylsulfonyl)amino]phenyl}propanoic acid | 1.6 | Calculated (M − H)$^-$ = 587.14; Found (M − H)− = 586.99. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[methyl(methylsulfonyl)amino]phenyl}propanoic acid | 1.3 | Calculated (M − H)$^-$ = 601.15; Found (M − H)− = 601.00. |
| (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[ethyl(methylsulfonyl)amino]phenyl}propanoic acid | 1 | Calculated (M − H)$^-$ = 601.15; Found (M − H)− = 601.00. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[ethyl(methylsulfonyl)amino]phenyl}propanoic acid | 1 | Calculated (M − H)$^-$ = 615.17; Found (M − H)− = 615.04. |
| (3S)-3-{[({1-[(2-chlorophenyl)methyl]-4-hydroxy-5-methyl-2-oxo-1,2-dihydro-3-pyridinyl}amino)carbonyl]amino}-3-(2'-fluoro[1,1'-biphenyl]-3-yl)propanoic acid | 25 | Calculated (M − H)$^-$ = 548.14; Found (M − H)− = 547.96. |
| (3S)-3-{[({1-[(2-chlorophenyl)methyl]-4-hydroxy-5-methyl-2-oxo-1,2-dihydro-3-pyridinyl}amino)carbonyl]amino}-3-[2'-(trifluoromethyl)[1,1'-biphenyl]-3-yl]propanoic acid | 157 | Calculated (M − H)$^-$ = 598.14; Found (M − H)− = 597.97. |
| (3S)-3-{[({1-[(2-chlorophenyl)methyl]-4-hydroxy-5-methyl-2-oxo-1,2-dihydro-3-pyridinyl}amino)carbonyl]amino}-3-(2-fluorophenyl)propanoic acid | 10 | Calculated (M − H)$^-$ = 472.11; Found (M − H)− = 471.98. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(1H-indol-5-yl)propanoic acid | 2 | Calculated (M − H)$^-$ = 533.16; Found (M − H)− = 533.01. |
| (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(3,5-difluorophenyl)propanoic acid | 11 | Calculated (M − H)$^-$ = 530.13; Found (M − H)− = 530.00. |

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A compound of the structure:

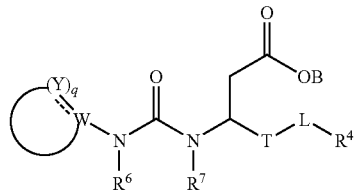

wherein

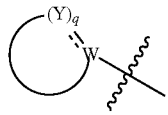

is

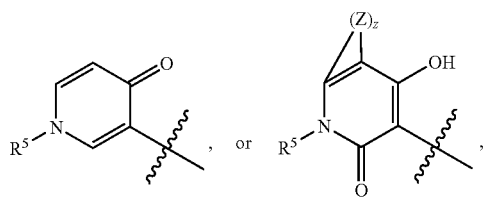

wherein each Z is independently selected from the group consisting of $CR^{30}$ and $C(R^{31})(R^{32})$;

z is an integer of from 3 to 5:

T is $(CH_2)_b$ wherein b is 0;

L is $(CH_2)_n$ wherein n is 0;

B and $R^6$ are independently selected from the group consisting of hydrogen and alkyl;

$R^4$ is selected from the group consisting of aryl, biaryl and alkyl wherein $R^4$ can be unsubstituted or substituted with one or more electron donating or electron withdrawing groups selected from the group consisting of alkyl, alkoxy, halogen, —O(haloalkyl), haloalkyl, —O(cycloalkylalkyl), cycloalkyl, dialkylamino, —O(cycloalkyl), —NHSO₂(alkyl), —N(alkyl)SO₂(alkyl);

$R^5$ is selected from the group consisting of aralkyl, —O(aryl), —NH(aralkyl), wherein $R^5$ can be unsubstituted or substituted with one or more electron donating or electron withdrawing groups selected from the group consisting of halogen, —CN, alkyl, alkoxy or alkoxyalkoxy; and $R^7$, $R^{30}$, $R^{31}$ and $R^{32}$ when present are each hydrogen;

or a pharmaceutically acceptable salt thereof.

2. The compound of claim 1 having the structure:

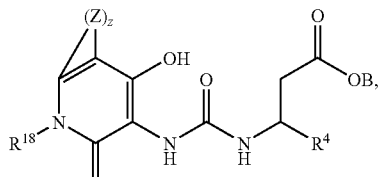

wherein

Z is selected from the group consisting of $CH_2$ and CH;

z is an integer of from 3 to 5;

$R^{18}$ is aralkyl, wherein $R^{18}$ can be unsubstituted or substituted with one or more electron donating or electron withdrawing groups selected from the group consisting of halogen, alkyl, alkoxy or alkoxyalkoxy;

or a pharmaceutically acceptable salt thereof.

3. The compound of claim 1 having the structure:

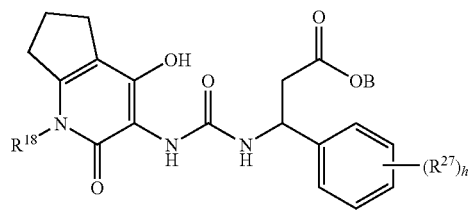

wherein $R^{18}$ is aralkyl wherein $R^{18}$ can be unsubstituted or substituted with one or more electron donating or electron withdrawing groups selected from the group consisting of halogen, alkyl, alkoxy or alkoxyalkoxy;

$R^{27}$ is selected from the group consisting of alkyl, alkoxy, halogen, —O(haloalkyl), haloalkyl, —O(cycloalkylalkyl), cycloalkyl, dialkylamino, —O(cycloalkyl), —NHSO$_2$(alkyl), —N(alkyl)SO$_2$(alkyl); and h is an integer of from 0 to 5;

or a pharmaceutically acceptable salt thereof.

4. A compound selected from the group consisting of:

(3S)-3-{[({1-[(2-chlorophenyl)methyl]-4-hydroxy-2-oxo-1,2-dihydro-3quinolinyl}amino)carbonyl]amino}-3-(4-methylphenyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-methylphenyl)propanoic acid, (3S)-3-[({[1-(2-chloro-6-methylbenzyl)-4-hydroxy-2-oxo-2,5,6,7-tetrahydro-1H-cyclopenta[b]pyridin-3-yl]amino}carbonyl)amino]-3-(3-ethoxyphenyl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-isopropoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-ethoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3,5-diethoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-(3-propoxyphenyl)propanoic acid, (3S)-3-[({[1-(2-chloro-6-ethoxybenzyl)-4-hydroxy-2-oxo-2,5,6,7-tetrahydro-1H-cyclopenta[b]pyridin-3-yl]amino}carbonyl)amino]-3-phenylpropanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1,3-diethyl-2-oxo-2,3-dihydro-1H-benzimidazole-5-yl)propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(1-methyl-1H-indol-5-yl)propanoic acid, (3S)-3-[({[1-(6-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopropyloxy)phenyl]propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid, (3S)-3-{[([1-(2-chloro-6-ethoxybenzyl)-4-hydroxy-2-oxo-2,5,6,7-tetrahydro-1H-cyclopenta[b]pyridin-3-yl]amino}carbonyl)amino]-3-[3-(cyclopropylmethoxy)phenyl]propanoic acid, (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(3-methylphenyl)propanoic acid, (3S)-3-{[([1-(2-chlorobenzyl)-4-hydroxy-2-oxo-2,5,6,7-tetrahydro-1H-cyclopenta[b]pyridin-3-yl]amino}carbonyl)amino]-3-(3,5-dimethylphenyl)propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(difluoromethyl)oxy]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(1,1,2,2-tetrafluoroethyl)oxy]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{1-ethyl-1H-indol-5-yl)propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-[1-methyl-1H-indol-5-yl)propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-[3-(diethylamino)phenyl]propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[(methylsulfonyl)amino]phenyl 1 propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[methyl(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[methyl(methylsulfonyl)amino]phenyl}propanoic acid, (3S)-3-{[({1-[(2-chlorophenyl)methyl]-4-hydroxy-2-oxo-2,5,6,7-tetrahydro-1H-cyclopenta[b]pyridin-3-yl}amino)carbonyl]amino}-3-{3-[ethyl(methylsulfonyl)amino]phenyl}propanoic acid, (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-{3-[ethyl(methylsulfonyl)amino]phenyl}propanoic acid, and (3S)-3-{[({1-[(2-chloro-6-methylphenyl)methyl]-4-hydroxy-2-oxo-2,5,6,7-tetrahydro-1H-cyclopenta[b]pyridin-3-yl}amino)carbonyl]amino}-3-(1H-indol-5-yl)propanoic acid.

5. (3S)-3-[({[1-(2-chlorobenzyl)-4-hydroxy-2-oxo-2,5,6,7-tetrahydro-1H-cyclopenta[b]pyridin-3-yl]amino}carbonyl)amino]-3-(4-methylphenyl) propanoic acid and pharmaceutically acceptable salts thereof.

6. A pharmaceutical composition comprising a therapeutically effective amount of the compound of claim 1 and a pharmaceutically acceptable carrier.

7. A method for treating asthma, multiple sclerosis or inflammatory bowel diseases in a mammal comprising administering to said mammal a therapeutically effective amount of a compound of claim 1.

* * * * *

SEQUENCE LISTING

<160> NUMBER OF SEQ ID NOS: 1

<210> SEQ ID NO 1
<211> LENGTH: 26
<212> TYPE: PRT
<213> ORGANISM: Homo Sapiens

<400> SEQUENCE: 1

Cys Asp Glu Leu Pro Gln Leu Val Thr Leu Pro His Pro Asn Leu His
 1               5                  10                  15

Gly Pro Glu Ile Leu Asp Val Pro Ser Thr
            20                  25